US012497396B2

(12) United States Patent
Liu et al.

(10) Patent No.: US 12,497,396 B2
(45) Date of Patent: Dec. 16, 2025

(54) NITROGEN-CONTAINING HETEROCYCLIC DERIVATIVES, METHOD THEREFOR AND APPLICATION THEREFOR AS INHIBITORS OF KRAS G12C FOR THE TREATMENT OF CANCERS

(71) Applicants: SHANGHAI HANSOH BIOMEDICAL CO., LTD., Shanghai (CN); JIANGSU HANSOH PHARMACEUTICAL GROUP CO., LTD., Lianyungang (CN)

(72) Inventors: Shiqiang Liu, Shanghai (CN); Yongsheng Wang, Shanghai (CN); Yida Yuan, Shanghai (CN); Cheng Cen, Shanghai (CN); Rudi Bao, Shanghai (CN)

(73) Assignees: SHANGHAI HANSOH BIOMEDICAL CO., LTD., Shanghai (CN); JIANGSU HANSOH PHARMACEUTICAL GROUP CO., LTD., Lianyungang (CN)

( * ) Notice: Subject to any disclaimer, the term of this patent is extended or adjusted under 35 U.S.C. 154(b) by 884 days.

(21) Appl. No.: 17/614,652

(22) PCT Filed: May 29, 2020

(86) PCT No.: PCT/CN2020/093285

§ 371 (c)(1),
(2) Date: Nov. 29, 2021

(87) PCT Pub. No.: WO2020/239077

PCT Pub. Date: Dec. 3, 2020

(65) Prior Publication Data

US 2022/0213100 A1 Jul. 7, 2022

(30) Foreign Application Priority Data

| | | |
|---|---|---|
| May 29, 2019 | (CN) | 201910457161.6 |
| Sep. 26, 2019 | (CN) | 201910918582.4 |
| Oct. 24, 2019 | (CN) | 201911018909.9 |
| Nov. 8, 2019 | (CN) | 201911090171.7 |
| Dec. 27, 2019 | (CN) | 201911382159.3 |
| May 25, 2020 | (CN) | 202010451270.X |

(51) Int. Cl.

| | |
|---|---|
| ***C07D 471/04*** | (2006.01) |
| ***A61P 35/00*** | (2006.01) |
| ***C07D 519/00*** | (2006.01) |

(52) U.S. Cl.

CPC ............ *C07D 471/04* (2013.01); *A61P 35/00* (2018.01); *C07D 519/00* (2013.01)

(58) Field of Classification Search

CPC ................ A61K 31/496; A61K 31/519; A61K 31/5365; A61K 31/5377; A61P 35/00; A61P 35/02; C07D 471/04; C07D 471/10; C07D 519/00; C07D 487/10

See application file for complete search history.

(56) References Cited

U.S. PATENT DOCUMENTS

| | | | |
|---|---|---|---|
| 2009/0099174 | A1 | 4/2009 | Smith |
| 2016/0297774 | A1 | 10/2016 | Li et al. |

FOREIGN PATENT DOCUMENTS

| | | | |
|---|---|---|---|
| CN | 106488910 | A | 3/2017 |
| CN | 107849022 | A | 3/2018 |
| RU | 2010118452 | A | 11/2011 |
| WO | 2015054572 | A1 | 4/2015 |
| WO | 2017201161 | A1 | 11/2017 |
| WO | 2018064510 | A1 | 4/2018 |
| WO | 2018119183 | A2 | 6/2018 |
| WO | 2018217651 | A1 | 11/2018 |
| WO | 2018218070 | A2 | 11/2018 |
| WO | 2019051291 | A1 | 3/2019 |

(Continued)

OTHER PUBLICATIONS

Office Action for Japan Patent Application No. 2021-571028, mailed Apr. 9, 2024.

(Continued)

*Primary Examiner* — Sarah Pihonak

*Assistant Examiner* — Padmaja S Rao

(74) *Attorney, Agent, or Firm* — Pilloff Passino & Cosenza LLP; Rachel Pilloff; Sean Passino

(57) ABSTRACT

Disclosed are a nitrogen-containing heterocyclic derivative regulator, a preparation method therefor and an application thereof. In particular, disclosed are a compound as represented by general formula (I), a preparation method for the compound and a pharmaceutical composition containing the compound, and the use thereof as a KRAS G12C mutation inhibitor in treatment of diseases or symptoms such as leukemia, neuroblastoma, melanoma, breast cancer, lung cancer and colon cancer, wherein the definitions of substituents in general formula (I) are the same as those in the description.

(I)

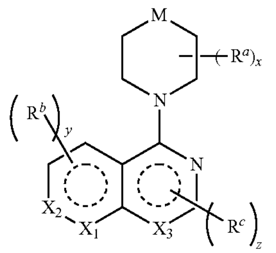

16 Claims, No Drawings

(56) References Cited

FOREIGN PATENT DOCUMENTS

| | | | |
|---|---|---|---|
| WO | 2019099524 | A1 | 5/2019 |
| WO | 2019213516 | A1 | 11/2019 |
| WO | 2020050890 | A2 | 3/2020 |

OTHER PUBLICATIONS

Office Action for Canada Patent Application No. 3,139,769, mailed Mar. 19, 2024.
First office Action issued Oct. 6, 2023 in Russian Patent Application No. 2021136926.
Klaus Kuemmerer, Pharmaceuticals in the Environment, Annu. Rev. Environ. Resour. 2010. 35:57-75 (call if you want a color copy via email (please use mail@pilloffpassino.com).
Second office Action issued Mar. 5, 2024 in Russian Patent Application No. 2021136926.
Second office Action issued Dec. 23, 2023 in China Patent Application No. 202080012820.6.
International Search Report and Written Opinion for PCT/CN2020/093285, mailed Aug. 27, 2020.
le;2qSupplementary Partial European Search Report issued in Patent Application of EP20815480.7, mailed Jan. 4, 2023.
José MA. Quintela et al., "A novel synthesis of pyrano[2,3-d]pyrimidine derivatives," Tetrahedron, May 1995, pp. 5,901-5,912, vol. 51, No. 20.
Kazuhiro Kobayashi et al., "Synthesis of 6,7-Dihydro-5H-Thiopyrano[2,3-d]Pyrimidin-5-One Derivatives Starting With 4,6-Dichloro-2-(Methylsulfanyl)Pyrimidine," Heterocycles, Dec. 2017, pp. 287-296, vol. 96, No. 2.
First Office Action issued in the counterpart Chinese application No. 202080012820.6 dated Mar. 8, 2023.
Supplementary Partial European Search Report issued in Patent Application of EP20815480.7, mailed Mar. 20, 2023.
Office action in TW application No. 109118156 dated Feb. 19, 2025.
Request for the Submission of an Opinion in KR application 20217043051 dated Apr. 7, 2025.
Examination report No. 1 for AU application 2020282473 dated Mar. 18, 2025.

NITROGEN-CONTAINING HETEROCYCLIC DERIVATIVES, METHOD THEREFOR AND APPLICATION THEREFOR AS INHIBITORS OF KRAS G12C FOR THE TREATMENT OF CANCERS

This application claims the priorities of the Chinese patent application CN2019104571616 filed on May 29, 2019, the Chinese patent application CN2019109185824 filed on Sep. 26, 2019, the Chinese patent application CN2019110189099 filed on Oct. 24, 2019, the Chinese patent application CN2019110901717 field on Nov. 8, 2019, the Chinese patent application CN2019113821593 filed on Dec. 27, 2019, the Chinese patent application CN202010451270X filed on May 25, 2020. The present disclosure refers to the full text of the above Chinese patent applications.

TECHNICAL FIELD

The present disclosure belongs to the field of drug synthesis, specifically related to a nitrogen-containing heterocyclic derivative inhibitor, a preparation method therefor and a use thereof.

PRIOR ART

Rat sarcoma (RAS), encoded by the proto-oncogenes HRAS, NRAS, and KRAS, is classified as 4 proteins, HRAS, NRAS, KRAS4A and KRAS4B, and is a GTP (guanosine triphosphate) binding protein. RAS is located on the inner surface of the cell membrane, upstream of which is receptor tyrosine kinase (RTK), after activation, it regulates downstream PI3K, RAF and other signaling pathways, thereby regulating cell growth, survival, migration and differentiation, etc.

RAS has two main states in the body: the inactive state combined with GDP (guanosine diphosphate) and the activated state combined with GTP. Its activity is regulated by two proteins, guanine nucleotide exchange factor (GEF) promotes the release of GDP from the RAS protein, allowing GTP to bind to activate RAS; GTPase activating protein (GAP) activates the GTPase activity of the RAS protein, hydrolyzing the GTP bound to the RAS protein into GDP and inactivates the RAS. Under normal circumstances, the RAS protein is in an inactive state, the conformation changes after mutation, RAS is continuously in an activated state, and downstream signaling pathways are also continuously activated, leading to the occurrence of various cancers.

As the first confirmed oncogene, RAS is the oncogene with the highest mutation rate, accounting for an average of 25% of human cancers. The most common oncogenic mutation in the RAS family is KRAS (85%), while NRAS (12%) and HRAS (3%) are relatively rare. KRAS mutations mainly occur in a series of cancers such as pancreatic cancer (95%), colorectal cancer (52%) and lung cancer (31%), etc. The most common mutation mode of KRAS is point mutation, which mostly occurs in G12, G13 in p-loop (aa 10-17) and Q61 in Switch II region (aa59-76), wherein G12 mutation is the most common (83%). KRAS G12C is one of the most common mutations in non-small cell lung cancer (NSCLC) and colorectal cancer.

Although there are great clinical needs, no drugs that directly target KRAS have been marketed so far, currently, patients with KRAS mutations in clinical treatment can only be treated with chemotherapy. The difficulty in the development of KRAS inhibitors is mainly due to two factors, first, the structure of RAS protein is smooth, and small molecules are difficult to bind to the protein surface; second, the affinity of RAS GTPase for GTP is as high as picomolar (pM) level, and the level of endogenous GTP is high, small molecule drugs are difficult to block the combination of the two. Recent studies have found that after the mutation of Glycine (Gly) at position 12 of KRAS to Cysteine (Cys), the conformation changes and a new pocket is formed for the covalent binding of small molecules, which irreversibly locks KRAS G12C in binding to GDP in an inactivated state. Therefore, KRAS G12C inhibitors are expected to be the first drugs that directly target KRAS.

At present, many KRAS G12C inhibitors have entered the clinical research stage, such as AMG 510 developed by Amgen, ARS-3248 developed by Wellspring Biosciences, and MTRX849 developed by Mirati, all of which are currently in the clinical phase I research stage, but none of them have been developed and marketed as KRAS G12C inhibitor.

There is no specific target drug for KRAS G12C, and there is a large clinical demand, KRAS G12C inhibitors with higher selectivity, better activity and better safety have the potential to treat a variety of cancers and have broad market prospects.

CONTENT OF THE PRESENT INVENTION

The object of the present disclosure is to provide a compound represented by general formula (I), a stereoisomer thereof or a pharmaceutically acceptable salt thereof, wherein the structure of the compound represented by general formula (I) is as follows:

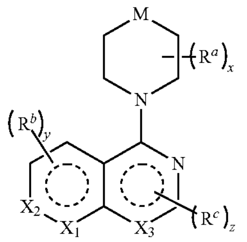

(I)

wherein:

M is selected from $CR_{aa}R_1$ or $NR_1$;

$X_1$ and $X_2$ are each independently selected from O, S, N, $NR_2$, $CR_2$ or $CR_{aa}R_2$;

$X_3$ is selected from N, $NR_3$ or $CR_3$;

$R_1$ is selected from hydrogen, deuterium, halogen, amino, hydroxyl, cyano, nitro, alkyl, alkenyl, alkynyl, deuterated alkyl, haloalkyl, alkoxy, haloalkoxy, hydroxyalkyl, cycloalkyl, heterocyclyl, aryl, heteroaryl or $-(CH_2)_nC(O)CH{=}CHR_{aa}$, the alkyl, alkenyl, alkynyl, deuterated alkyl, haloalkyl, alkoxy, haloalkoxy, hydroxyalkyl, cycloalkyl, heterocyclyl, aryl and heteroaryl can be optionally further substituted;

$R_2$ is selected from hydrogen, deuterium, halogen, amino, hydroxyl, cyano, nitro, alkyl, alkenyl, alkynyl, deuterated alkyl, haloalkyl, alkoxy, haloalkoxy, hydroxyalkyl, cycloalkyl, heterocyclyl, aryl or heteroaryl, the alkyl, alkenyl, alkynyl, deuterated alkyl, haloalkyl, alkoxy, haloalkoxy, hydroxyalkyl, cycloalkyl, heterocyclyl, aryl and heteroaryl can be optionally further substituted;

$R_3$ is selected from hydrogen, deuterium, halogen, amino, hydroxyl, cyano, nitro, alkyl, alkenyl, alkynyl, deuterated alkyl, haloalkyl, alkoxy, haloalkoxy, hydroxyalkyl, cycloalkyl, heterocyclyl, aryl or heteroaryl, wherein the alkyl, alkenyl, alkynyl, deuterated alkyl, haloalkyl, alkoxy, haloalkoxy, hydroxyalkyl, cycloalkyl, heterocyclyl, aryl and heteroaryl can be optionally further substituted;

$R^a$ is selected from hydrogen, deuterium, halogen, amino, hydroxyl, cyano, nitro, alkyl, alkenyl, alkynyl, oxo, thio, deuterated alkyl, haloalkyl, alkoxy, haloalkoxy, hydroxyalkyl, cyano-substituted alkyl, cycloalkyl, heterocyclyl, aryl or heteroaryl, the alkyl, alkenyl, alkynyl, deuterated alkyl, haloalkyl, alkoxy, haloalkoxy, hydroxyalkyl, cyano-substituted alkyl, cycloalkyl, heterocyclyl, aryl and heteroaryl can be optionally further substituted;

$R^b$ is selected from hydrogen, deuterium, halogen, amino, hydroxyl, cyano, nitro, alkyl, alkenyl, alkynyl, oxo, thio, deuterated alkyl, haloalkyl, alkoxy, haloalkoxy, hydroxyalkyl, cyano-substituted alkyl, cycloalkyl, heterocyclyl, aryl or heteroaryl, the alkyl, alkenyl, alkynyl, deuterated alkyl, haloalkyl, alkoxy, haloalkoxy, hydroxyalkyl, cyano-substituted alkyl, cycloalkyl, heterocyclyl, aryl and heteroaryl can be optionally further substituted;

or, any two adjacent or non-adjacent $R^b$ are connected to form a cycloalkyl, heterocyclyl, aryl or heteroaryl, the cycloalkyl, heterocyclyl, aryl and heteroaryl can be optionally further substituted;

$R^c$ is selected from hydrogen, deuterium, halogen, amino, hydroxyl, cyano, nitro, alkyl, alkenyl, alkynyl, oxo, thio, deuterated alkyl, haloalkyl, alkoxy, haloalkoxy, hydroxyalkyl, cyano-substituted alkyl, cycloalkyl, heterocyclyl, aryl, heteroaryl, $—CH{=}CH(CH_2)_nR_{bb}$, $—CH{=}CH(CH_2)_nNR_{bb}R_{cc}$, $—O(CH_2)_nR_{bb}$, $—OC(R_{bb}R_{cc})_n(CH_2)_mR_{aa}$, $—CH{=}CH(CH_2)_nNR_{bb}(CH_2)_mC(O)R_{cc}$, $—CH{=}CH(CH_2)_nNR_{bb}(CH_2)_mC(O)NR_{cc}R_{aa}$, $—NR_{bb}(CH_2)_nR_{cc}$, $—(CH_2)_{n1}—$, $—(CH_2)_nR_{bb}$, $—(CH_2)_nOR_{bb}$, $—(CH_2)_nSR_{bb}$, $—(CH_2)_nC(O)R_{bb}$, $—(CH_2)_nC(O)OR_{bb}$, $—(CH_2)_{n1}S(O)_mR_{bb}$, $—(CH_2)_nNR_{bb}R_{cc}$, $—(CH_2)_nC(O)NR_{bb}R_{cc}$, $—(CH_2)_nNR_{bb}C(O)R_{cc}$ or $—(CH_2)_nNR_{bb}S(O)_mR_{cc}$, the alkyl, alkenyl, alkynyl, deuterated alkyl, haloalkyl, alkoxy, haloalkoxy, hydroxyalkyl, cyano-substituted alkyl, cycloalkyl, heterocyclyl, aryl and heterocyclyl can be optionally further substituted;

$R_{aa}$ is selected from hydrogen, deuterium, halogen, amino, hydroxyl, cyano, nitro, alkyl, alkenyl, alkynyl, deuterated alkyl, haloalkyl, alkoxy, haloalkoxy, hydroxyalkyl, cycloalkyl, heterocyclyl, aryl or heteroaryl, the amino, alkyl, alkenyl, alkynyl, deuterated alkyl, haloalkyl, alkoxy, haloalkoxy, hydroxyalkyl, cyano-substituted alkyl, cycloalkyl, heterocyclyl, aryl and heteroaryl can be optionally further substituted;

$R_{bb}$ and $R_{cc}$ are each independently selected from hydrogen, deuterium, halogen, amino, hydroxyl, cyano, nitro, alkyl, alkenyl, alkynyl, deuterated alkyl, haloalkyl, alkoxy, haloalkoxy, hydroxyalkyl, cyano-substituted alkyl, cycloalkyl, heterocyclyl, aryl or heteroaryl, the amino, alkyl, alkenyl, alkynyl, deuterated alkyl, haloalkyl, alkoxy, haloalkoxy, hydroxyalkyl, cyano-substituted alkyl, cycloalkyl, heterocyclyl, aryl and heteroaryl can be optionally further substituted;

or, $R_{bb}$ and $R_{cc}$ together with the adjacent atoms form a cycloalkyl, heterocyclyl, aryl or heteroaryl, the cycloalkyl, heterocyclyl, aryl and heteroaryl can be optionally further substituted;

$R_{dd}$ is selected from hydrogen, deuterium, halogen, amino, hydroxyl, cyano, nitro, alkyl, alkenyl, alkynyl, deuterated alkyl, haloalkyl, alkoxy, haloalkoxy, hydroxyalkyl, cyano-substituted alkyl, cycloalkyl, heterocyclyl, aryl or heteroaryl, the amino, alkyl, alkenyl, alkynyl, deuterated alkyl, haloalkyl, alkoxy, haloalkoxy, hydroxyalkyl, cyano-substituted alkyl, cycloalkyl, heterocyclyl, aryl and heteroaryl can be optionally further substituted;

or, $R_{cc}$ and $R_{dd}$ together with the adjacent atoms form a cycloalkyl, heterocyclyl, aryl or heteroaryl, the cycloalkyl, heterocyclyl, aryl and heteroaryl can be optionally further substituted;

x is an integer from 0 to 6;

y is an integer from 0 to 6;

z is an integer from 0 to 6;

m is 0, 1 2 or 3;

n is 0, 1, 2 or 3;

n1 is 0, 1, 2 or 3;

wherein, when $X_3$ is $NR_3$, $R^c$ is oxo or thio, and $R^c$ is connected to a carbon atom in the same ring adjacent to $X_3$, $X_1$ is $CH_2$, and $X_2$ is $NR_2$;

when $X_3$ is N, $X_1$ is $CH_2$ and $X_2$ is $NR_2$; or $X_1$ is N, $X_2$ is $CR_2$.

In a preferred embodiment of the present disclosure, when $X_3$ is $NR_3$, $R^c$ is oxo or thio, and $R^c$ is connected to a carbon atom in the same ring adjacent to $X_3$, $X_1$ is selected from N, $NR_2$ or $CH_2$; $X_2$ is selected from N, $CR_2$ or $NH_2$;

or, when $X_3$ is N, $X_1$ is selected from N, $CH_2$ or $NR_2$, and $X_2$ is selected from $CR_2$ or $NR_2$;

preferably, when $X_3$ is $NR_3$, $R^c$ is oxo or thio, $X_1$ is $CH_2$, $X_2$ is $NR_2$;

when $X_3$ is N, $X_1$ is $CH_2$ and $X_2$ is $NR_2$; or $X_1$ is N, $X_2$ is $CR_2$;

in addition, when $X_1$ and $X_2$ are both $CR_2$ or $NR_2$, $R_2$ is not necessarily the same group, but can be independently selected from hydrogen, deuterium, halogen, amino, hydroxyl, cyano, nitro, alkyl, alkenyl, alkynyl, deuterated alkyl, haloalkyl, alkoxy, haloalkoxy, hydroxyalkyl, cycloalkyl, heterocyclyl, aryl or heteroaryl, the alkyl, alkenyl, alkynyl, deuterated alkyl, haloalkyl, alkoxy, haloalkoxy, hydroxyalkyl, cycloalkyl, heterocyclyl, aryl and heteroaryl can be optionally further substituted.

In a preferred embodiment of the present disclosure, $R_1$ is selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, $C_{3-12}$ cycloalkyl, 3-12 membered heterocyclyl, $C_{6-12}$ aryl, 5-12 membered heteroaryl or $—(CH_2)_nC(O)CH{=}CHR_{aa}$;

preferably 3-12 membered heterocyclyl and $—(CH_2)_nC(O)CH{=}CHR_{aa}$;

more preferably 3-10 membered heterocyclyl and $—C(O)CH{=}CR_{aa}$; the 3-10 heterocyclyl is selected from 5-6 membered heterocyclyl containing 1-2 of nitrogen atoms, oxygen atoms or sulfur atoms, and optionally substituted by one or more substituents selected from deuterium, halogen, amino, hydroxyl, cyano, nitro, oxo and methylenyl;

$R_{aa}$ is selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl; preferably hydrogen or $C_{1-3}$ alkyl;

In a preferred embodiment of the present disclosure, $R_1$ is selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, $C_{3-12}$ cycloalkyl, 3-12 membered heterocyclyl, $C_{6-12}$ aryl, 5-12 membered heteroaryl or $-(CH_2)_nC(O)CH=CHR_{aa}$, the $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, $C_{3-12}$ cycloalkyl, 3-12 membered heterocyclyl, $C_{6-12}$ aryl and 5-12 membered heteroaryl are optionally substituted by one or more substituents selected from hydrogen, deuterium, halogen, amino, hydroxyl, cyano, nitro, oxo, methylene, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl, more preferably,

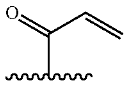,
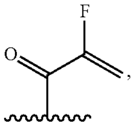,
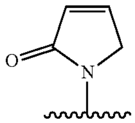
or
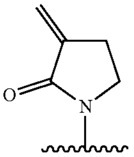;

most preferably

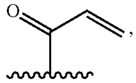,
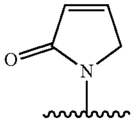
or
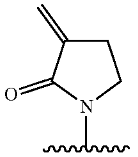;

$R_{aa}$ is selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl; preferably hydrogen or $C_{1-3}$ alkyl.

In a further preferred embodiment of the present disclosure, $R_1$ is selected from 3-12 membered heterocyclyl or $-(CH_2)_nC(O)CH=CHR_{aa}$, and the 3-12 membered heterocyclyl is optionally substituted by one or more substituents selected from hydrogen, deuterium, halogen, amino, hydroxyl, cyano, nitro, oxo and methylene.

In a further preferred embodiment of the present disclosure, $R_1$ is selected from 3-10 membered heterocyclyl or $-C(O)CH=CHR_{aa}$, and the 3-12 membered heterocyclyl is optionally substituted by one or more substituents selected from hydrogen, deuterium, halogen, amino, hydroxyl, cyano, nitro, oxo and methylene.

In a preferred embodiment of the present disclosure, $R_2$ is selected from $C_{3-12}$ cycloalkyl, 3-12 membered heterocyclyl, $C_{6-12}$ aryl or 5-12 membered heteroaryl, the $C_{3-12}$ cycloalkyl, 3-12 membered heterocyclyl, $C_{6-12}$ aryl and 5-12 membered heteroaryl are optionally substituted by one or more substituents selected from hydrogen, hydroxyl, halogen, amino and $C_{1-6}$ alkyl;

preferably phenyl, pyridyl, naphthyl, biphenyl, benzoheteroaryl, pyridophenyl or pyrazolophenyl, the phenyl, pyridyl, naphthyl, biphenyl, benzoheteroaryl, pyridophenyl and pyrazolophenyl are optionally substituted by one or more substituents selected from hydrogen, hydroxyl, halogen, amino and $C_{1-6}$ alkyl.

In a preferred embodiment of the present disclosure, $R_2$ is selected from $C_{3-12}$ cycloalkyl, 3-12 membered heterocyclyl, $C_{6-12}$ aryl or 5-12 membered heteroaryl, the $C_{3-12}$ cycloalkyl, 3-12 membered heterocyclyl, $C_{6-12}$ aryl or 5-12 membered heteroaryl are optionally substituted by one or more substituents selected from hydrogen, hydroxyl, halogen, amino, cyano, sulfhydryl, $C_{1-6}$ hydroxyalkyl, $C_{1-6}$ alkoxy, $C_{1-6}$ alkylthio, $C_{1-6}$ alkylthio-alkylene, $C_{1-6}$ haloalkylthio, $C_{3-12}$ cycloalkyl, $C_{1-6}$ alkylamino, carbamoyl, $C_{1-6}$ alkylacylamino, $C_{1-6}$ alkylsulfonylamino, $C_{3-12}$ cycloalkylamino, $C_{3-12}$ cycloalkylsulfonamino, $C_{1-6}$ alkylcarbamoyl, $C_{1-6}$ alkylsulfinyl, $C_{1-6}$ alkylsulfonyl and $C_{1-6}$ alkyl.

In a further preferred embodiment of the present disclosure, $R_2$ is selected from phenyl, pyridyl, naphthyl, indolyl, biphenyl, benzoheteroaryl, pyridophenyl or pyrazolophenyl, the phenyl, pyridyl, naphthyl, indolyl, biphenyl, benzoheteroaryl, pyridophenyl and pyrazolophenyl are optionally substituted by one or more substituents selected from hydrogen, hydroxyl, halogen, amino, cyano, sulfhydryl, $C_{1-6}$ hydroxyalkyl, $C_{1-6}$ alkoxy, $C_{1-6}$ alkylthio, $C_{1-6}$ alkylthio-alkylene, $C_{1-6}$ haloalkylthio, $C_{3-12}$ cycloalkyl, $C_{1-6}$ alkylamino, carbamoyl, $C_{1-6}$ alkylacylamino, $C_{1-6}$ alkylsulfonylamino, $C_{3-12}$ cycloalkylamino, $C_{3-12}$ cycloalkylsulfonamino, $C_{1-6}$ alkylcarbamoyl, $C_{1-6}$ alkylsulfinyl, $C_{1-6}$ alkylsulfonyl and $C_{1-6}$ alkyl. Specifically, the $C_{1-6}$ alkylamino can be $(CH_3)_2N-$, $(CH_3CH_2)_2NH-$,

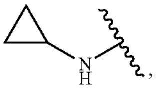 [SMILES: *NC1CC1], the carbamoyl can be $NH_2C(O)-$, the $C_{1-6}$ alkylacylamino can be $CH_3C(O)NH-$, the $C_{1-6}$ alkylsulfonamino can be $CH_3SO_2NH-$, the $C_{1-6}$ alkylcarbamoyl can be $CH_3CH_2NHC(O)-$, $(CH_3)_2NC(O)-$, $CH_3NHC(O)-$, the $C_{1-6}$ alkylsulfinyl can be $CH_3SO-$, the $C_{1-6}$ alkylsulfonyl can be $CH_3SO_2-$, etc.

In a preferred embodiment of the present disclosure, $R_3$ is selected from $C_{3-12}$ cycloalkyl, 3-12 membered heterocyclyl, $C_{6-12}$ aryl or 5-12 membered heteroaryl, the $C_{3-12}$ cycloalkyl, 3-12 membered heterocyclyl, $C_{6-12}$ aryl and 5-12 membered heteroaryl are optionally substituted by one or more substituents selected from hydrogen, hydroxyl, halogen, amino and $C_{1-6}$ alkyl; preferably phenyl and pyridyl, and the phenyl and pyridyl are optionally substituted by one or more substituents selected from hydrogen, hydroxyl, halogen, amino and $C_{1-6}$ alkyl.

In a preferred embodiment of the present disclosure, $R_3$ is selected from $C_{3-12}$ cycloalkyl, 3-12 membered heterocyclyl, $C_{6-12}$ aryl or 5-12 membered heteroaryl, the $C_{3-12}$ cycloalkyl, 3-12 membered heterocyclyl, $C_{6-12}$ aryl and 5-12 membered heteroaryl are optionally substituted by one or more substituents selected from hydrogen, hydroxyl, halogen, amino, sulfhydryl, $C_{1-6}$ alkylthio, $C_{1-6}$ alkylthio-alkylene, $C_{1-6}$ haloalkylthio, $C_{1-6}$ alkylamino-carbonyl and $C_{1-6}$ alkyl.

In a preferred embodiment of the present disclosure, $R_3$ is selected from phenyl, naphthyl, indolyl or pyridyl, the phenyl, naphthyl, indolyl and pyridyl are optionally substituted by one or more substituents selected from hydrogen, hydroxyl, halogen, amino, sulfhydryl, $C_{1-6}$ alkylthio, $C_{1-6}$ alkylthio-alkylene, $C_{1-6}$ haloalkylthio, $C_{1-6}$ alkylaminocarbonyl and $C_{1-6}$ alkyl.

In a preferred embodiment of the present disclosure, $R^a$ is selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl or cyano-substituted $C_{1-6}$ alkyl.

In a further preferred embodiment of the present disclosure, $R^a$ is selected from hydrogen, $C_{1-3}$ alkyl or cyano-substituted $C_{1-3}$ alkyl.

In a preferred embodiment of the present disclosure, $R^a$ is selected from hydrogen, deuterium, halogen, amino, hydroxyl, sulfhydryl, cyano, nitro, $C_{1-6}$ alkyl, $C_{2-6}$ alkenyl, $C_{2-6}$ alkynyl, oxo, thio, $C_{1-6}$ deuterated alkyl, $C_{1-6}$ haloalkyl, $C_{1-6}$ alkoxy, $C_{1-6}$ alkylthio, $C_{1-6}$ alkylsulfinyl, $C_{1-6}$ alkylsulfonyl, $C_{1-6}$ haloalkoxy, $C_{1-6}$hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl, the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ alkylthio, $C_{1-6}$ alkylsulfinyl, $C_{1-6}$ alkylsulfonyl, $C_{1-6}$ haloalkoxy, $C_{1-6}$ hydroxyalkyl, $C_{3-12}$ cycloalkyl, 3-12 membered heterocyclyl, $C_{6-12}$ aryl and 5-12 membered heteroaryl are optionally substituted by one or more substituents selected from hydrogen, deuterium, halogen, amino, hydroxyl, cyano, hydroxyl, sulfhydryl, nitro, oxo, methylene, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ alkylthio, $C_{1-6}$ alkylsulfinyl, $C_{1-6}$ alkylsulfonyl, $C_{1-6}$ haloalkoxy, $C_{1-6}$ hydroxyalkyl, cyano-substituted $C_{1-6}$ alkyl, $C_{3-12}$ cycloalkyl, 3-12 heterocyclyl, $C_{6-12}$ aryl, and 5-12 membered heteroaryl.

In a preferred embodiment of the present disclosure, $R^b$ is selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl or cyano-substituted $C_{1-6}$ alkyl.

In a further preferred embodiment of the present disclosure, $R^b$ is selected from hydrogen, halogen or $C_{1-3}$ alkyl.

Or, two adjacent $R^b$ together with the adjacent carbon atoms form a $C_{3-8}$ cycloalkyl, 3-8 membered heterocyclyl, $C_{6-14}$ aryl or 5-14 membered heteroaryl.

In a further preferred embodiment of the present disclosure, two adjacent $R^b$ together with the adjacent carbon atoms form a $C_{3-8}$ cycloalkyl.

In a further preferred embodiment of the present disclosure, two adjacent $R^b$ together with the adjacent carbon atoms form a cyclopropyl.

In a further preferred embodiment of the present disclosure, $R^c$ is selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl, 5-12 membered heteroaryl, $—CH{=}CH(CH_2)_nR_{bb}$, $—CH{=}CH(CH_2)_nNR_{bb}R_{cc}$, $—O(CH_2)_nR_{bb}$, $—OC(R_{bb}R_{cc})_n(CH_2)_mR_{aa}$, $—CH{=}CH(CH_2)_nNR_{bb}(CH_2)_mC(O)R_{cc}$, $—CH{=}CH(CH_2)_nNR_{bb}(CH_2)_mC(O)NR_{cc}R_{aa}$ or $—NR_{bb}(CH_2)_nR_{cc}$; the $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl are optionally substituted by one or more substituents selected from hydrogen, hydroxyl, halogen, amino, $C_{1-6}$ alkyl and 3-12 membered heterocyclyl;

preferably hydrogen, oxo, thio, $C_{3-12}$ cycloalkyl, 3-12 membered heterocyclyl, $—CH{=}CH(CH_2)_nR_{bb}$, $—CH{=}CH(CH_2)_nNR_{bb}R_{cc}$, $—O(CH_2)_nR_{bb}$ or $—OC(R_{bb}R_{cc})_n(CH_2)_mR_{aa}$, the $C_{3-12}$ cycloalkyl and 3-12 membered heterocyclyl are optionally substituted by one or more substituents selected from hydrogen, $C_{1-6}$ alkyl and 3-12 membered heterocyclyl;

$R_{bb}$ and $R_{cc}$ are each independently hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl, 5-12 membered heteroaryl, the amino, $C_{1-6}$ alkyl, $C_{2-6}$ alkenyl, $C_{2-6}$ alkynyl, $C_{1-6}$ deuterated alkyl, $C_{1-6}$ haloalkyl $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl are optionally substituted by one or more substituents selected from hydrogen, hydroxyl, halogen, amino, $C_{1-6}$ alkyl and 3-12 membered heterocyclyl;

or, $R_{bb}$ and $R_{cc}$ together with the adjacent atoms form a $C_{3-12}$ cycloalkyl, 3-12 membered heterocyclyl, $C_{6-12}$ aryl or 5-12 membered heteroaryl, the $C_{3-12}$ cycloalkyl, 3-12 membered heterocyclyl, $C_{6-12}$ aryl and 5-12 membered heteroaryl are optionally substituted by one or more substituents selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl;

$R_{dd}$ is selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl, 5-12 membered heteroaryl, the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl are optionally substituted by one or more substituents selected from hydrogen, hydroxyl, halogen, amino, cyano, $C_{1-6}$ alkyl and 3-12 membered heterocyclyl;

or, $R_{cc}$ and $R^{dd}$ together with the adjacent atoms form a $C_{3-12}$ cycloalkyl, 3-12 membered heterocyclyl, $C_{6-12}$ aryl or 5-12 membered heteroaryl, the $C_{3-12}$ cycloalkyl, 3-12 membered heterocyclyl, $C_{6-12}$ aryl and 5-12 membered heteroaryl are optionally substituted by hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl.

In a further preferred embodiment of the present disclosure, $R^c$ is selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl, 5-12 membered heteroaryl, $—CH=CH(CH_2)_nR_{bb}$, $—CH=CH(CH_2)_nNR_{bb}R_{cc}$, $—O(CH_2)_nR_{bb}$, $—CH=CH(CH_2)_nNR_{bb}(CH_2)_mC(O)R_{cc}$, $—CH=CH(CH_2)_n NR_{bb}(CH_2)_mC(O)NR_{cc}R_{aa}$, $—OC(R_{bb}R_{cc})_n(CH_2)_m R_{aa}$ or $—NR_{bb}(CH_2)_nR_{cc}$; the $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl are optionally substituted by one or more substituents selected from hydrogen, hydroxyl, halogen, amino, $C_{1-6}$ alkyl and 3-12 membered heterocyclyl.

In a further preferred embodiment of the present disclosure, $R^c$ is selected from hydrogen, $C_{1-3}$ alkyl, $C_{1-3}$ alkoxy, oxo, thio, $C_{3-12}$ cycloalkyl, 3-12 membered heterocyclyl, $—CH=CH(CH_2)_nR_{bb}$, $—CH=CH(CH_2)_nNR_{bb}R_{cc}$, $—O(CH_2)_nR_{bb}$ or $—O(CR_{bb}R_{cc})_n(CH_2)_mR_{aa}$, the $C_{1-3}$ alkyl, $C_{1-3}$ alkoxy, $C_{3-12}$ cycloalkyl and 3-12 membered heterocyclyl are optionally substituted by one or more substituents selected from hydrogen, $C_{1-6}$ alkyl and 3-12 membered heterocyclyl.

In a further preferred embodiment of the present disclosure, $R_{bb}$ and $R_{cc}$ are each independently hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl, the amino, $C_{1-6}$ alkyl, $C_{2-6}$ alkenyl, $C_{2-6}$ alkynyl, $C_{1-6}$ deuterated alkyl, $C_{1-6}$ haloalkyl $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl are optionally substituted by one or more substituents selected from hydrogen, hydroxyl, halogen, amino, $C_{1-6}$ alkyl and 3-12 membered heterocyclyl;

or, $R_{bb}$ and $R_{cc}$ together with the adjacent atoms form a $C_{3-12}$ cycloalkyl, 3-12 membered heterocyclyl, $C_{6-12}$ aryl or 5-12 membered heteroaryl, the $C_{3-12}$ cycloalkyl, 3-12 membered heterocyclyl, $C_{6-12}$ aryl and 5-12 membered heteroaryl are optionally substituted by one or more substituents selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl.

In a further preferred embodiment of the present disclosure, $R^{dd}$ is selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl, the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl are optionally substituted by one or more substituents selected from hydrogen, hydroxyl, halogen, amino, cyano, $C_{1-6}$ alkyl and 3-12 membered heterocyclyl;

or, $R_{cc}$ and $R^{dd}$ together with the adjacent atoms form a $C_{3-12}$ cycloalkyl, 3-12 membered heterocyclyl, $C_{6-12}$ aryl or 5-12 membered heteroaryl, the $C_{3-12}$ cycloalkyl, 3-12 membered heterocyclyl, $C_{6-12}$ aryl and 5-12 membered heteroaryl are optionally substituted by one or more substituents selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl.

In a further preferred embodiment of the present disclosure, the present disclosure provides a compound represented by formula (II), a stereoisomer thereof or a pharmaceutically acceptable salt thereof, the specific structure of the compound is as follows:

(II)

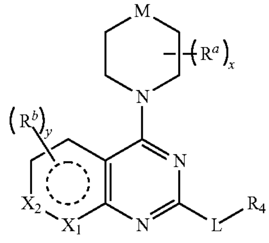

wherein:

L is selected from a bond, $—CH=CH(CH_2)_n—$, $—CH=CH(CH_2)NR_{bb}—$, $—O(CH_2)_n—$, $—CH=CH(CH_2)_nNR_{bb}(CH_2)_mC(O)—$, $—CH=CH(CH_2)_nNR_{bb}(CH_2)_m C(O)NR_{cc}—$, $—OC(R_{bb}R_{cc})_n(CH_2)_m—$, $—NR_{bb}(CH_2)_nR_{cc}$, $—(CH_2)_{n1}—$, $—(CH_2)_nR_{bb}—$, $—(CH_2)_nOR_{bb}$, $—(CH_2)_nS—$, $—(CH_2)_nC(O)—$, $—(CH_2)_nC(O)O—$, $—(CH_2)_{n1}S(O)_m—$, $—(CH_2)_nNR_{bb}—$, $—(CH_2)_nC(O)NR_{bb}—$, $—(CH_2)_nNR_{bb}C(O)—$ or $—(CH_2)_nNR_{bb}S(O)_m—$;

$R_4$ is selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl, the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl are optionally substituted by one or more substituents selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl.

In a further preferred embodiment of the present disclosure, the present disclosure provides a compound represented by formula (III), a stereoisomer thereof or a pharmaceutically acceptable salt thereof, the specific structure of the compound is as follows:

(III)

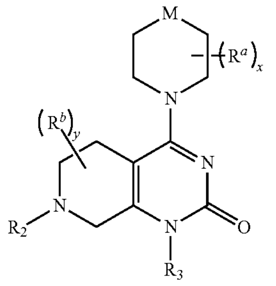

In a further preferred embodiment of the present disclosure, the present disclosure provides a compound represented by formula (IV), a stereoisomer thereof or a pharmaceutically acceptable salt thereof, the specific structure of the compound is as follows:

(IV)

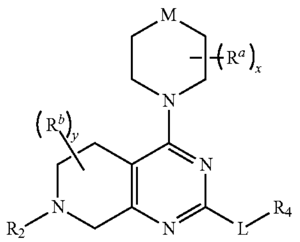

In a further preferred embodiment of the present disclosure, the present disclosure provides a compound represented by formula (V), a stereoisomer thereof or a pharmaceutically acceptable salt thereof, the specific structure of the compound is as follows:

(V)

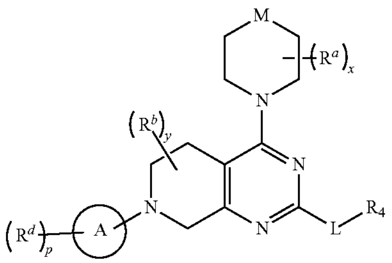

wherein:

ring A is selected from $C_{3-12}$ cycloalkyl, 3-14 membered heterocyclyl, $C_{6-14}$ aryl or 5-14 membered heteroaryl; preferably $C_{6-12}$ aryl and 5-12 membered heteroaryl;

$R_d$ is selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl, the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl are optionally substituted by one or more substituents selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl;

p is an integer from 0 to 6.

In a further preferred embodiment of the present disclosure, the present disclosure provides a compound represented by formula (VI), a stereoisomer thereof or a pharmaceutically acceptable salt thereof, the specific structure of the compound is as follows:

(VI)

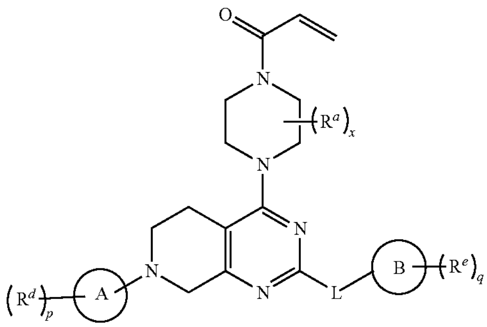

wherein:

ring B is selected from $C_{3-12}$ cycloalkyl, 3-14 membered heterocyclyl, $C_{6-14}$ aryl or 5-14 membered heteroaryl; preferably $C_{3-12}$ cycloalkyl or 3-12 membered heteroaryl;

$R^e$ is selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl, the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl are optionally substituted by one or more substituents selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl;

q is an integer from 0 to 6.

In a further preferred embodiment of the present disclosure, the present disclosure provides a compound represented by formula (VII), a stereoisomer thereof or a pharmaceutically acceptable salt thereof, the specific structure of the compound is as follows:

(VII)

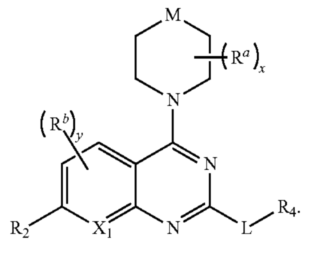

In a further preferred embodiment of the present disclosure, the present disclosure provides a compound represented by formula (VIII), a stereoisomer thereof or a pharmaceutically acceptable salt thereof, the specific structure of the compound is as follows:

(VIII)

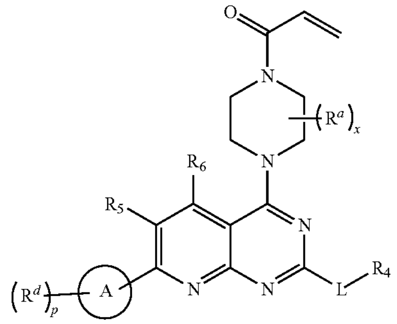

wherein:

$R_5$ is selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl, 5-12 membered heteroaryl, preferably hydrogen, halogen or $C_{1-3}$ alkyl;

$R_6$ is selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl, or 5-12 membered heteroaryl; preferably hydrogen.

In a further preferred embodiment of the present disclosure, the present disclosure provides a compound represented by formula (IX), a stereoisomer thereof or a pharmaceutically acceptable salt thereof, the specific structure of the compound is as follows:

(IX)

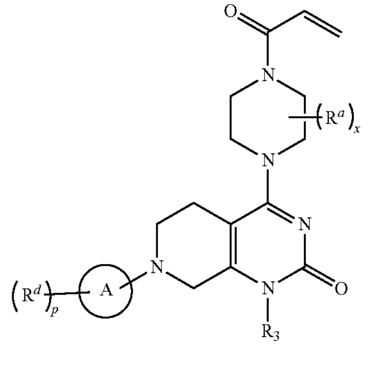

wherein:

ring A is selected from $C_{3-12}$ cycloalkyl, 3-14 membered heterocyclyl, $C_{6-14}$ aryl or 5-14 membered heteroaryl; preferably $C_{6-12}$ aryl or 5-12 membered heteroaryl;

$R^d$ is selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl, the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl are optionally substituted by one or more substituents selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl;

preferably hydrogen, halogen, hydroxyl, amino or $C_{1-3}$ alkyl;

p is an integer from 0 to 6.

In a further preferred embodiment of the present disclosure, the present disclosure provides a compound represented by formula (X), a stereoisomer thereof or a pharmaceutically acceptable salt thereof, the specific structure of the compound is as follows:

(X)

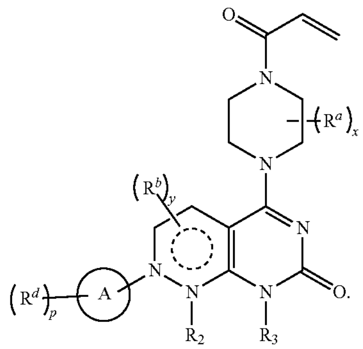

In a further preferred embodiment of the present disclosure, the present disclosure provides a compound represented by formula (X-A), a stereoisomer thereof or a pharmaceutically acceptable salt thereof, the specific structure of the compound is as follows:

(X-A)

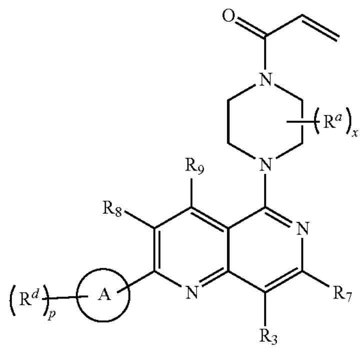

wherein:

$R_7$ is selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl, the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl are optionally substituted by one or more substituents selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl;

preferably $C_{1-3}$ alkyl or $C_{1-3}$ haloalkoxy;

$R_8$ and $R_9$ are each independently selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl, the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl are optionally substituted by one or more substituents selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl.

In a preferred embodiment of the present disclosure, a compound represented by general formula (XI), a stereoisomer thereof or a pharmaceutically acceptable salt thereof:

(XI)

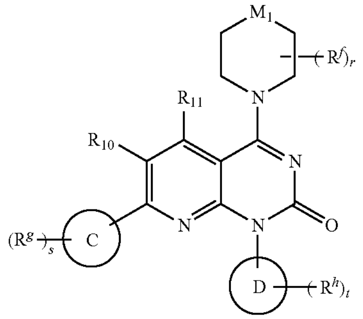

wherein:

$M_1$ is selected from $CR_{12}R_{13}$ or $NR_{12}$; preferably the following groups:

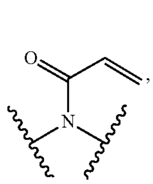,
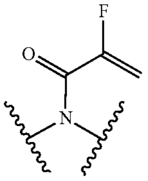,
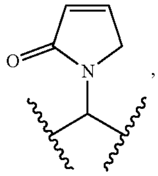, or
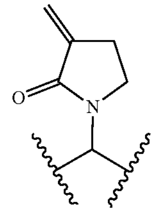;

preferably, the following groups:

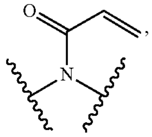,
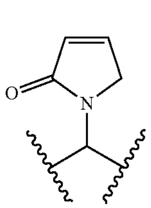 or
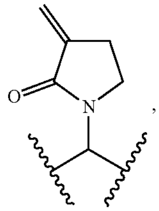, ring C is selected from $C_{6-14}$ aryl or 5-14 membered heteroaryl;

preferably phenyl or pyridyl, more preferably the following groups:

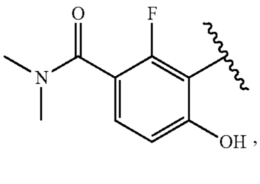,
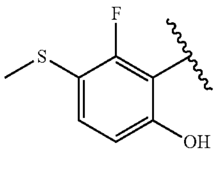,

-continued
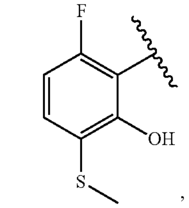,
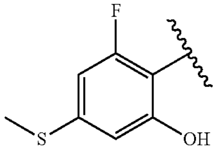,
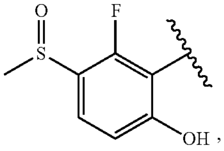,
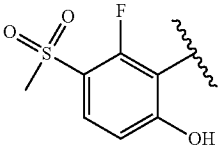,
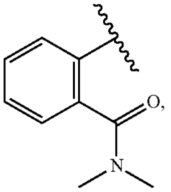,
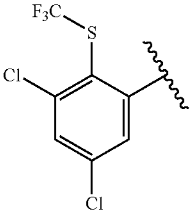,
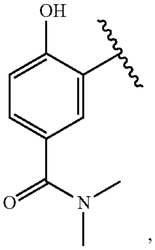,
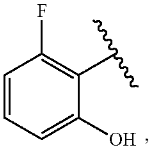,
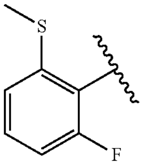,
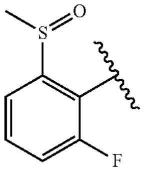,
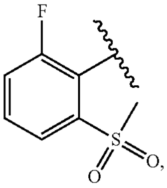,
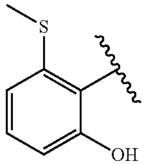,
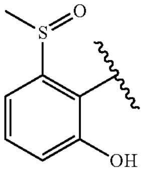,
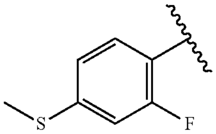,
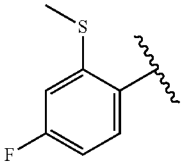,
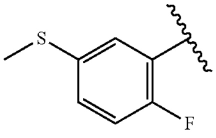,
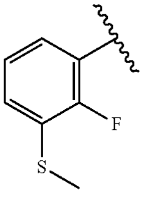,
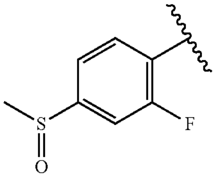,
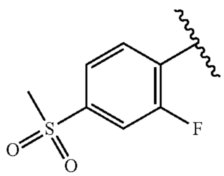,
-continued
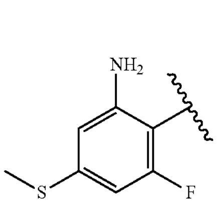,
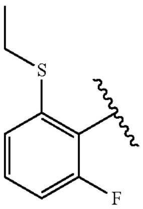,
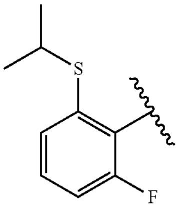,
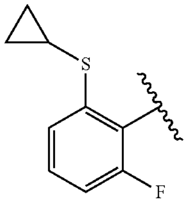,
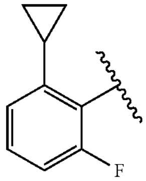,
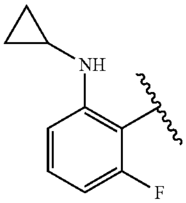,
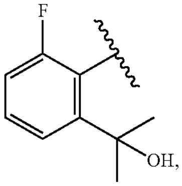,
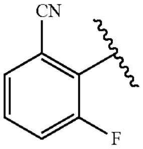,
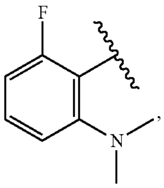,
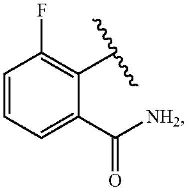,
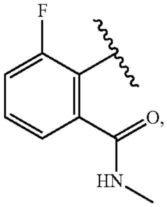,
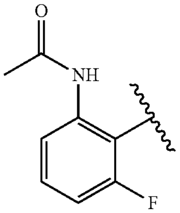,
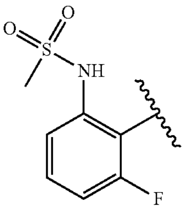,
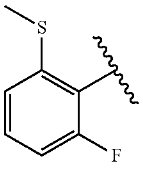,
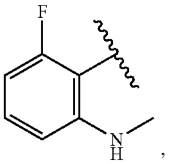,
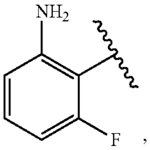,
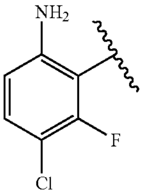, -continued
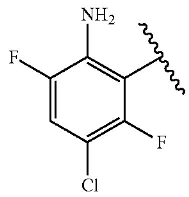 , 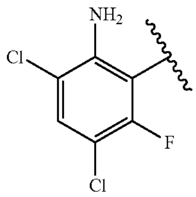 ,
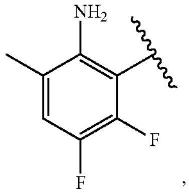 , 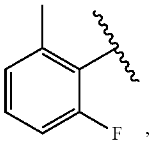 , 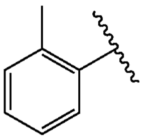 ,
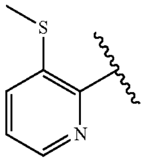 , 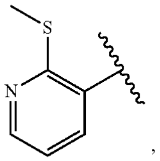 ,
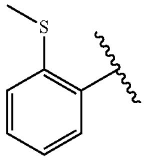 or 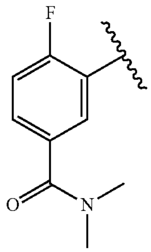 ;
further preferably selected from the following groups:
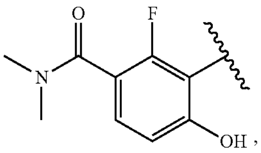 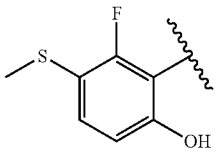
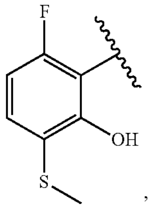 , 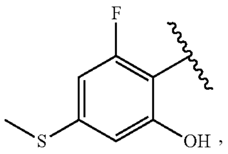
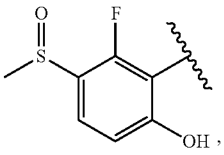 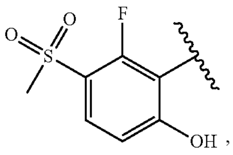
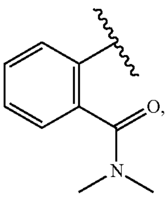 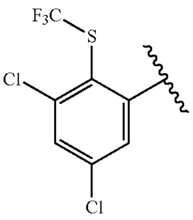 ,
-continued
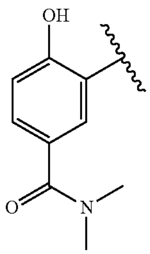 , 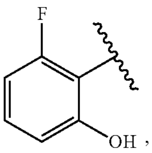 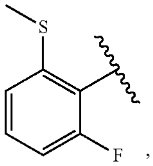 ,
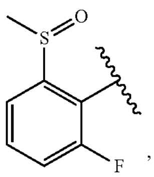 , 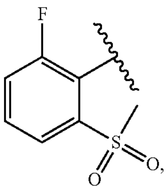
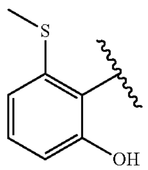 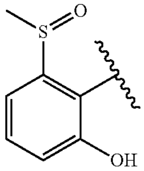
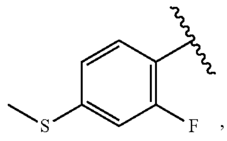 , 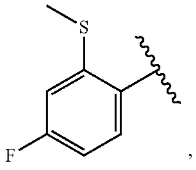 ,
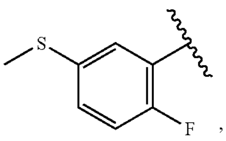 , 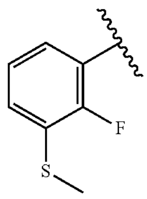 ,
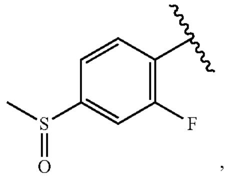 , 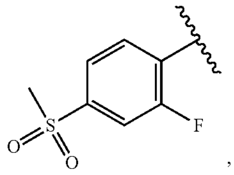 ,
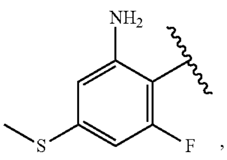 , 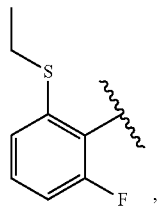 ,
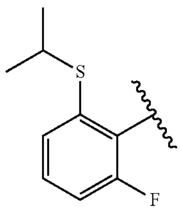 , 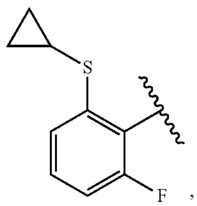 , -continued
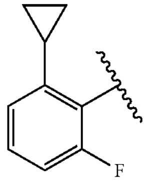 , 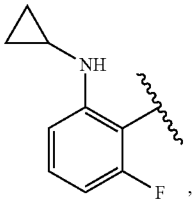 ,
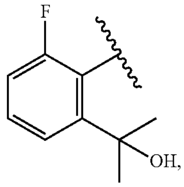 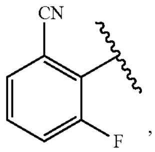 ,
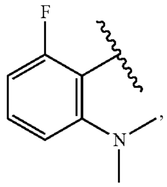 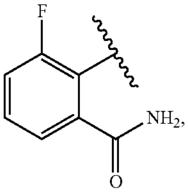
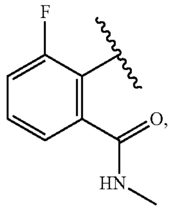 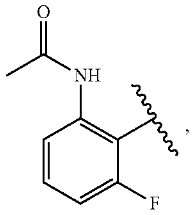 ,
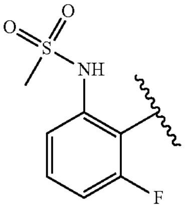 , 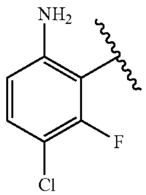 ,
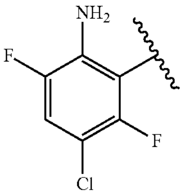 , 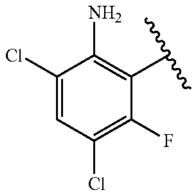 ,
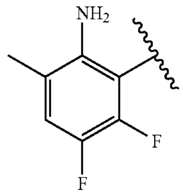 , 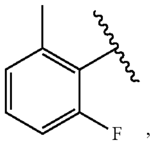 ,
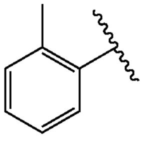 or 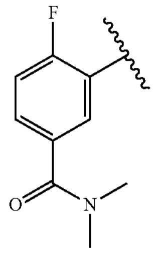 ;
ring D is selected from $C_{6-14}$ aryl or 5-14 membered heteroaryl;
preferably phenyl or pyridyl, more preferably the following groups:
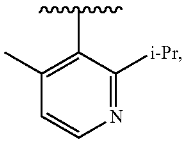 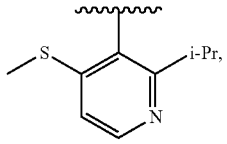
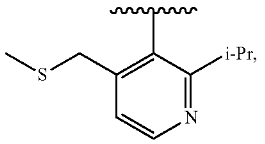 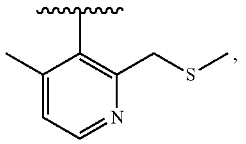
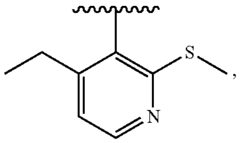 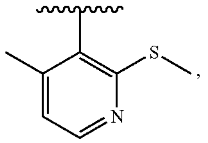
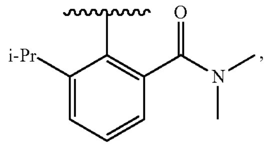 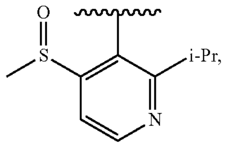
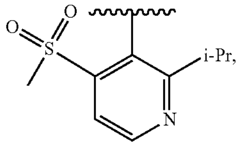 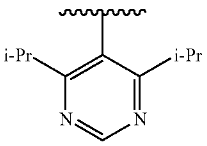 or
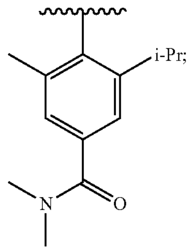
further preferably selected from the following groups:
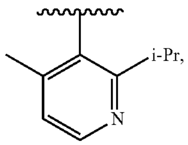 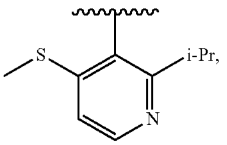
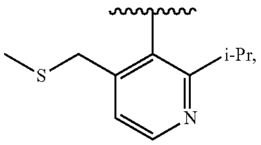 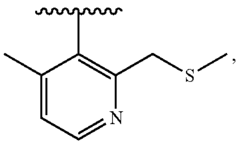
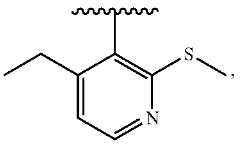 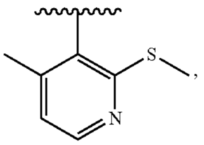

-continued

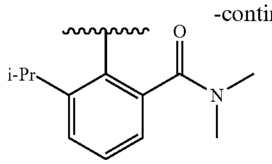

or

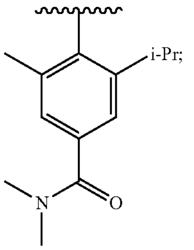

$R_{10}$ and $R_{11}$ are each independently selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl, the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl are optionally substituted by one or more substituents selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl;

$R_{12}$ is selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, $C_{3-12}$ cycloalkyl, 3-12 membered heterocyclyl, $C_{6-12}$ aryl or 5-12 membered heteroaryl or $-(CH_2)_{n2}C(O)CR_{ee}{=}CR_{ff}R_{gg}$, the $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, $C_{3-12}$ cycloalkyl, 3-12 membered heterocyclyl, $C_{6-12}$ aryl or 5-12 membered heteroaryl are optionally substituted by one or more substituents selected from hydrogen, deuterium, halogen, amino, hydroxyl, cyano, nitro, oxo, methylene, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl;

preferably 3-12 membered heterocyclyl or $-(CH_2)_{n2}C(O)CR_{ee}{=}CR_{ff}R_{gg}$, and the 3-12 membered heterocyclyl is optionally substituted by one or more substituents selected from hydrogen, deuterium, halogen, amino, hydroxyl, cyano, nitro, oxo and methylene;

$R_{13}$ is selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl, the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl are optionally substituted by one or more substituents selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl;

$R^f$ is selected from hydrogen, deuterium, halogen, amino, hydroxyl, sulfhydryl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ alkylthio, $C_{1-6}$ alkylsulfinyl, $C_{1-6}$ alkylsulfonyl, $C_{1-6}$ haloalkoxy, $C_{1-6}$ hydroxyalkyl, $C_{3-12}$ cycloalkyl, 3-12 membered heterocyclyl, $C_{6-12}$ aryl, 5-12 membered heteroaryl or $-(CH_2)_nC(O)CH{=}CHR_{aa}$, the $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ alkylthio, $C_{1-6}$ alkylsulfinyl, $C_{1-6}$ alkylsulfonyl, $C_{1-6}$ haloalkoxy, $C_{1-6}$ hydroxyalkyl, $C_{3-12}$ cycloalkyl, 3-12 membered heterocyclyl, $C_{6-12}$ aryl and 5-12 membered heteroaryl are optionally substituted by one or more substituents selected from hydrogen, deuterium, halogen, amino, hydroxyl, sulfhydryl, cyano, nitro, oxo, methylene, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ alkylthio, $C_{1-6}$ alkylsulfinyl, $C_{1-6}$ alkylsulfonyl, $C_{1-6}$ haloalkoxy, $C_{1-6}$ hydroxyalkyl, cyano-substituted $C_{1-6}$ alkyl, $C_{3-12}$ cycloalkyl, 3-12 heterocyclyl, $C_{6-12}$ aryl, and 5-12 membered heteroaryl;

$R^g$ is selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl, 5-12 membered heteroaryl, $-O(CH_2)_{n2}R_{ee}$, $-OC(R_{ee}R_{ff})_{n2}(CH_2)_{m1}R_{gg}$, $-NR_{ee}(CH_2)_{n2}R_{ff}$, $-(CH_2)_{n2}SR_{ee}$, $-(CH_2)_{n2}R_{ee}$, $-(CH_2)_{n2}OR_{ee}$, $-(CH_2)_{n2}SR_{ee}$, $-(CH_2)_{n2}C(O)R_{ee}$, $-(CH_2)_{n2}C(O)OR_{ee}$, $-(CH_2)_{n2}S(O)_{m1}R_{ee}$, $-(CH_2)_{n2}NR_{bb}R_{ee}$, $-(CH_2)_{n2}C(O)NR_{ee}R_{ff}$, $-(CH_2)_{n2}NR_{ee}C(O)R_{ff}$ or $-(CH_2)_{n2}NR_{ee}S(O)_{m1}R_{ff}$, the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl are optionally substituted by one or more substituents selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl;

$R^h$ is selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl, 5-12 membered heteroaryl, $-O(CH_2)_{n2}R_{ee}$, $-OC(R_{ee}R_{ff})_{n2}(CH_2)_{m1}R_{gg}$, $-NR_{ee}(CH_2)_{n2}R_{ff}$, $-(CH_2)_{n2}SR_{ee}$, $-(CH_2)_{n2}R_{ee}$, $-(CH_2)_{n2}OR_{ee}$, $-(CH_2)_{n2}SR_{ee}$, $-(CH_2)_{n2}C(O)R_{ee}$, $-(CH_2)_{n2}C(O)OR_{ee}$, $-(CH_2)_{n2}S(O)_{m1}R_{ee}$, $-(CH_2)_{n2}NR_{bb}R_{ee}$, $-(CH_2)_{n2}C(O)NR_{ee}R_{ff}$, $-(CH_2)_{n2}NR_{ee}C(O)R_{ff}$ or $-(CH_2)_{n2}NR_{ee}S(O)_{m}R_{ff}$, the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl are optionally substituted by one or more substituents selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl;

$R_{aa}$ is selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl, the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl are optionally substituted by one or more substituents selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl;

$R_{ee}$, $R_{ff}$ and $R_{gg}$ are each independently selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl, the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl are optionally substituted by one or more substituents selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl;

r is an integer from 0 to 5;

s is an integer from 0 to 5;

t is an integer from 0 to 5;

n2 is an integer from 0 to 5; and m1 is 0, 1 or 2.

In a further preferred embodiment of the present disclosure,

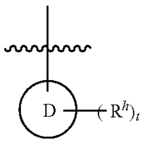

is selected from

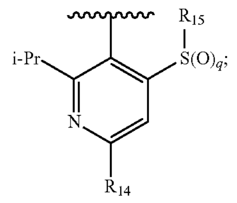

$R_{14}$ is selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl, the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl are optionally substituted by one or more substituents selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl;

preferably hydrogen, halogen, amino, $C_{1-3}$ alkyl or 3-8 membered heterocyclyl, the amino, $C_{1-3}$ alkyl and 3-8 membered heterocyclyl are optionally substituted by one or more substituents selected from hydrogen, halogen, $C_{1-3}$ alkoxy and $C_{3-8}$ cycloalkyl;

more preferably hydrogen, chlorine, fluorine, bromine, amino, methyl, methoxy, cyclopropyl, azetidinyl, morpholinyl, the amino, methyl, methoxy, cyclopropyl, azetidinyl and morpholinyl are optionally substituted by one or more substituents selected from hydrogen, fluorine, chlorine, bromine and cyclopropyl;

$R_{15}$ is selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl, or 5-12 membered heteroaryl;

preferably hydrogen or $C_{1-3}$ alkyl;

more preferably methyl.

In a preferred embodiment of the present disclosure, the present disclosure provides a compound represented by general formula (XI-A), a stereoisomer thereof or a pharmaceutically acceptable salt thereof:

(XI-A)

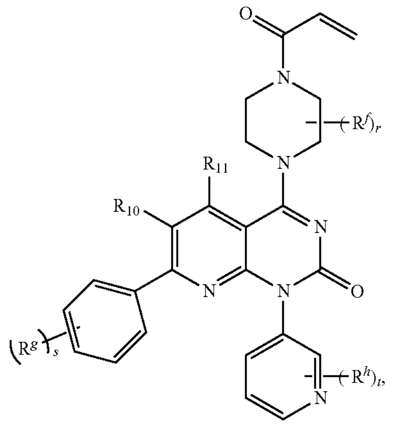

wherein, $R^f$ is independently selected from hydrogen, deuterium, halogen, amino, hydroxyl, sulfhydryl, cyano, nitro, $C_{1-3}$ alkyl, $C_{2-4}$ alkenyl, $C_{2-4}$ alkynyl, $C_{1-3}$ deuterated alkyl, $C_{1-3}$ haloalkyl, $C_{1-3}$ alkoxy, $C_{1-3}$ alkylthio, $C_{1-3}$ alkylsulfinyl, $C_{1-3}$ alkylsulfonyl, $C_{1-3}$ haloalkoxy or $C_{1-3}$ hydroxyalkyl, preferably $C_{1-3}$ alkyl;

$R_{10}$ and $R_{11}$ are each independently selected from hydrogen, deuterium, halogen, amino, hydroxyl, cyano, nitro, $C_{1-3}$ alkyl, $C_{2-4}$ alkenyl, $C_{2-4}$ alkynyl, oxo, thio, $C_{1-3}$ deuterated alkyl, $C_{1-3}$ haloalkyl, $C_{1-3}$ alkoxy, $C_{1-3}$ haloalkoxy, $C_{1-3}$ hydroxyalkyl or cyano-substituted $C_{1-3}$ alkyl, preferably halogen;

$R^g$ is each independently selected from hydrogen, deuterium, halogen, amino, hydroxyl, cyano, nitro, $C_{1-3}$ alkyl, $C_{2-4}$ alkenyl, $C_{2-4}$ alkynyl, oxo, thio, $C_{1-3}$ deuterated alkyl, $C_{1-3}$ haloalkyl, $C_{1-3}$ alkoxy, $C_{1-3}$ haloalkoxy, $C_{1-3}$ hydroxyalkyl or cyano-substituted $C_{1-3}$ alkyl, preferably hydroxyl, amino or halogen;

$R^h$ is each independently selected from hydrogen, deuterium, halogen, amino, hydroxyl, cyano, nitro, $C_{1-3}$ alkyl, $C_{1-3}$ alkylthio, $C_{1-3}$ alkoxy, $C_{2-4}$ alkenyl, $C_{2-4}$ alkynyl, oxo, thio, $C_{1-3}$ deuterated alkyl, $C_{1-3}$ haloalkyl, $C_{1-3}$ alkoxy, $C_{1-3}$ haloalkoxy, $C_{1-3}$ hydroxyalkyl, cyano-substituted $C_{1-3}$ alkyl, preferably $C_{1-3}$ alkyl or $C_{1-3}$ alkylthio, more preferably methylthio or isopropyl;

r is an integer from 1 to 3;

s is an integer from 1 to 3;

t is an integer from 1 to 3, preferably 2.

In a preferred embodiment of the present disclosure, the present disclosure provides a compound represented by general formula (XI-A), a stereoisomer thereof or a pharmaceutically acceptable salt thereof:

(XI-A)

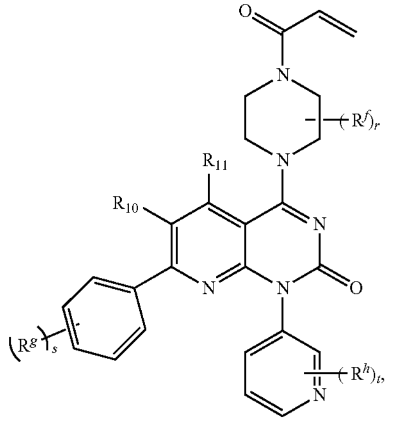

wherein, $R^f$ is independently selected from hydrogen, deuterium, halogen, amino, hydroxyl, sulfhydryl, cyano, nitro, $C_{1-3}$ alkyl, $C_{2-4}$ alkenyl, $C_{2-4}$ alkynyl, $C_{1-3}$ deuterated alkyl, $C_{1-3}$ haloalkyl, $C_{1-3}$ alkoxy, $C_{1-3}$ alkylthio, $C_{1-3}$ alkylsulfinyl, $C_{1-3}$ alkylsulfonyl, $C_{1-3}$ haloalkoxy or $C_{1-3}$ hydroxyalkyl, preferably $C_{1-3}$ alkyl;

$R_{10}$ and $R_{11}$ are each independently selected from hydrogen, deuterium, halogen, amino, hydroxyl, cyano, nitro, $C_{1-3}$ alkyl, $C_{2-4}$ alkenyl, $C_{2-4}$ alkynyl, oxo, thio, $C_{1-3}$ deuterated alkyl, $C_{1-3}$ haloalkyl, $C_{1-3}$ alkoxy, $C_{1-3}$ haloalkoxy, $C_{1-3}$ hydroxyalkyl or cyano-substituted $C_{1-3}$ alkyl, preferably halogen;

$R^g$ is each independently selected from hydrogen, deuterium, halogen, amino, hydroxyl, cyano, nitro, $C_{1-3}$ alkyl, $C_{2-4}$ alkenyl, $C_{2-4}$ alkynyl, oxo, thio, $C_{1-3}$ deuterated alkyl, $C_{1-3}$ haloalkyl, $C_{1-3}$ alkoxy, $C_{1-6}$ haloalkoxy, $C_{1-3}$ hydroxyalkyl or cyano-substituted $C_{1-3}$ alkyl, preferably hydroxyl, amino or halogen;

$R^h$ is each independently selected from hydrogen, deuterium, halogen, amino, hydroxyl, cyano, nitro, $C_{1-3}$ alkyl, $C_{1-3}$ alkylthio, $C_{1-3}$ alkoxy, $C_{2-4}$ alkenyl, $C_{2-4}$ alkynyl, oxo, thio, $C_{1-3}$ deuterated alkyl, $C_{1-3}$ haloalkyl, $C_{1-3}$ alkoxy, $C_{1-3}$ haloalkoxy, $C_{1-3}$ hydroxyalkyl, cyano-substituted $C_{1-3}$ alkyl, preferably $C_{1-3}$ alkyl or $C_{1-3}$ alkylthio, more preferably methylthio or isopropyl;

r is an integer from 1 to 3;

s is an integer from 1 to 4;

t is an integer from 1 to 3, preferably 2.

In a further preferred embodiment of the present disclosure, the present disclosure provides a compound represented by formula (XI-B), a stereoisomer thereof or a pharmaceutically acceptable salt thereof, the structure of the compound is as follows:

(XI-B)

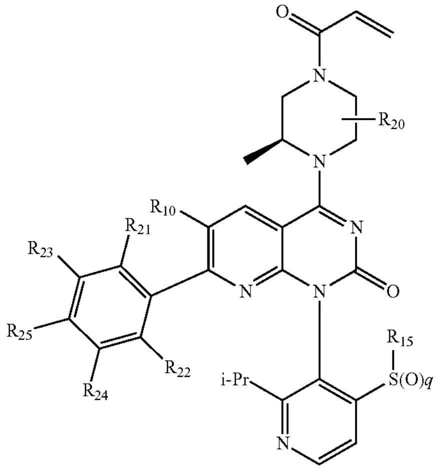

wherein:

wherein, $R_{10}$ is independently selected from hydrogen, deuterium, halogen, amino, hydroxyl, sulfhydryl, cyano, nitro, $C_{1-3}$ alkyl, $C_{2-4}$ alkenyl, $C_{2-4}$ alkynyl, $C_{1-3}$ deuterated alkyl, $C_{1-3}$ haloalkyl, $C_{1-3}$ alkoxy, $C_{1-3}$ alkylthio, $C_{1-3}$ alkylsulfinyl, $C_{1-3}$ alkylsulfonyl, $C_{1-3}$ haloalkoxy or $C_{1-3}$ hydroxyalkyl;

preferably fluorine or chlorine;

$R_{15}$ is selected from hydrogen, deuterium, halogen, amino, hydroxyl, sulfhydryl, cyano, nitro, $C_{1-3}$ alkyl, $C_{2-4}$ alkenyl, $C_{2-4}$ alkynyl, $C_{1-3}$ deuterated alkyl, $C_{1-3}$ haloalkyl, $C_{1-3}$ alkoxy, $C_{1-3}$ alkylthio, $C_{1-3}$ alkylsulfinyl, $C_{1-3}$ alkylsulfonyl, $C_{1-3}$ haloalkoxy or $C_{1-3}$ hydroxyalkyl;

preferably methyl;

$R_{20}$ is selected from hydrogen, deuterium, halogen, amino, hydroxyl, sulfhydryl, cyano, nitro, $C_{1-3}$ alkyl, $C_{2-4}$ alkenyl, $C_{2-4}$ alkynyl, $C_{1-3}$ deuterated alkyl, $C_{1-3}$ haloalkyl, $C_{1-3}$ alkoxy, $C_{1-3}$ alkylthio, $C_{1-3}$ alkylsulfinyl, $C_{1-3}$ alkylsulfonyl, $C_{1-3}$ haloalkoxy or $C_{1-3}$ hydroxyalkyl;

preferably hydrogen or methyl;

$R_{21}$ and $R_{22}$ are each independently selected from hydrogen, deuterium, halogen, amino, hydroxyl, sulfhydryl, cyano, nitro, $C_{1-3}$ alkyl, $C_{2-4}$ alkenyl, $C_{2-4}$ alkynyl, $C_{1-3}$ deuterated alkyl, $C_{1-3}$ haloalkyl, $C_{1-3}$ alkoxy, $C_{1-3}$ alkylthio, $C_{1-3}$ alkylsulfinyl, $C_{1-3}$ alkylsulfonyl, $C_{1-3}$ haloalkoxy or $C_{1-3}$ hydroxyalkyl;

preferably hydrogen, hydroxyl, amino, fluorine, methyl, trifluoromethyl, methylthio, methylamino, aminoacyl or dimethylamino;

$R_{23}$ and $R_{24}$ are each independently selected from hydrogen, deuterium, halogen, amino, hydroxyl, sulfhydryl, cyano, nitro, $C_{1-3}$ alkyl, $C_{2-4}$ alkenyl, $C_{2-4}$ alkynyl, $C_{1-3}$ deuterated alkyl, $C_{1-3}$ haloalkyl, $C_{1-3}$ alkoxy, $C_{1-3}$ alkylthio, $C_{1-3}$ alkylsulfinyl, $C_{1-3}$ alkylsulfonyl, $C_{1-3}$ haloalkoxy or $C_{1-3}$ hydroxyalkyl;

preferably hydrogen, chloride, fluorine or methyl;

$R_{25}$ is selected from hydrogen, deuterium, halogen, amino, hydroxyl, sulfhydryl, cyano, nitro, $C_{1-3}$ alkyl, $C_{2-4}$ alkenyl, $C_{2-4}$ alkynyl, $C_{1-3}$ deuterated alkyl, $C_{1-3}$ haloalkyl, $C_{1-3}$ alkoxy, $C_{1-3}$ alkylthio, $C_{1-3}$ alkylsulfinyl, $C_{1-3}$ alkylsulfonyl, $C_{1-3}$ haloalkoxy or $C_{1-3}$ hydroxyalkyl;

preferably hydrogen, fluorine or methyl;

q is an integer from 0 to 2.

In a further preferred embodiment of the present disclosure, the compound represented by formula (XI-B), the stereoisomer thereof or the pharmaceutically acceptable salt thereof, wherein:

$R^f$ is selected from hydrogen, deuterium, halogen, amino, hydroxyl, sulfhydryl, cyano, nitro, methyl, ethyl, propyl, isopropyl, deuterated methyl, deuterated ethyl, deuterated propyl, deuterium isopropyl, halomethyl, haloethyl, halopropyl, haloisopropyl, methoxy, ethoxy, propoxy, isopropoxy, methylthio, ethylthio, propylthio, isopropylthio, halomethoxy, haloethoxy, halopropoxy, hydroxymethyl, hydroxyethyl, hydroxypropyl, hydroxyisopropyl, cyclopropyl, cyclobutyl, cyclopentyl or cyclohexyl, preferably hydrogen or methyl;

$R_{10}$ is selected from hydrogen, deuterium, fluorine, chlorine, bromine, iodine, amino, hydroxyl, cyano, nitro, methyl, ethyl, propyl, isopropyl, deuterated methyl, deuterated ethyl, deuterated propyl, deuterium isopropyl, halomethyl, haloethyl, halopropyl, haloisopropyl, methoxy, ethoxy, propoxy, isopropoxy, halomethoxy, haloethoxy, halopropoxy, haloisopropoxy, hydroxymethyl, hydroxyethyl, hydroxypropyl, hydroxyisopropyl, cyclopropyl, cyclobutyl, cyclopentyl or cyclohexyl, preferably fluorine or chlorine;

$R_{15}$ is selected from methyl, ethyl, propyl, isopropyl, cyclopropyl, cyclobutyl, cyclopentyl or cyclohexyl, preferably methyl;

$R_{21}$ and $R_{22}$ are each independently selected from hydrogen, deuterium, fluorine, chlorine, bromine, iodine, amino, hydroxyl, cyano, nitro, methyl, ethyl, propyl, isopropyl, deuterated methyl, deuterated ethyl, deuterated propyl, deuterium isopropyl, halomethyl, haloethyl, halopropyl, haloisopropyl, methoxy, ethoxy, propoxy, isopropoxy, hydroxymethyl, hydroxyethyl, hydroxypropyl, hydroxyisopropyl, cyclopropyl, cyclobutyl, cyclopentyl or cyclohexyl, preferably hydroxyl, amino, fluorine, chlorine or methyl;

$R_{23}$ and $R_{24}$ are each independently selected from hydrogen, deuterium, fluorine, chlorine, bromine, iodine, amino, hydroxyl, sulfhydryl, cyano, nitro, $C_{1-3}$ alkyl, methyl, ethyl, propyl, isopropyl, deuterated methyl, deuterated ethyl, deuterated propyl, deuterium isopropyl, halomethyl, haloethyl, halopropyl, haloisopropyl, methoxy, ethoxy, propoxy, isopropoxy, hydroxymethyl, hydroxyethyl, hydroxypropyl, hydroxyisopropyl, cyclopropyl, cyclobutyl, cyclopentyl or cyclohexyl, preferably hydrogen, fluorine, chlorine or methyl;

$R_{25}$ is selected from hydrogen, deuterium, fluorine, chlorine, bromine, iodine, amino, hydroxyl, sulfhydryl, cyano, nitro, methyl, ethyl, propyl, isopropyl, deuterated methyl, deuterated ethyl, deuterated propyl, deuterium isopropyl, halomethyl, haloethyl, halopropyl, haloisopropyl, methoxy, ethoxy, propoxy, isopropoxy, hydroxymethyl, hydroxyethyl, hydroxypropyl or hydroxyisopropyl, cyclopropyl, cyclobutyl, cyclopentyl or cyclohexyl, preferably hydrogen, fluorine or methyl.

In a further preferred embodiment of the present disclosure, the compound represented by formula (XI-B), the stereoisomer thereof or the pharmaceutically acceptable salt thereof, wherein:

$R^f$ is selected from hydrogen, deuterium, halogen, amino, hydroxyl, sulfhydryl, cyano, nitro, methyl, ethyl, propyl, isopropyl, deuterated methyl, deuterated ethyl, deuterated propyl, deuterium isopropyl, halomethyl, haloethyl, halopropyl, haloisopropyl, methoxy, ethoxy, propoxy, isopropoxy, methylthio, ethylthio, propylthio, isopropylthio, halomethoxy, haloethoxy, halopropoxy, hydroxymethyl, hydroxyethyl, hydroxypropyl or hydroxyisopropyl, preferably hydrogen or methyl;

$R_{10}$ is selected from hydrogen, deuterium, fluorine, bromine, iodine, amino, hydroxyl, cyano, nitro, methyl, ethyl, propyl, isopropyl, deuterated methyl, deuterated ethyl, deuterated propyl, deuterium isopropyl, halomethyl, haloethyl, halopropyl, haloisopropyl, methoxy, ethoxy, propoxy, isopropoxy, halomethoxy, haloethoxy, halopropoxy, haloisopropoxy, hydroxymethyl, hydroxyethyl, hydroxypropyl or hydroxyisopropyl, preferably fluorine or chlorine;

$R_{15}$ is selected from methyl, ethyl, propyl or isopropyl, preferably methyl;

$R_{21}$ and $R_{22}$ are each independently selected from hydrogen, deuterium, fluorine, bromine, iodine, amino, hydroxyl, cyano, nitro, methyl, ethyl, propyl, isopropyl, deuterated methyl, deuterated ethyl, deuterated propyl, deuterium isopropyl, halomethyl, haloethyl, halopropyl, haloisopropyl, methoxy, ethoxy, propoxy, isopropoxy, hydroxymethyl, hydroxyethyl, hydroxypropyl or hydroxyisopropyl, preferably hydroxyl, amino, fluorine, chlorine or methyl;

$R_{23}$ and $R_{24}$ are each independently selected from hydrogen, deuterium, fluorine, bromine, iodine, amino, hydroxyl, sulfhydryl, cyano, nitro, $C_{1-3}$ alkyl, methyl, ethyl, propyl, isopropyl, deuterated methyl, deuterated ethyl, deuterated propyl, deuterium isopropyl, halomethyl, haloethyl, halopropyl, haloisopropyl, methoxy, ethoxy, propoxy, isopropoxy, hydroxymethyl, hydroxyethyl, hydroxypropyl or hydroxyisopropyl, preferably hydrogen, fluorine, chlorine or methyl;

$R_{25}$ is selected from hydrogen, deuterium, fluorine, bromine, iodine, amino, hydroxyl, sulfhydryl, cyano, nitro, methyl, ethyl, propyl, isopropyl, deuterated methyl, deuterated ethyl, deuterated propyl, deuterium isopropyl, halomethyl, haloethyl, halopropyl, haloisopropyl, methoxy, ethoxy, propoxy, isopropoxy, hydroxymethyl, hydroxyethyl, hydroxypropyl or hydroxyisopropyl, preferably hydrogen, fluorine or methyl.

In a further preferred embodiment of the present disclosure, the present disclosure provides a compound represented by formula (XI-C) or (XI-D), a stereoisomer thereof or a pharmaceutically acceptable salt thereof, the specific structure of the compound is as follows:

(XI-C)

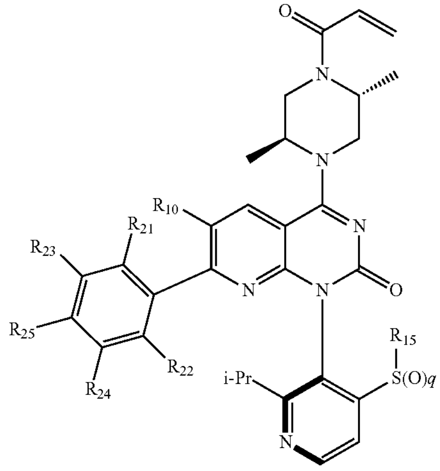

-continued (XI-D)

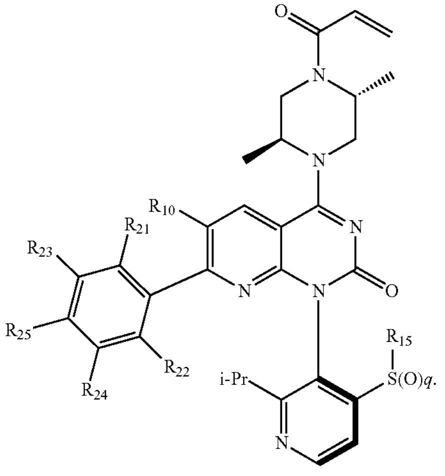

In a further preferred embodiment of the present disclosure, the structure of the compound represented by formula (XI-C) or (XI-D) is as follows:

(XI-C)

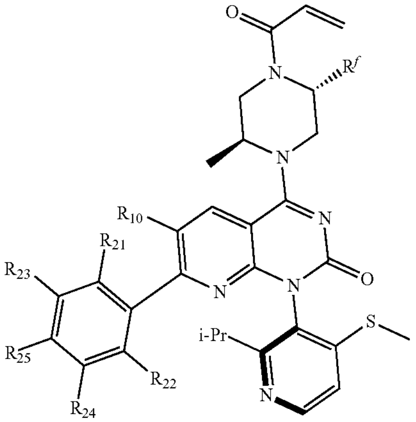

or (XI-D)

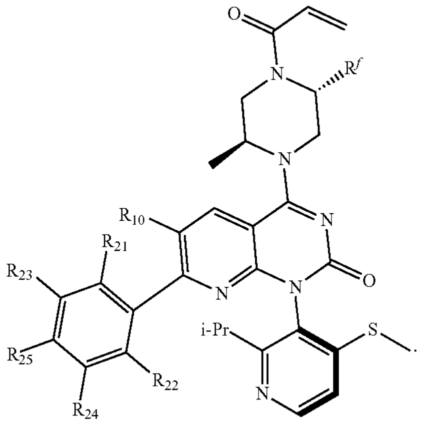

In a further preferred embodiment of the present disclosure, the compound represented by (XI-C) or formula (XI-D), the stereoisomer thereof or the pharmaceutically acceptable salt thereof, wherein:

$R_{21}$ and $R_{22}$ are each independently selected from amino or fluorine, and $R_{23}$ and $R_{24}$ are each independently selected from hydrogen, fluorine, chlorine, bromine, methyl, ethyl, propyl or isopropyl;

or, $R_{21}$ and $R_{22}$ are each independently selected from hydroxyl or fluorine, and $R_{23}$ and $R_{24}$ are each independently selected from hydrogen, fluorine, chlorine, bromine, methyl, ethyl, propyl or isopropyl.

Preferably, $R_{21}$ is amino, $R_{22}$ is selected from fluorine, or $R_{21}$ is hydroxyl, $R_{22}$ is selected from fluorine.

In a preferred embodiment of the present disclosure, ring A is selected from $C_{6-10}$ aryl or 5-12 membered heteroaryl, wherein 5-12 membered heteroaryl is selected from heteroaryl containing 1-3 of nitrogen atoms, preferably 5-7 membered nitrogen-containing heteroaryl, benzo 5-7 membered nitrogen-containing heteroaryl or 5-7 membered nitrogen-containing heteroaryl phenyl; more preferably the following groups:

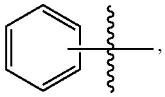, 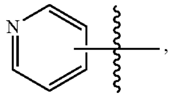,

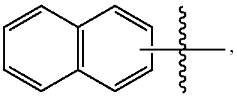, 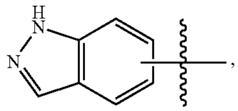,

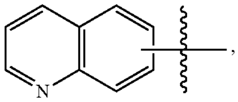, 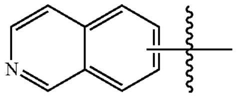,

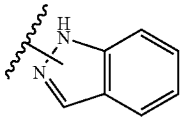, 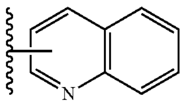 or

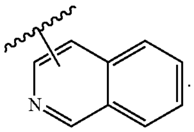.

optionally substituted by one or more substituents selected from hydroxyl, halogen, amino, sulfhydryl, $C_{1-6}$ hydroxyalkyl, $C_{1-6}$ alkoxy, $C_{1-6}$ alkylthio, $C_{1-6}$ alkylthioalkyl, $C_{1-6}$ haloalkylthio, $C_{1-6}$ alkylcarbamoyl, $C_{1-6}$ alkylsulfinyl, $C_{1-6}$ alkylsulfonyl and $C_{1-6}$ alkyl.

In a preferred embodiment of the present disclosure, ring B is selected from 5-12 membered heterocyclyl containing 1-3 of nitrogen atoms, including the following groups:

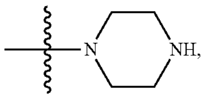, 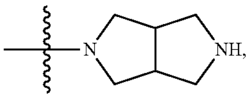,

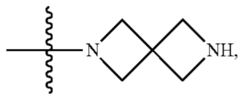, 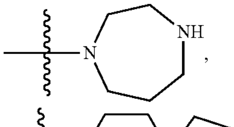,

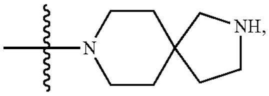, 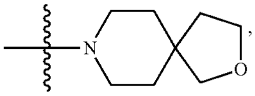,

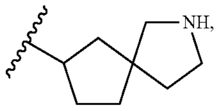, 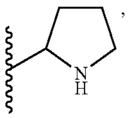,

-continued

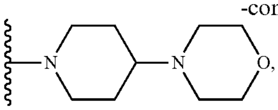, 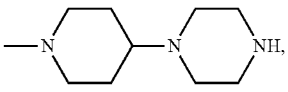,

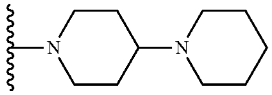 or 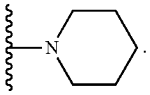.

In a further preferred embodiment of the present disclosure, the present disclosure provides a compound represented by formula (XII), a stereoisomer thereof or a pharmaceutically acceptable salt thereof, the specific structure of the compound is as follows:

(XII)

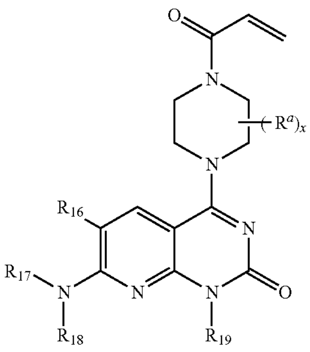

$R_{16}$ is selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl, the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl are optionally substituted by one or more substituents selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl;

preferably hydrogen, deuterium, halogen, amino, hydroxyl, cyano, $C_{1-3}$ alkyl, $C_{2-5}$ alkenyl, $C_{2-5}$ alkynyl, $C_{1-3}$ deuterated alkyl, $C_{1-3}$ haloalkyl, $C_{1-3}$ hydroxyalkyl, $C_{1-3}$ alkoxy, $C_{1-3}$ haloalkoxy, $C_{3-6}$ cycloalkyl, 3-10 membered heterocyclyl, $C_{6-12}$ aryl or 5-12 membered heteroaryl;

more preferably hydrogen, deuterium, fluorine, chlorine, bromine, amino, hydroxyl, cyano, methyl, ethyl, propyl, vinyl, propenyl, allyl, ethynyl, propynyl, propargyl, deuterium methyl, deuterated ethyl, deuterated propyl, fluoromethyl, fluoroethyl, fluoropropyl, chloromethyl, chloroethyl, chloropropyl, bromomethyl, bromoethyl, bromopropyl, hydroxymethyl, hydroxyethyl, hydroxypropyl, methoxy, ethoxy, propoxy, fluoromethoxy, fluoroethoxy, fluoropropoxy, chloromethoxy, chloroethoxy, chloropropoxy, cyclopropyl, cyclobutyl, cyclopentyl, cyclohexyl, cycloheptyl, epoxypropyl, epoxybutyl, epoxypentyl, epoxyhexyl, epoxyheptyl, aziridinyl, azetidinyl, azacyclopentyl, azacyclohexyl, azepanyl, thiophenyl, pyrrolyl, pyridyl, pyranyl, piperazinyl, phenyl or naphthyl;

$R_{17}$ is selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl, the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl are optionally substituted by one or more substituents selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl;

preferably $C_{3-8}$ cycloalkyl, 3-8 membered heterocyclyl, $C_{6-10}$ aryl or 5-10 membered heteroaryl, the $C_{3-8}$ cycloalkyl, 3-8 membered heterocyclyl, $C_{6-10}$ aryl and 5-10 membered heteroaryl are optionally further substituted by one or more substituents selected from hydrogen, deuterium, halogen, amino, hydroxyl, cyano, nitro, $C_{1-3}$ alkyl, $C_{2-3}$ alkenyl, $C_{2-3}$ alkynyl, oxo, thio, $C_{1-3}$ deuterated alkyl, $C_{1-3}$ haloalkyl, $C_{1-3}$ alkoxy, $C_{1-3}$ haloalkoxy, $C_{1-3}$ hydroxyalkyl, cyano-substituted $C_{1-3}$ alkyl, $C_{3-10}$ cycloalkyl, 3-10 membered heterocyclyl, $C_{6-10}$ aryl and 5-10 membered heteroaryl;

more preferably $C_{3-6}$ cycloalkyl, 3-8 membered heterocyclyl containing 1-3 of N, O or S atoms, $C_{6-10}$ aryl or 5-10 membered heteroaryl containing 1-3 of N, O or S atoms, the $C_{3-6}$ cycloalkyl, 3-8 membered heterocyclyl containing 1-3 of N, O or S atoms, $C_{6-10}$ aryl and 5-10 membered heteroaryl containing 1-3 of N, O or S atoms are optionally further substituted by one or more substituents selected from hydrogen, deuterium, halogen, amino, hydroxyl, cyano, nitro, $C_{1-3}$ alkyl, $C_{2-3}$ alkenyl, $C_{2-3}$ alkynyl, oxo, thio, $C_{1-3}$ deuterated alkyl, $C_{1-3}$ haloalkyl, $C_{1-3}$ alkoxy, $C_{1-3}$ haloalkoxy, $C_{1-3}$ hydroxyalkyl, cyano-substituted $C_{1-3}$ alkyl, $C_{3-10}$ cycloalkyl, 3-10 membered heterocyclyl, $C_{6-10}$ aryl and 5-10 membered heteroaryl;

more preferably cyclohexyl, tetrahydropyranyl, phenyl, pyrimidinyl, naphthyl, pyridyl or benzimidazolyl, the cyclohexyl, tetrahydropyranyl, phenyl, pyrimidinyl, naphthyl, pyridyl and benzimidazolyl are optionally further substituted by one or more substituents selected from hydrogen, fluorine, chlorine, amino, hydroxyl or methyl;

$R_{18}$ is selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl, or 5-12 membered heteroaryl;

preferably hydrogen, deuterium, halogen, amino, hydroxyl, cyano, $C_{1-3}$ alkyl, $C_{2-5}$ alkenyl, $C_{2-5}$ alkynyl, $C_{1-3}$ deuterated alkyl, $C_{1-3}$ haloalkyl, $C_{1-3}$ hydroxyalkyl, $C_{1-3}$ alkoxy, $C_{1-3}$ haloalkoxy, $C_{3-6}$ cycloalkyl, 3-10 membered heterocyclyl, $C_{6-12}$ aryl or 5-12 membered heteroaryl;

more preferably hydrogen, deuterium, fluorine, chlorine, bromine, amino, hydroxyl, cyano, methyl, ethyl, propyl, vinyl, propenyl, allyl, ethynyl, propynyl, propargyl, deuterium methyl, deuterated ethyl, deuterated propyl, fluoromethyl, fluoroethyl, fluoropropyl, chloromethyl, chloroethyl, chloropropyl, bromomethyl, bromoethyl, bromopropyl, hydroxymethyl, hydroxyethyl, hydroxypropyl, methoxy, ethoxy, propoxy, fluoromethoxy, fluoroethoxy, fluoropropoxy, chloromethoxy, chloroethoxy, chloropropoxy, cyclopropyl, cyclobutyl, cyclopentyl, cyclohexyl, cycloheptyl, epoxypropyl, epoxybutyl, epoxypentyl, epoxyhexyl, epoxyheptyl, aziridinyl, azetidinyl, azacyclopentyl, azacyclohexyl, azepanyl, thiophenyl, pyrrolyl, pyridyl, pyranyl, piperazinyl, phenyl or naphthyl;

$R_{19}$ is selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl, the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl are optionally substituted by one or more substituents selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl;

preferably $C_{3-8}$ cycloalkyl, 3-8 membered heterocyclyl, $C_{6-10}$ aryl or 5-10 membered heteroaryl, the $C_{3-8}$ cycloalkyl, 3-8 membered heterocyclyl, $C_{6-10}$ aryl and 5-10 membered heteroaryl are optionally further substituted by one or more substituents selected from hydrogen, deuterium, halogen, amino, hydroxyl, cyano, nitro, $C_{1-3}$ alkyl, $C_{2-3}$ alkenyl, $C_{2-3}$ alkynyl, oxo, thio, $C_{1-3}$ deuterated alkyl, $C_{1-3}$ haloalkyl, $C_{1-3}$ alkoxy, $C_{1-3}$ haloalkoxy, $C_{1-3}$ hydroxyalkyl, cyano-substituted $C_{1-3}$ alkyl, $C_{3-10}$ cycloalkyl, 3-10 membered heterocyclyl, $C_{6-10}$ aryl and 5-10 membered heteroaryl;

more preferably $C_{3-6}$ cycloalkyl, 3-8 membered heterocyclyl containing 1-3 of N, O or S atoms, $C_{6-10}$ aryl or 5-10 membered heteroaryl containing 1-3 of N, O or S atoms, the $C_{3-6}$ cycloalkyl, 3-8 membered heterocyclyl containing 1-3 of N, O or S atoms, $C_{6-10}$ aryl and 5-10 membered heteroaryl containing 1-3 of N, O or S atoms are optionally further substituted by one or more substituents selected from hydrogen, deuterium, halogen, amino, hydroxyl, cyano, nitro, $C_{1-3}$ alkyl, $C_{2-3}$ alkenyl, $C_{2-3}$ alkynyl, oxo, thio, $C_{1-3}$ deuterated alkyl, $C_{1-3}$ haloalkyl, $C_{1-3}$ alkoxy, $C_{1-3}$ haloalkoxy, $C_{1-3}$ hydroxyalkyl, cyano-substituted $C_{1-3}$ alkyl, $C_{3-10}$ cycloalkyl, 3-10 membered heterocyclyl, $C_{6-10}$ aryl and 5-10 membered heteroaryl;

more preferably cyclohexyl, tetrahydropyranyl, phenyl, pyrimidinyl, naphthyl, pyridyl or benzimidazolyl, the cyclohexyl, tetrahydropyranyl, phenyl, pyrimidinyl, naphthyl, pyridyl and the benzimidazolyl are optionally further substituted by one or more substituents selected from hydrogen, fluorine, chlorine, amino, hydroxyl or methyl.

In the most preferred embodiment of the present disclosure, the present disclosure includes the following specific compounds:
1
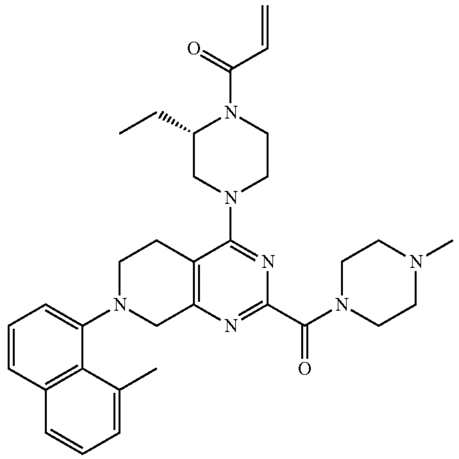
2
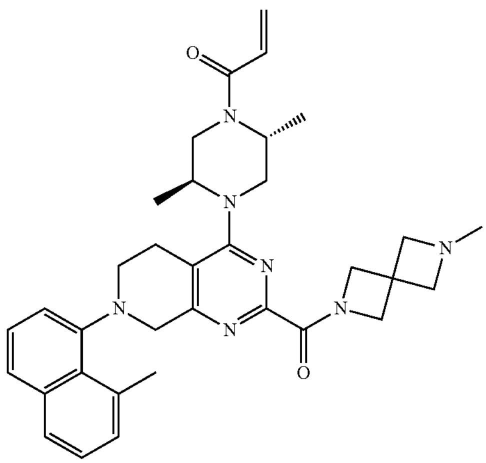
3
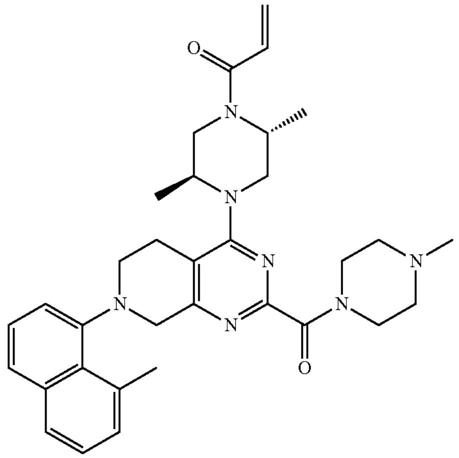
-continued
4
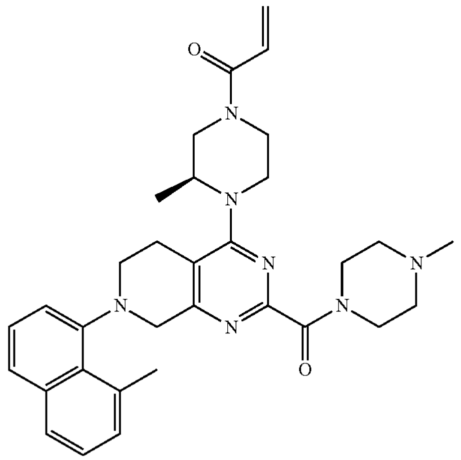
5
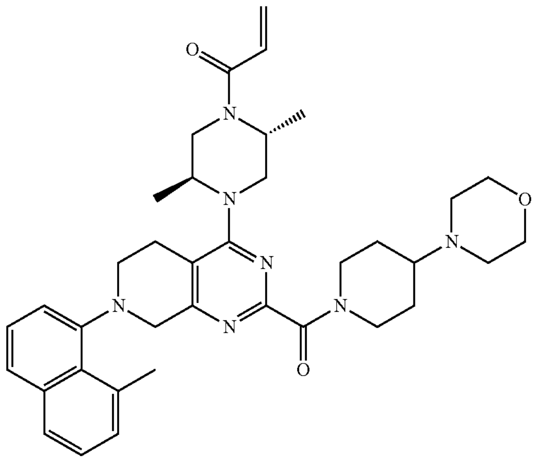
6
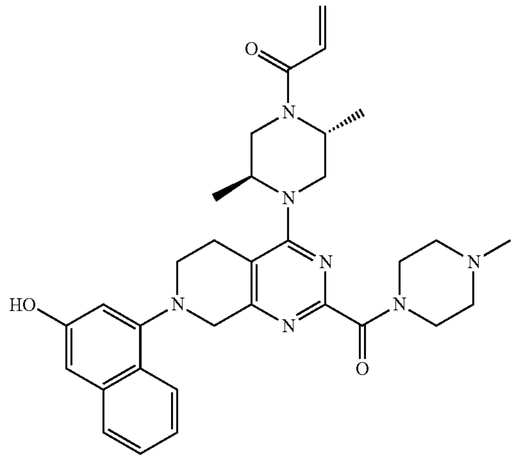

-continued
7
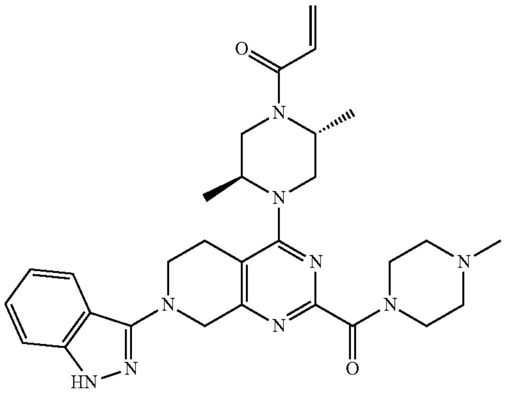
8
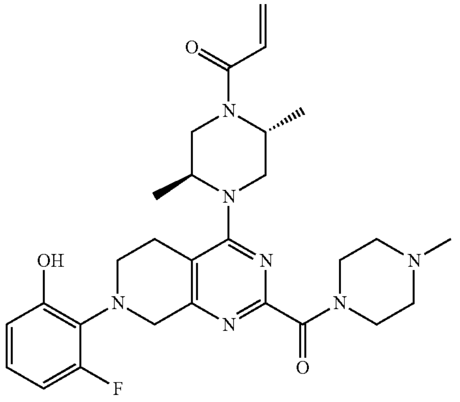
9
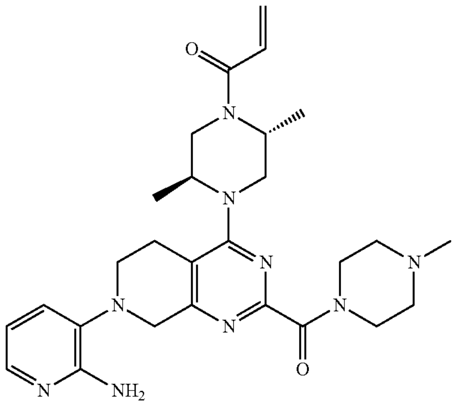
-continued
10
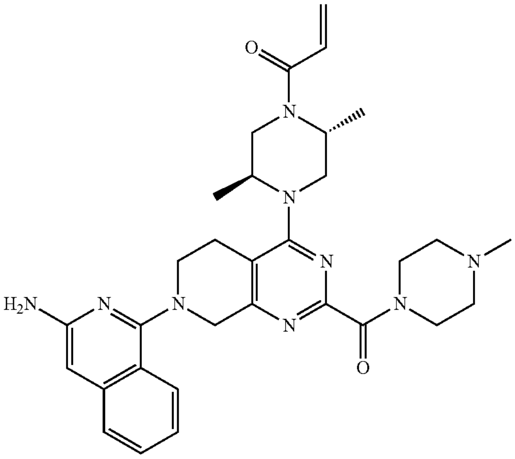
11
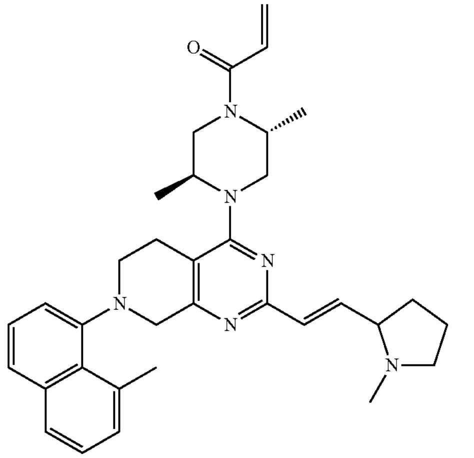
12
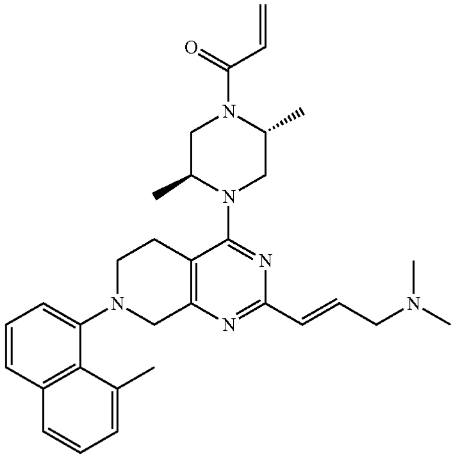

-continued
13
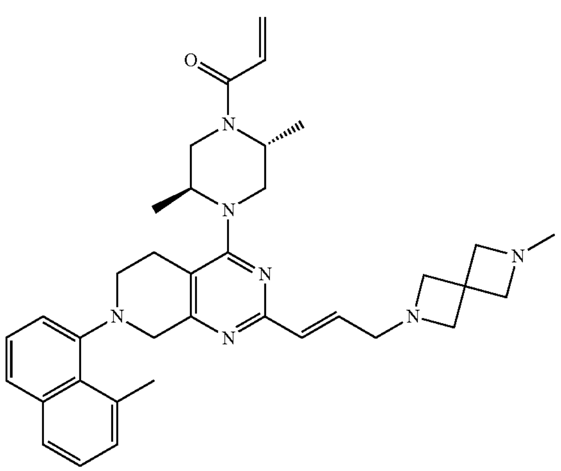
14
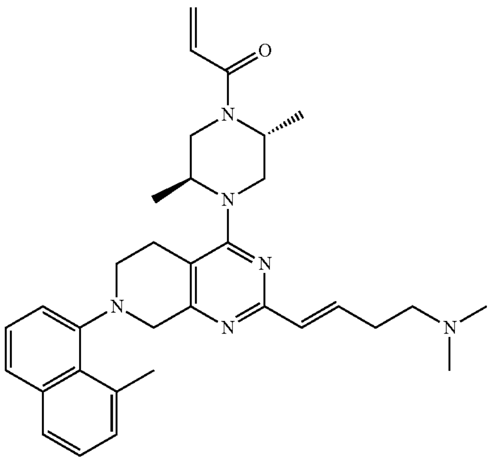
15
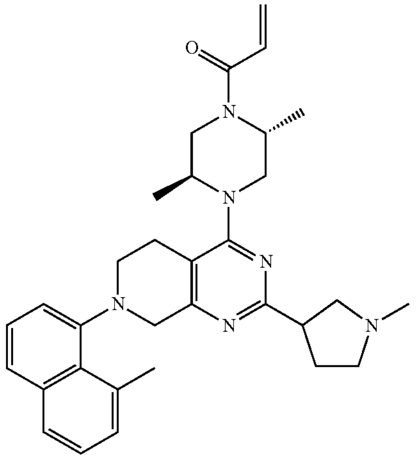
-continued
16
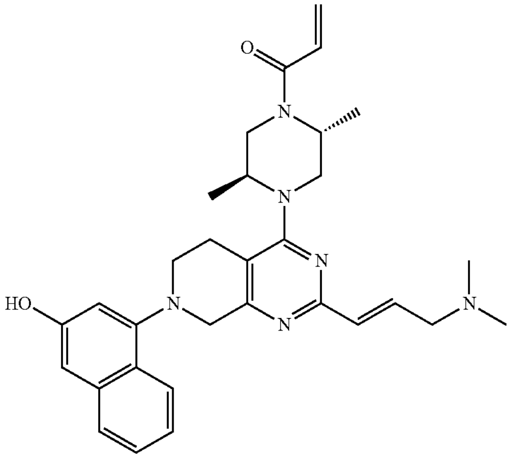
17
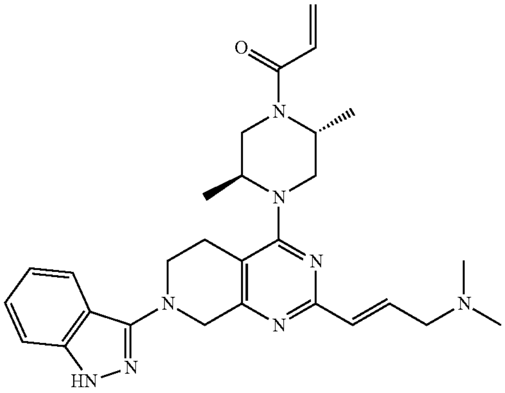
18
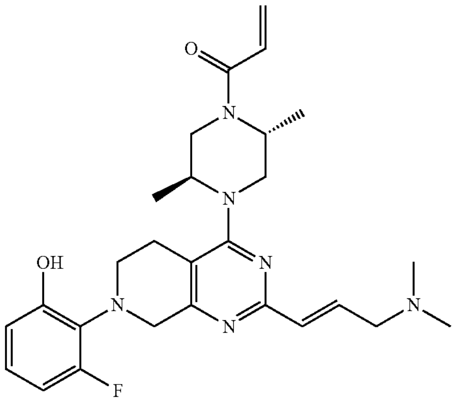

-continued
19
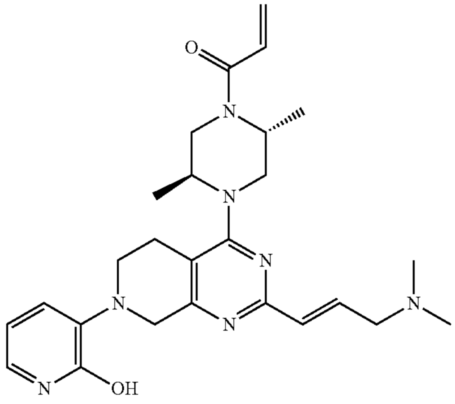
20
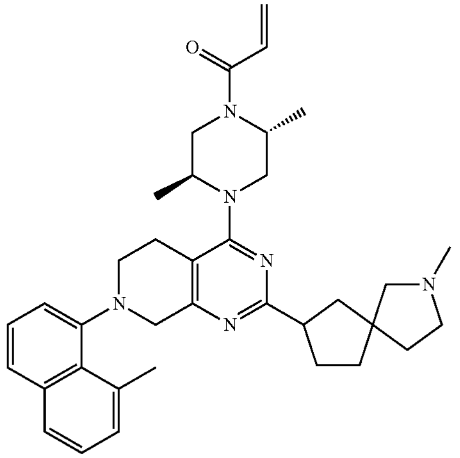
21
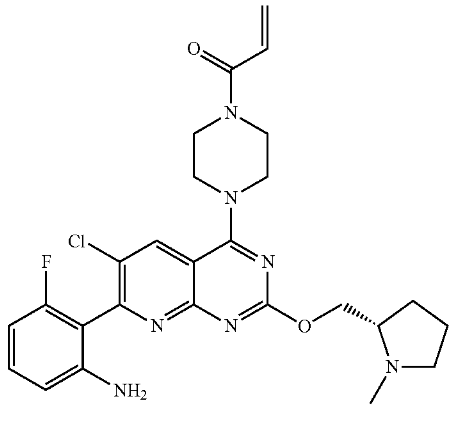
-continued
22
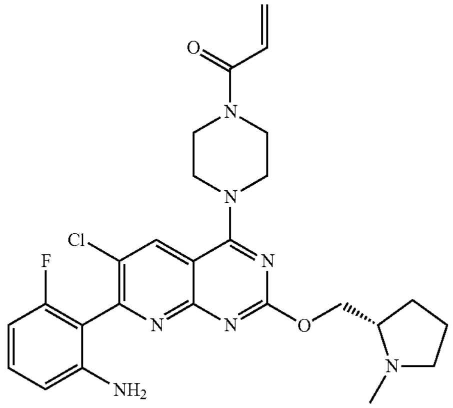
23
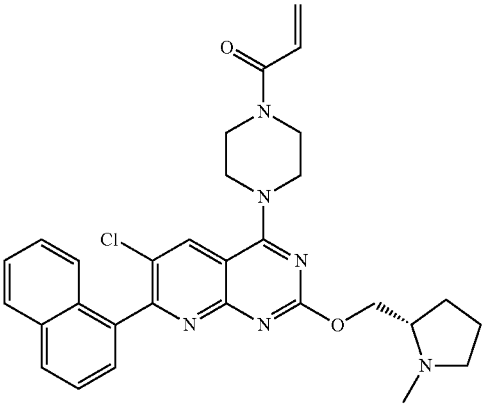
24
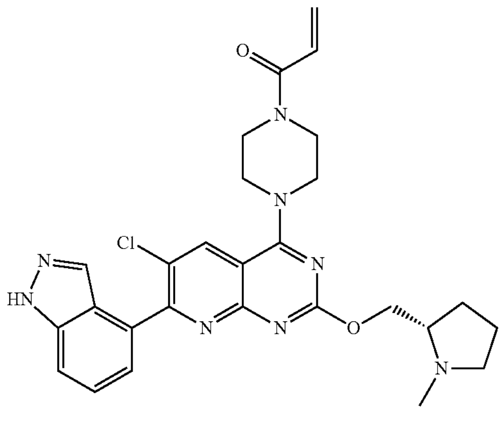

-continued
25
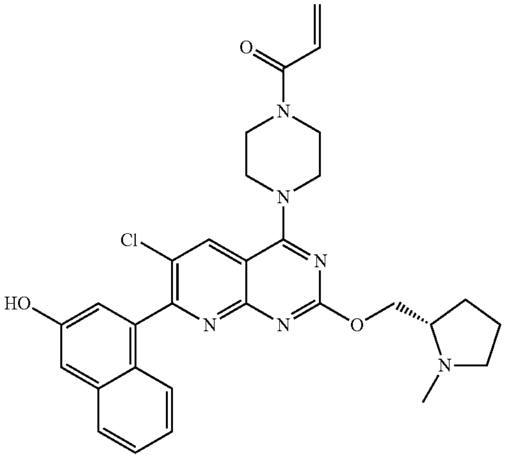
26
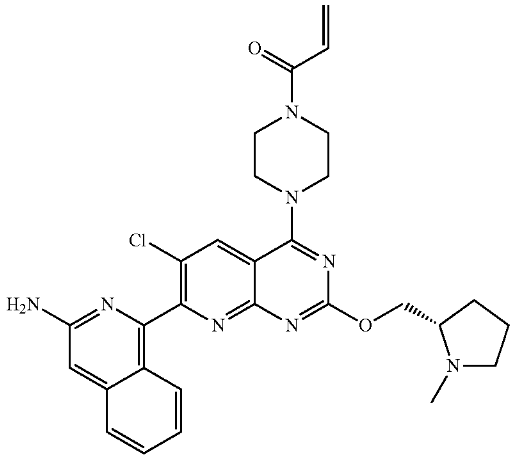
27
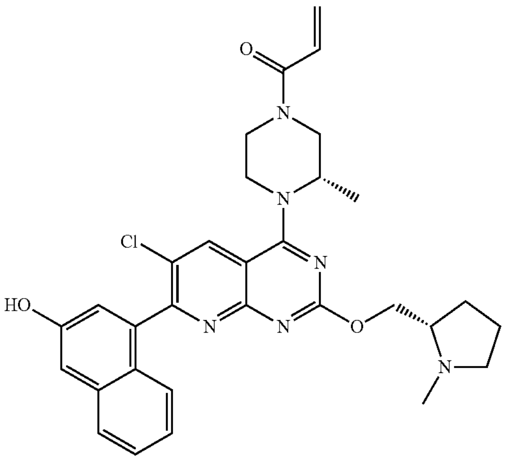
-continued
28
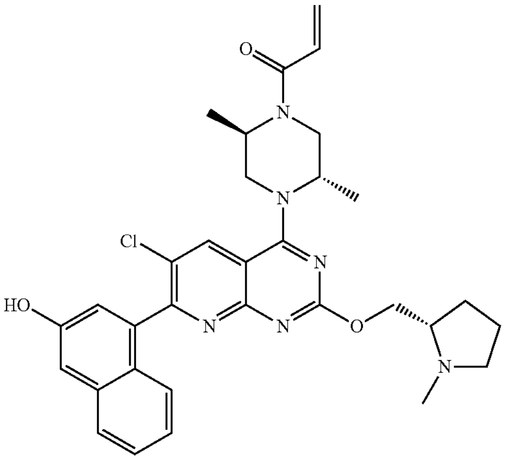
29
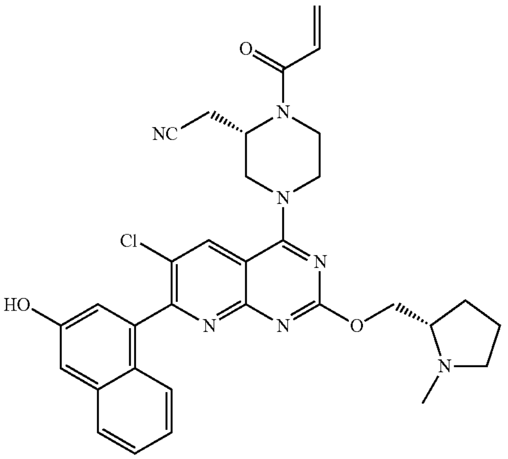
30
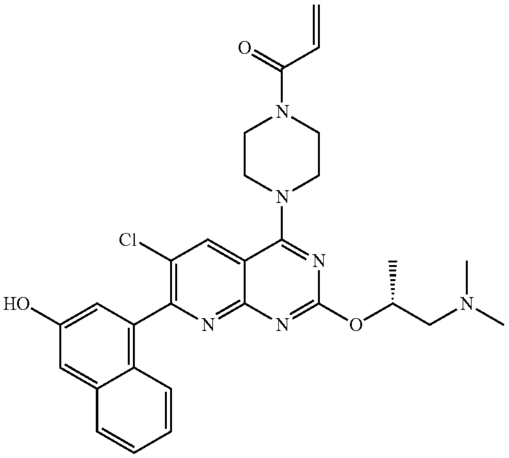

-continued
31
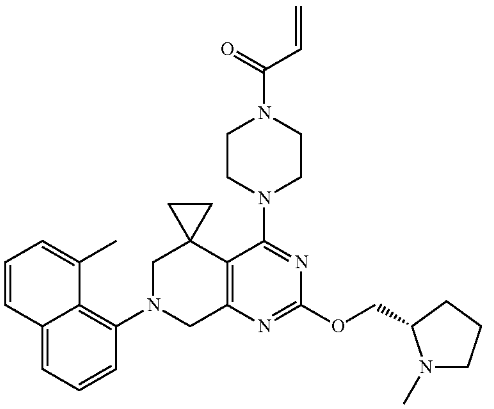
32
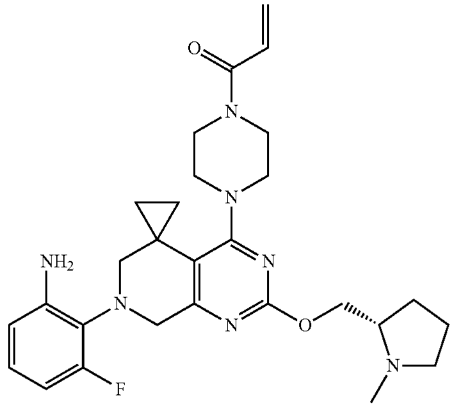
33
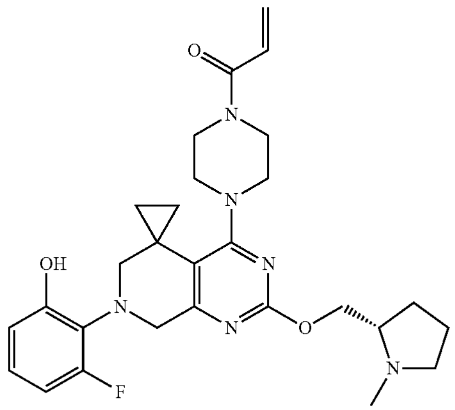
-continued
34
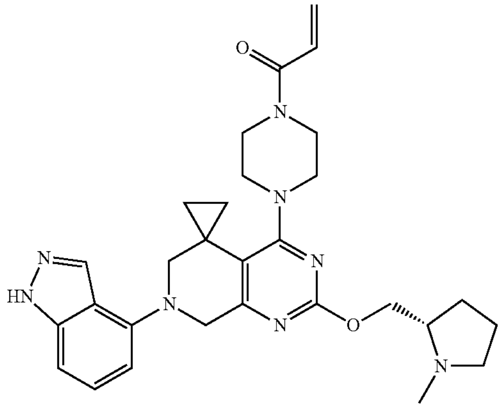
35
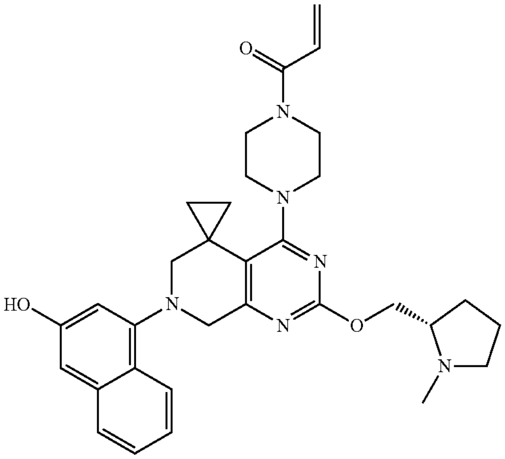
36
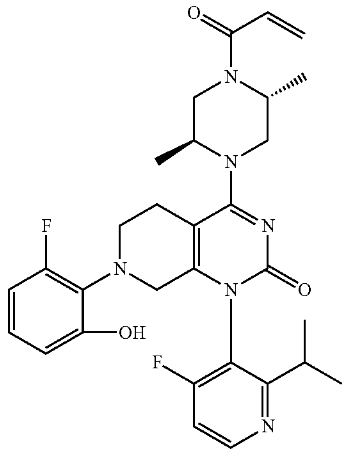

-continued
37
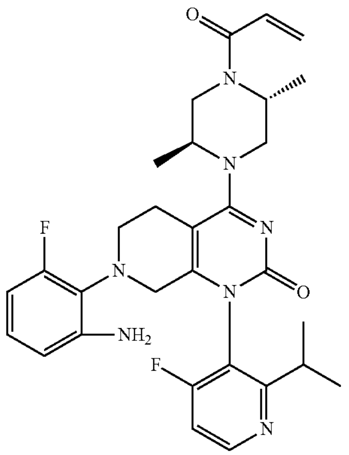
38
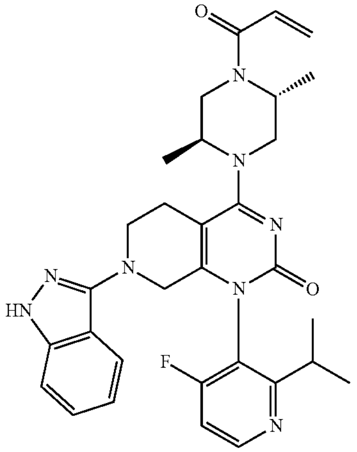
39
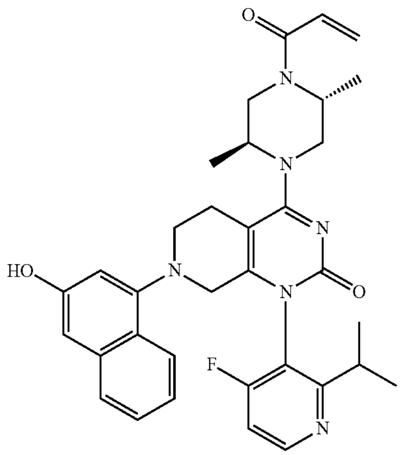
-continued
40
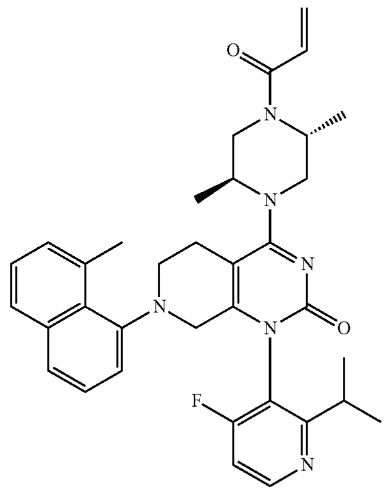
41
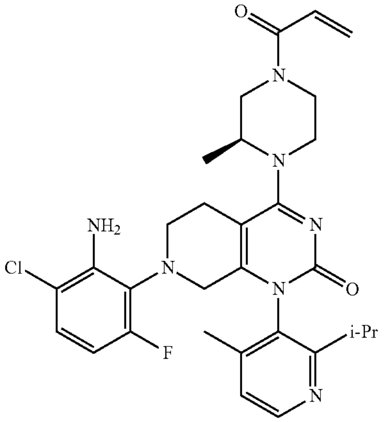
42
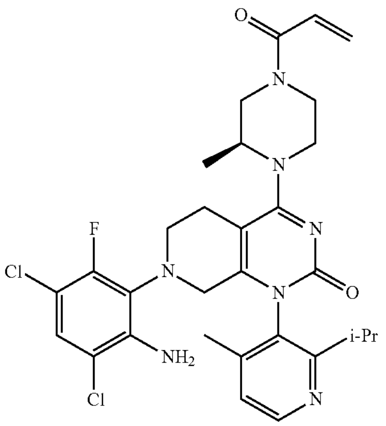

-continued
43
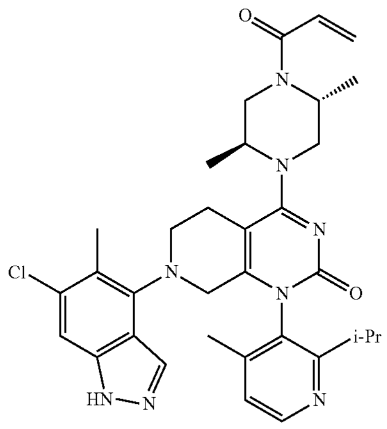
44
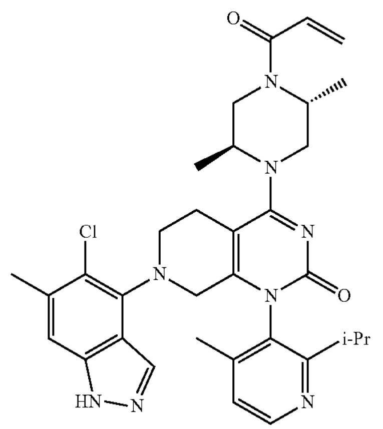
45
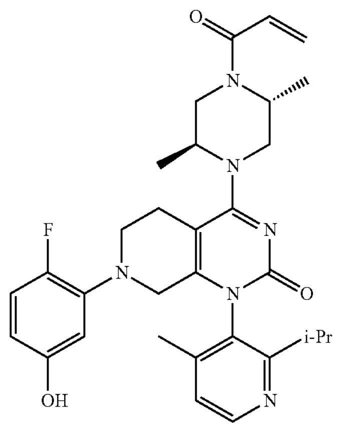
-continued
46
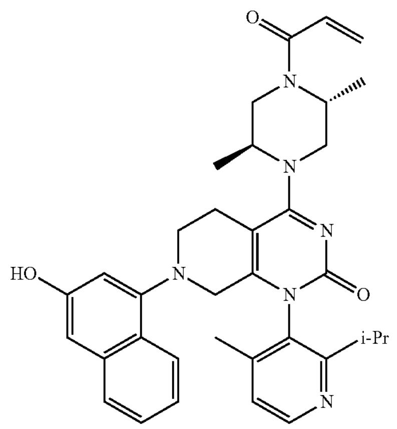
47
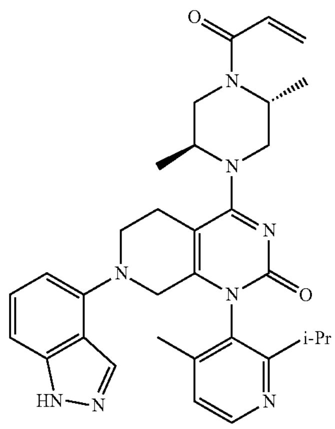
48
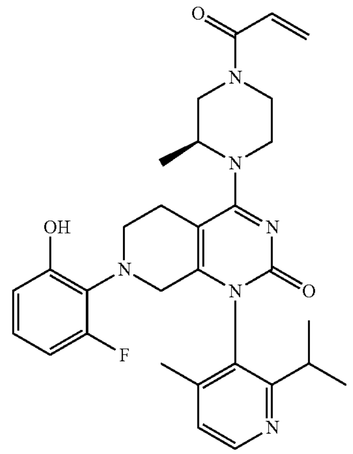

-continued
49
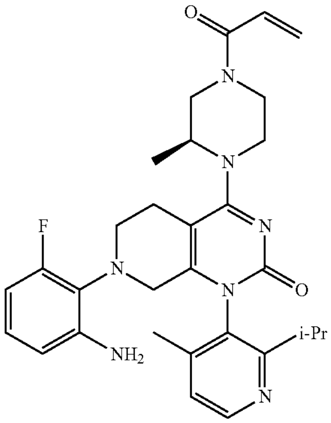
50
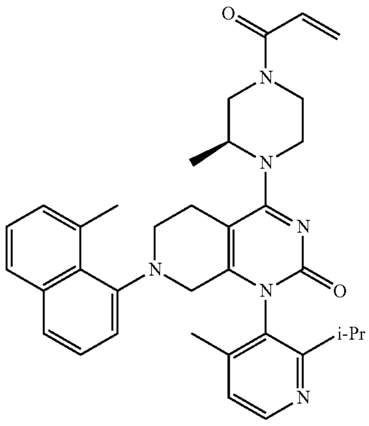
51
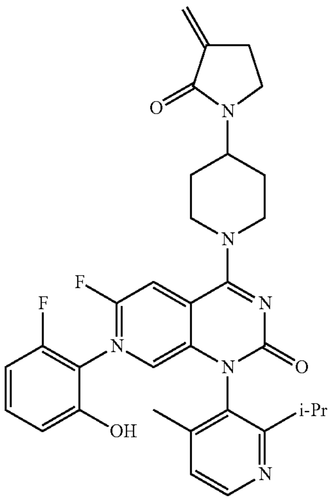
-continued
52
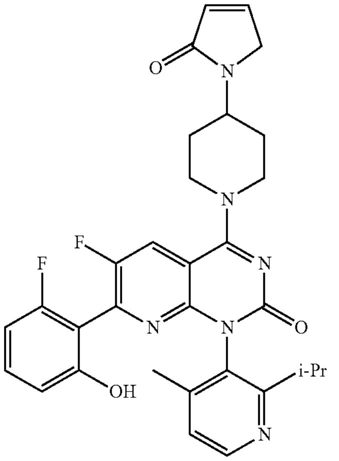
53
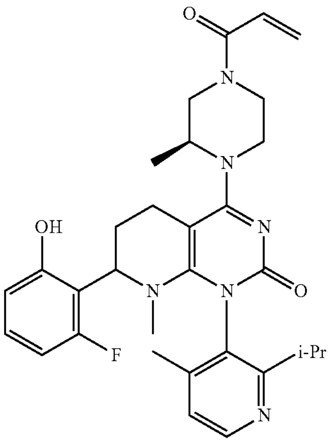
54
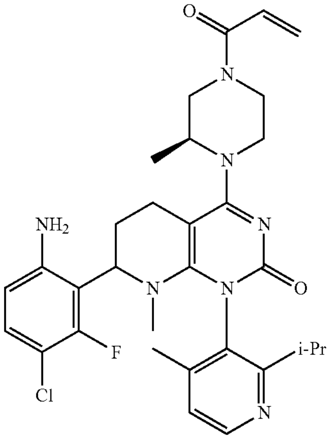

-continued
55
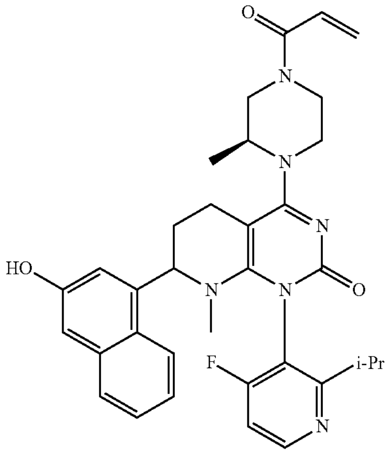
56
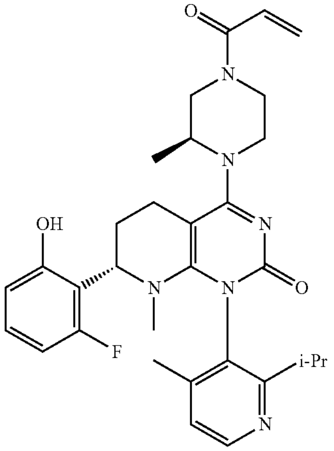
57
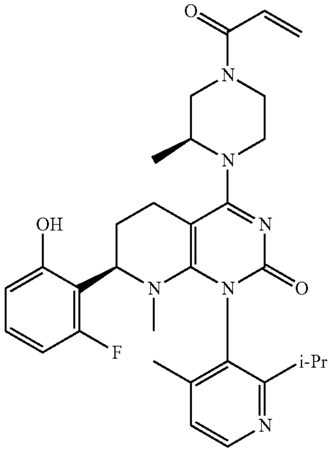
-continued
58
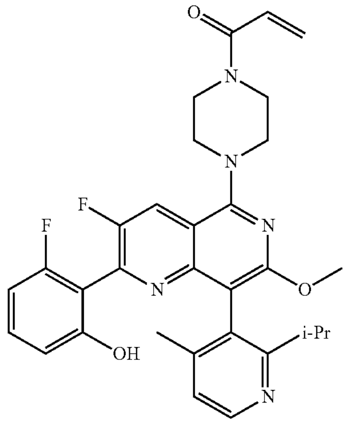
59
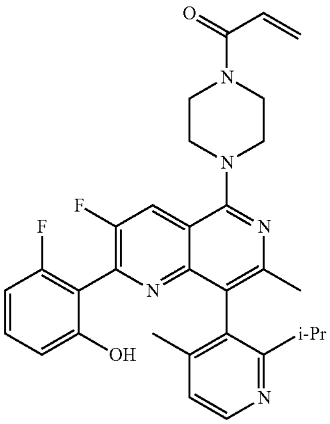
60
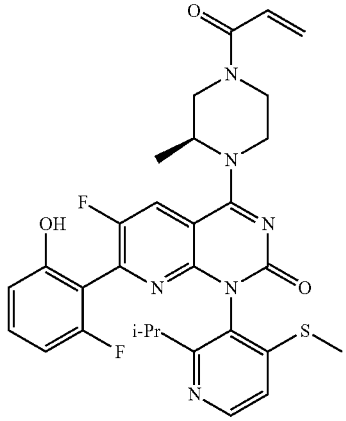

-continued
61
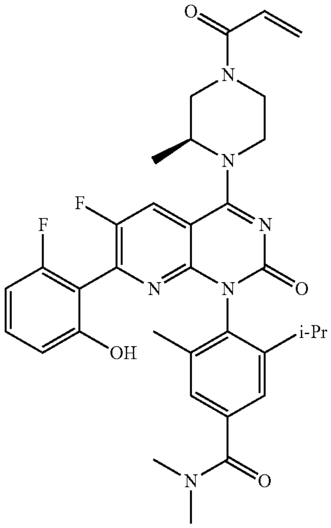
62
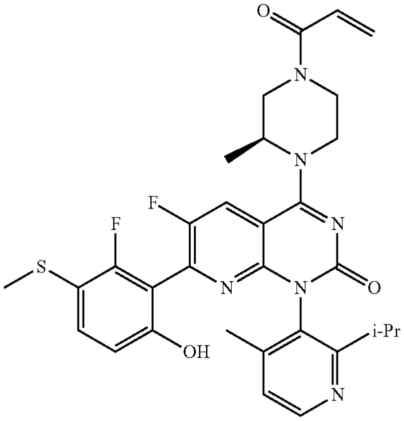
63
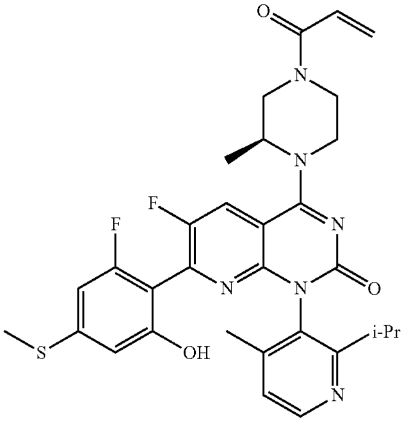
-continued
64
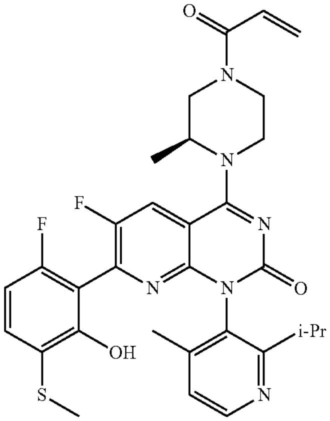
65
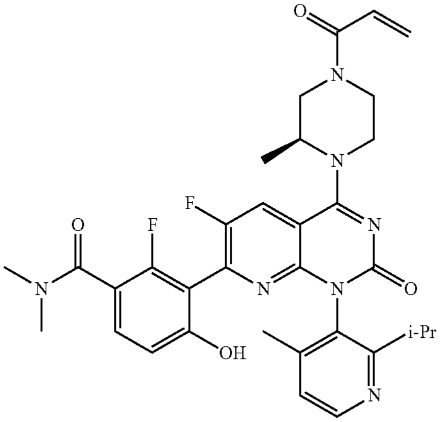
66
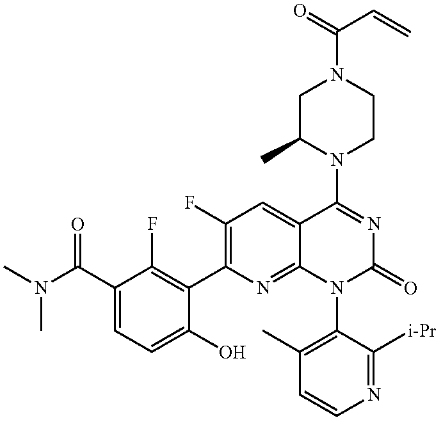

-continued
67
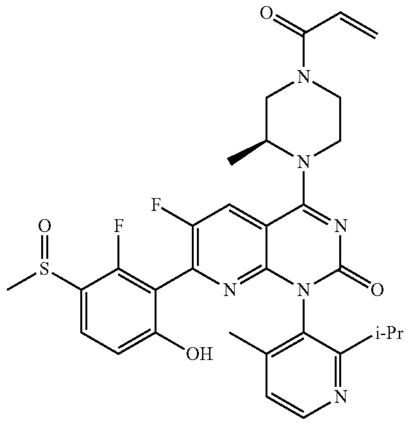
68
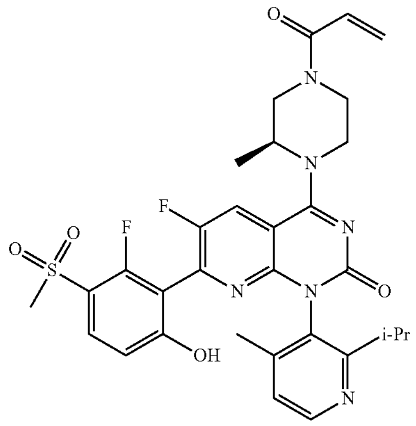
69
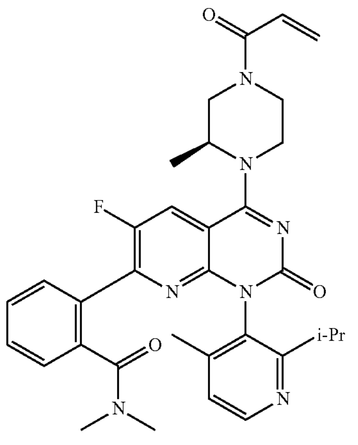
-continued
70
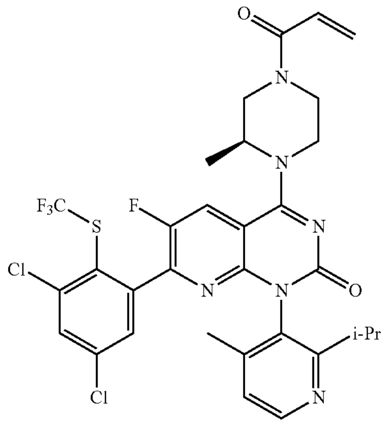
71
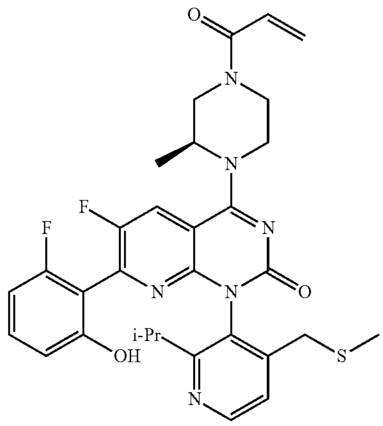
72
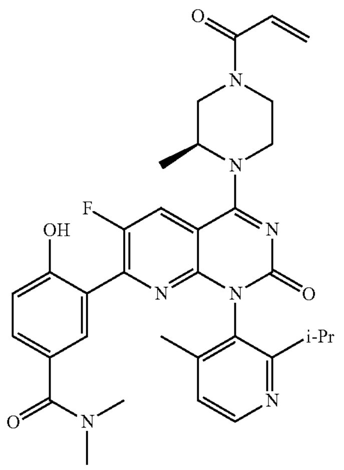

-continued
73
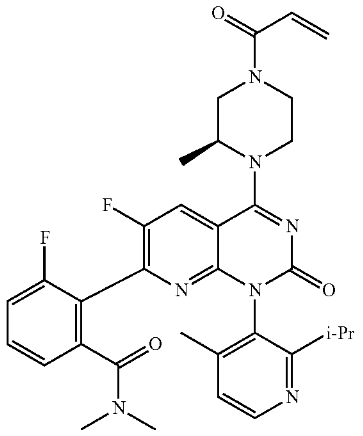
74
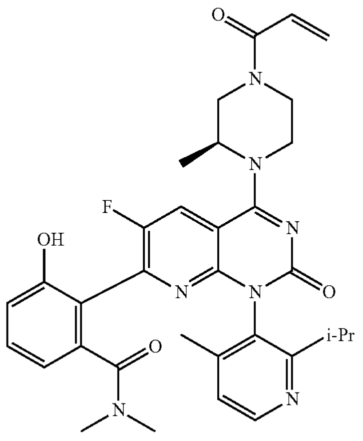
75
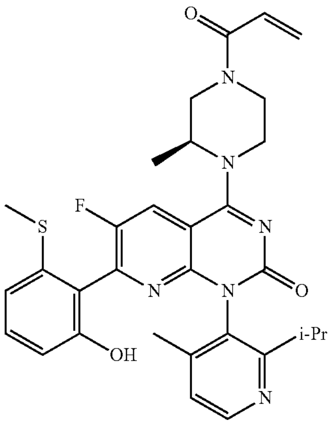
-continued
76
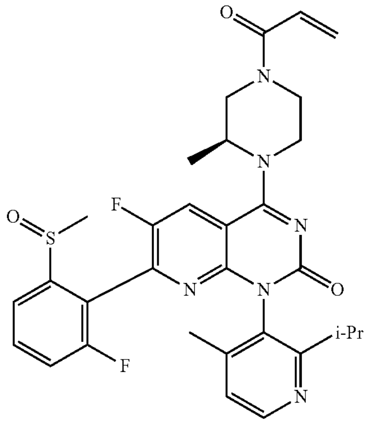
77
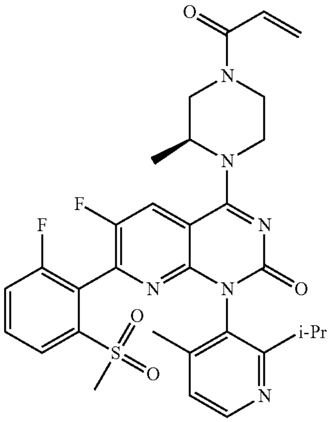
78
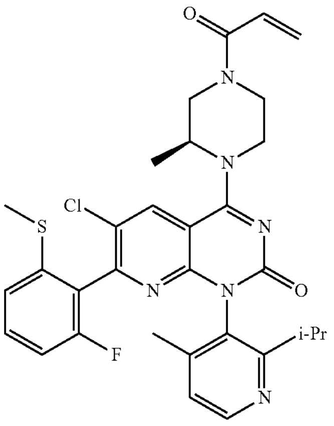

-continued
79
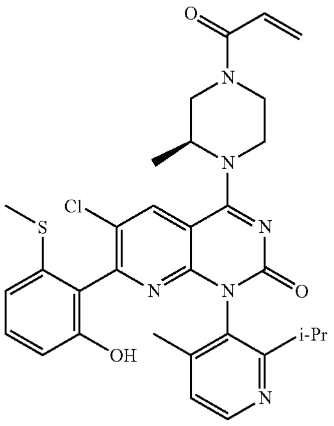
80
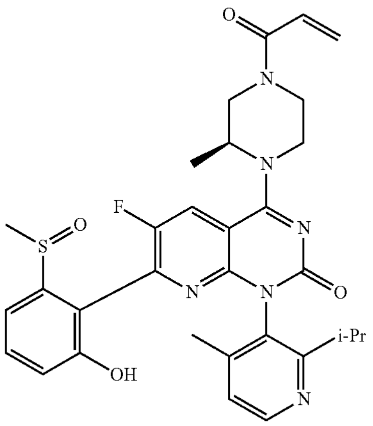
81
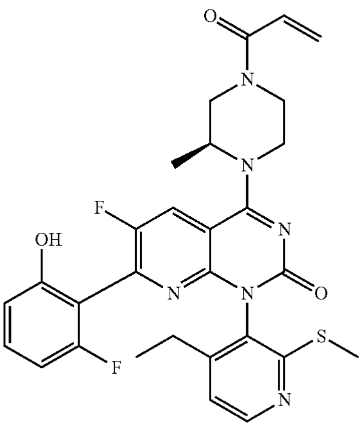
-continued
82
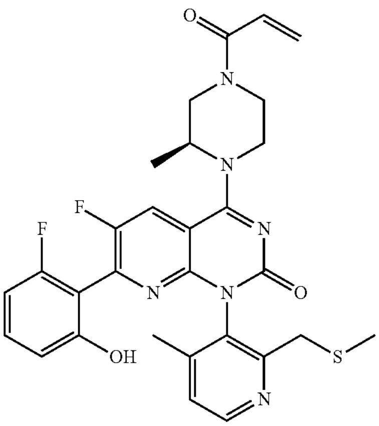
83
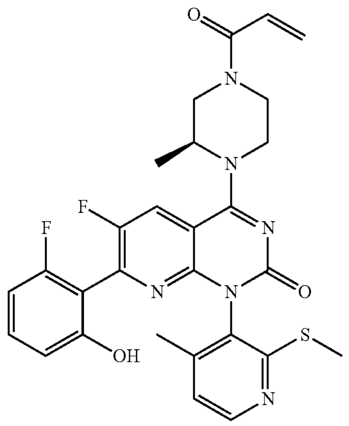
84
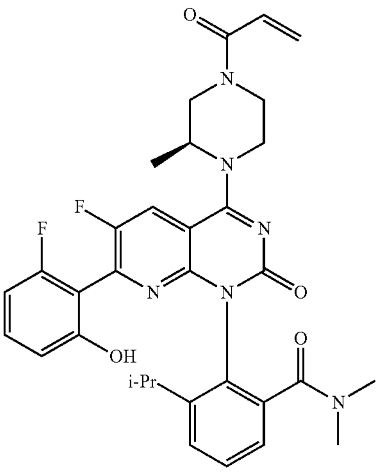

-continued
85
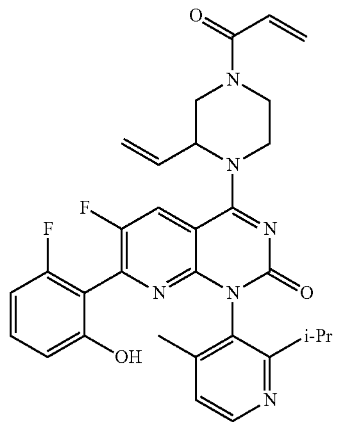
86
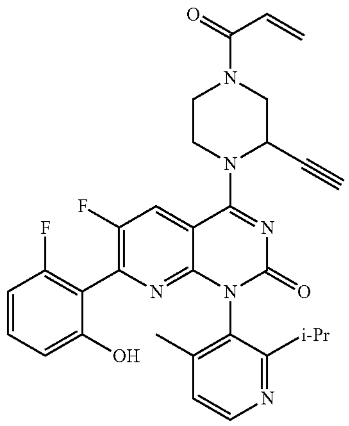
87
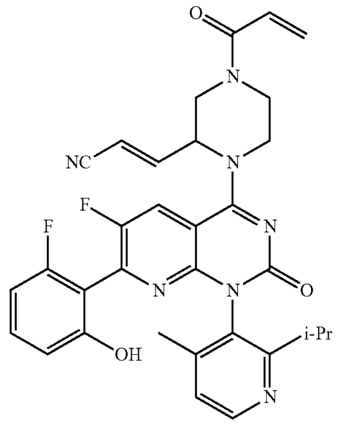
-continued
88
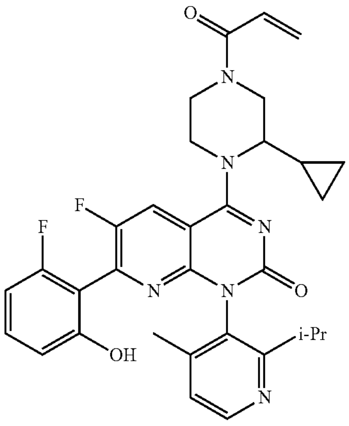
89
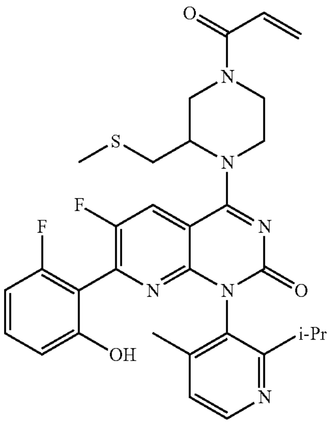
90
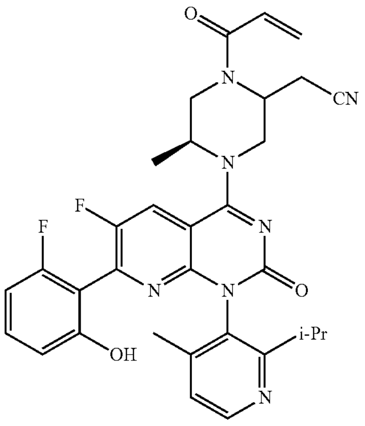

-continued
91
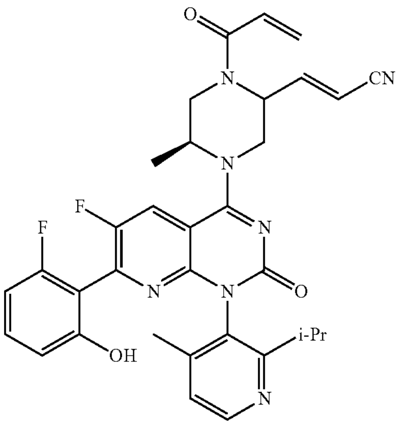
92
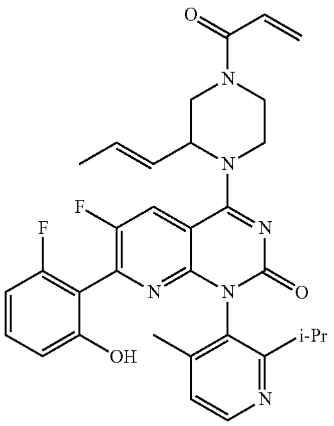
93
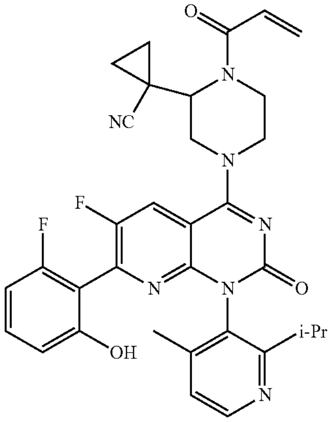
-continued
94
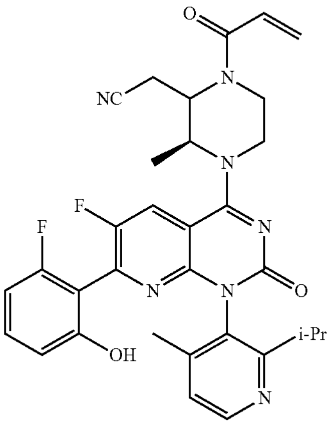
95
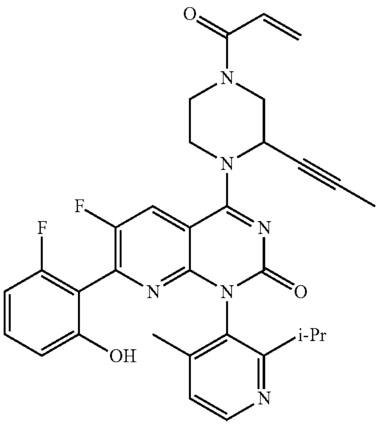
96
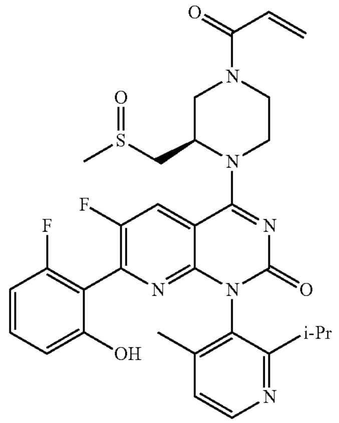

-continued
97
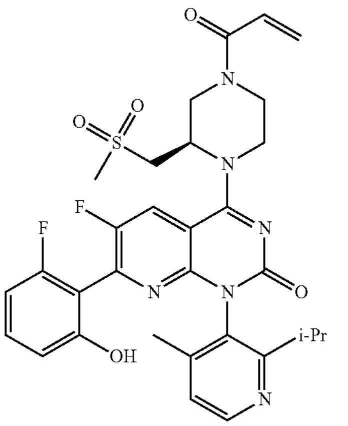
98
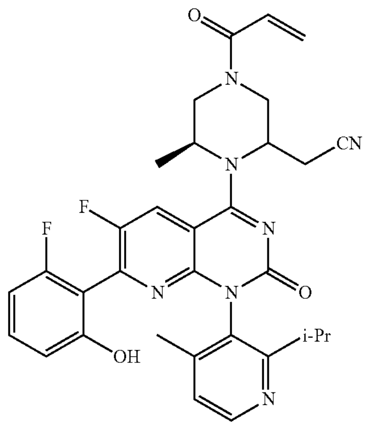
99
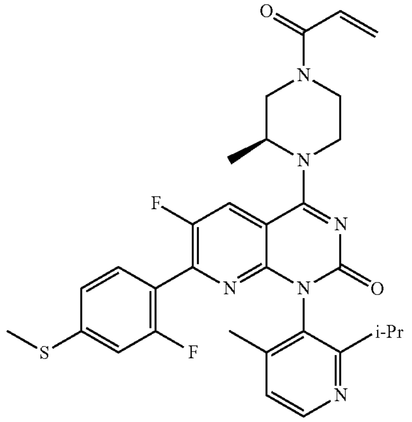
-continued
100
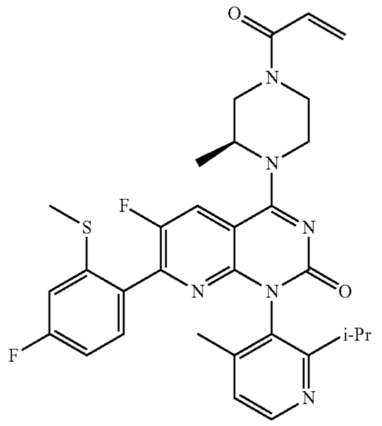
101
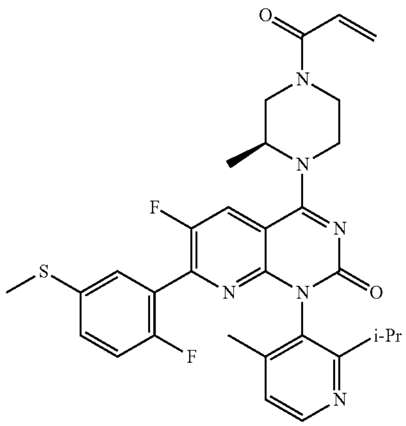
102
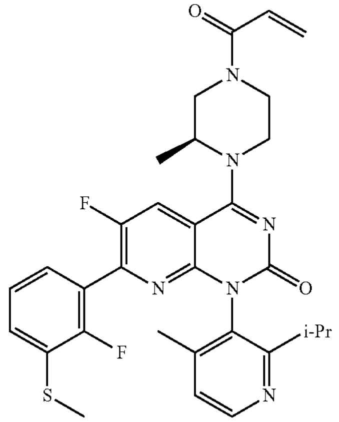

-continued
103
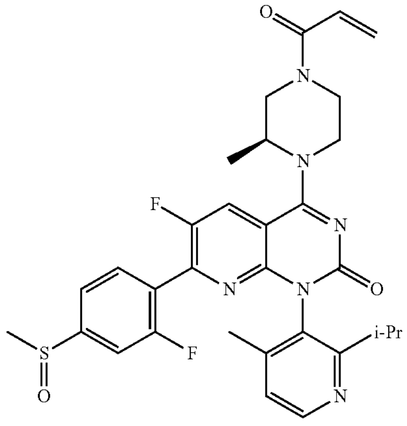
104
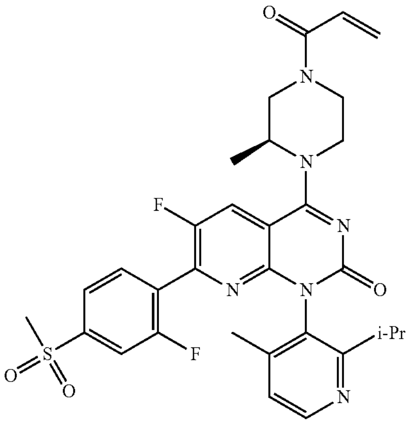
105
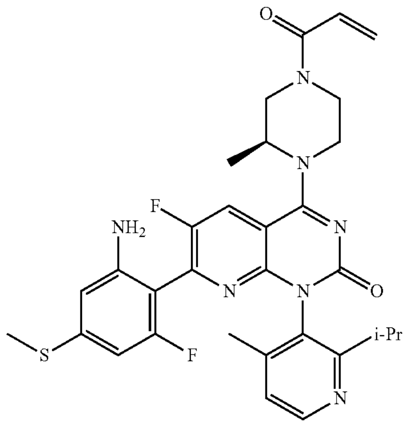
-continued
106
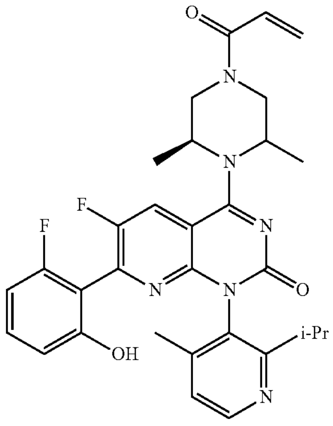
107
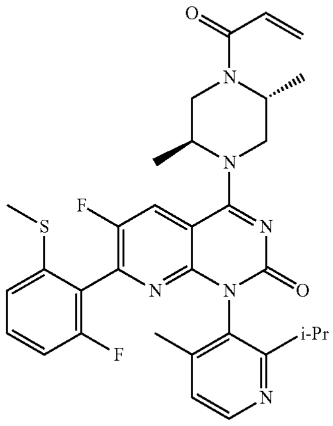
108
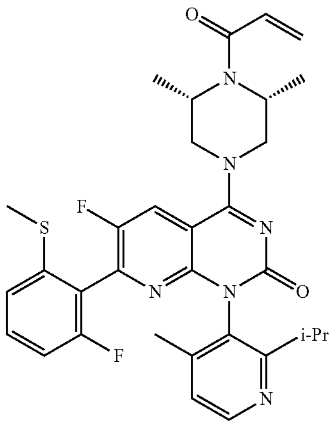

-continued
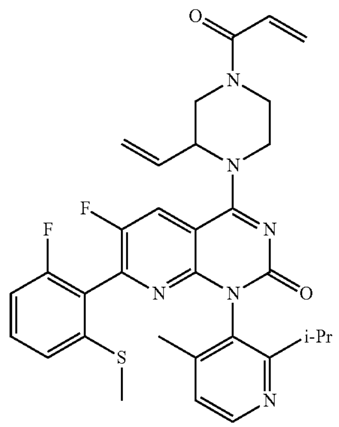
109
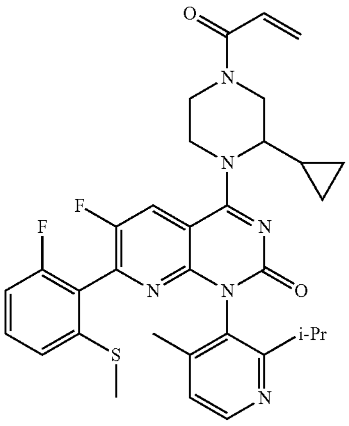
112
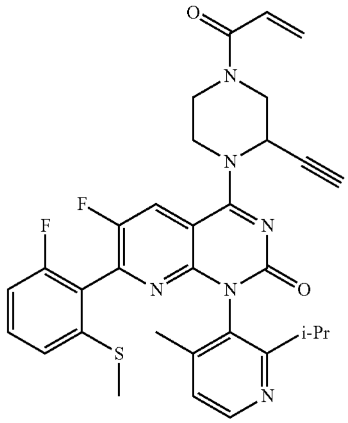
110
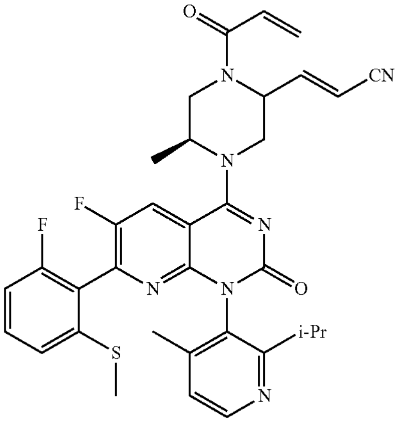
113
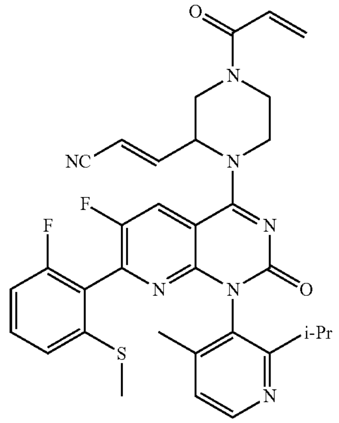
111
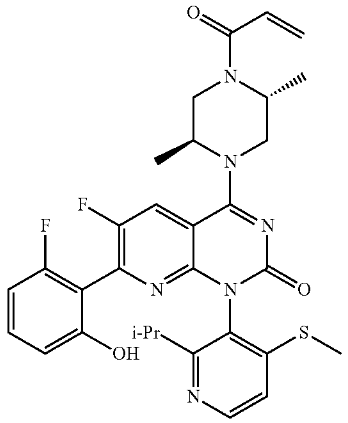
114

-continued
115
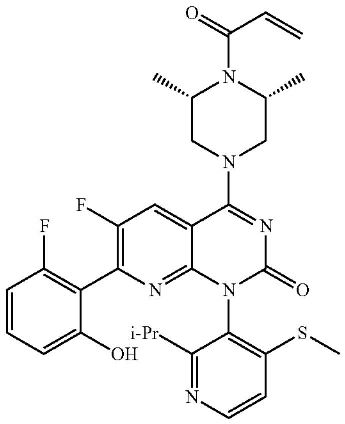
116
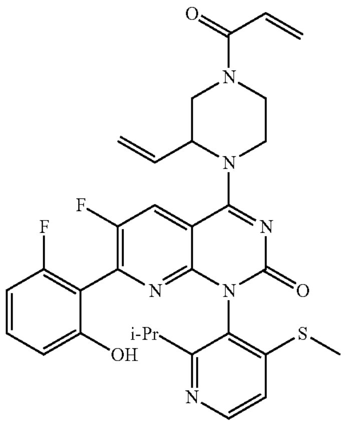
117
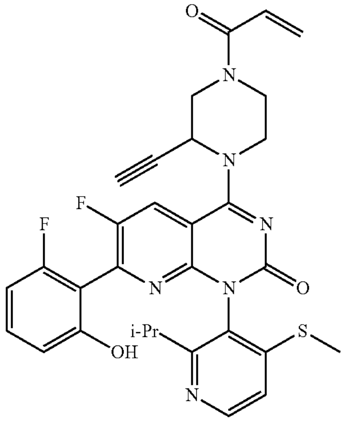
-continued
118
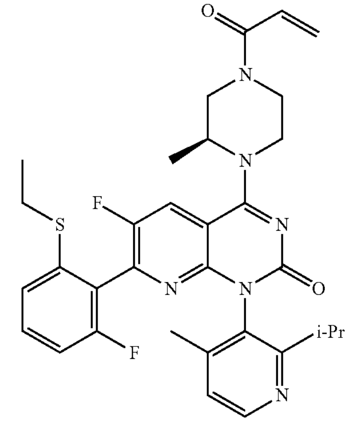
119
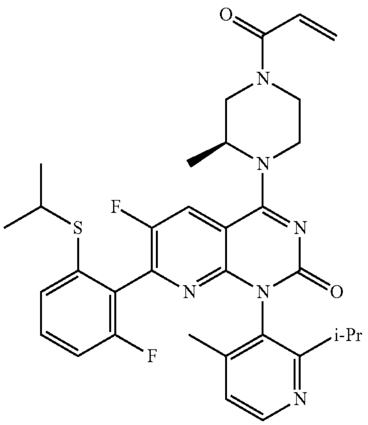
120
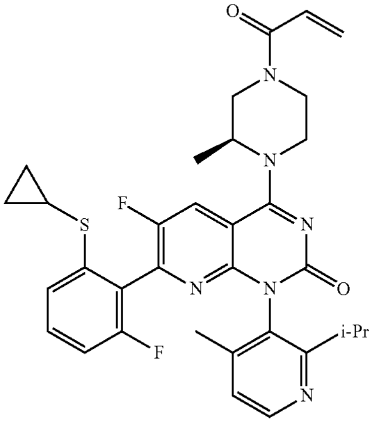

-continued
121
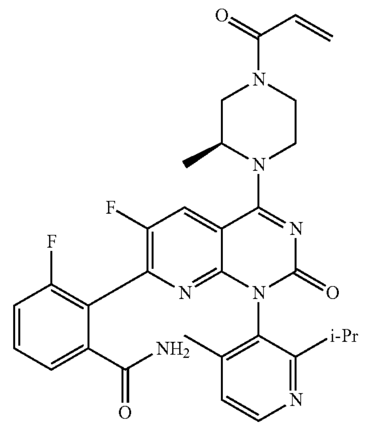
122
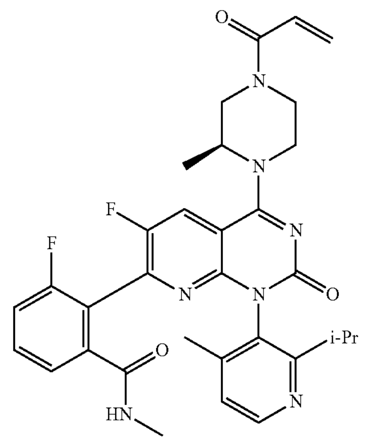
123
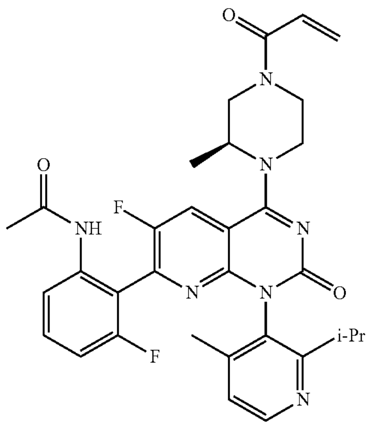
-continued
124
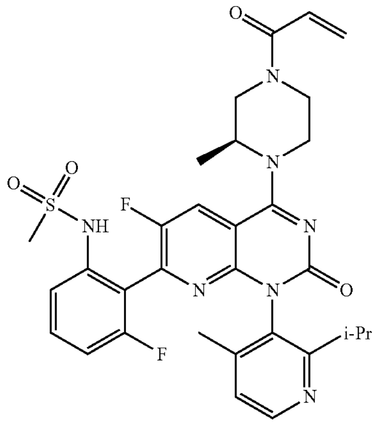
125
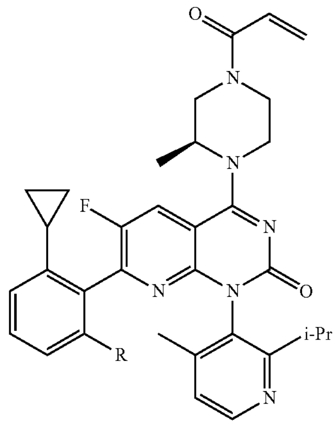
126
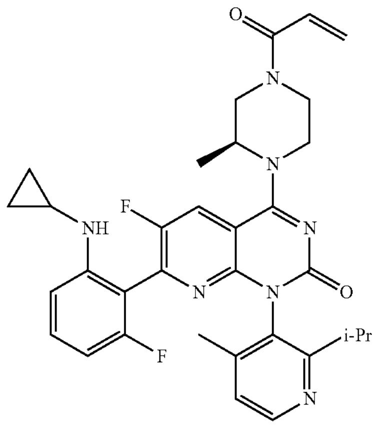

-continued
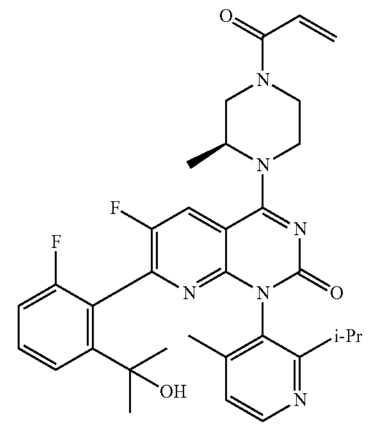
127
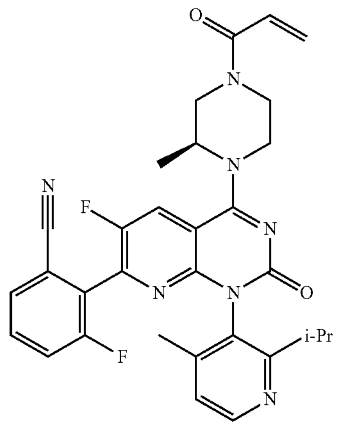
128
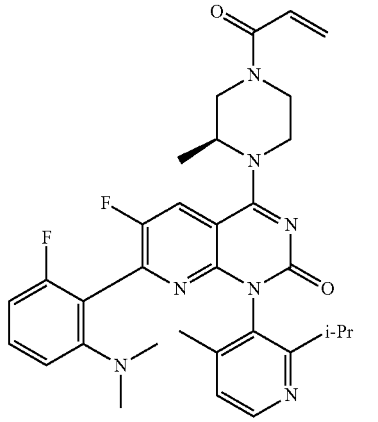
129
-continued
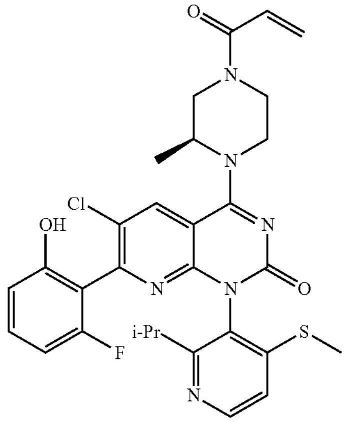
130
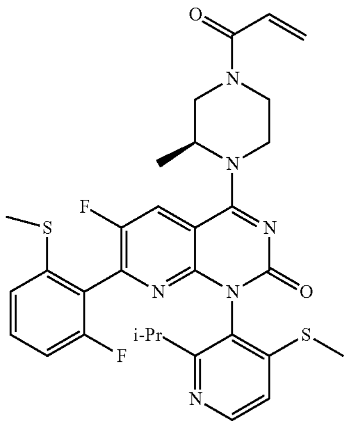
131
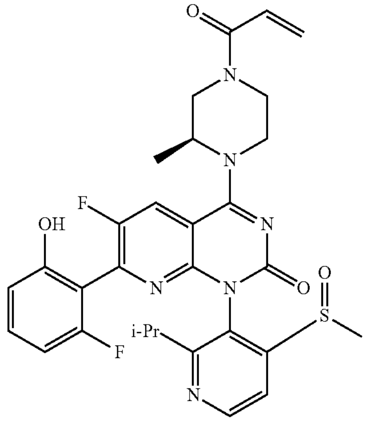
132

-continued
133
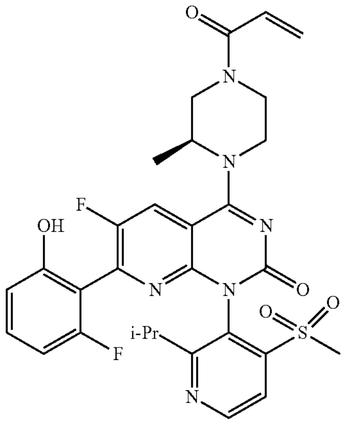
134
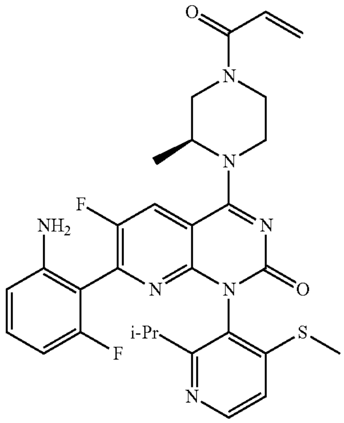
135
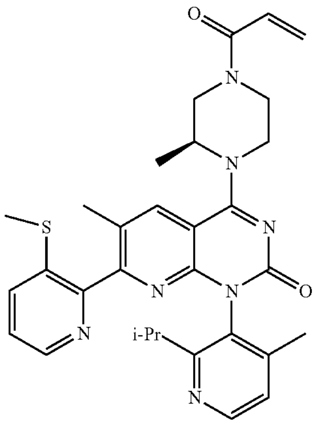
-continued
136
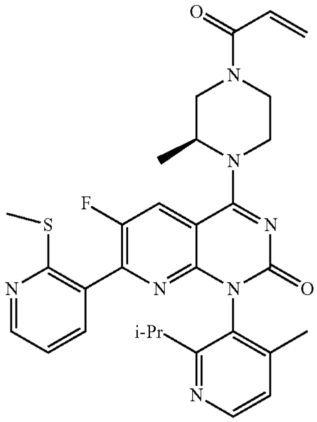
137
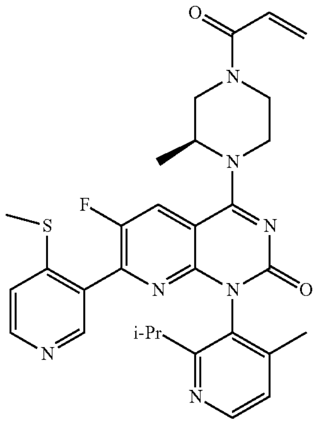
138
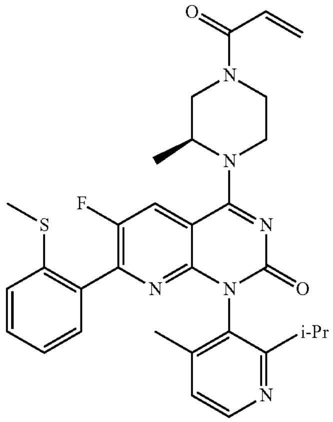

139
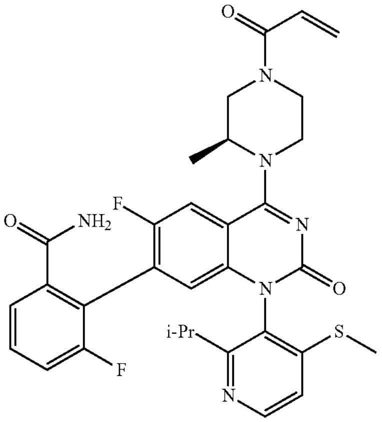
140
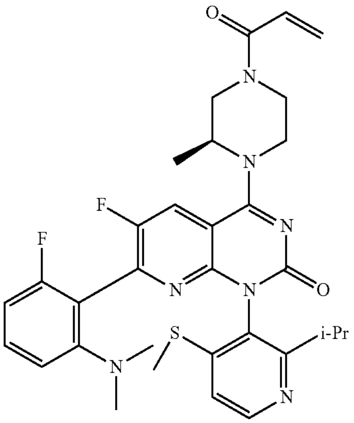
141
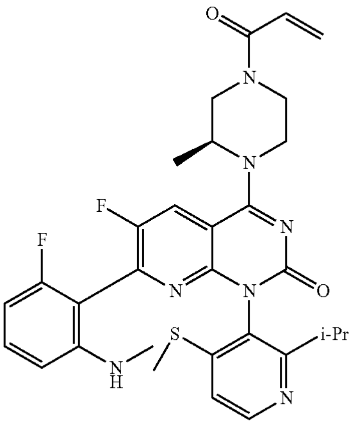
142
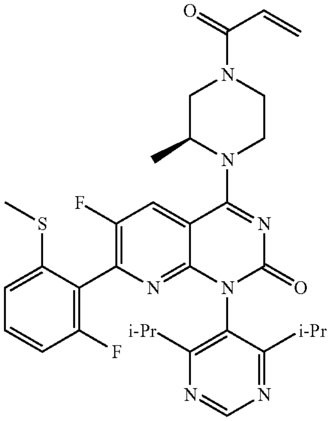
143
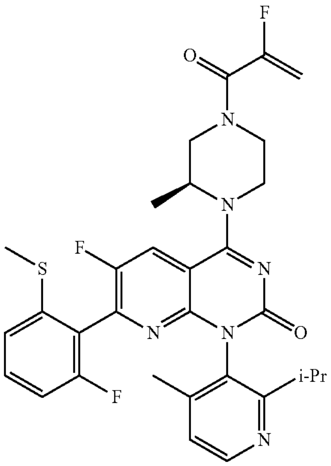
144
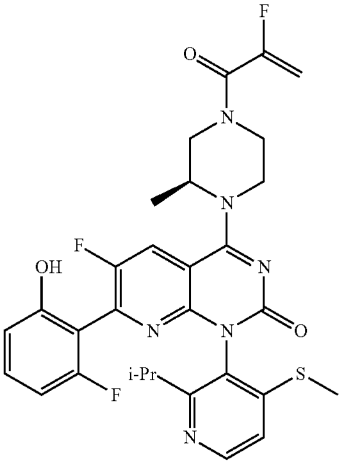

-continued
145
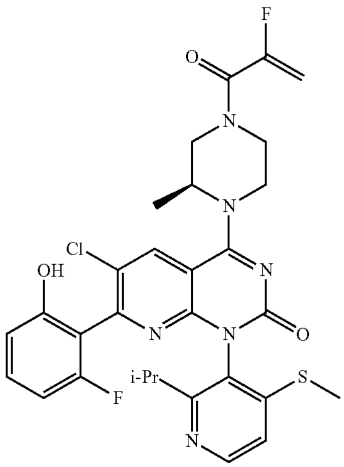
146
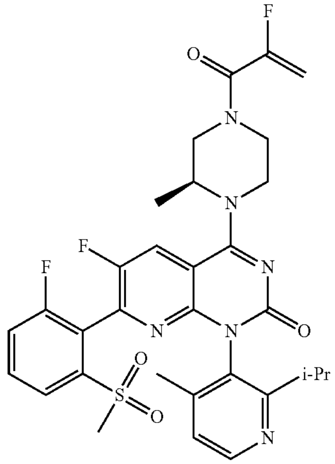
147
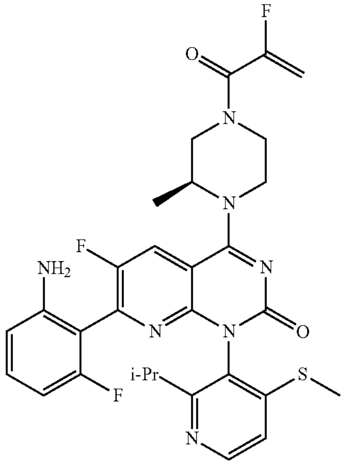
-continued
148
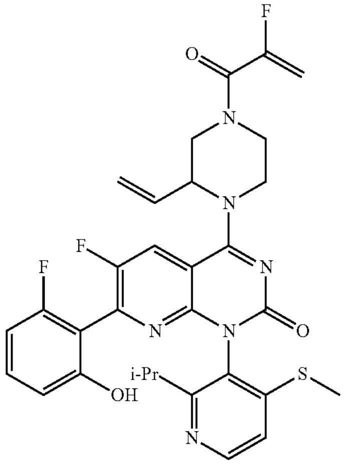
149
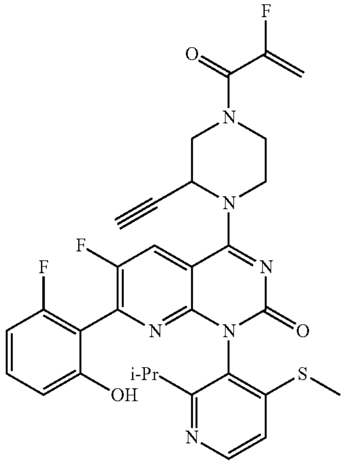
150
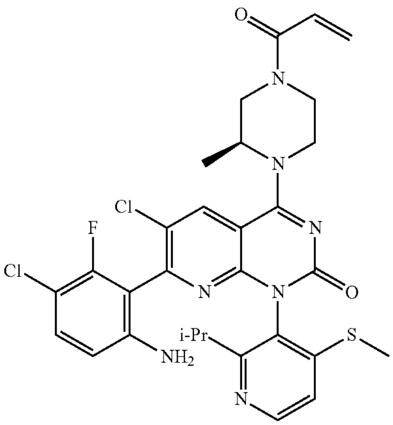

-continued
151
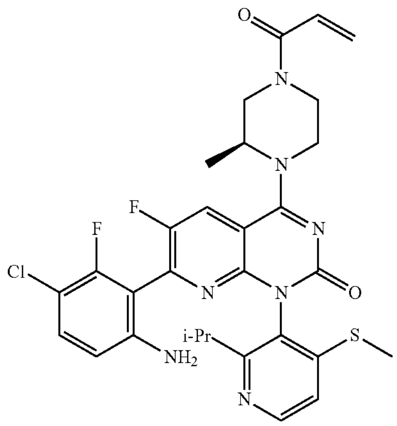
152
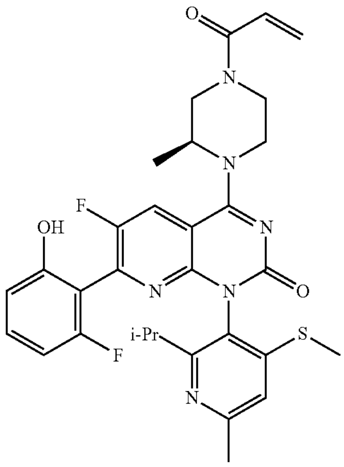
153
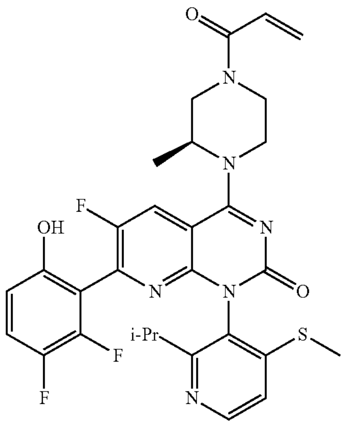
-continued
154
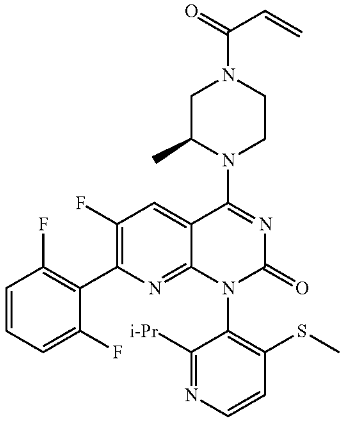
155
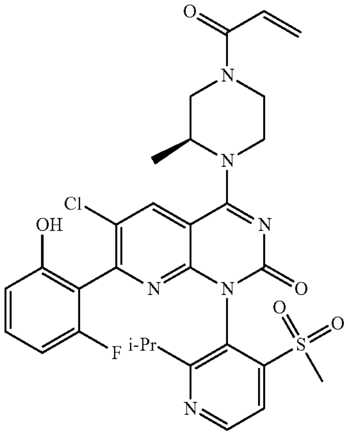
156
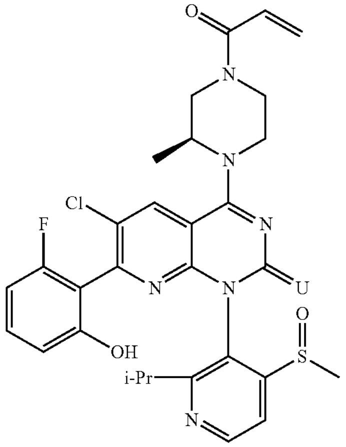

-continued
157
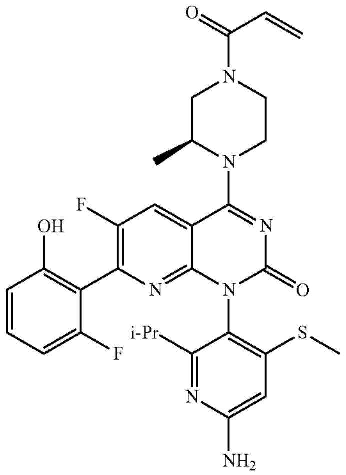
158
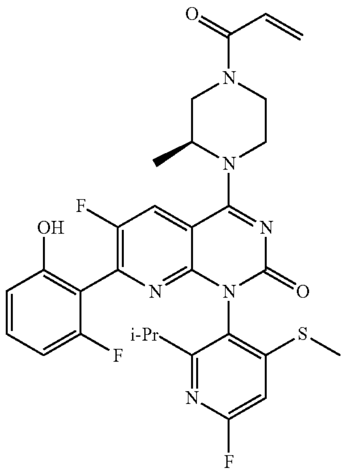
159
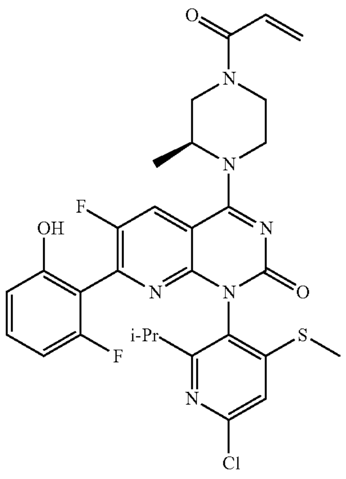
-continued
160
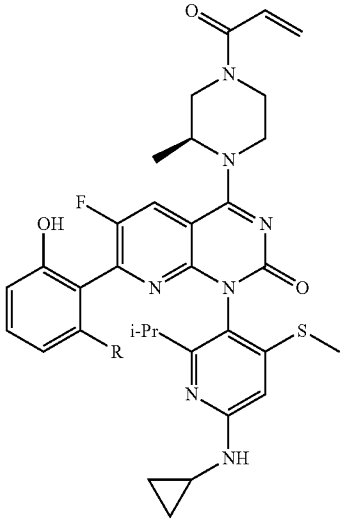
161
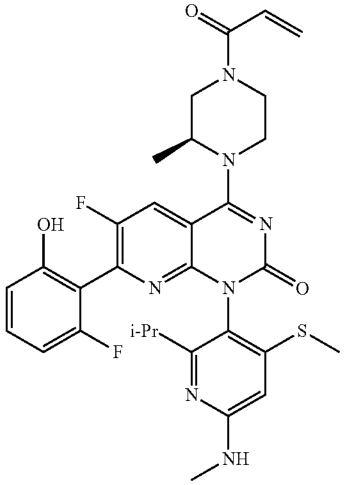
162
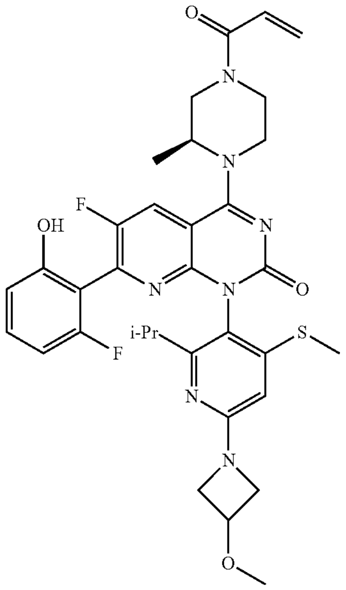

-continued
163
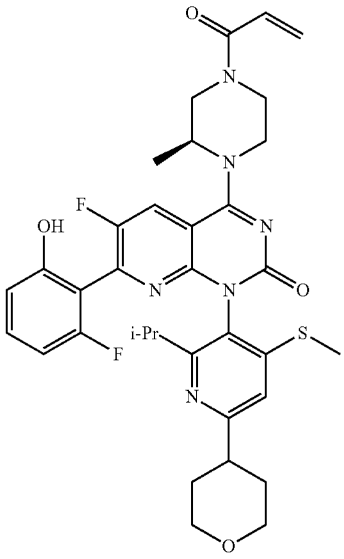
164
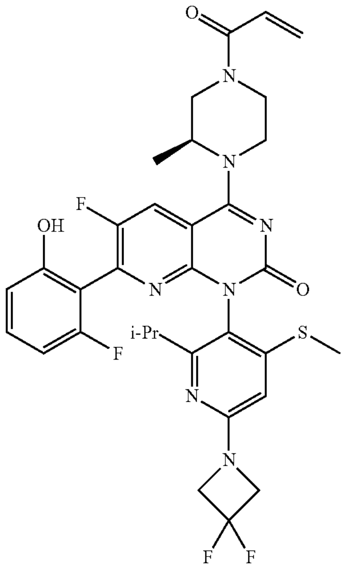
165
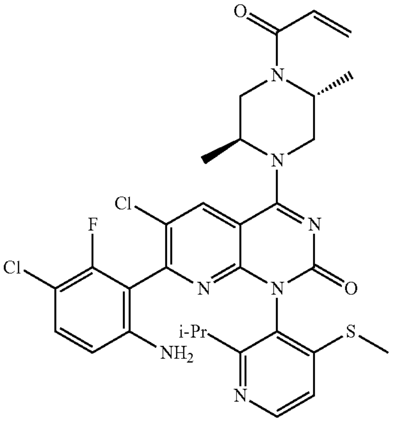
-continued
166
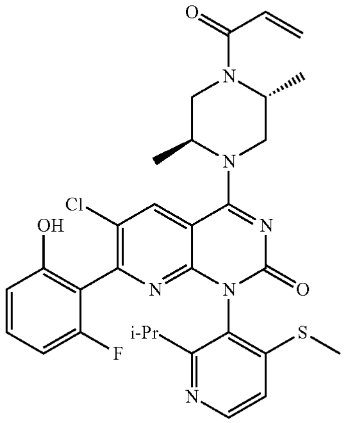
167
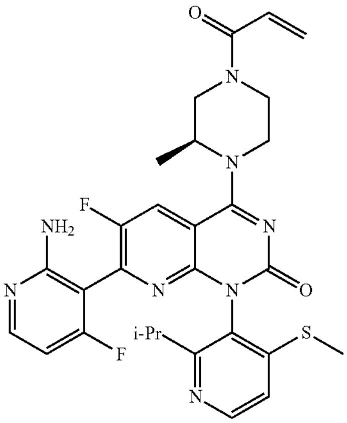
168
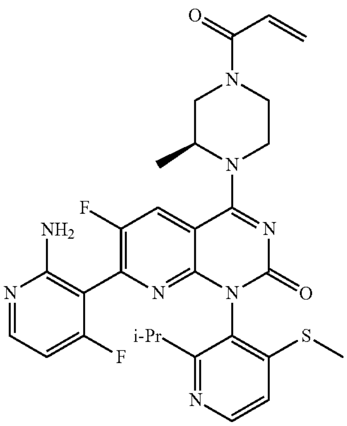

-continued
169
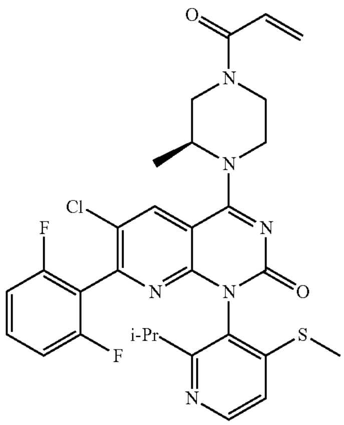
170
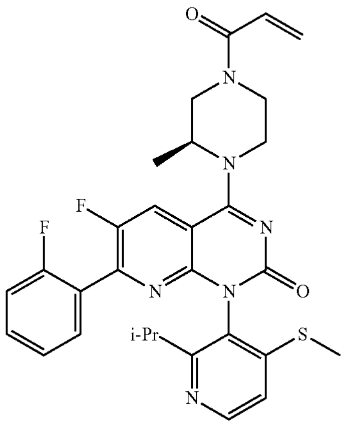
171
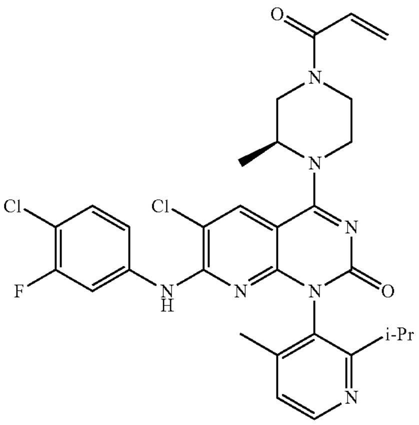
-continued
172
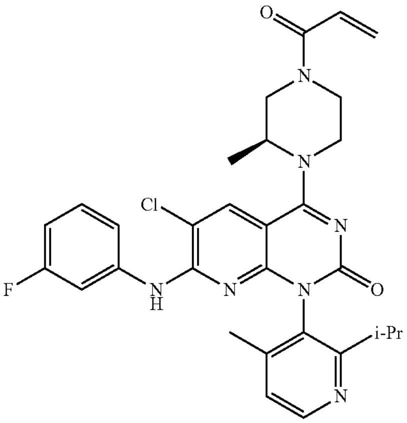
173
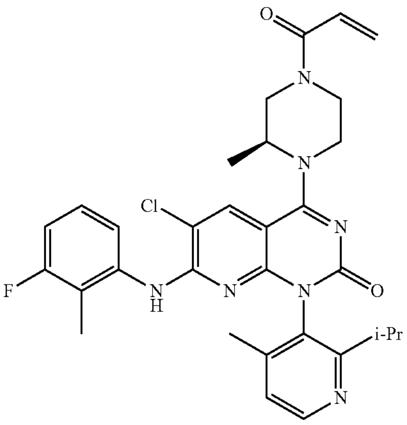
174
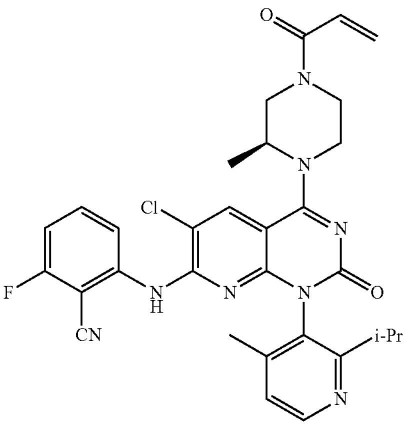

-continued
175
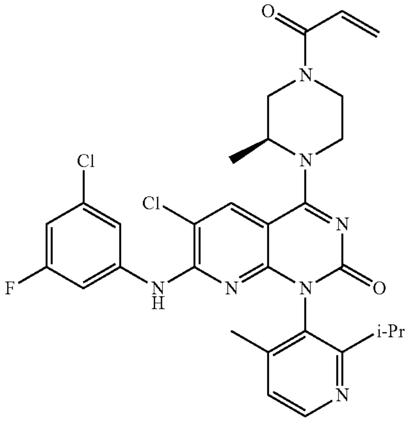
176
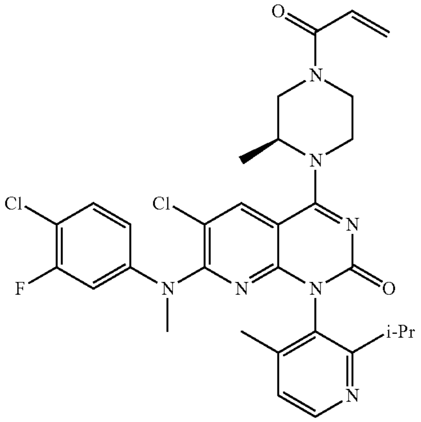
177
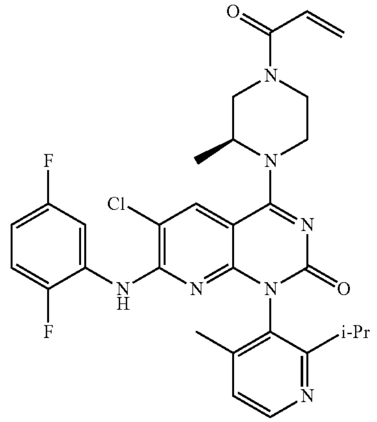
-continued
178
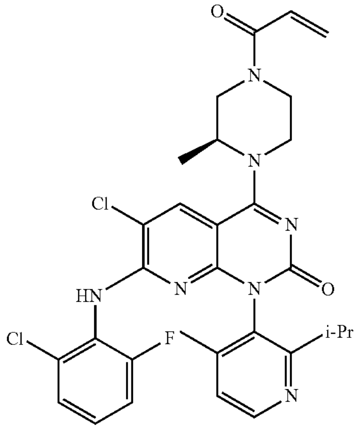
179
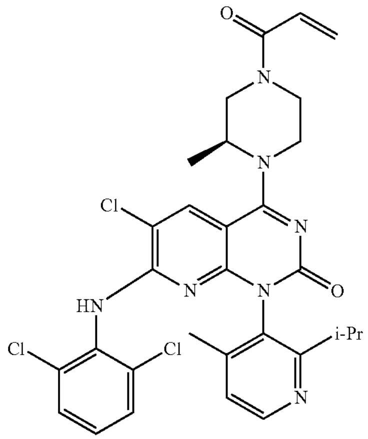
180
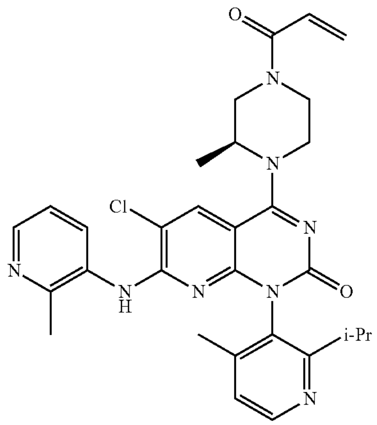

-continued
181
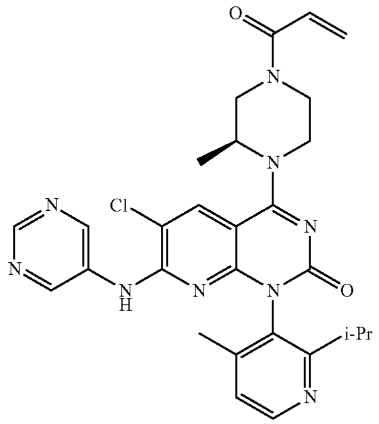
182
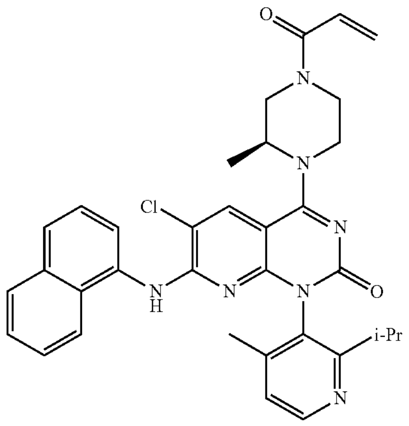
183
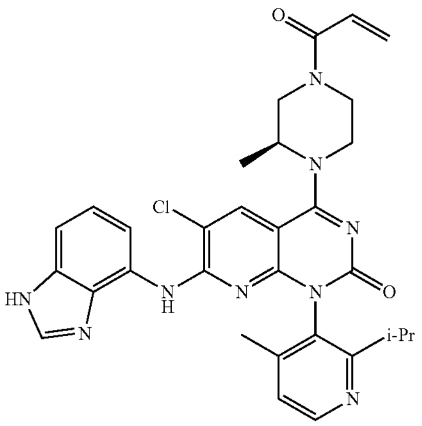
-continued
184
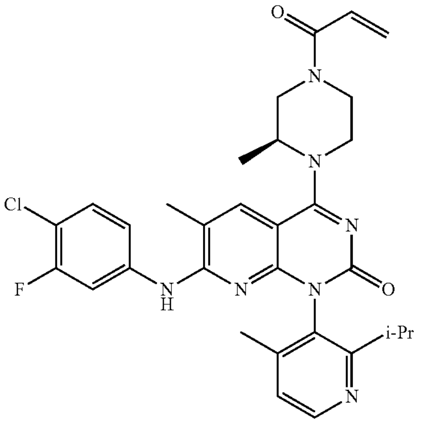
185
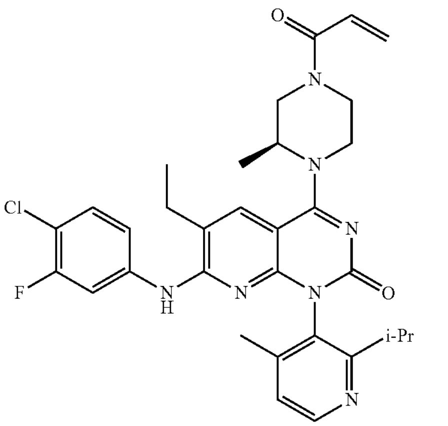
186
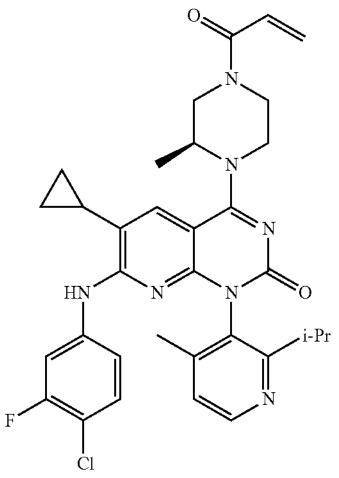

-continued
187
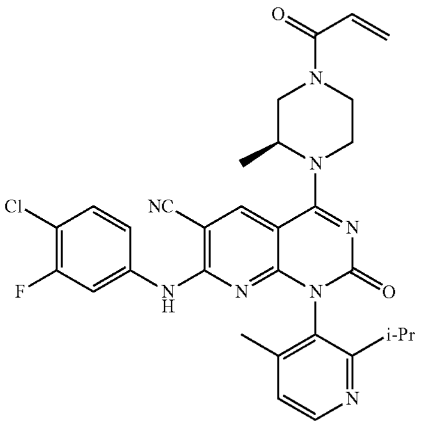
188
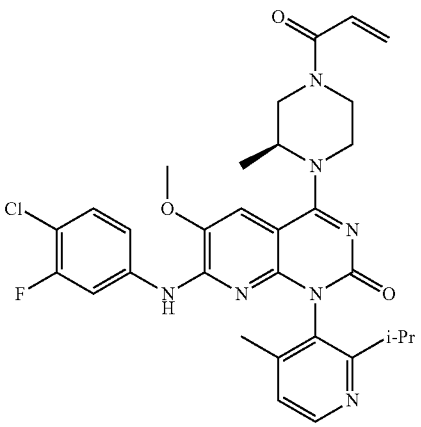
189
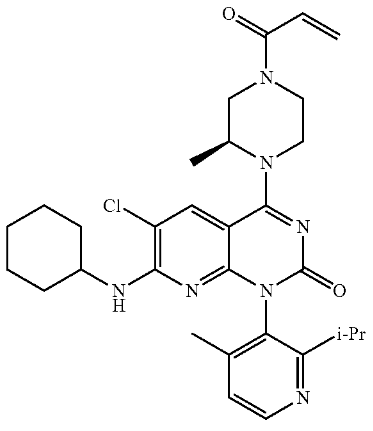
-continued
190
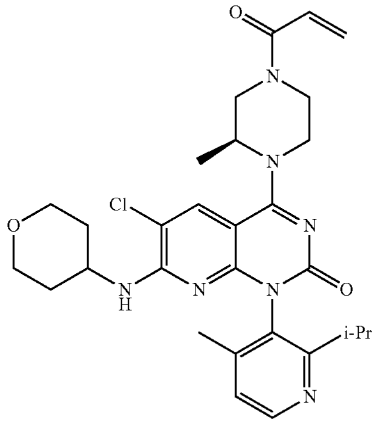
191
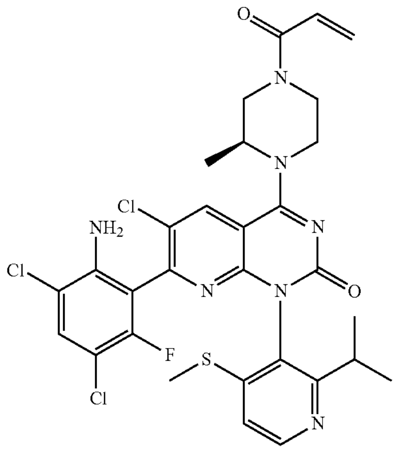
192
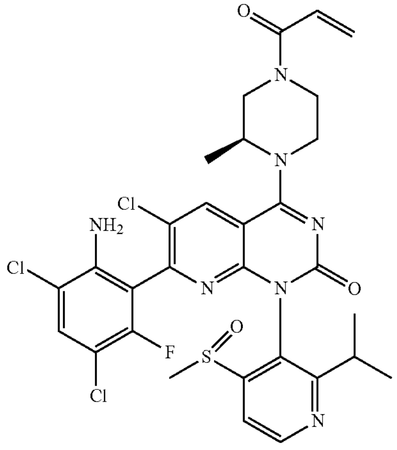

-continued
193
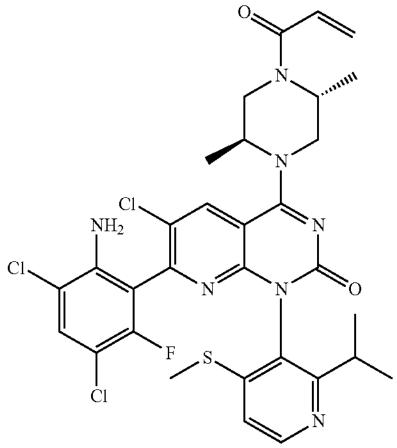
194
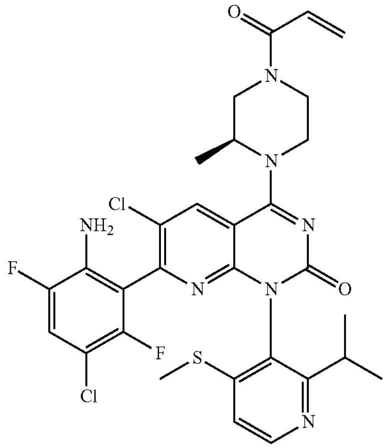
195
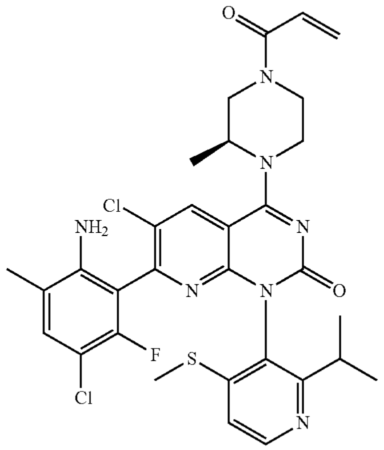
-continued
196
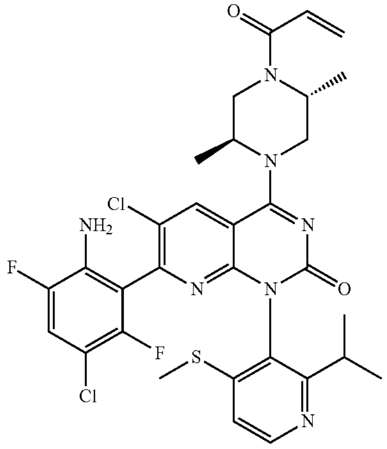
197
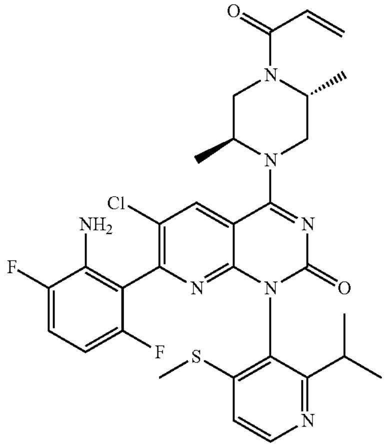
198
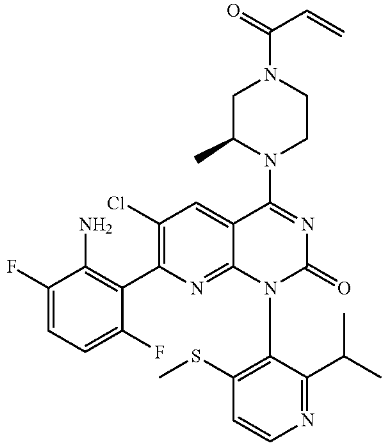

-continued
199
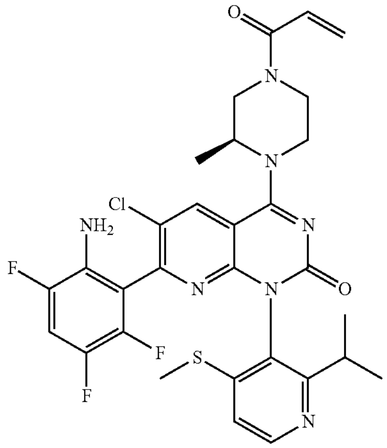
200
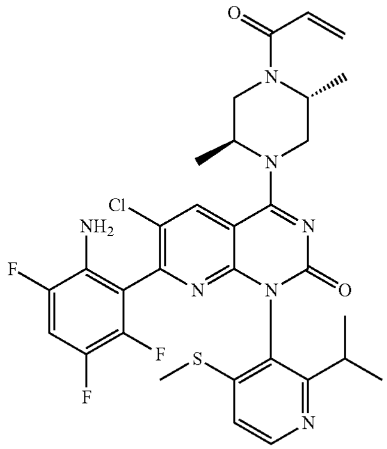
201
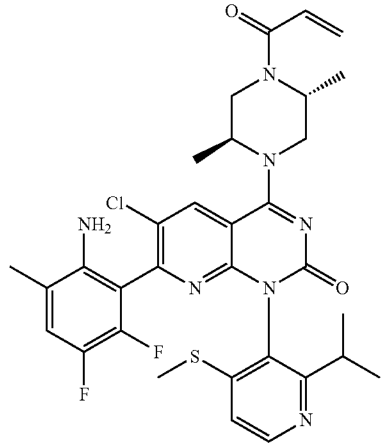
-continued
202
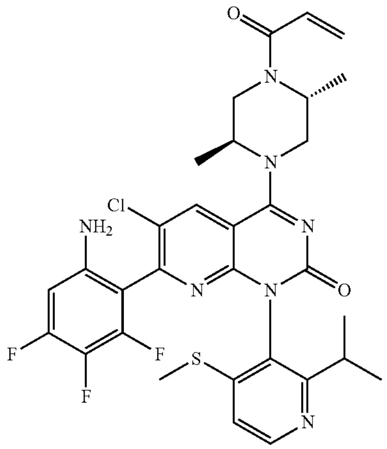
203
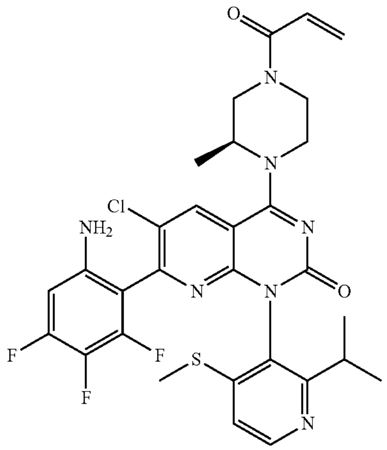
204
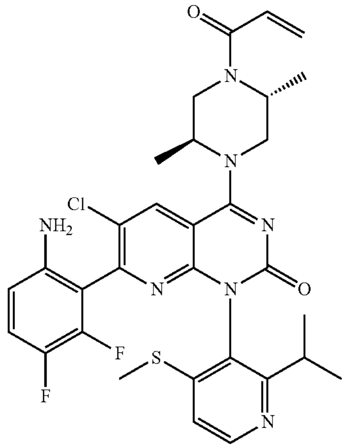

-continued
205
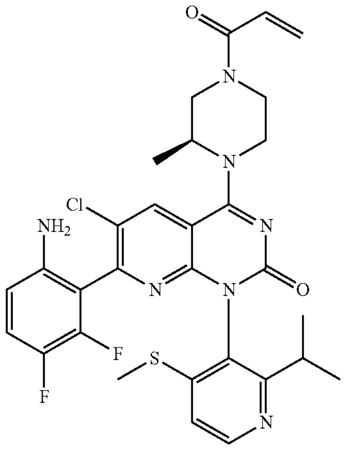
206
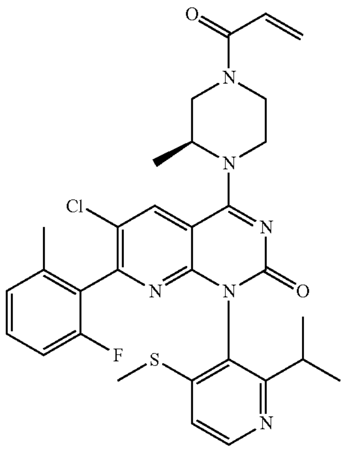
207
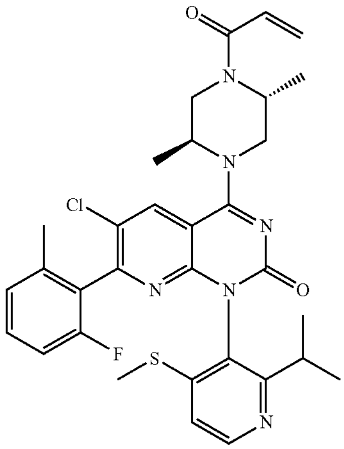
-continued
208
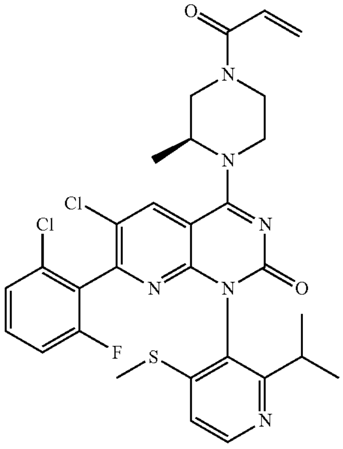
209
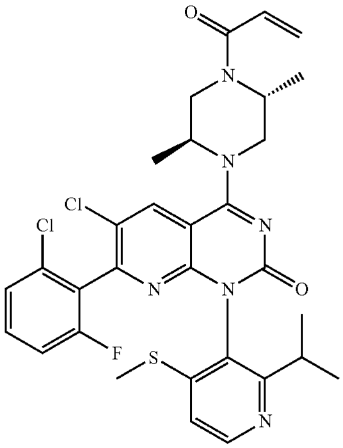
210
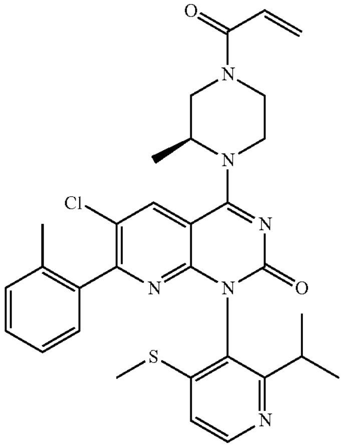

211
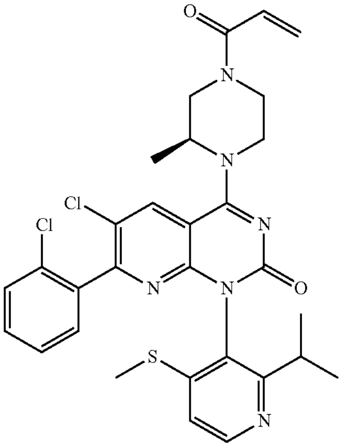
212
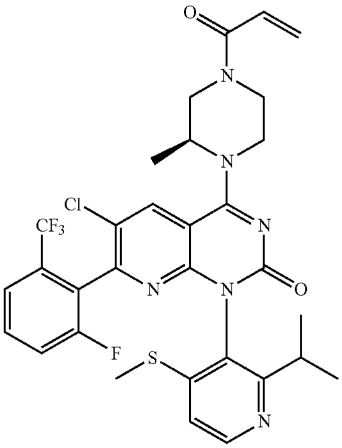
213
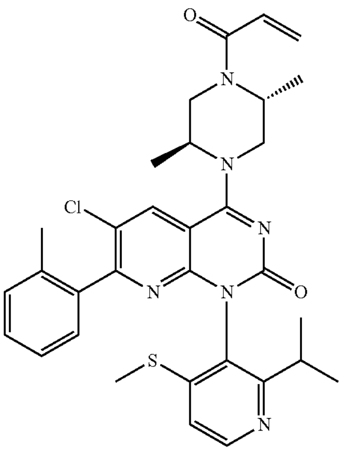
214
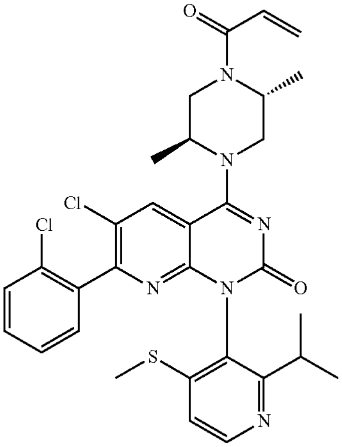
or
215
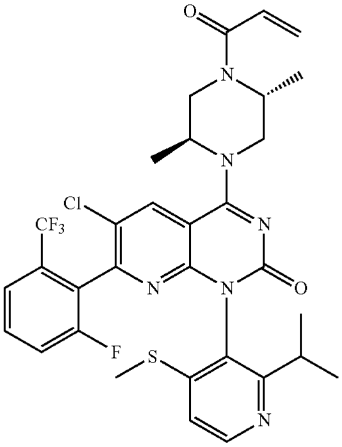
.
Preferably, when selected from the following compound structures, the compound can be further separated into enantiomeric axial chiral compounds,
60
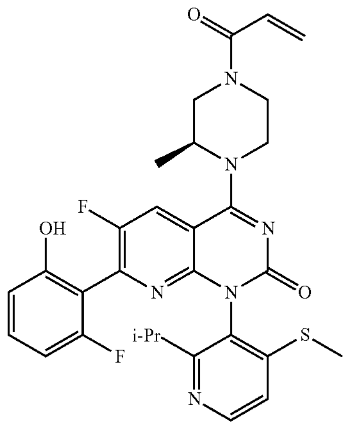

-continued
75
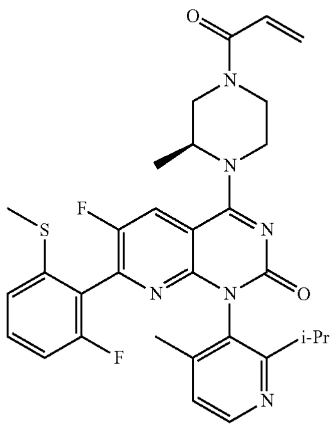
114
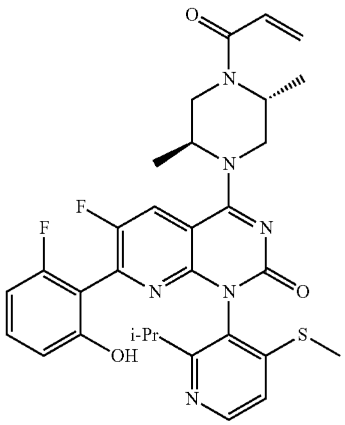
150
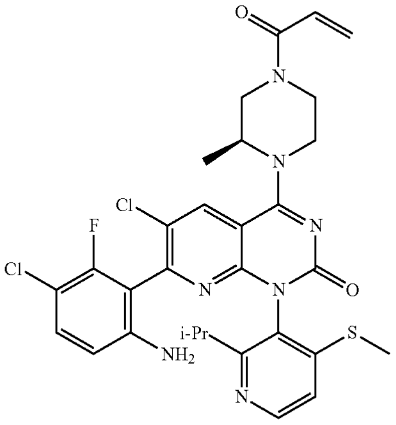
-continued
165
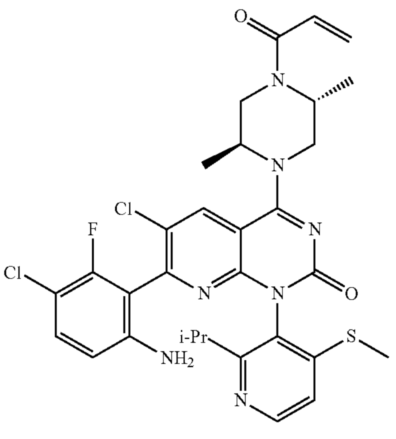
166
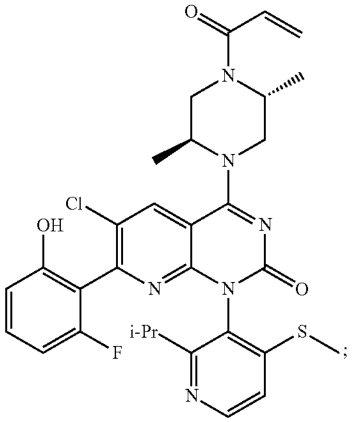
Further, the axial chiral compound structures of the compounds are as follows:
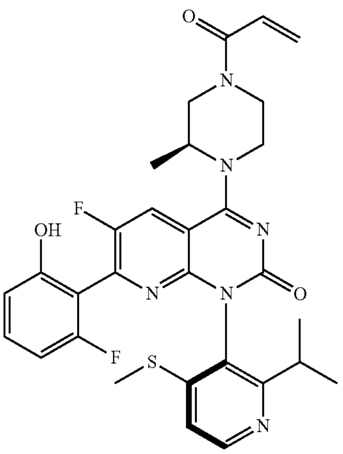

-continued
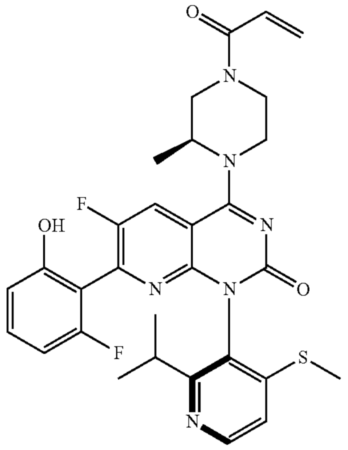
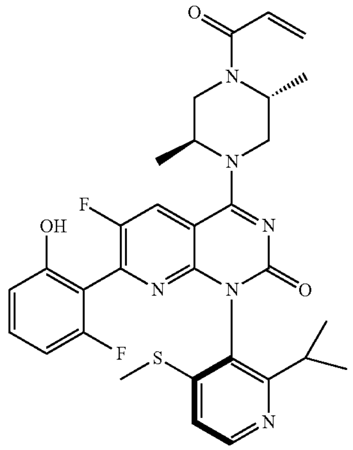
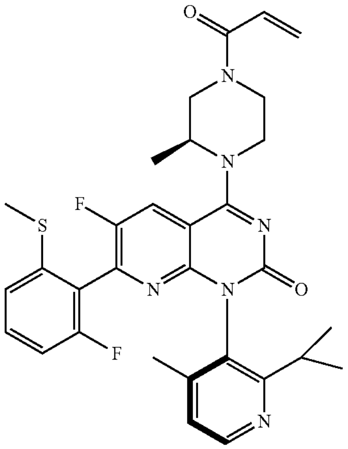
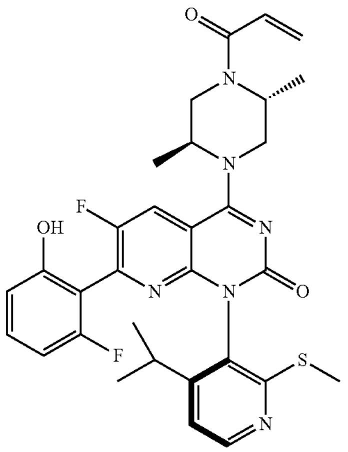
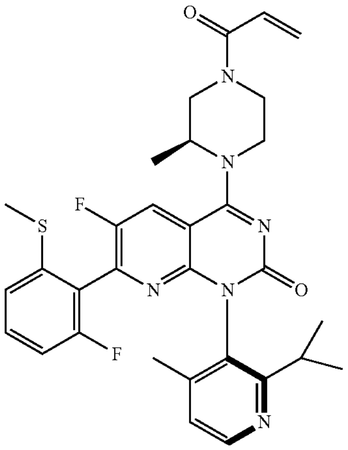
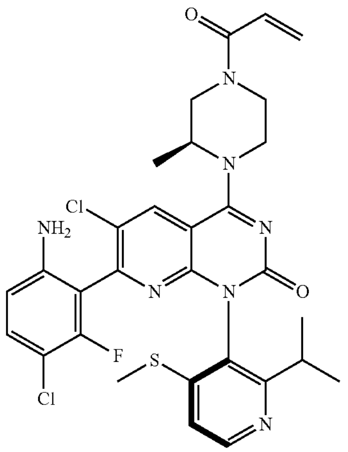
-continued -continued

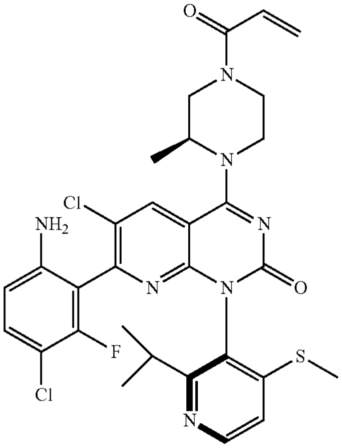

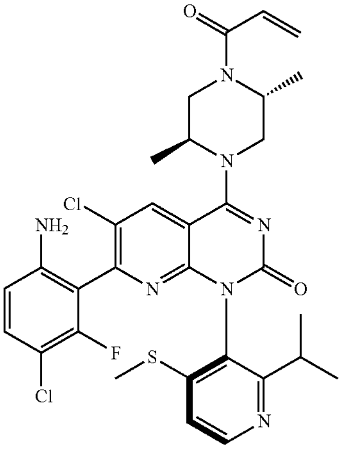

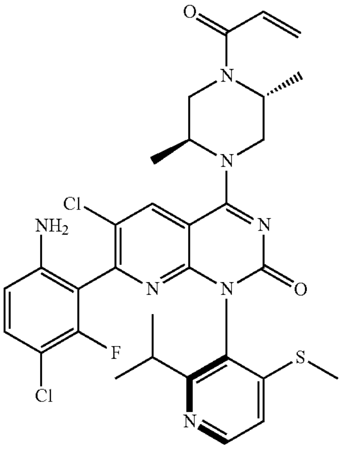

-continued

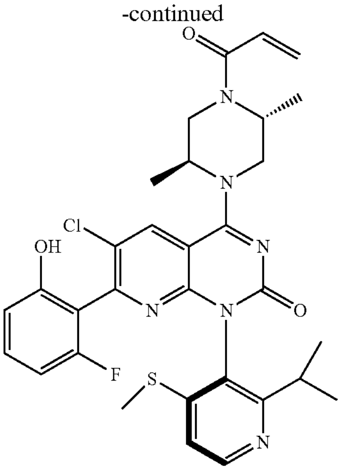

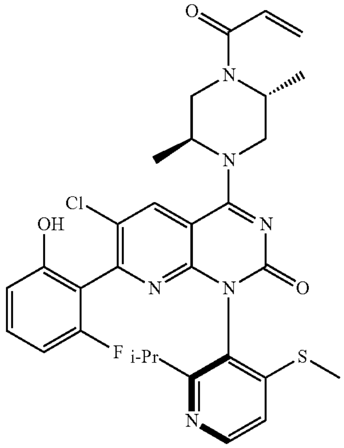

.

In a further preferred embodiment of the present disclosure, when the structure of the compound is

60

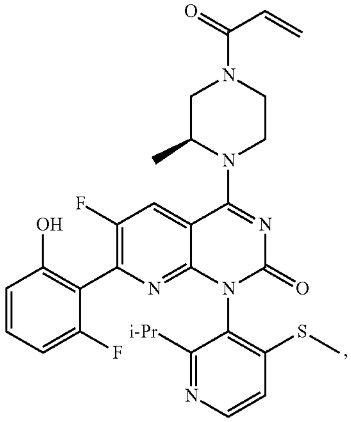

, the compound contains two axial chiral isomers 60-1 and 60-2, and the compounds 60-1 and 60-2 have the following parameters:

the compound 60-1 is the first axially chiral compound to be washed down with an earlier retention time than compound 60-2, preferably the retention time of the compound 60-1 is $t_R$=1.92 min and the retention time of the compound 60-2 is $t_R$=2.43 min, the detection conditions are as follows:

TABLE 1

| | |
|---|---|
| Instrument | SFC Method Station (Thar, Waters) |
| Column type | Celluloe-SC 4. 6 × 100 mm, 5 um (YMC) |
| Column pressure | 120 bar |
| Mobile phase | A: $CO_2$; B: Methanol [0. 2% $NH_3$(7M in methanol)]; A:B = 60:40 |
| Flow rate | 4 mL/min |
| Detection wavelength | UV 214 nm |
| Column temperature | 40° C. |

or, when the structure of the compound is

75

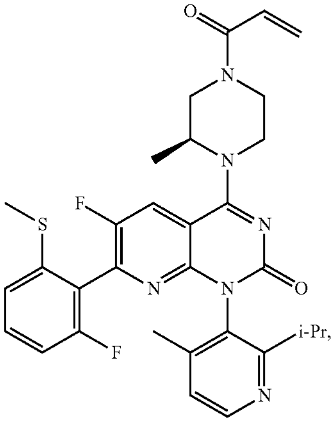

the compound contains two axial chiral isomers 75-1 and 75-2, and the compounds 75-1 and 75-2 have the following parameters:

the compound 75-1 is the first axially chiral compound to be washed down with an earlier retention time than compound 75-2, preferably the retention time of the compound 75-1 is $t_R$=1.97 min and the retention time of the compound 75-2 is $t_R$=3.75 min, the detection conditions are as follows:

TABLE 2

| | |
|---|---|
| Instrument | SFC Method Station (Thar, Waters) |
| Column type | Celluloe-SC 4. 6 × 100 mm, 5 um (YMC) |
| Column pressure | 120 bar |
| Mobile phase | A: $CO_2$; B: Methanol [0. 2% $NH_3$(7M in methanol)]; A:B = 60:40 |
| Flow rate | 4 mL/min |
| Detection wavelength | UV 214 nm |
| Column temperature | 40° C. |

or, when the structure of the compound is

114

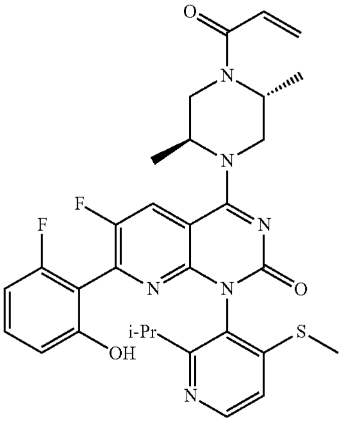

, the compound contains two axial chiral isomers 114-1 and 114-2, and the compounds 114-1 and 114-2 have the following parameters:

the compound 114-1 is the first axially chiral compound to be washed down with an earlier retention time than compound 114-2, preferably the retention time of the compound 114-1 is $t_R$=1.99 min and the retention time of the compound 114-2 is $t_R$=2.87 min, the detection conditions are as follows:

TABLE 3

| | |
|---|---|
| Instrument | SFC Method Station (Thar, Waters) |
| Column type | Celluloe-SC 4. 6 ×100 mm, 5 um (YMC) |
| Column pressure | 120 bar |
| Mobile phase | A: $CO_2$; B: Ethanol [1. 0% $NH_3$(7M in methanol)]; A:B = 65:35 |
| Flow rate | 4 mL/min |
| Detection wavelength | UV 214 nm |
| Column temperature | 40° C. |

or, when the structure of the compound is

150

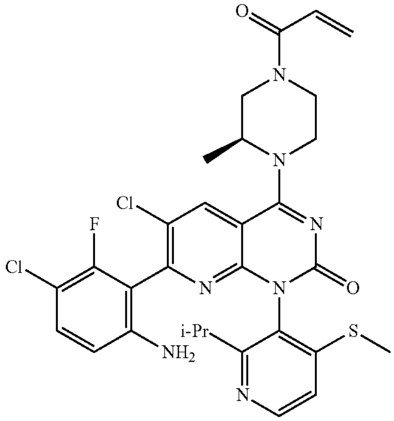

, the compound contains two axial chiral isomers 150-1 and 150-2, and the compounds 150-1 and 150-2 have the following parameters:

the compound 150-1 is the first axially chiral compound to be washed down with an earlier retention time than compound 150-2, preferably the retention time of the compound 150-1 is $t_R$=1.87 min and the retention time of the compound 150-2 is $t_R$=2.80 min, the detection conditions are as follows:

TABLE 4

| | |
|---|---|
| Instrument | SFC Method Station (Thar, Waters) |
| Column type | OX-H 4. 6*100 mm, 5 μm (Daicel) |
| Column pressure | 120 bar |
| Mobile phase | A: $CO_2$; B: Methanol [0. 2% $NH_3$(7M in methanol)]; A:B = 65:35 |
| Flow rate | 4 mL/min |
| Detection wavelength | UV 214 nm |
| Column temperature | 40° C. |

or, when the structure of the compound is

165

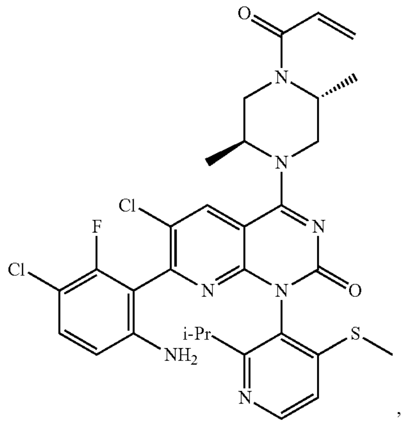

, the compound contains two axial chiral isomers 165-1 and 165-2, and the compounds 165-1 and 165-2 have the following parameters:

the compound 165-1 is the first axially chiral compound to be washed down with an earlier retention time than compound 165-2, preferably the retention time of the compound 165-1 is $t_R$=1.74 min and the retention time of the compound 165-2 is $t_R$=2.49 min, the detection conditions are as follows:

TABLE 5

| | |
|---|---|
| Instrument | SFC Method Station (Thar, Waters) |
| Column type | OX-H 4. 6*100 mm, 5 μm (Daicel) |
| Column pressure | 120 bar |
| Mobile phase | A: $CO_2$; B: Methanol [0. 2% $NH_3$(7M in methanol)]; A:B = 65:35 |
| Flow rate | 4 mL/min |
| Detection wavelength | UV 214 nm |
| Column temperature | 40° C. |

or, when the structure of the compound is

166

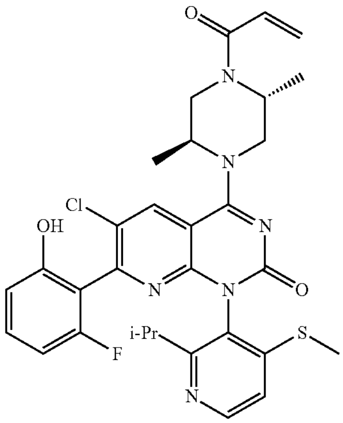

, the compound contains two axial chiral isomers 166-1 and 166-2, and the compounds 166-1 and 166-2 have the following parameters:

the compound 166-1 is the first axially chiral compound to be washed down with an earlier retention time than compound 166-2, preferably the retention time of the compound 166-1 is $t_R$=2.46 min and the retention time of the compound 166-2 is $t_R$=3.08 min, the detection conditions are as follows:

TABLE 6

| | |
|---|---|
| Instrument | SFC Method Station (Thar, Waters) |
| Column type | IC 4. 6*100 mm, 5 μm (Daicel) |
| Column pressure | 120 bar |
| Mobile phase | A: $CO_2$; B: Ethanol [1. 0% $NH_3$(7M in methanol)]; A:B = 55:45 |
| Flow rate | 4 mL/min |
| Detection wavelength | UV 214 nm |
| Column temperature | 40° C. |

In a further preferred embodiment of the present disclosure, when the structure of the compound is

60

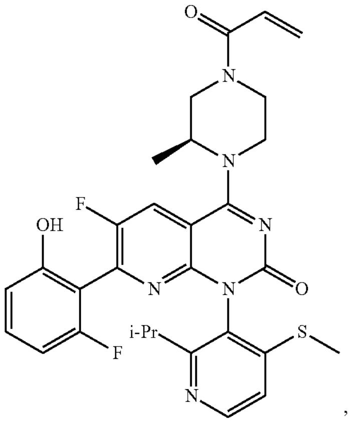

, two axial chiral isomers 60-1 and 60-2 can be obtained by the following SFC chiral preparation resolution conditions, wherein the compound 60-1 is the first axial chiral compound to be washed down with an earlier retention time than compound 60-2, preferably the retention time of the compound 60-1 is $t_R$=1.92 min and the retention time of the compound 60-2 is $t_R$=2.43 min, the SFC chiral preparation conditions were as follows:

TABLE 7

| | |
|---|---|
| Instrument | SFC Method Station (Thar, Waters) |
| Column type | Celluloe-SC 4. 6 x 100 mm, 5 um (YMC) |
| Column pressure | 120 bar |
| Mobile phase | A: $CO_2$; B: Methanol [0. 2% $NH_3$(7M in methanol)]; A:B = 60:40 |
| Flow rate | 4 mL/min |
| Detection wavelength | UV 214 nm |
| Column temperature | 40° C. |

or, when the structure of the compound is

75

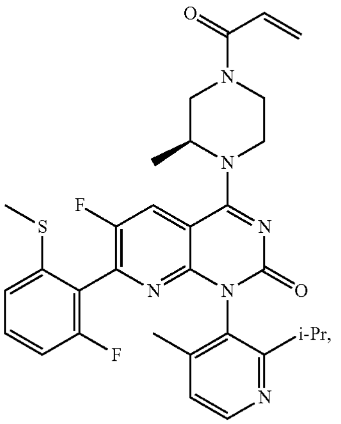

two axial chiral isomers 75-1 and 75-2 can be obtained by the following SFC chiral preparation resolution conditions, wherein the compound 75-1 is the first axial chiral compound to be washed down with an earlier retention time than compound 75-2, preferably the retention time of the compound 75-1 is $t_R$=1.97 min and the retention time of the compound 75-2 is $t_R$=3.75 min, the SFC chiral preparation conditions were as follows:

TABLE 8

| | |
|---|---|
| Instrument | SFC Method Station (Thar, Waters) |
| Column type | Celluloe-SC 4. 6 x 100 mm, 5 um (YMC) |
| Column pressure | 120 bar |
| Mobile phase | A: $CO_2$; B: Methanol [0. 2% $NH_3$(7M in methanol)]; A:B = 60:40 |
| Flow rate | 4 mL/min |
| Detection wavelength | UV 214 nm |
| Column temperature | 40° C. |

or, when the structure of the compound is

114

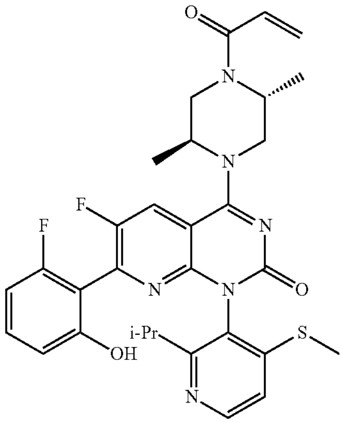

, two axial chiral isomers 114-1 and 114-2 can be obtained by the following SFC chiral preparation resolution conditions, wherein the compound 114-1 is the first axial chiral compound to be washed down with an earlier retention time than compound 114-2, preferably the retention time of the compound 114-1 is $t_R$=1.99 min and the retention time of the compound 114-2 is $t_R$=2.87 min, the SFC chiral preparation conditions were as follows:

TABLE 9

| | |
|---|---|
| Instrument | SFC Method Station (Thar, Waters) |
| Column type | Celluloe-SC 4. 6 x 100 mm, 5 um (YMC) |
| Column pressure | 120 bar |
| Mobile phase | A: $CO_2$; B: Ethanol [1. 0% $NH_3$(7M in methanol)]; A:B = 65:35 |
| Flow rate | 4 mL/min |
| Detection wavelength | UV 214 nm |
| Column temperature | 40° C. |

or, when the structure of the compound is

150

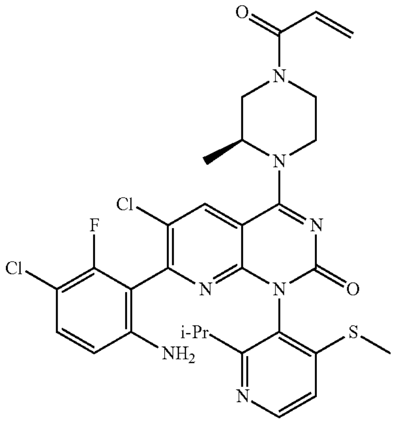

, two axial chiral isomers 150-1 and 150-2 can be obtained by the following SFC chiral preparation resolution conditions, wherein the compound 150-1 is the first axial chiral compound to be washed down with an earlier retention time than compound 150-2, preferably the retention time of the compound 150-1 is $t_R$=1.87 min and the retention time of the compound 150-2 is $t_R$=2.80 min, the SFC chiral preparation conditions were as follows.

TABLE 10

| | |
|---|---|
| Instrument | SFC Method Station (Thar, Waters) |
| Column type | OX-H 4. 6*100 mm, 5 μm (Daicel) |
| Column pressure | 120 bar |
| Mobile phase | A: $CO_2$; B: Methanol [0. 2% $NH_3$(7M in methanol)]; A:B = 65:35 |
| Flow rate | 4 mL/min |
| Detection wavelength | UV 214 nm |
| Column temperature | 40° C. |

or, when the structure of the compound is

165

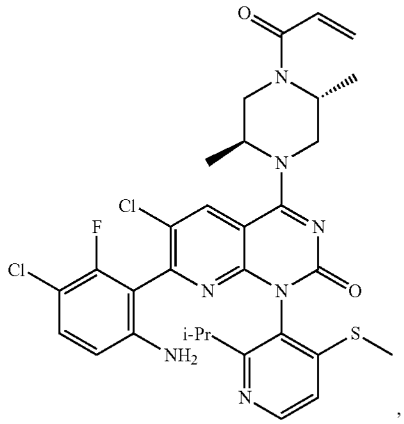

, two axial chiral isomers 165-1 and 165-2 can be obtained by the following SFC chiral preparation resolution conditions, wherein the compound 165-1 is the first axial chiral compound to be washed down with an earlier retention time than compound 165-2, preferably the retention time of the compound 165-1 is $t_R$=1.74 min and the retention time of the compound 165-2 is $t_R$=2.49 min, the SFC chiral preparation conditions were as follows:

TABLE 11

| | |
|---|---|
| Instrument | SFC Method Station (Thar, Waters) |
| Column type | OX-H 4. 6*100 mm, 5 μm (Daicel) |
| Column pressure | 120 bar |
| Mobile phase | A: $CO_2$: B: Methanol [0. 2% $NH_3$(7M in methanol)]; A:B = 65:35 |
| Flow rate | 4 mL/min |
| Detection wavelength | UV 214 nm |
| Column temperature | 40° C. |

or, when the structure of the compound is

166

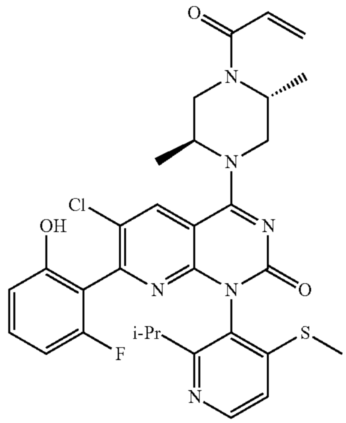

, two axial chiral isomers 166-1 and 166-2 can be obtained by the following SFC chiral preparation resolution conditions, wherein the compound 166-1 is the first axial chiral compound to be washed down with an earlier retention time than compound 166-2, preferably the retention time of the compound 166-1 is $t_R$=2.46 min and the retention time of the compound 166-2 is $t_R$=3.08 min, the SFC chiral preparation conditions were as follows:

TABLE 12

| | |
|---|---|
| Instrument | SFC Method Station (Thar, Waters) |
| Column type | IC 4. 6*100 mm, 5 μm (Daicel) |
| Column pressure | 120 bar |
| Mobile phase | A: $CO_2$; B: Ethanol [1. 0% $NH_3$(7M in methanol)]; A:B = 55:45 |
| Flow rate | 4 mL/min |
| Detection wavelength | UV 214 nm |
| Column temperature | 40° C. |

It can be understood by those ordinarily skilled in the art that the axial chiral isomer of the disclosure can also be resolved by other common resolution methods or different resolution conditions, and different resolution methods or conditions may lead to changes in the retention time of the compound, those ordinarily skilled in the art can obtain the axial chiral isomer of the corresponding compound of the present disclosure through common resolution methods, the corresponding racemate and the axial chiral isomer obtained by resolution under different conditions fall in the contents protected by the present disclosure.

As another embodiment, the axial chiral isomer of the present disclosure has the following inhibitory activities:

(1) Two axial chiral isomers compound 60-1 and 60-2 are obtained by chiral resolution to the compound 60, wherein the $IC_{50}$ value of the NCI-H358 cell proliferation inhibitory activity of the compound 60-1 is ≤100 nM, preferably ≤50 nm, more preferably ≤30 nM, further preferably 28 nM; or, the $IC_{50}$ value of the Mia PaCa-2 cell proliferation inhibitory activity of the compound 60-1 is ≤100 nM, preferably ≤80 nM, more preferably ≤60 nM, further preferably 55 nM;

or, (2) Two axial chiral isomers compound 75-1 and 75-2 are obtained by chiral resolution to the compound 75, wherein the $IC_{50}$ value of the NCI-H358 cell proliferation inhibitory activity of the compound 75-1 is ≤100 nM, preferably ≤50, more preferably ≤30 nM, further preferably 25 nM; or, the $IC_{50}$ value of the Mia PaCa-2 cell proliferation inhibitory activity of the compound 75-1 is ≤100 nM, preferably ≤80 nM, more preferably ≤60 nM, further preferably ≤60 nM, the most preferably 36 nM;

or, (3) Two axial chiral isomers compound 114-1 and 114-2 are obtained by chiral resolution to the compound 114, wherein the $IC_{50}$ value of the NCI-H358 cell proliferation inhibitory activity of the compound 114-1 is ≤100 nM, preferably ≤50, more preferably ≤40 nM, further preferably 35 nM; or, the $IC_{50}$ value of the Mia PaCa-2 cell proliferation inhibitory activity of the compound 114-1 is ≤100 nM, preferably ≤80 nM, more preferably ≤60 nM, further preferably ≤50 nM, still further preferably ≤30 nM, the most preferably 29 nM;

or, (4) Two axial chiral isomers compound 150-1 and 150-2 are obtained by chiral resolution to the compound 150, wherein the $IC_{50}$ value of the NCI-H358 cell proliferation inhibitory activity of the compound 150-1 is ≤100 nM, preferably ≤50 nM, more preferably ≤20 nM, further preferably 10 nM, the most preferably 6.6 nM; or, the $IC_{50}$ value of the Mia PaCa-2 cell proliferation inhibitory activity of the compound 150-1 is ≤100 nM, preferably ≤50 nM, more preferably ≤20 nM, further preferably 10 nM, the most preferably 3.5 nM;

or, (5) Two axial chiral isomers compound 165-1 and 165-2 are obtained by chiral resolution to the compound 165, wherein the $IC_{50}$ value of the NCI-H358 cell proliferation inhibitory activity of the compound 165-1 is ≤100 nM, preferably ≤50 nM, more preferably ≤30 nM, further preferably A10 nM, the most preferably 6.6 nM; or, the $IC_{50}$ value of the Mia PaCa-2 cell proliferation inhibitory activity of the compound 165-1 is ≤80 nM, preferably ≤50 nM, more preferably ≤20 nM, further preferably ≤10 nM, still further preferably ≤5 nM, the most preferably 3.3 nM;

or, (6) Two axial chiral isomers compound 166-1 and 166-2 are obtained by chiral resolution to the compound 166, wherein the $IC_{50}$ value of the NCI-H358 cell proliferation inhibitory activity of the compound 166-1 is 50 nM, preferably ≤30 nM, more preferably ≤20 nM, further preferably 17 nM; or, the $IC_{50}$ value of the Mia PaCa-2 cell proliferation inhibitory activity of the compound 166-1 is ≤50 nM, preferably ≤30 nM, more preferably ≤20 nM, further preferably ≤15 nM, the most preferably 11 nM;

As a preferred embodiment of the present disclosure, the detection method of NCI-H358 cell proliferation inhibitory activity and Mia PaCa-2 cell proliferation inhibitory activity is as follows: through cell culture, adding different concentrations of compound solutions to the cultured cells, continuing the culture for a period of time and measuring the cell proliferation;

further, the method of cell culture is: adjusting the cells to a suitable cell concentration with complete medium and spreading the cell suspension in well plates for culture; preferably, the culture conditions are 37° C., 5% $CO_2$ incubator overnight; preferably, the cell suspension is spread in 96-well plates, 48-well plates, 24-well plates, 12-well plates or 6-well plates, more preferably 96-well plates; preferably, the suitable cell concentration is 1500-4000 cells/well, with 90 μL of cell suspension added to each well;

further, the compound solution is prepared with DMSO and may be further diluted with medium; preferably, the compound solution has a concentration gradient starting from 100 μM at 4-fold dilution, more preferably starting from 30 μM at 4-fold dilution, most preferably starting from 10 μM at 4-fold dilution;

further, the volume of the compound solution or solvent added to each well is 1-10 μL, preferably 10 μL;

further, after adding the compound solution, the conditions for continuing the culture are 37° C., 5% $CO_2$ incubator; preferably, the culture time is 24-72 h, more preferably 72 h;

further, the method for measuring cell proliferation is MTT, CCK8, CellTiter-Glo; preferably the method is CellTiter-Glo;

further, the cell proliferation is read using a microplate reader, more preferably a BioTek Synergy H1 microplate reader.

As another embodiment, the $IC_{50}$ value of the axial chiral isomer 114-1 of the compound of the present disclosure for pERK inhibition in Mia PaCa-2 cells is ≤100 nM, preferably ≤50 nM, more preferably ≤40 nM, and most preferably 38 nM;

or, the $IC_{50}$ value of the axial chiral isomer 150-1 of the compound for pERK inhibition in Mia PaCa-2 cells is ≤50 nM, preferably ≤30 nM, more preferably ≤10 nM, still more preferably ≤5 nM, the most preferably 5 nM;

or, the $IC_{50}$ value of the axial chiral isomer 165-1 of the compound for pERK inhibition in Mia PaCa-2 cells is ≤50 nM, preferably ≤30 nM, more preferably ≤10 nM, further preferably ≤5 nM, the most preferably 4.2 nM;

or, the $IC_{50}$ value of the axial chiral isomer 166-1 of the compound for pERK inhibition in Mia PaCa-2 cells is ≤50 nM, preferably ≤30 nM, more preferably ≤20 nM, the most preferably 20 nM.

As a preferred embodiment of the present disclosure, the method for detecting the inhibitory activity of phosphorylated ERK level is as follows: through cell culture, adding different concentrations of compound solutions to the cultured cells, continuing the culture for a period of time, lysing the cells, followed by centrifugation and determining the affinity of the compound for the enzyme;

further, the method of cell culture is: adjusting the cells to a suitable cell concentration with a complete medium, preferably the cell concentration is $1\times10^6$/mL, and spreading the cell suspension on a well plate for culture. Preferably, the culture conditions are 37° C., 5% $CO_2$ incubator overnight; preferably, the cell suspension is spread in 96-well plates, 48-well plates, 24-well plates, 12-well plates or 6-well plates, more preferably 96-well plates; preferably, the suitable cell concentration is 50000 cells/well;

further, the compound solution is prepared with DMSO and may be further diluted with medium; preferably, the compound solution has a concentration gradient starting from 100 μM at 4-fold dilution, more preferably starting from 30 μM at 4-fold dilution, most preferably starting from 10 μM at 4-fold dilution;

further, the volume of the compound solution or solvent added to each hole is 1-50 μL, preferably 20-25 μL, further preferably 25 μL;

further, after adding the compound solution, the conditions for continuing the culture are 37° C., 5% $CO_2$ incubator; preferably, the culture time is 1-6 h, more preferably 2 h;

further, the cell lysis is performed by adding lysis solution, or preferably lysis solution is added at 50-100 μL, more preferably 50 μL; or preferably the lysis is performed under shaking conditions at room temperature, more preferably the lysis time is 30 minutes;

further, the centrifugal conditions are: centrifuge at 1000 rpm for 1 minute;

further, the method for determining the affinity between the compound and the enzyme is: transferring the supernatant to a well plate, adding the detection mixture, and measuring with a microplate reader after the reaction; preferably, the volume of the supernatant is 10-30 μL, preferably 15 μL; preferably, the detection mixture is Eu-labeled anti-ERK1/2 (T202-Y204) Antibody and ULight labeled anti-ERK1/2 Antibody; more preferably, the detection mixture is Eu-labeled anti-ERK1/2 (T202-Y204) Antibody with a final concentration of 0.5 nM and ULight labeled anti-ERK1/2 Antibody with a final detection concentration of 5 nM; further preferably, the volume of the detection mixture is 5-10 μL, more preferably 5 μL;

further, after lysis and centrifugation, the reaction between the supernatant and the detection mixed solution is performed for a period of time, preferably overnight at room temperature;

further, the cell proliferation is read using a microplate reader, more preferably a BioTek Synergy H1 microplate reader.

It is understood by those of ordinary skill in the art that the axial chiral isomers of the present disclosure can also be measured for inhibitory activity by other common activity assay methods, and that different detection methods or adjustment of detection conditions can lead to fluctuations or large changes in the inhibitory activity of the compounds, and that the axial chiral isomers measured by different activity detection methods are all protected by the present invention.

The present disclosure also relates to a method for preparing the compound represented by general formula (IX-A), the stereoisomer thereof or the pharmaceutically acceptable salt thereof, comprising the following steps,

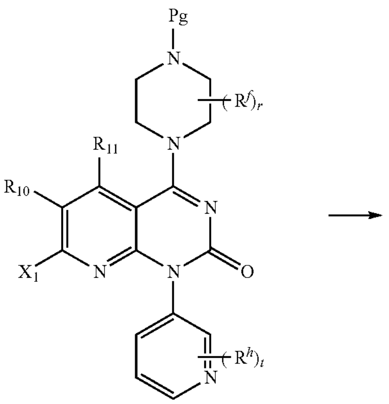

(XI-A5)

-continued

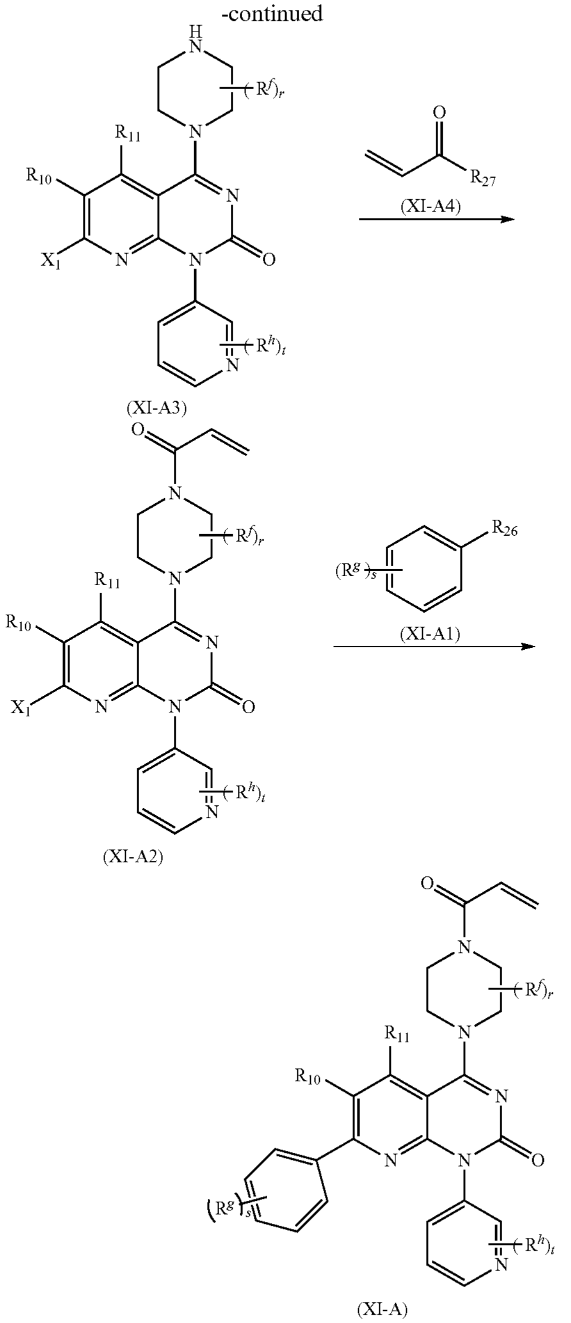

a compound represented by general formula (IX-A5) is deprotected to obtain a compound represented by general formula (IX-A3) or a stereoisomer thereof and a pharmaceutically acceptable salt thereof;

a condensation reaction is carried out between the compound represented by general formula (IX-A3) and a compound represented by general formula (IX-A4) to obtain a compound represented by general formula (IX-A2) or a stereoisomer thereof and a pharmaceutically acceptable salt thereof;

a coupling reaction is carried out between the compound represented by general formula (IX-A2) and a compound represented by general formula (IX-A1) to obtain the compound represented by general formula (IX-A) or the stereoisomer thereof and the pharmaceutically acceptable salt thereof;

wherein:

Pg is an amino protecting group, preferably allyloxycarbonyl, trifluoroacetyl, tert-butylsulfinyl 2, 4-dimethoxybenzyl, nitrophenylsulfonyl, triphenylmethyl, fluorenylmethyloxycarbonyl, 9-fluorenylmethyloxycarbonyl, benzyl, p-toluenesulfonyl, p-methoxybenzyl, formate, acetyl, benzyloxycarbonyl, phthaloyl, tert-butoxycarbonyl, benzyl or p-methoxyphenyl; more preferably tert-butoxycarbonyl;

$X_1$ is selected from halogen; preferably fluorine, chlorine, bromine or iodine; more preferably chlorine;

$R_{26}$ is selected from halogen, boric acid or boric acid ester; preferably fluorine, chlorine, bromine, iodine, $—B(OH)_2$ or

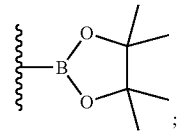 [SMILES: *B1OC(C)(C)C(C)(C)O1]

;

when $X_1$ is halogen, $R_{26}$ is selected from boric acid or boric acid ester;

when $X_1$ is selected from boric acid or boric acid ester, $R_{26}$ is halogen;

$R_{27}$ is selected from halogen, hydroxyl, or alkylcarbonyloxy; preferably chlorine or hydroxyl.

The present disclosure also relates to a method for preparing the compound represented by general formula (IX-A), the stereoisomer thereof or the pharmaceutically acceptable salt thereof, comprising the following steps,

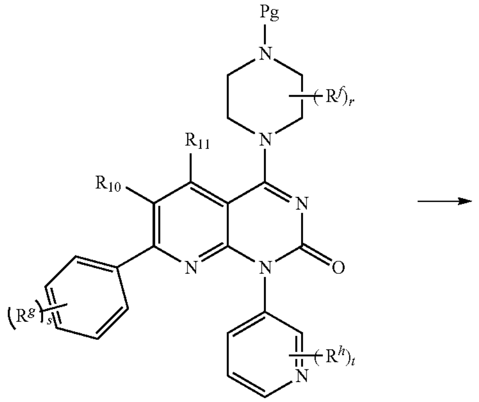

(XI-A7)

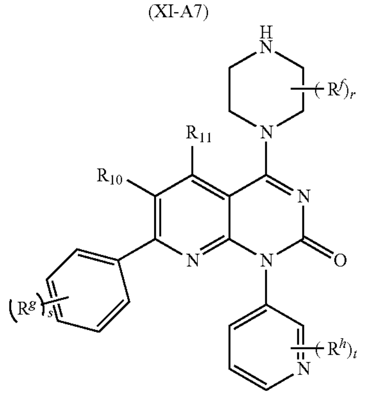

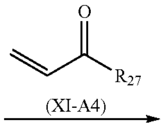

(XI-A6)

-continued

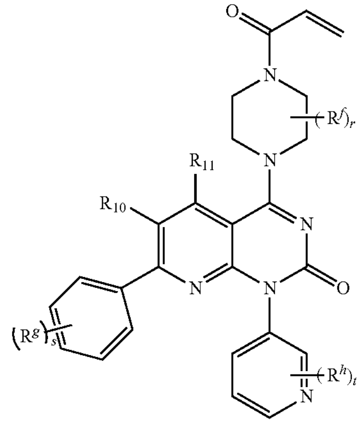

(XI-A)

a compound represented by general formula (IX-A7) is deprotected to obtain a compound represented by general formula (IX-A6) or a stereoisomer thereof and a pharmaceutically acceptable salt thereof;

a condensation reaction is carried out between the compound represented by general formula (IX-A6) and the compound represented by general formula (IX-A4) to obtain the compound represented by the general formula (IX-A) or the stereoisomer thereof and the pharmaceutically acceptable salt thereof.

The present disclosure also relates to a method for preparing the compound represented by general formula (IX-B), the stereoisomer thereof or the pharmaceutically acceptable salt thereof, comprising the following steps,

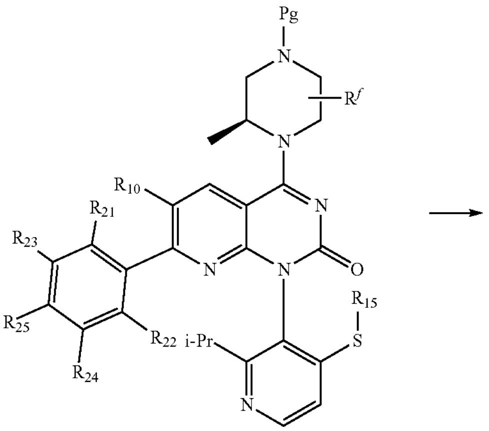

(XI-B4)

-continued

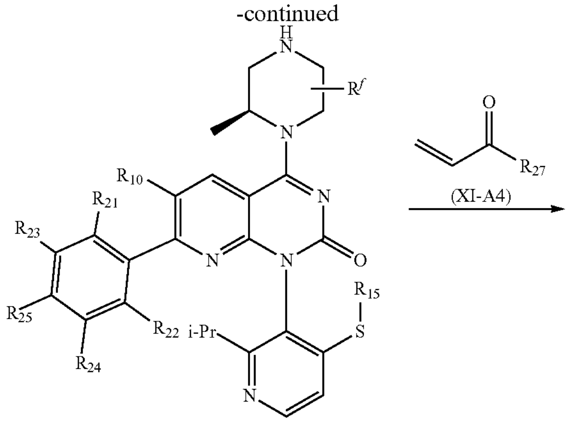

(XI-B3)

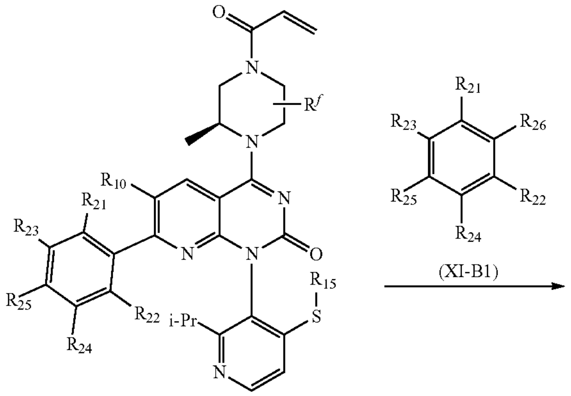

(XI-B2)

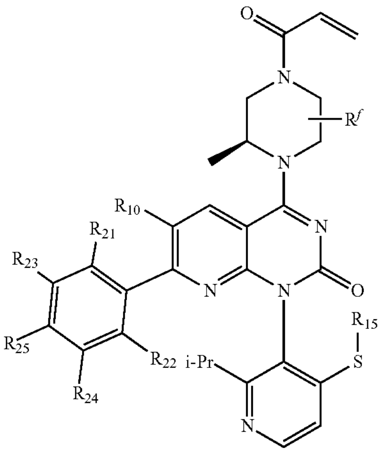

(XI-B)

a compound represented by general formula (IX-B4) is deprotected to obtain a compound represented by general formula (IX-B3) or a stereoisomer thereof and a pharmaceutically acceptable salt thereof;

a condensation reaction is carried out between the compound represented by general formula (IX-B3) and the compound represented by general formula (IX-A4) to obtain a compound represented by the 5' general formula (IX-B2) or a stereoisomer thereof and a pharmaceutically acceptable salt thereof;

a coupling reaction is carried out between the compound represented by general formula (IX-B2) and a compound represented by general formula (IX-B1) to obtain the compound represented by general formula (IX-B) or the stereoisomer thereof and the pharmaceutically acceptable salt thereof.

The present disclosure also relates to a method for preparing the compound represented by general formula (IX-B), the stereoisomer thereof or the pharmaceutically acceptable salt thereof, comprising the following steps,

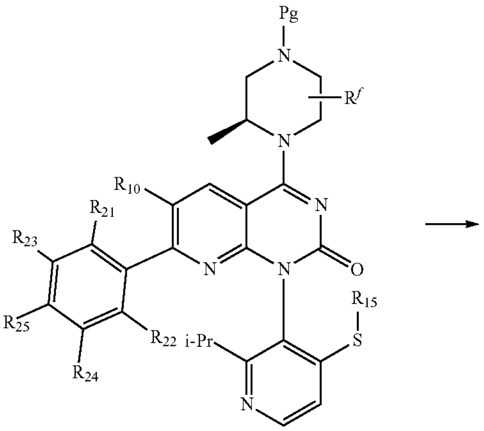

(XI-B6)

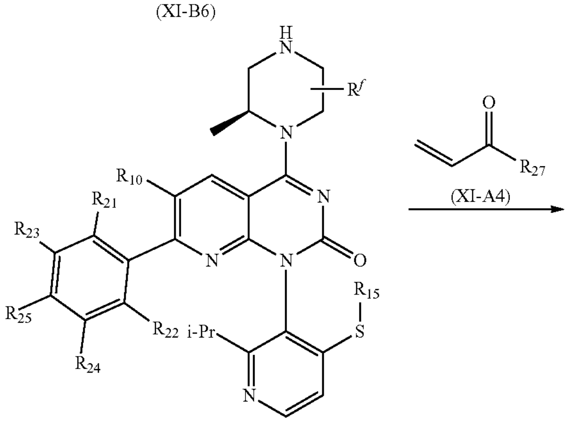

(XI-B5)

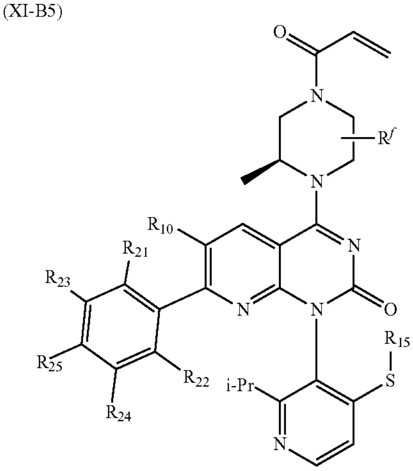

(XI-B)

a compound represented by general formula (IX-B6) is deprotected to obtain a compound represented by general formula (IX-B5) or a stereoisomer thereof and a pharmaceutically acceptable salt thereof;

a condensation reaction is carried out between the compound represented by general formula (IX-B5) and the compound represented by general formula (IX-A4) to obtain the compound represented by the general formula (IX-B) or the stereoisomer thereof and the pharmaceutically acceptable salt thereof.

The present invention also provides preferred embodiment, and relates to a pharmaceutical composition comprising a therapeutically effective amount of the compound represented by general formula (I) and the stereoisomer thereof or the pharmaceutically acceptable salt thereof, and one or more pharmaceutically acceptable carriers, diluents or excipients.

The present disclosure further relates to a use of any one of the compounds of general formula (I), the stereoisomer thereof or the pharmaceutically acceptable salt thereof, or the pharmaceutical composition in the preparation of a medicament of KRAS inhibitor; preferably the use in KRAS G12C mutant medicament.

The present disclosure also provides a preferred embodiment, and relates to a method of the compound of the general formula (I), the stereoisomer thereof or the pharmaceutically acceptable salt thereof, or the pharmaceutical composition in the treatment, prevention and/or treating pre-prepared treatment of a condition mediated by a KRAS inhibitor, the method comprising administering a therapeutically effective dose of the compound represented by general formula (I), the stereoisomer thereof or the pharmaceutically acceptable salt thereof, or the pharmaceutical composition to a patient.

In some embodiments, the compound and the composition of the present disclosure can be used in the treatment of Noonan syndrome, leopard syndrome, leukemia, neuroblastoma, melanoma, breast cancer, esophageal cancer, head and neck tumor, gastric cancer, lung cancer and colon cancer and other diseases or conditions.

The compound and the composition of the present disclosure can be used in the method for the treatment of Noonan syndrome, leopard syndrome, leukemia, neuroblastoma, melanoma, breast cancer, esophageal cancer, head and neck tumor, lung cancer and colon cancer and other diseases or conditions.

In some embodiments, the present disclosure provides a method for treating a cancer condition, comprising administering the compound or the composition of the present disclosure to a patient suffering from a cancer condition.

In some embodiments, the cancer treated by the compound and the composition of the present disclosure is Noonan syndrome, leopard syndrome, leukemia, neuroblastoma, melanoma, breast cancer, esophageal cancer, head and neck tumor, gastric cancer, lung cancer and colon cancer; preferably non-small cell lung cancer, colon cancer, esophagus cancer, head and neck tumor.

DETAILED DESCRIPTION OF THE INVENTION

Unless otherwise stated, the terms used in the description and claims have the following meanings.

The term "alkyl" refers to a saturated aliphatic hydrocarbon group, which is a straight or branched chain group containing 1 to 20 carbon atoms, preferably alkyl containing 1 to 8 carbon atoms, more preferably alkyl containing 1 to 6 carbon atoms, the most preferably alkyl containing 1 to 3 carbon atoms. Non-limiting examples include methyl, ethyl, n-propyl, isopropyl, n-butyl, isobutyl, tert-butyl, sec-butyl, n-pentyl, 1, 1-dimethylpropyl, 1, 2-dimethylpropyl, 2, 2-dimethylpropyl, 1-ethylpropyl, 2-methylbutyl, 3-methylbutyl, n-hexyl, 1-ethyl-2-methylpropyl, 1, 1, 2-trimethylpropyl, 1, 1-dimethylbutyl, 1, 2-dimethylbutyl, 2, 2-dimethylbutyl, 1, 3-dimethylbutyl, 2-ethylbutyl, 2-methylpentyl, 3-methylpentyl, 4-methylpentyl, 2, 3-dimethylbutyl, n-heptyl, 2-methylhexyl, 3-methylhexyl, 4-methylhexyl, 5-methylhexyl, 2, 3-dimethylpentyl, 2, 4-dimethylpentyl, 2, 2-dimethylpentyl, 3, 3-dimethylpentyl, 2-ethylpentyl, 3-ethylpentyl, n-octyl, 2, 3-dimethylhexyl, 2, 4-dimethylhexyl, 2, 5-dimethylhexyl, 2, 2-dimethylhexyl, 3, 3-dimethylhexyl, 4, 4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2, 2-diethylpentyl, n-decyl, 3, 3-diethylhexyl, 2, 2-diethylhexyl, and various branched isomers. More preferrably lower alkyl containing 1 to 6 carbon atoms, non-limiting examples include methyl, ethyl, n-propyl, isopropyl, n-butyl, isobutyl, tert-butyl, sec-butyl, n-pentyl, 1, 1-dimethylpropyl, 1, 2-dimethylpropyl, 2, 2-dimethylpropyl, 1-ethylpropyl, 2-methylbutyl, 3-methylbutyl, n-hexyl, 1-ethyl-2-methylpropyl, 1, 1, 2-trimethylpropyl, 1, 1-dimethylbutyl, 1, 2-dimethylbutyl, 2, 2-dimethylbutyl, 1, 3-dimethylbutyl, 2-ethylbutyl, 2-methylpentyl, 3-methylpentyl, 4-methylpentyl, 2, 3-dimethylbutyl, etc. The alkyl may be substituted or unsubstituted, when substituted, the substituents may be substituted at any available attachment point, the substituents are preferably one or more of the following groups, which are independently selected from alkyl, alkenyl, alkynyl, alkoxyl, alkylthio, alkylamino, halogen, sulfhydryl, hydroxyl, nitro, cyano, cycloalkyl, heterocycloalkyl, aryl, heteroaryl, cycloalkoxy, heterocycloalkoxy, cycloalkylthio, heterocycloalkylthio, oxo, carboxyl, or carboxylate, preferably alkyl substituted by methyl, ethyl, isopropyl, tert-butyl, haloalkyl, deuterated alkyl, alkoxy-substituted alkyl and hydroxyl-substituted alkyl.

The term "alkylene" refers to that one hydrogen atom of an alkyl is further substituted, for example: "methylene" refers to $—CH_2—$, "ethylene" refers to $—(CH_2)_2—$, and "propylene" refers to $—(CH_2)_3—$, "butylene" refers to $—(CH_2)_4—$, etc. The term "alkenyl" refers to an alkyl as defined above containing at least two carbon atoms and at least one carbon-carbon double bond, such as vinyl, 1-propenyl, 2-propenyl, 1-, 2-, or 3-butenyl etc. The alkenyl may be substituted or unsubstituted, when substituted, the substituents are preferably one or more of the following groups, which are independently selected from alkyl, alkenyl, alkynyl, alkoxy, alkylthio, alkylamino, halogen, sulfhydryl, hydroxyl, nitro, cyano, cycloalkyl, heterocycloalkyl, aryl, heteroaryl, cycloalkoxy, heterocycloalkoxy, cycloalkylthio, heterocycloalkylthio.

The term "cycloalkyl" refers to a saturated or partially unsaturated monocyclic or polycyclic cyclic hydrocarbon substituent, the cycloalkyl ring contains 3 to 20 carbon atoms, preferably 3 to 12 carbon atoms, more preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctanyl, etc., polycylic cycloalkyl includes spiro, fused and bridged cycloalkyl, preferably cyclopropyl, cyclobutyl, cyclohexyl, cyclopentyl and cycloheptyl.

The term "spirocycloalkyl" refers to polycyclyl that shares one carbon atom (called a spiro atom) between 5- to 20-membered monocyclic rings, which may contain one or more double bonds, but none of the rings has a complete conjugate π electron system. Preferably 6-14 membered, more preferably 7-10 membered. According to the number of shared spiro atoms between the rings, the spirocycloalkyl is classified into monospirocycloalkyl, bispirocycloalkyl or polyspirocycloalkyl, preferably monospirocycloalkyl and bispirocycloalkyl. More preferably, 3-membered/6-membered, 3-membered/5-membered, 4-membered/4-membered, 4-membered/5-membered, 4-membered/6-membered, 5-membered/5-membered, or 5-membered/6-membered monospirocycloalkyl. Non-limiting examples of spirocycloalkyl include:

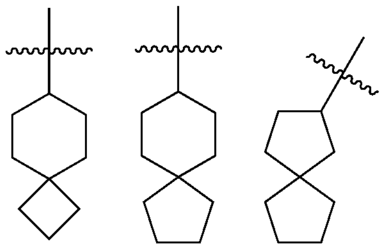

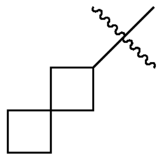

and

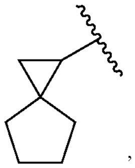

, etc.;

also include spirocycloalkyl in which monospirocycloalkyl and heterocycloalkyl share a spiro atom, non-limiting examples include:

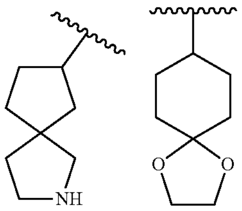

and

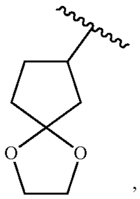

, etc.

The term "fused cycloalkyl" refers to a 5-20 membered all-carbon polycyclic group in which each ring in the system shares an adjacent pair of carbon atoms with other rings in the system, wherein one or more of the rings may comprise one or multiple double bonds, but none of the rings has a fully conjugated i-electron system. Preferably 6-14 membered, more preferably 7-10 membered. According to the number of constituent rings, it can be classified into bicyclic, tricyclic, tetracyclic or polycyclic fused cycloalkyl, preferably bicyclic or tricyclic, and more preferably 5-membered/5-membered or 5-membered/6-membered bicyclic alkyl. Non-limiting examples of fused cycloalkyls include:

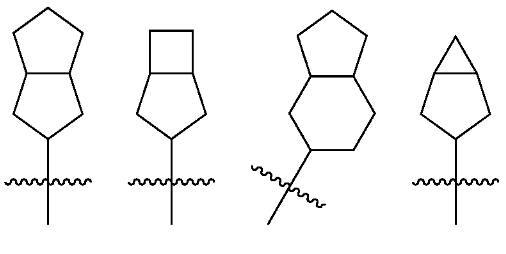

-continued

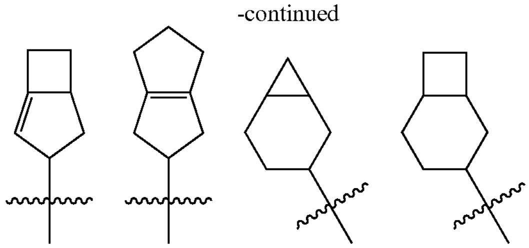

and

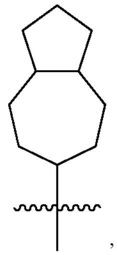

, etc.

The term "bridged cycloalkyl" refers to 5-20 membered all-carbon polycyclic group, in which any two rings share two carbon atoms that are not directly connected, it may contain one or more double bonds, but none of the rings has a complete conjugated π electron system. Preferably 6-14 membered, more preferably 7-10 membered. According to the number of constituent rings, it can be classified into bicyclic, tricyclic, tetracyclic or polycyclic bridged cycloalkyl, preferably bicyclic, tricyclic, or tetracyclic, and more preferably bicyclic or tricyclic. Non-limiting examples of bridge ring alkyl include:

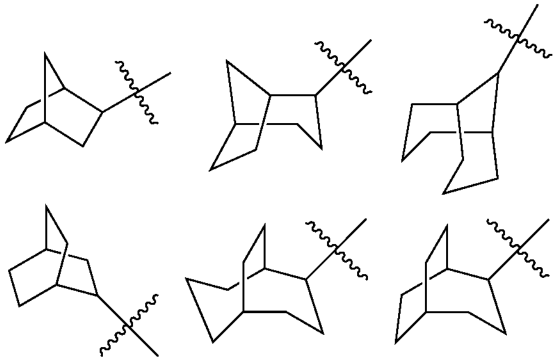

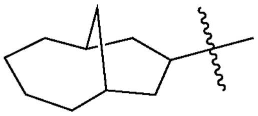

and

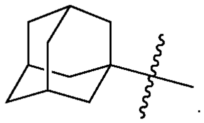

.

The cycloalkyl ring may be fused to an aryl, heteroaryl or heterocycloalkyl ring, wherein the ring connected to the parent structure is cycloalkyl, non-limiting examples include indanyl, tetrahydronaphthyl, benzocycloheptanyl, etc. The cycloalkyl may be substituted or unsubstituted, when substituted, the substituents are preferably one or more of the following groups, which are independently selected from alkyl, alkenyl, alkynyl, alkoxy, alkylthio, alkylamino, halogen, sulfhydryl, hydroxyl, nitro, cyano, cycloalkyl, heterocycloalkyl, aryl, heteroaryl, cycloalkoxy, heterocycloalkoxy, cycloalkylthio, heterocycloalkylthio, oxo, carboxyl or carboylate.

The term "heterocyclyl" refers to saturated or partially unsaturated monocyclic or polycyclic hydrocarbon substituent containing 3 to 20 ring atoms, wherein one or more of the ring atoms are heteroatoms selected from nitrogen, oxygen or $S(O)_m$ (wherein m is an integer of 0 to 2), but not including the ring part of —O—O—, —O—S— or —S—S—, and the remaining ring atoms are carbon. It preferably contains 3 to 12 ring atoms, wherein 1 to 4 ring atoms are heteroatoms; more preferably contains 3 to 8 ring atoms; most preferably contains 3 to 8 ring atoms; further preferably 3-8-membered heterocyclyl containing 1 to 3 of nitrogen atoms optionally substituted by 1-2 of oxygen atoms, sulfur atoms or oxo, including nitrogen-containing monocyclic heterocyclyl, nitrogen-containing spiro heterocyclyl or nitrogen-containing fused heterocyclyl.

Non-limiting examples of monocyclic heterocyclyl include pyrrolidinyl, imidazolidinyl, tetrahydrofuranyl, tetrahydrothienyl, dihydroimidazolyl, dihydrofuranyl, dihydropyrazolyl, dihydropyrrolyl, piperidinyl, piperazinyl, morpholinyl, thiomorpholinyl, homopiperazinyl, azepyl, 1, 4-diazepanyl, pyranyl, etc., preferably pyrrolidinyl, morpholinyl, piperidinyl, azepanyl, 1, 4-diazepanyl and piperazinyl. Polycyclic heterocyclyl include spiro, fused and bridged heterocyclyl; the spiro, fused and bridged heterocyclyl are optionally connected to other groups through a single bond, or to connected to other cycloalkyl, heterocyclyl, aryl and heteroaryl through any two or more of ring atoms.

The term "spiroheterocyclyl" refers to polycyclic heterocyclyl sharing one atom (called a spiro atom) between 5-20 membered monocyclic ring, wherein one or more ring atoms are selected from nitrogen, oxygen or $S(O)_m$ (wherein m is an integer of 0 to 2) heteroatoms, and the remaining ring atoms are carbon. It may contain one or more double bonds, but none of the rings has complete conjugate 71 electron system. Preferably 6-14 membered, more preferably 7-10 membered. According to the number of spiro atoms shared between the rings, the spiro heterocyclyl is classified into monospiroheterocyclyl, dispiro heterocyclyl or polyspiroheterocyclyl, preferably monospiroheterocyclyl and dispiroheterocyclyl. More preferably, 3-membered/5-membered, 3-membered/6-membered, 4-membered/4-membered, 4-membered/5-membered, 4-membered/6-membered, 5-membered/5-membered, or 5-membered/6-membered monospiroheterocyclyl. Non-limiting examples of spiroheterocyclyl include:

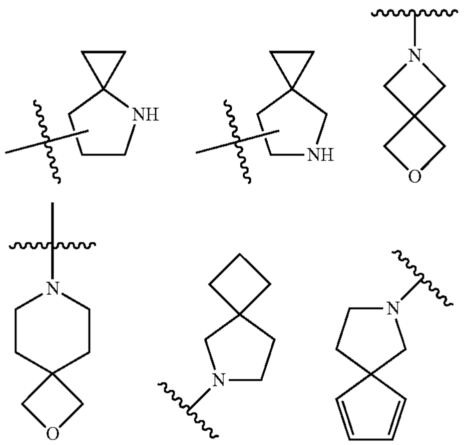

-continued

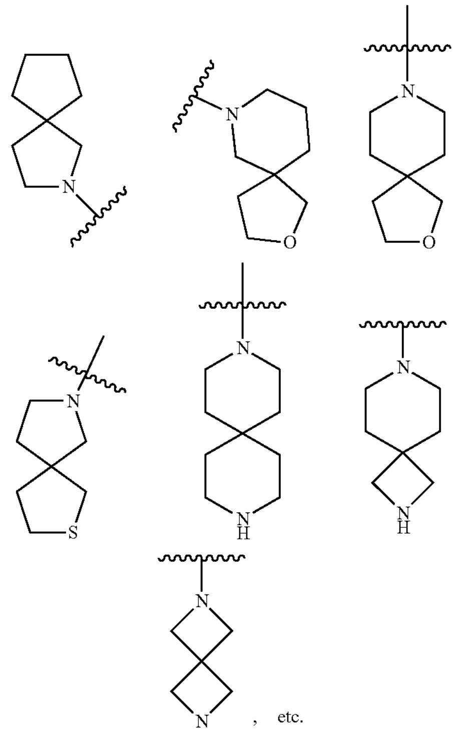

, etc.

The term "fused heterocyclyl" refers to a 5-20 membered polycyclic heterocylic group in which each ring in the system shares an adjacent pair of atoms with other rings in the system, one or more of the rings may comprise one or multiple double bonds, but none of the rings has a fully conjugated π-electron system, wherein one or more of the ring atoms are heteroatoms selected from nitrogen, oxygen or $S(O)_m$ (wherein m is an integer of 0 to 2), the rest of the ring atoms are carbon. Preferably 6-14 membered, more preferably 7-10 membered. According to the number of constituent rings, it can be classified into bicyclic, tricyclic, tetracyclic or polycyclic fused heterocyclyl, preferably bicyclic or tricyclic, and more preferably 5-membered/5-membered or 5-membered/6-membered bicyclic fused heterocylyl. Non-limiting examples of fused heterocylyl include:

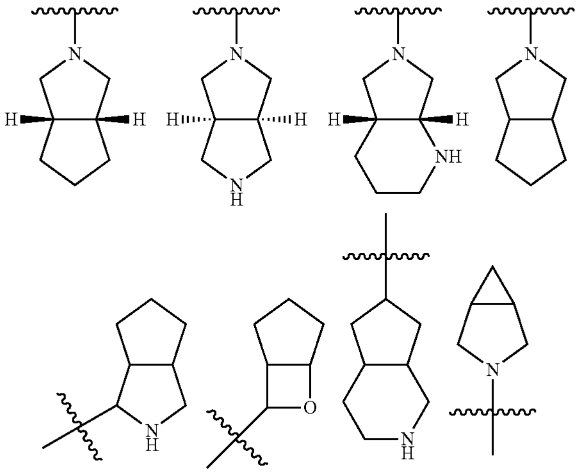

-continued

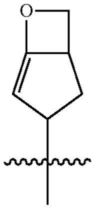 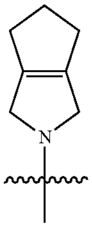 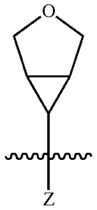 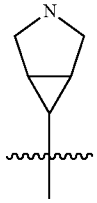 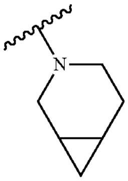

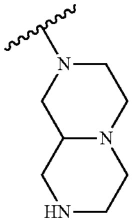 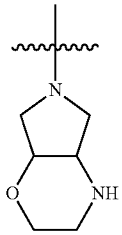 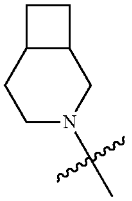 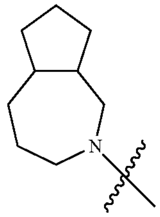

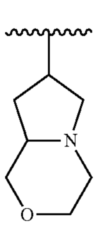 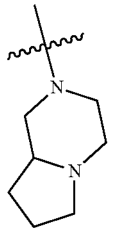 and 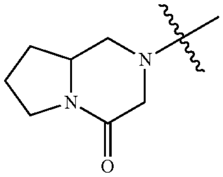 etc.

The term "bridged heterocyclyl" refers to polycyclic heterocylic group in which any two rings share two atoms that are not directly connected, it may contain one or multiple double bonds, but none of the rings has a fully conjugated π-electron system, wherein one or more of the ring atoms are heteroatoms selected from nitrogen, oxygen or $S(O)_m$ (wherein m is an integer of 0 to 2), the rest of the ring atoms are carbon. Preferably 6-14 membered, more preferably 7-10 membered. According to the number of constituent rings, it can be classified into bicyclic, tricyclic, tetracyclic or polycyclic bridged heterocyclyl, preferably bicyclic, tricyclic, or tetracyclic, and more preferably bicyclic or tricyclic. Non-limiting examples of bridged heterocylyl include:

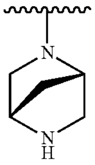 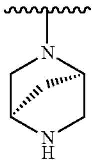 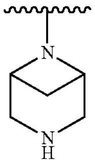

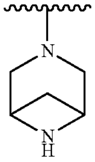 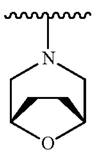 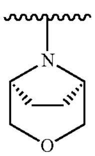

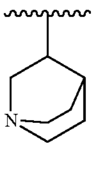 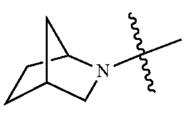 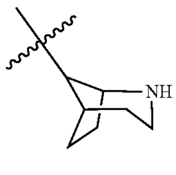

-continued

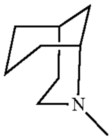 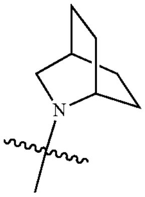 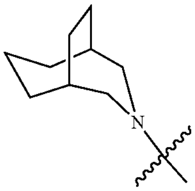

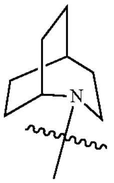 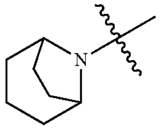 and

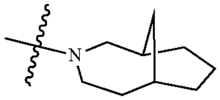 etc.

The heterocyclic ring may be fused to an aryl, heteroaryl or cycloalkyl ring, wherein the ring connected to the parent structure is heterocyclyl, non-limiting examples include:

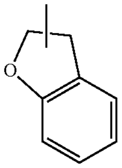 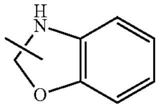 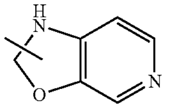 and

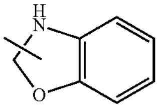 etc.

The heterocyclyl may be substituted or unsubstituted, when substituted, the substituents are preferably one or more of the following groups, which are independently selected from alkyl, alkenyl, alkynyl, alkoxy, alkylthio, alkylamino, halogen, sulfhydryl, hydroxyl, nitro, cyano, cycloalkyl, heterocycloalkyl, aryl, heteroaryl, cycloalkoxy, heterocycloalkoxy, cycloalkylthio, heterocycloalkylthio, oxo, carboxyl or carboylate.

The term "aryl" refers to a 6-14 membered all-carbon monocyclic or fused polycyclic (that is, rings sharing adjacent pairs of carbon atoms) with conjugated i-electron system, preferably 6-12 membered, such as phenyl and naphthyl. More preferably phenyl. The aryl ring may be fused on a heteroaryl, heterocyclyl or cycloalkyl ring, including benzo 5-10 membered heteroaryl, benzo 3-8 membered cycloalkyl and benzo 3-8 membered heteroalkyl, preferably benzo 5-6 membered heteroaryl, benzo 3-6 membered cycloalkyl and benzo 3-6 membered heteroalkyl, wherein the heterocyclyl is a heterocyclyl containing 1-3 of heteroatoms selected from nitrogen atoms, oxygen atoms and sulfur atoms; or 3-membered nitrogen-containing fused ring containing benzene ring.

Wherein the ring connected to the parent structure is aryl ring, non-limiting examples include:

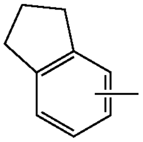
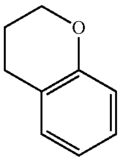
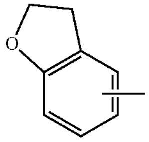
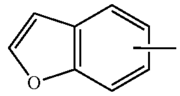
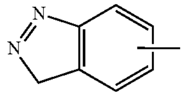
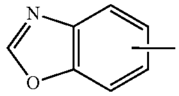
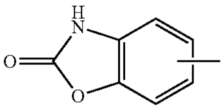
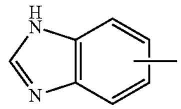
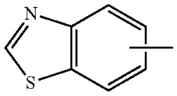
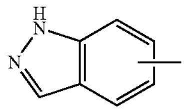
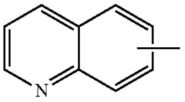
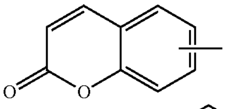
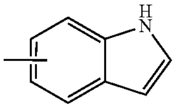

and

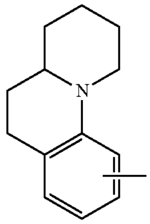

etc.

The aryl may be substituted or unsubstituted, when substituted, the substituents are preferably one or more of the following groups, which are independently selected from alkyl, alkenyl, alkynyl, alkoxy, alkylthio, alkylamino, halogen, sulfhydryl, hydroxyl, nitro, cyano, cycloalky, heterocycloalky, aryl, heteroaryl, cycloalkoxyl, heterocycloalkoxyl, cycloalkylthio, heterocycloalkylthio, carboxyl or carboylate.

The term "heteroaryl" refers to heteroaromatic system containing 1 to 4 heteroatoms and 5 to 14 ring atoms, wherein the heteroatoms are selected from oxygen, sulfur, and nitrogen. The heteroaryl is preferably 5-12 membered, more preferably 5 or 6 membered, such as imidazole, furanyl, thiophenyl, thiazolyl, pyrazolyl, oxazolyl, pyrrolyl, triazolyl, tetrazolyl, pyridyl, pyrimidinyl, thiadiazole, pyrazinyl, etc., preferably triazolyl, thiophenyl, imidazolyl, pyrazolyl, oxazolyl, pyrimidinyl or thiazole; more preferably pyrazolyl, pyrrolyl and oxazolyl. The heteroaryl ring may be fused to an aryl, heteroaryl or cycloalkyl ring, wherein the ring connected to the parent structure is an aryl ring, non-limiting examples include:

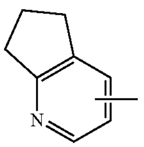
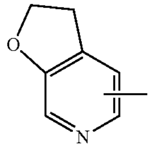
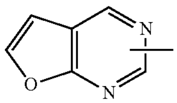
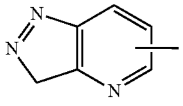
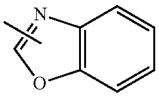

-continued

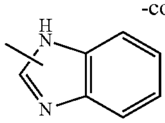
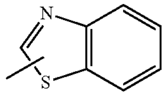
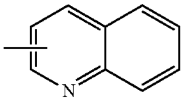
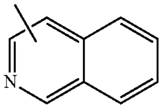
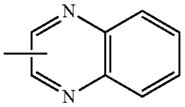
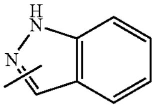

and

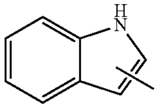

etc.

The heteroaryl may be optionally substituted or unsubstituted, when substituted, the substituents are preferably one or more of the following groups, which are independently selected from alkyl, alkenyl, alkynyl, alkoxy, alkylthio, alkylamino, halogen, sulfhydryl, hydroxyl, nitro, cyano, cycloalky, heterocycloalky, aryl, heteroaryl, cycloalkoxyl, heterocycloalkoxyl, cycloalkylthio, heterocycloalkylthio, carboxyl or carboylate.

The term "alkoxy" refers to —O— (alkyl) and —O— (unsubstituted cycloalkyl), wherein the definition of alkyl is as described above. Non-limiting examples of alkoxy include: methoxy, ethoxy, propoxy, butoxy, cyclopropoxy, cyclobutoxy, cyclopentyloxy, cyclohexyloxy. The alkoxy may be optionally substituted or unsubstituted, when substituted, the substituents are preferably one or more of the following groups, which are independently selected from alkyl, alkenyl, alkynyl, alkoxy, alkylthio, alkylamino, halogen, sulfhydryl, hydroxyl, nitro, cyano, cycloalkyl, heterocycloalkyl, aryl, heteroaryl, cycloalkoxy, heterocycloalkoxy, cycloalkylthio, heterocycloalkylthio, carboxyl or carboylate.

The term "alkylthio" refers to —S— (alkyl) and —S— (unsubstituted cycloalkyl), wherein the definition of alkyl is as described above. Non-limiting examples of alkoxy groups include: methylthio, ethylthio, propylthio, butylthio, cyclopropylthio, cyclobutylthio, cyclopentylthio, cyclohexylthio. The alkylthio may be optionally substituted or unsubstituted, when substituted, the substituents are preferably one or more of the following groups, which are independently selected from alkyl, alkenyl, alkynyl, alkoxy, alkylthio, alkylamino, halogen, sulfhydryl, hydroxyl, nitro, cyano, cycloalkyl, heterocycloalkyl, aryl, heteroaryl, cycloalkoxy, heterocycloalkoxy, cycloalkylthio, heterocycloalkylthio, carboxyl or carboylate.

"Alkylthio-alkyl" refers to an alkylthio attached to an alkyl, wherein the alkyl and the alkylthio are as defined above.

"Alkylaminocarbonyl" refers to (alkyl)-N—C(O)—, wherein the alkyl is as defined above.

"Haloalkyl" refers to alkyl substituted by one or more halogens, wherein the alkyl is as defined above.

"Haloalkoxy" refers to alkoxy substituted by one or more halogens, wherein the alkoxy is as defined above.

"Haloalkylthio" refers to alkylthio substituted by one or more halogens, wherein the alkylthio is as defined above.

"Hydroxyalky" refers to alkyl substituted by one or more hydroxyl, wherein the alkyl is as defined above.

"Alkenyl" refers to chain alkenyl, also known as olefinic group, wherein the alkenyl may be further substituted with other related groups, such as: alkyl, alkenyl, alkynyl, alkoxy, alkylthio, alkylamino, halogen, sulfhydryl, hydroxyl, nitro, cyano, cycloalky, heterocycloalkyl, aryl, heteroaryl, cycloalkoxy, heterocycloalkoxy, cycloalkylthio, heterocycloalkylthio, carboxyl or carboxylate.

"Alknyl" refers to (CH≡C—), wherein the alknyl may be further substituted by other related groups, for example: alkyl, alkenyl, alkynyl, alkoxy, alkylthio, alkylamino, halogen, sulfhydryl, hydroxyl, nitro, cyano, cycloalkyl, heterocycloalkyl, aryl, heteroaryl, cycloalkoxy, heterocycloalkoxy, cycloalkylthio, heterocycloalkylthio, carboxyl or carboylate.

The term "alkenylcarbonyl" refers to —C(O)-(alkenyl), wherein the alkenyl is as defined above. Non-limiting examples of alkenylcarbonyl include: vinylcarbonyl, propenylcarbonyl, butenylcarbonyl. The alkenylcarbonyl may be optionally substituted or unsubstituted, when substituted, the substituents are preferably one or more of the following groups, which are independently selected from alkyl, alkenyl, alkynyl, alkoxy, alkylthio, alkylamino, halogen, sulfhydryl, hydroxyl, nitro, cyano, cycloalkyl, heterocycloalkyl, aryl, heteroaryl, cycloalkoxy, heterocycloalkoxy, cycloalkylthio, heterocycloalkylthio, carboxyl or carboylate.

"Hydroxyl" refers to the —OH group.

"Halogen" refers to fluorine, chlorine, bromine or iodine.

"Amino" refers to $—NH_2$.

"Cyano" refers to —CN.

"Nitro" refers to $—NO_2$.

"Carbonyl" refers to —C(O)—.

"Carboxyl" refers to —C(O)OH.

"THF" refers to tetrahydrofuran.

"EtOAc" refers to ethyl acetate.

"MeOH" refers to methanol.

"DMF" refers to N, N-dimethylformamide.

"DIPEA" refers to diisopropylethylamine.

"TFA" refers to trifluoroacetic acid.

"MeCN" refers to acetonitrile.

"DMA" refers to N, N-dimethylacetamide.

"$Et_2O$" refers to diethyl ether.

"DCE" refers to 1, 2 dichloroethane.

"DIPEA" refers to N, N-diisopropylethylamine.

"NBS" refers to N-bromosuccinimide.

"NIS" refers to N-iodosuccinimide.

"Cbz-Cl" refers to benzyl chloroformate.

"$Pd_2(dba)_3$" refers to tris(dibenzylideneacetone)dipalladium.

"Dppf" refers to 1, 1'-bis(diphenylphosphino)ferrocene.

"HATU" refers to 2-(7-azabenzotriazol-1-yl)-N,N,N',N'-tetramethyluronium hexafluorophosphate.

"KHMDS" refers to potassium hexamethyldisilazide.

"LiHMDS" refers to lithium bistrimethylsilylamide.

"MeLi" refers to methyl lithium.

"N-BuLi" refers to n-butyl lithium.

"$NaBH(OAc)_3$" refers to sodium triacetoxyborohydride.

"X is selected from A, B, or C", "X is selected from A, B and C", "X is A, B or C", "X is A, B and C" and other terms all express the same meaning, which means that X can be any one or more of A, B, and C.

The hydrogen atom described in the present disclosure can be replaced by its isotope deuterium, and any hydrogen atom in the embodiment compounds of the present disclosure can also be replaced by a deuterium atom.

"Optional" or "optionally" refers to that the event or environment described later can but does not have to occur, and the description includes occasions where the event or environment occurs or does not occur. For example, "heterocyclic group optionally substituted by alkyl" refers to that alkyl may but does not have to be present, and the description includes the case where the heterocyclic group is substituted by alkyl and the case where the heterocyclic group is not substituted by alkyl.

"Substituted" refers to one or more hydrogen atoms in the group, preferably up to 5, more preferably 1 to 3 hydrogen atoms, independently substituted by a corresponding number of substituents. It goes without saying that the substituents are only in their possible chemical positions, and those skilled in the art can determine (by experiment or theory) possible or impossible substitutions without too much effort. For example, amino or hydroxyl having free hydrogen may be unstable when combined with a carbon atom having an unsaturated (e.g., olefinic) bond.

"Pharmaceutical composition" refers to a mixture containing one or more of the compounds described herein or the physiologically/pharmaceutically acceptable salt or prodrug thereof and other chemical components, and the other component is, for example, physiological/pharmaceutically acceptable carrier and excipient. The purpose of the pharmaceutical composition is to promote the administration to the organism, facilitate the absorption of the active ingredient and then exert the biological activity.

"Pharmaceutically acceptable salt" refers to the salt of the compound of the present disclosure, which is safe and effective when used in mammals, and has due biological activity.

DETAILED DESCRIPTION OF THE PREFERRED EMBODIMENT

The following embodiments will further describe the present disclosure, but these embodiments do not limit the scope of the present disclosure.

Embodiment

The structures of the compounds of the present disclosure were determined by nuclear magnetic resonance (NMR) or/and liquid chromatography-mass spectrometry (LC-MS). NMR chemical shift (δ) was given in units of parts per million (ppm). NMR was determined using a Bruker AVANCE-400 NMR instrument with deuterated dimethyl sulfoxide (DMSO-$d_6$), deuterated methanol ($CD_3OD$) and deuterated chloroform ($CDCl_3$) as solvents and tetramethylsilane (TMS) as internal standard.

Liquid chromatography-mass spectrometry LC-MS was determined with an Agilent 1200 Infinity Series mass spectrometer. HPLC determinations were performed using an Agilent 1200DAD high pressure liquid chromatograph (Sunfire C18 150×4.6 mm column) and a Waters 2695-2996 high pressure liquid chromatograph (Gimini $C_{18}$ 150×4.6 mm column).

Yantai Huanghai HSGF254 or Qingdao GF254 silica gel plate was used as thin layer chromatography silica gel plate, the specification of TLC was 0.15 mm-0.20 mm, and the specification of thin layer chromatography separation and purification products was 0.4 mm-0.5 mm. Generally, Yantai Huanghai silica gel 200-300 mesh silica gel was used as carrier for column chromatography.

The starting materials in the embodiments of the present disclosure are known and commercially available, or can be synthesized by using or following methods known in the art.

Unless otherwise specified, all reactions of the present disclosure were carried out under continuous magnetic stirring under dry nitrogen or argon atmosphere, the solvent is a dry solvent, and the unit of the reaction temperature was degrees Celsius.

Embodiment 1
The Preparation of (S)-2-(1-acryloyl-4-(7-(8-methylnaphthalen-1-yl)-2-(4-methylpiperazine-1-carbonyl)-5, 6, 7, 8-tetrahydropyrido[3, 4-d]pyrimidin-4-yl)piperazin-2-yl)acetonitrile
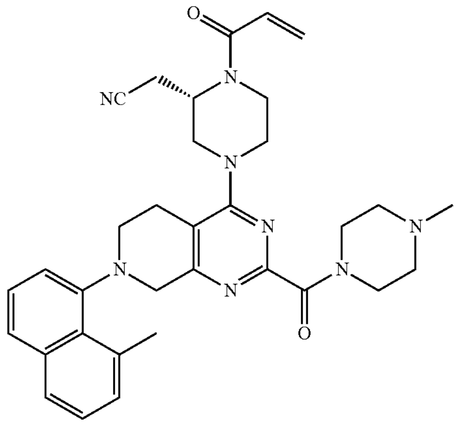
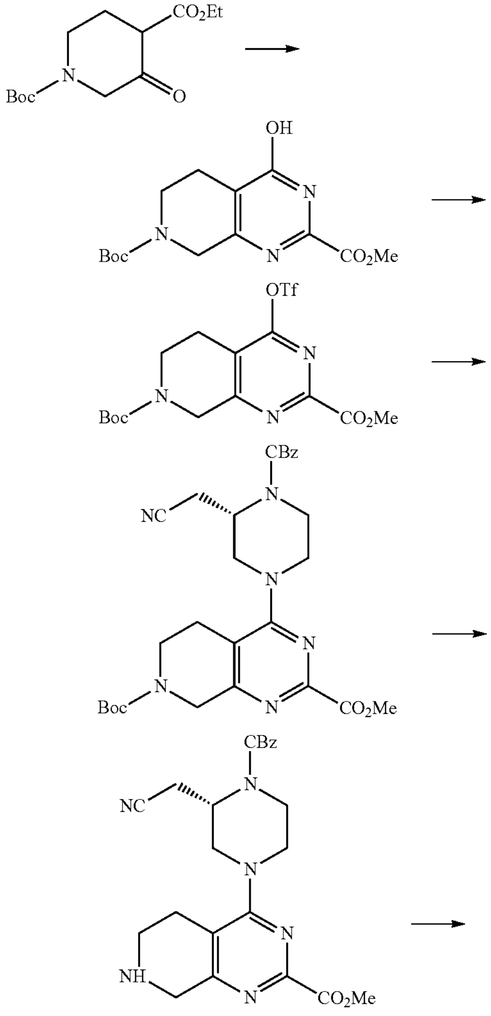
-continued
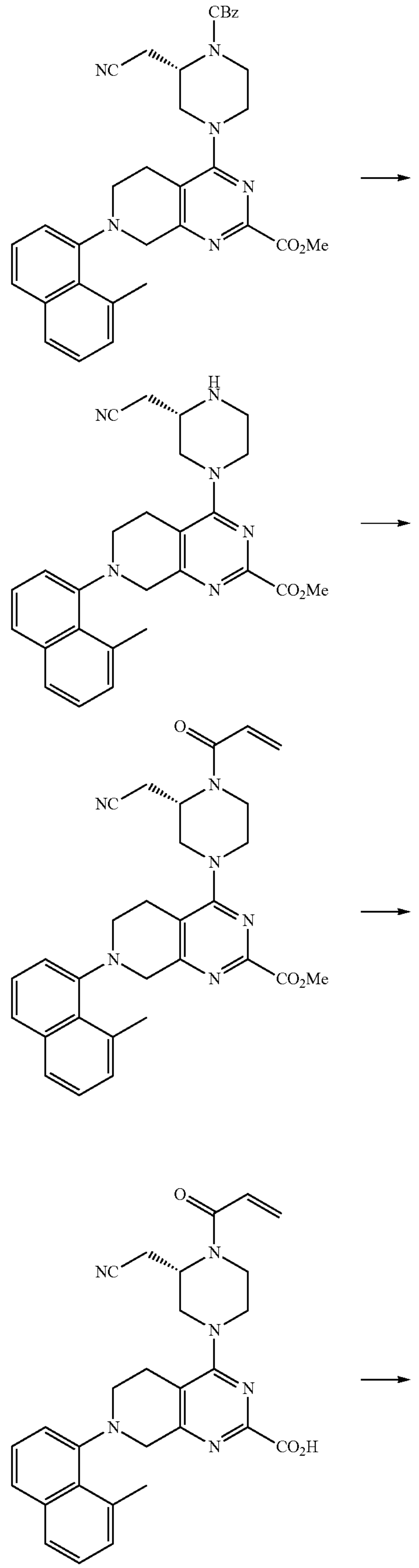

-continued

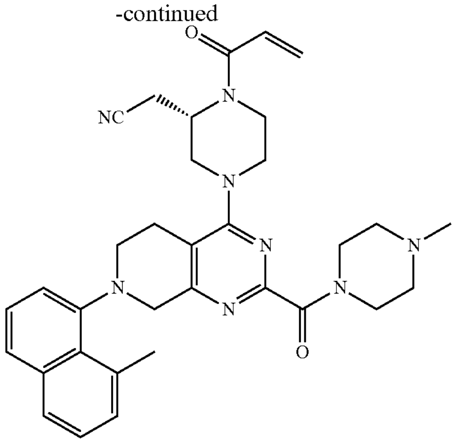

Step 1: Preparation of 7-(tert-butyl) 2-methyl 4-hydroxy-5, 8-dihydropyrido[3, 4-d]pyrimidine-2, 7(6H)-dicarboxylate

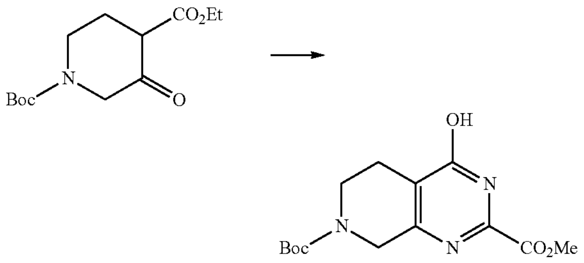

(Tert-butyl) 4-ethyl 3-carbonylpiperidine-1, 4-dicarboxylate (10 g, 37 mmol) and methyl 2-amino-2-iminoacetate hydrochloride (5.1 g, 37 mmol) were dissolved in ethanol (100 mL), and sodium ethoxide (2.7 g, 40 mmol) was added, the mixture was heated to 75° C. and stirred for 15 hours, then concentrated under reduced pressure to remove excess solvent, water was added thereto, and the pH value was adjusted to neutral with 1M diluted hydrochloric acid, a solid was precipitated, and the mixture was filtered and washed with water, then the solid was dried to obtain the target product 7-(tert-butyl) 2-methyl 4-hydroxy-5, 8-dihydropyrido[3, 4-d]pyrimidine-2, 7(6H)-dicarboxylate (3.8 g, yield: 33%).

MS m/z (ESI): 310.1 $[M+H]^+$.

Step 2: Preparation of 7-(tert-butyl) 2-methyl 4-(((trifluoromethyl)sulfonyl)oxo)-5, 8-dihydropyrido[3, 4-d]pyrimidine-2, 7(6H)-dicarboxylate

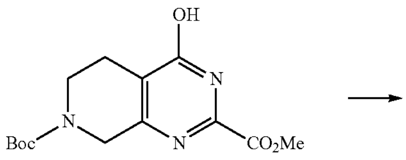

-continued

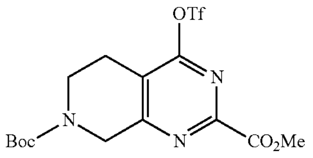

7-(Tert-butyl) 2-methyl 4-hydroxy-5, 8-dihydropyrido[3, 4-d]pyrimidin-2, 7(6H)-dicarboxylate (3.7 g, 12.0 mmol) was dissolved in dichloromethane (100 mL), and the mixture was cooled to 0° C., DIPEA (2.7 g, 24.1 mmol) and $Tf_2O$ (5.1 g, 18.1 mmol) were added thereto, and the mixture was stirred at room temperature overnight. The mixture was concentrated and purified by column chromatography (EtOAc/Petro ether=5:1) to obtain the target product 7-(tert-butyl) 2-methyl 4-(((trifluoromethyl)sulfonyl)oxo)-5, 8-dihydropyrido[3, 4-d]pyrimidine-2, 7(6H)-dicarboxylate (4.5 g, yield: 85%).

Step 3: Preparation of 7-(tert-butyl) 2-methyl (S)-4-(4-((benzyloxy)carbonyl)-3-(cyanomethyl)piperazin-1-yl)-5, 8-dihydropyrido[3, 4-d]pyrimidin-2, 7(6H)-dicarboxylate

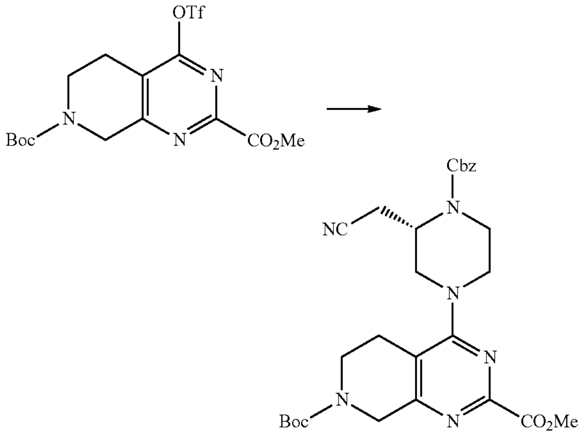

7-(Tert-butyl) 2-methyl 4-(((trifluoromethyl)sulfonyl)oxo)-5, 8-dihydropyrido[3, 4-d]pyrimidine-2, 7 (6H)-dicarboxylate (3.5 g, 7.9 mmol) was dissolved in DMF (50 mL), and benzyl (S)-2-(cyanomethyl)piperazine-1-carboxylate (2.5 g, 9.7 mmol), DIPEA (2.7 g, 24.1 mmol) were added thereto, the mixture was heated to 100° C. under nitrogen protection, and stirred for 3 hours. The mixture was cooled down, water was added thereto, and the mixture was extracted with ethyl acetate (3*50 mL). The organic phase was combined, dried over anhydrous sodium sulfate, and concentrated to obtain the crude product, then purified by column chromatography (EtOAc/Petro ether=3:1) to obtain the target product 7-(tert-butyl) 2-methyl(S)-4-(4-((benzyloxy)carbonyl)-3-(cyanomethyl)piperazin-1-yl)-5, 8-dihydropyrido[3, 4-d]pyrimidine-2, 7(6H)-dicarboxylate (3.7 g, yield: 85%).

MS m/z (ESI): 551.1 $[M+H]^+$.

Step 4: Preparation of methyl (S)-4-(4-((benzyloxy) carbonyl)-3-(cyanomethyl)piperazin-1-yl)-5, 6, 7, 8-tetrahydropyrido[3, 4-d]pyrimidine-2-carboxylate

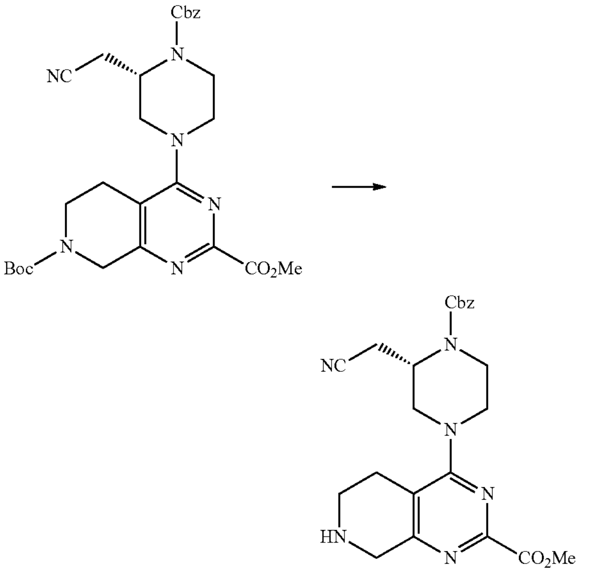

7-(Tert-butyl) 2-methyl (S)-4-(4-((benzyloxy)carbonyl)-3-(cyanomethyl)piperazin-1-yl)-5, 8-dihydropyrido[3, 4-d] pyrimidine-2, 7(6H)-dicarboxylate (1.5 g, 2.7 mmol) was dissolved in dichloromethane (30 mL), and TFA (2 mL, 27.2 mmol) was added thereto, the mixture was stirred at room temperature for 2 hours. The mixture was adjusted to neutral with saturated $NaHCO_3$ aqueous solution and extracted three times with ethyl acetate (3*50 mL). The organic phases were combined, dried over anhydrous sodium sulfate and concentrated to obtain the target product methyl (S)-4-(4-((benzyloxy)carbonyl)-3-(cyanomethyl)piperazin-1-yl)-5, 6, 7, 8-tetrahydropyrido[3, 4-d]pyrimidine-2-carboxylate (1.3 g, crude product).

MS m/z (ESI): 451.1 $[M+H]^+$.

Step 5: Preparation of methyl (S)-4-(4-((benzyloxy) carbonyl)-3-(cyanomethyl)piperazin-1-yl)-7-(8-methylnaphthalen-1-yl)-5, 6, 7, 8-tetrahydropyrido [3, 4-d]pyrimidine-2-carboxylate

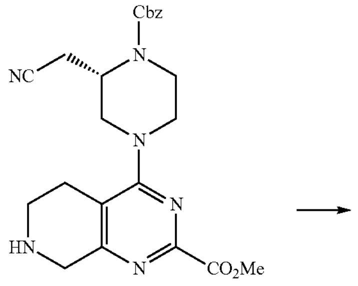

-continued

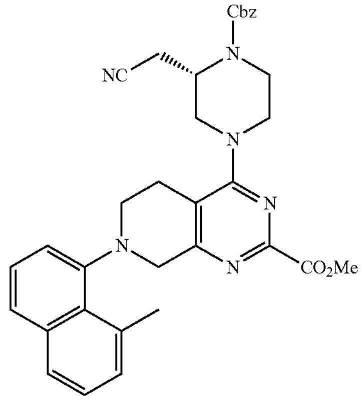

Methyl (S)-4-(4-((benzyloxy)carbonyl)-3-(cyanomethyl) piperazin-1-yl)-5, 6, 7, 8-tetrahydropyrido[3, 4-d]pyrimidine-2-carboxylate (1.3 g, 2.7 mmol) was dissolved in toluene (50 mL); 1-bromo-8-methylnaphthalene (1.2 g, 5.4 mmol), $Pd_2(dba)_3$ (275 mg, 0.3 mmol), RuPhos (280 mg, 0.6 mmol) and $Cs_2CO_3$ (326 mg, 1.0 mmol) were added thereto, and the reaction mixture was replaced with nitrogen 3 times, the reaction mixture was stirred at 100° C. for 15 hours. The mixture was concentrated to remove toluene and extracted with water and ethyl acetate (3*30 mL). The organic phases were combined, dried over anhydrous sodium sulfate, concentrated to obtain the crude product, and purified by column chromatography (EtOAc/Petro ether=3:1) to obtain the target product methyl (S)-4-(4-((benzyloxy)carbonyl)-3-(cyanomethyl)piperazin-1-yl)-7-(8-methylnaphthalen-1-yl)-5, 6, 7, 8-tetrahydropyrido[3, 4-d]pyrimidine-2-carboxylate (550 mg, yield: 35%).

MS m/z (ESI): 591.1 $[M+H]^+$.

Step 6: Preparation of methyl (S)-4-(3-(cyanomethyl)piperazin-1-yl)-7-(8-methylnaphthalen-1-yl)-5, 6, 7, 8-tetrahydropyrido[3, 4-d]pyrimidine-2-carboxylate

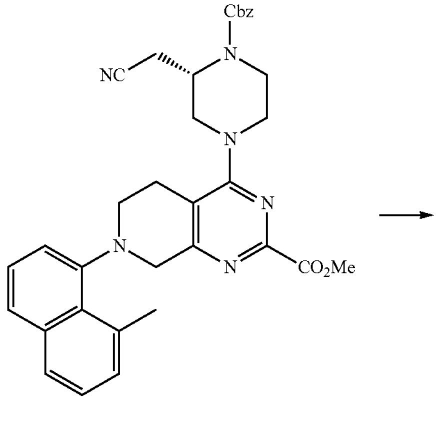

-continued

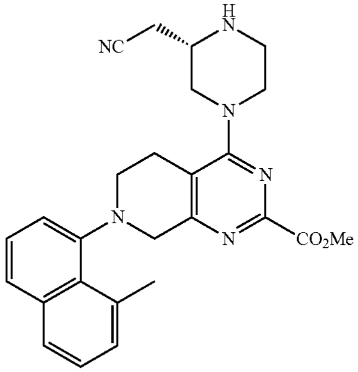

-continued

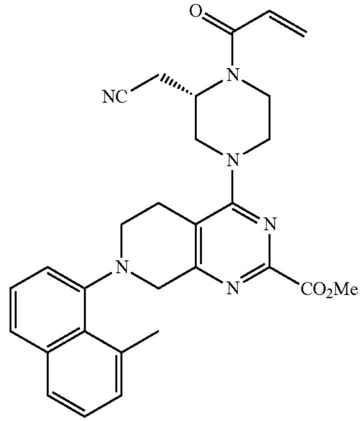

Ammonia was passed into MeOH (20 mL) for 30 min at −70° C., then methyl (S)-4-(4-((benzyloxy)carbonyl)-3-(cyanomethyl)piperazin-1-yl)-7-(8-methylnaphthalen-1-yl)-5, 6, 7, 8-tetrahydropyrido[3, 4-d]pyrimidin-2-carboxylate (500 mg, 0.85 mmol), Pd/C (250 mg, 10% water) were added thereto, the mixture was replaced with hydrogen, and then stirred for 1 hour at room temperature under 15 Psi of hydrogen. The reaction was complete, and the mixture was filtered to remove the catalyst, washed with MeOH, and the organic phase was concentrated to obtain the target product methyl (S)-4-(3-(cyanomethyl)piperazin-1-yl)-7-(8-methylnaphthalen-1-yl)-5, 6, 7, 8-tetrahydropyrido[3, 4-d]pyrimidine-2-carboxylate (320 mg, yield: 83%).

MS m/z (ESI): 457.1 $[M+H]^+$.

Step 7: Preparation of methyl (S)-4-(4-acryloyl-3-(cyanomethyl)piperazin-1-yl)-7-(8-methylnaphthalen-1-yl)-5, 6, 7, 8-tetrahydropyrido[3, 4-d]pyrimidin-2-carboxylate

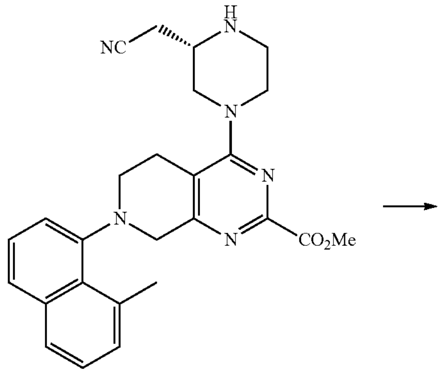

Methyl (S)-4-(3-(cyanomethyl)piperazin-1-yl)-7-(8-methylnaphthalen-1-yl)-5, 6, 7, 8-tetrahydropyrido[3, 4-d] pyrimidine-2-carboxylate (300 mg, 0.66 mmol) was dissolve in dichloromethane (10 mL), DIPEA (220 mg, 2.0 mmol) was added, then acryloyl chloride (66 mg, 0.73 mmol) was added dropwise at room temperature, the stirring was continued after the addition for 1 hour. The reaction mixture was quenched with water and extracted three times with dichloromethane (10 mL). The organic phases were combined, dried over anhydrous sodium sulfate, concentrated to obtain the crude product, and purified by column chromatography (EtOAc/Petro ether=5:1) to obtain the target product methyl (S)-4-(4-acryloyl-3-(cyanomethyl)piperazin-1-yl)-7-(8-methylnaphthalen-1-yl)-5, 6, 7, 8-tetrahydropyrido[3, 4-d]pyrimidine-2-carboxylate (275 mg, yield: 82%).

MS m/z (ESI): 511.1 $[M+H]^+$.

Step 8: Preparation of (S)-4-(4-acryloyl-3-(cyanomethyl)piperazin-1-yl)-7-(8-methylnaphthalen-1-yl)-5, 6, 7, 8-tetrahydropyrido[3, 4-d]pyrimidine-2-carboxylic acid

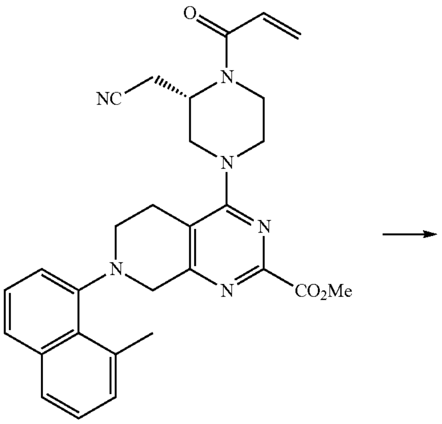

-continued

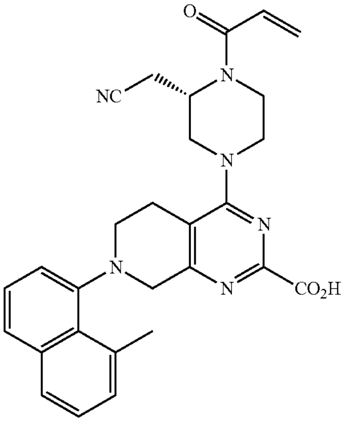

Methyl (S)-4-(4-acryloyl-3-(cyanomethyl)piperazin-1-yl)-7-(8-methylnaphthalen-1-yl)-5, 6, 7, 8-tetrahydropyrido[3, 4-d]pyrimidine-2-carboxylate (270 mg, 0.53 mmol) was dissolved in THF/$H_2O$ (10 mL/5 mL), and LiOH—$H_2O$ (220 mg, 5.3 mmol) was added thereto, the mixture was stirred at room temperature for 5 hours. The mixture was adjusted to neutral with 1M hydrochloric acid, extracted three times with ethyl acetate (3*20 mL), and the organic phases were combined, dried over anhydrous sodium sulfate, and concentrated to obtain the crude target product (S)-4-(4-acryloyl-3-(cyanomethyl)piperazin-1-yl)-7-(8-methylnaphthalen-1-yl)-5, 6, 7, 8-tetrahydropyrido[3, 4-d] pyrimidine-2 carboxylic acid (280 mg, crude product).

MS m/z (ESI): 497.1 $[M+H]^+$.

Step 9: Preparation of (S)-2-(1-acryloyl-4-(7-(8-methylnaphthalen-1-yl)-2-(4-methylpiperazine-1-carbonyl)-5, 6, 7, 8-tetrahydropyrido[3, 4-d]pyrimidin-4-yl)piperazin-2-yl)acetonitrile

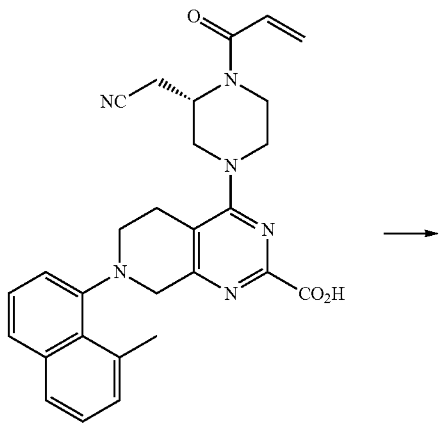

-continued

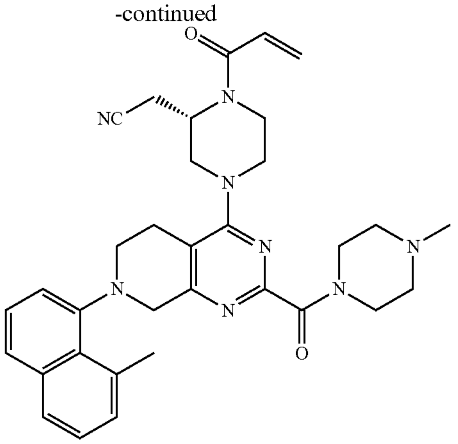

(S)-4-(4-acryloyl-3-(cyanomethyl)piperazin-1-yl)-7-(8-methylnaphthalen-1-yl)-5, 6, 7, 8-tetrahydropyrido[3, 4-d] pyrimidine-2-carboxylic acid (30 mg, 0.05 mmol) was dissolved in DMF (10 mL); DIPEA (0.5 mL) and HATU (20 mg, 0.06 mmol) were added thereto, and the mixture was stirred for 0.5 hours at room temperature. N-methylpiperazine (10 mg, 0.1 mmol) was added and stirring was continued for 3 hours, water was added thereto, and the mixture was extracted with dichloromethane (3*20 mL), washed with water (20 mL) and saturated saline (20 mL), the organic phase was dried over anhydrous sodium sulfate, concentrated and purified by column chromatography ($CH_2Cl_2$/MeOH=10:1) to obtain the target product (S)-2-(1-acryloyl-4-(7-(8-methylnaphthalen-1-yl)-2-(4-methylpiperazine-1-carbonyl)-5, 6, 7, 8-tetrahydropyrido[3, 4-d]pyrimidin-4-yl) piperazin-2-yl)acetonitrile (10 mg, yield: 35%).

MS m/z (ESI): 579.1 $[M+H]^+$.

The synthesis of embodiments 2-20 were carried out with reference to embodiment 1.

Embodiment 21

Preparation of 1-(4-(6-chloro-7-(2-fluoro-6-hydroxyphenyl)-2-(((S)-1-methylpyrrolidin-2-yl) methoxy)pyrido[2, 3-d]pyrimidin-4-yl)piperazin-1-yl)prop-2-en-1-one

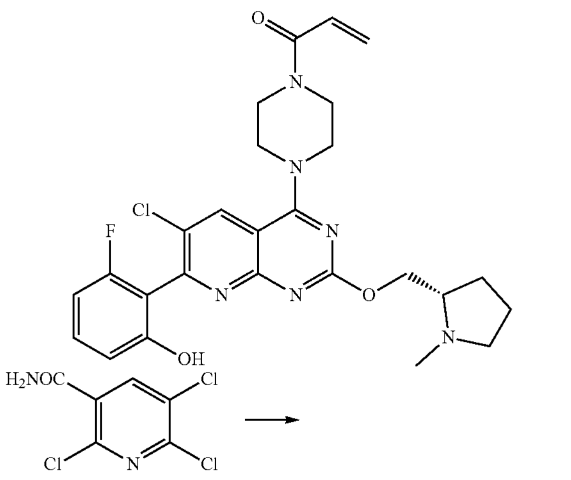

-continued

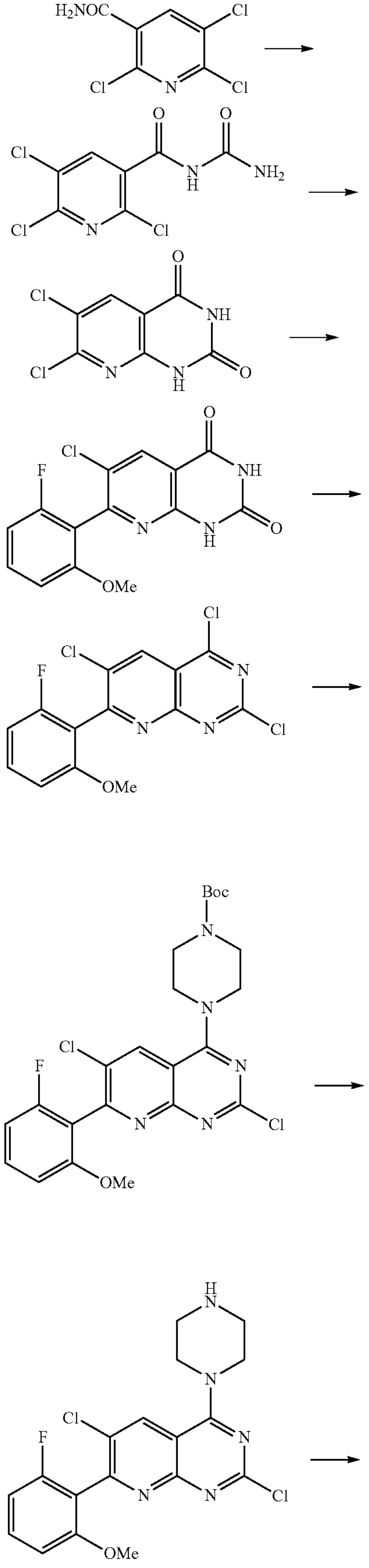

-continued

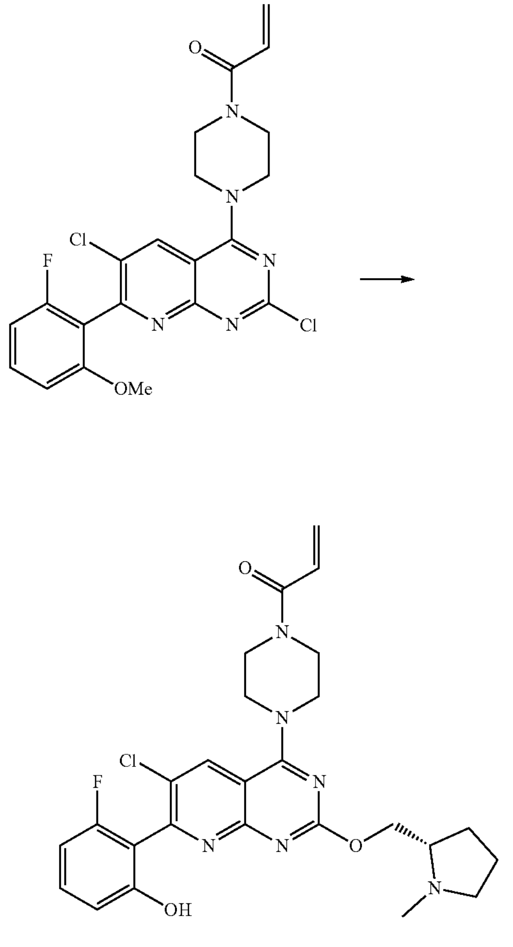

Step 1: Preparation of 2, 5, 6-trichloronicotinamide

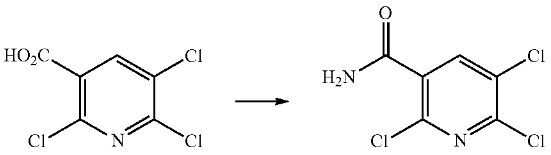 [SMILES: O=C(O)c1cc(Cl)c(Cl)nc1Cl ; NC(=O)c1cc(Cl)c(Cl)nc1Cl]

2, 5, 6-Trichloronicotinic acid (8 g, 35.5 mmol) was dissolved in 80 mL of anhydrous tetrahydrofuran, N'N-carbonyldiimidazole (6.3 g, 39 mmol) was added to the reaction mixture in batches, the mixture was heated to 50° C. and stirred for 1 hour, then toluene was added thereto and the mixture was concentrated to 50 mL under reduced pressure. After cooling to 0° C., ammonia water (9.5 mL, 22 mmol) was slowly added dropwise to the reaction, and the mixture was stirred at room temperature for 1 hour. After the reaction was completed, the mixture was concentrated and extracted three times with ethyl acetate/petroleum ether (1/3), the organic phases were combined, dried over anhydrous sodium sulfate, and concentrated to obtain a white solid. The white solid was slurried by ethyl acetate/petroleum ether (1/5) to obtain the target product 2, 5, 6-trichloronicotinamide (5.6 g, yield: 70%).

Step 2: Preparation of N-carbamoyl-2, 5, 6-trichloronicotinamide

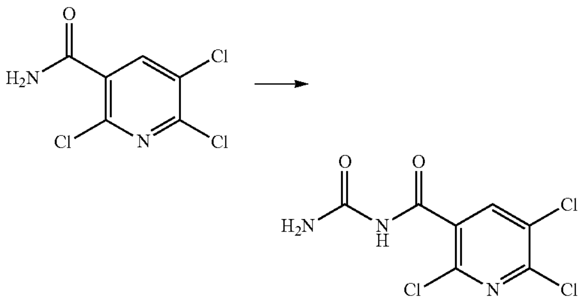

2, 5, 6-Trichloronicotinamide (5 g, 22.3 mmol) was dissolved in 40 mL of anhydrous tetrahydrofuran, oxalyl chloride (2.0 mL, 23.8 mmol) was added dropwise at −78° C., and the mixture was stirred at 60° C. for 3.5 hours. Then the mixture was cooled to −78° C., triethylamine (9.7 mL, 68.9 mmol) and ammonia (22 mL, 51 mmol) were added thereto, and the mixture was stirred at room temperature for 1 hour, the reaction was complete. The mixture was concentrated, extracted three times with ethyl acetate, the organic phases were combined, dried over anhydrous sodium sulfate, concentrated again, and slurried with ethyl acetate/petroleum ether (1/5) to obtain the target product N-carbamoyl-2, 5, 6-trichloronicotinamide (3.5 g, yield: 58%).

Step 3: Preparation of 6, 7-dichloropyrido[2, 3-d]pyrimidine-2, 4(1H, 3H)-dione

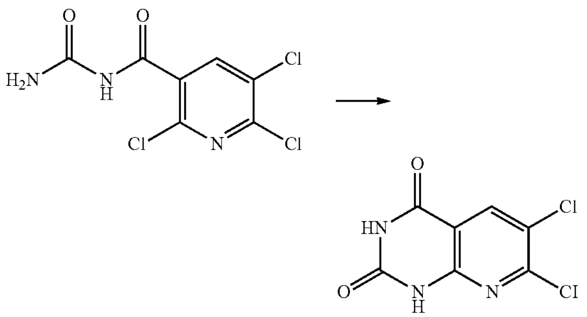

N-carbamoyl-2, 5, 6-trichloronicotinamide (3.2 g, 12.0 mmol) was dissolved in THF (100 mL) under the protection of nitrogen, and KHMDS (24.0 mL, 1 M THF solution, 24.0 mmol) was added dropwise thereto under an ice-water bath, and gradually brought to room temperature after the addition and stirred for 1 hour. The reaction mixture was quenched with saturated $NH_4Cl$ aqueous solution and extracted with ethyl acetate (3*30 mL). The organic phases were combined, dried over anhydrous sodium sulfate, concentrated to obtain the crude product, and purified by column chromatography ($CH_2Cl_2$/MeOH=10:1) to obtain the target product 6, 7-dichloropyrido[2, 3-d]pyrimidine-2, 4(1H, 3H)-dione (2.1 g, yield: 76%).

MS m/z (ESI): 232.1 $[M+H]^+$, 234.1$[M+2+H]^+$.

Step 4: Preparation of 6-chloro-7-(2-fluoro-6-methoxyphenyl)pyrido[2, 3-d]pyrimidine-2, 4(1H, 3H)-dione

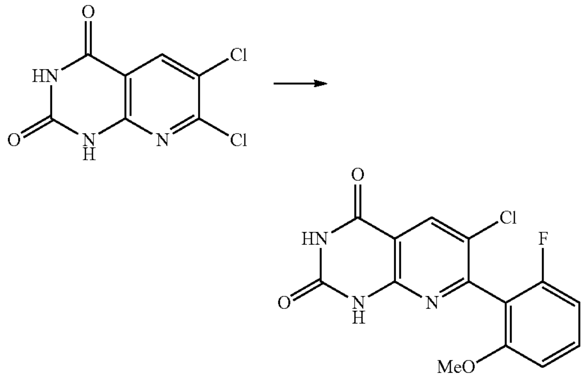

6, 7-Dichloropyrido[2, 3-d]pyrimidine-2, 4(1H, 3H)-dione (2 g, 8.6 mmol) was dissolved in dioxane (100 mL), 2-fluoro-6-methoxyphenylboronic acid (2.2 g, 12.9 mmol), tris(dibenzylideneacetone)dipalladium (459 mg, 0.5 mmol), Xantphos (580 mg, 1 mmol), and $Cs_2CO_3$ (8.5 g, 25.9 mmol) were added thereto, and the mixture was replaced with nitrogen. The reaction mixture was heated to 110° C. and the reaction was carried out overnight. After cooling to room temperature, the mixture was diluted with 200 mL of ethyl acetate, filtered through celite, the filtrate was evaporated to dryness, and purify by column chromatography ($CH_2Cl_2$/MeOH=10:1) to obtain the target product 6-chloro-7-(2-fluoro-6)-methoxyphenyl)pyrido[2, 3-d]pyrimidine-2, 4(1H, 3H)-dione (1.9 g, yield: 68%).

MS m/z (ESI): 322.1 $[M+H]^+$, 324.1$[M+2+H]^+$.

Step 5: Preparation of 2, 4, 6-trichloro-7-(2-fluoro-6-methoxyphenyl)pyrido[2, 3-d]pyrimidine

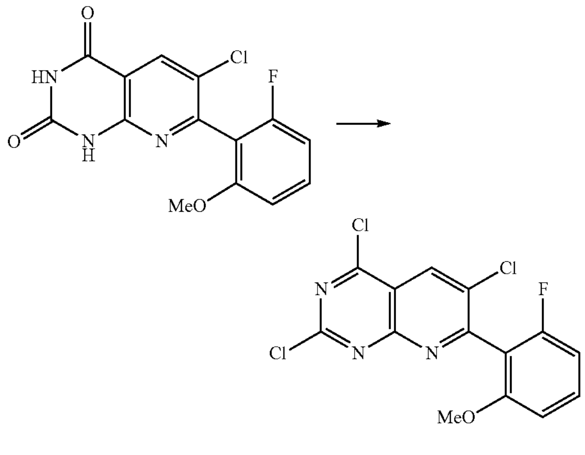

6-Chloro-7-(2-fluoro-6-methoxyphenyl)pyrido[2, 3-d]pyrimidine-2, 4(1H, 3H)-dione (1.8 g, 5.6 mmol) was dissolved in $POCl_3$ (50 mL), under the protection of nitrogen, the mixture was stirred at 80° C. for 10 hours. Then the mixture was quenched by adding ice water dropwise, filtered to obtain the solid product, the solid product was washed with water, and dried to obtain the crude target product 2, 4, 6-trichloro-7-(2-fluoro-6-methoxyphenyl)pyrido[2, 3-d]pyrimidine (1.5 g, yield: 75%).

Step 6: Preparation of tert-butyl 4-(2, 6-dichloro-7-(2-fluoro-6-methoxyphenyl)pyrido[2, 3-d]pyrimidin-4-yl)piperazin-1-carboxylate

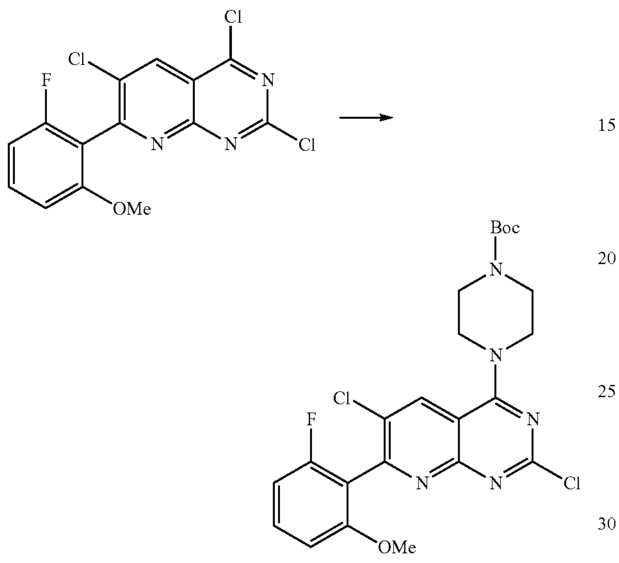

2, 4, 6-Trichloro-7-(2-fluoro-6-methoxyphenyl)pyrido[2, 3-d]pyrimidine (1.5 g, 4.2 mmol) was dissolved in dichloromethane (30 mL), N-tert-butoxyformyl-piperazine (940 mg, 5.0 mmol), TEA (1.3 g, 12.9 mmol) were added thereto, and the reaction mixture was stirred at 0° C. for 1 hour. The reaction mixture was poured into ice water and extracted three times with dichloromethane (30 mL). The organic phases were combined, dried over anhydrous sodium sulfate and concentrated to obtain the crude product, the crude product was purified by column chromatography (EtOAc/Petro ether=3:1) to obtain the target product tert-butyl 4-(2, 6-dichloro-7-(2-fluoro-6-methoxyphenyl)pyrido[2, 3-d]pyrimidin-4-yl)piperazin-1-carboxylate (1.4 g, yield: 65%).

MS m/z (ESI): 508.1 $[M+H]^+$, 510.1$[M+2+H]^+$.

Step 7: Preparation of 2, 6-dichloro-7-(2-fluoro-6-methoxyphenyl)-4-(piperazine-1-yl)pyrido[2, 3-d] pyrimidine

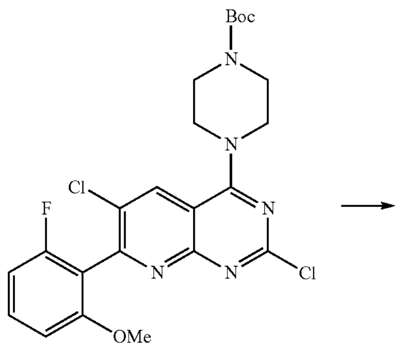

-continued

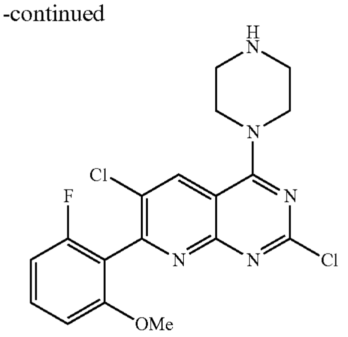

Tert-butyl 4-(2, 6-dichloro-7-(2-fluoro-6-methoxyphenyl) pyrido[2, 3-d]pyrimidin-4-yl)piperazin-1-carboxylate (1.4 g, 2.8 mmol) was dissolved in dichloromethane (20 mL), TFA (2 mL) was added thereto and stirred at room temperature for 2 hours. The mixture was adjusted to neutral with saturated $NaHCO_3$ aqueous solution and extracted three times with ethyl acetate (3*50 mL). The organic phases were combined, dried over anhydrous sodium sulfate, and concentrated to obtain the target product 2, 6-dichloro-7-(2-fluoro-6-methoxyphenyl)-4-(piperazin-1-yl)pyrido[2, 3-d] pyrimidine (1.4 g, crude product).

MS m/z (ESI): 408.1 $[M+H]^+$, 410.1$[M+2+H]^+$.

Step 8: Preparation of 1-(4-(2, 6-dichloro-7-(2-fluoro-6-methoxyphenyl)pyrido[2, 3-d]pyrimidin-4-yl)piperazin-1-yl)prop-2-en-1-one

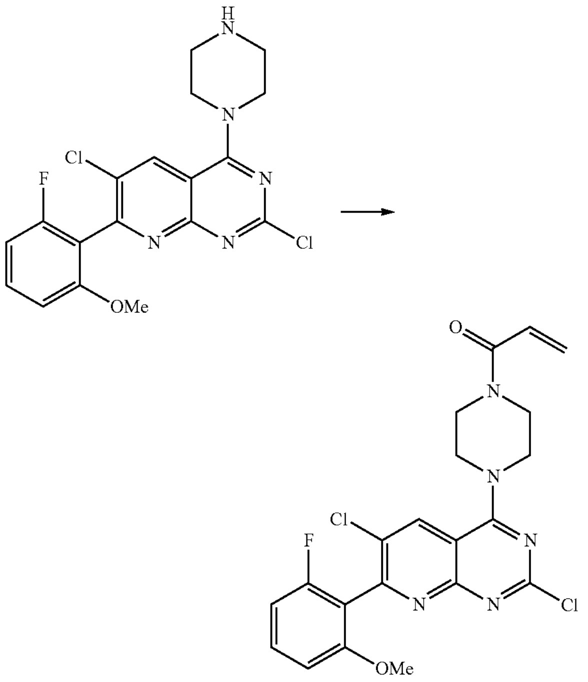

2, 6-Dichloro-7-(2-fluoro-6-methoxyphenyl)-4-(piperazin-1-yl)pyrido[2, 3-d]pyrimidine (1.4 g, 2.8 mmol) was dissolve in dichloromethane (30 mL), DIPEA (1.1 g, 8.5 mmol) was added, then acryloyl chloride (305 mg, 3.4 mmol) was added dropwise at room temperature, the stirring was continued after the addition for 1 hour. The reaction mixture was quenched with water and extracted three times with dichloromethane (10 mL). The organic phases were combined, dried over anhydrous sodium sulfate and concentrated to obtain the crude product, the crude product was purified by column chromatography (EtOAc/Petro ether=3:1) to obtain the target product 1-(4-(2, 6-dichloro-7-(2-fluoro-6-methoxyphenyl)pyrido[2, 3-d]pyrimidin-4-yl)piperazin-1-yl)prop-2-en-1-one (1 g, yield: 77%).

MS m/z (ESI): 462.1 $[M+H]^+$, 464.1$[M+2+H]^+$.

Step 9: Preparation of 1-(4-(6-chloro-7-(2-fluoro-6-methoxyphenyl)-2-(((S)-1-methylpyrrolidin-2-yl)methoxy)pyrido[2, 3-d]pyrimidin-4-yl)piperazin-1-yl)prop-2-en-1-one

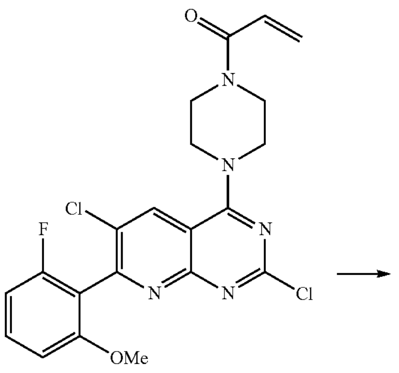

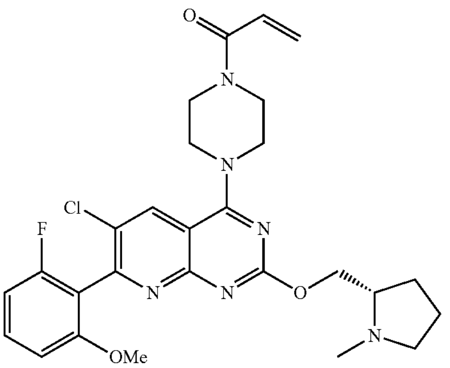

1-(4-(2, 6-Dichloro-7-(2-fluoro-6-methoxyphenyl)pyrido[2, 3-d]pyrimidin-4-yl)piperazin-1-yl)prop-2-en-1-one (200 mg, 0.43 mmol) was dissolved in THF (20 mL), (S)-(1-methylpyrrolidin-2-yl)methanol (100 mg, 0.86 mmol) and sodium tert-butoxide (124 mg, 1.29 mmol) were added thereto, and the mixture was stirred for 2 hours at room temperature under nitrogen protection. The reaction mixture was then quenched with water and extracted three times with ethyl acetate (10 mL). The organic phases were combined, dried over anhydrous sodium sulfate, concentrated to obtain the crude product, and purified by column chromatography ($CH_2Cl_2$/MeOH=10:1) to obtain the target product 1-(4-(6-chloro-7-(2-fluoro-6-methoxyphenyl))-2-(((S)-1-methylpyrrolidine2-yl)methoxy)pyrido[2, 3-d]pyrimidin-4-yl)piperazin-1-yl)prop-2-en-1-one (40 mg, yield: 18%).

MS m/z (ESI): 541.1 $[M+H]^+$, 543.1$[M+2+H]^+$.

Step 10: Preparation of 1-(4-(6-chloro-7-(2-fluoro-6-hydroxyphenyl)-2-(((S)-1-methylpyrrolidin-2-yl)methoxy)pyrido[2, 3-d]pyrimidin-4-yl)piperazin-1-yl)prop-2-en-1-one

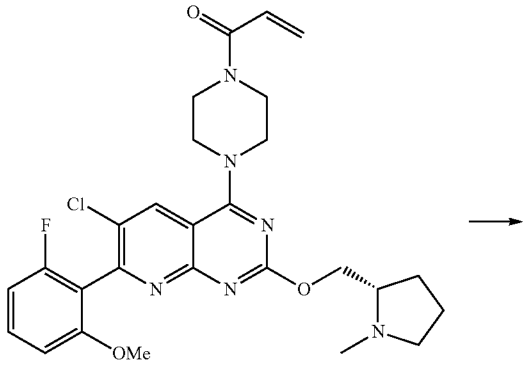

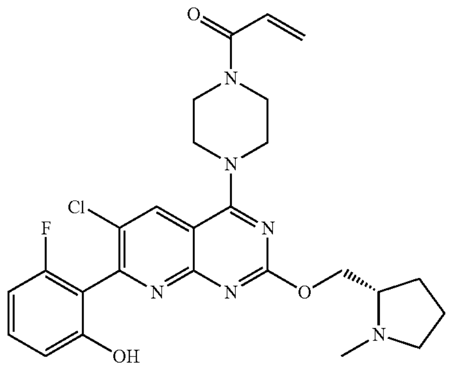

1-(4-(6-Chloro-7-(2-fluoro-6-methoxyphenyl)-2-(((S)-1-methylpyrrolidin-2-yl)methoxy)pyrido[2, 3-d]pyrimidin-4-yl)piperazin-1-yl)prop-2-en-1-one (40 mg, 0.07 mmol) was dissolved in dichloromethane (10 mL), the mixture was cooled to −40° C., and $BBr_3$ (35 mg, 0.14 mmol) was added thereto, the mixture was gradually warmed to room temperature, and stirred for 2 hours. The mixture was then quenched by adding saturated $NaHCO_3$ aqueous solution and extracted three times with ethyl acetate (10 mL). The organic phases were combined, dried over anhydrous sodium sulfate, concentrated to obtain the crude product, and purified by preparative HPLC to obtain the target product 1-(4-(6-chloro-7-(2-fluoro-6-hydroxyphenyl)-2-(((S)-1-methylpyrrolidin-2-yl)methoxy)pyrido[2, 3-d]pyrimidin-4-yl)piperazin-1-yl)prop-2-en-1-one (13 mg, yield: 33%).

MS m/z (ESI): 527.1 $[M+H]^+$, 529.1$[M+2+H]^+$.

The synthesis of embodiments 22-30 were carried out with reference to embodiment 21.

Embodiment 31

Preparation of (S)-1-(4-(7'-(8-methylnaphthalen-1-yl)-2'-((1-methylpyrrolidin-2-yl)methoxy)-7', 8'-dihydro-6'H-spiro[cyclopropane-1, 5'-pyrido[3, 4-d]pyrimidin]-4'-yl)piperazin-1-yl)prop-2-en-1-one

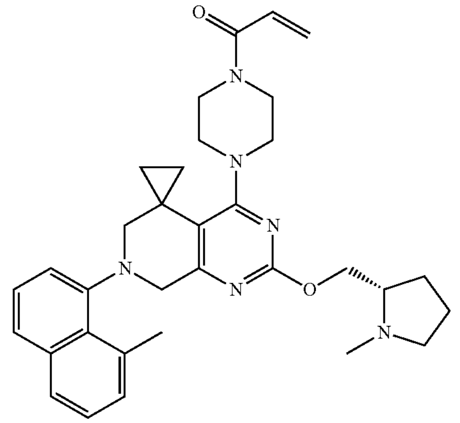

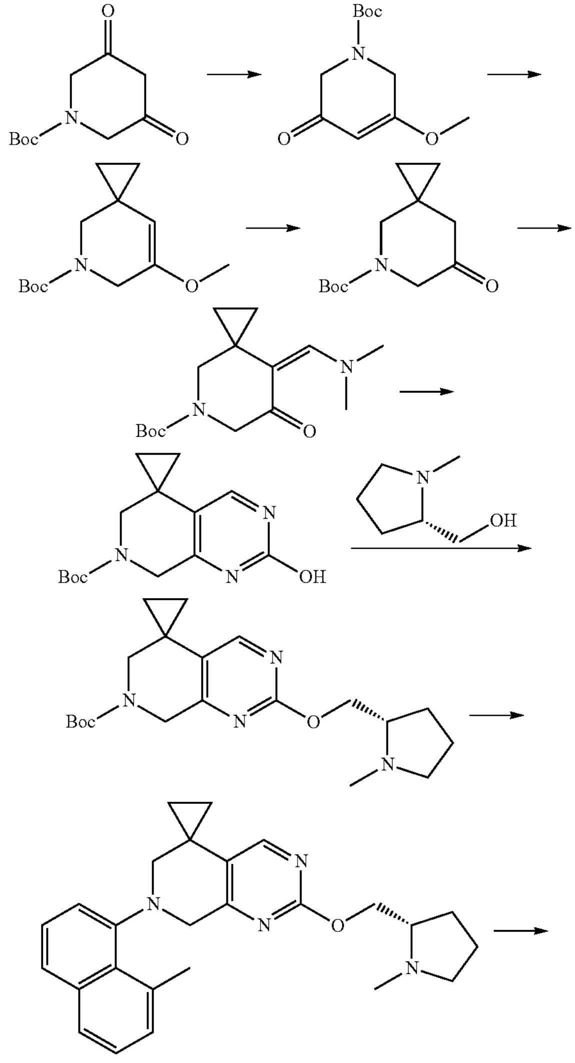

-continued

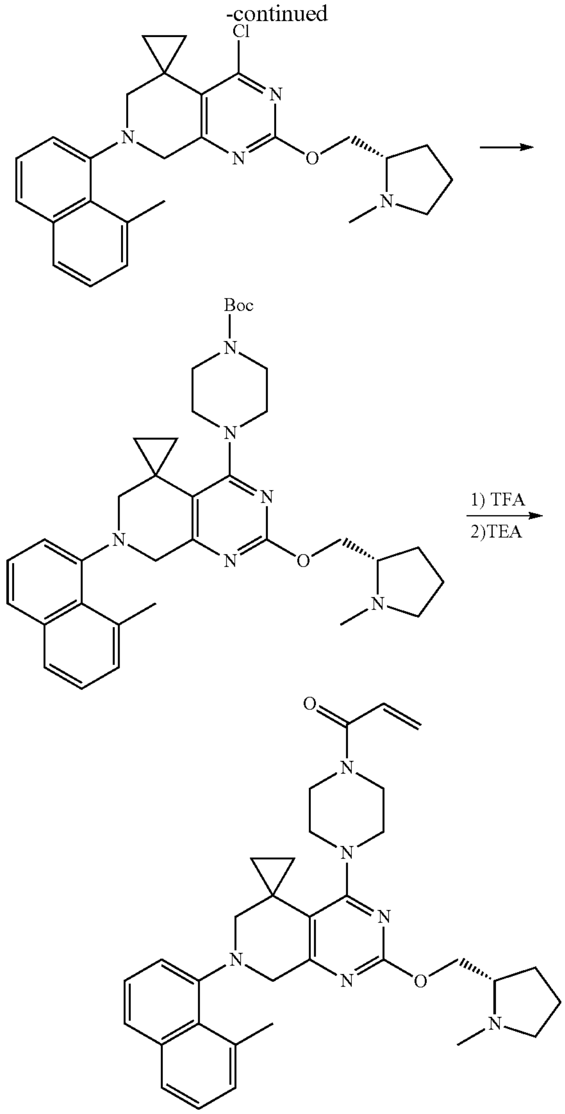

Step 1: Preparation of tert-butyl 5-methoxy-3-carbonyl-3, 6-dihydropyridine-1(2H)-carboxylate

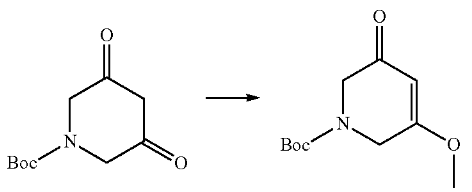 [SMILES: CC(C)(C)OC(=O)N1CC(=O)CC(=O)C1 ; COC1=CC(=O)CN(C(=O)OC(C)(C)C)C1]

Tert-butyl 3, 5-dicarbonylpyridine-1-carboxylate (10 g, 46.9 mmol) and triethyl orthoformate (6 mL) were dissolved in methanol/toluene (50 mL/150 mL), p-toluenesulfonic acid (400 mg, 2.3 mmol) was added thereto, and the mixture was stirred at 110° C. for 5 hours, cooled to room temperature, washed with saturated NaCl aqueous solution with 10% NaOH, the organic phase was dried over anhydrous sodium sulfate and concentrated to obtain the crude product, then purified by column chromatography (EtOAc/Petro ether=10:1) to obtain the target product tert-butyl 5-methoxy-3-carbonyl-3, 6-dihydropyridine-1(2H)-carboxylate (7.8 g, yield: 73%).

Step 2: Preparation of tert-butyl 7-methoxy-5-azaspiro[2. 5]oct-7-ene-5-carboxylate

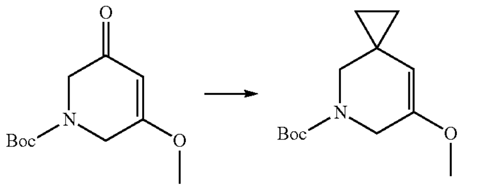 [SMILES: COC1=CC(=O)CN(C(=O)OC(C)(C)C)C1 ; COC1=CC2(CC2)CN(C(=O)OC(C)(C)C)C1]

Tert-butyl 5-methoxy-3-carbonyl-3, 6-dihydropyridine-1 (2H)-carboxylate (7.6 g, 33.5 mmol) was dissolved in 100 mL of ether, tetraisopropyl titanium oxide (10 mL) was added thereto, and ethylmagnesium bromide (33.5 mL, 3M ether solution, 100.5 mmol) was added dropwise at room temperature, and stirring was continued after the addition for 3 hours. After the reaction was completed, the reaction mixture was quenched by adding water dropwise, filtered through celite, washed with ethyl acetate and extracted with ethyl acetate three times, the organic phases were combined, dried over anhydrous sodium sulfate, and concentrated to obtain the target product tert-butyl 7-methoxy-5-azaspiro[2. 5]oct-7-ene-5-carboxylate (8.8 g, crude product).

Step 3: Preparation of tert-butyl 7-carbonyl-5-azaspiro[2. 5]octane-5-carboxylate

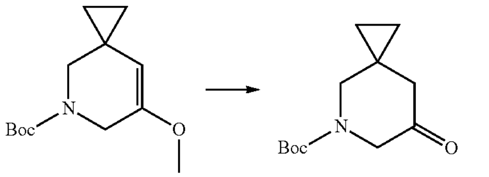 [SMILES: COC1=CC2(CC2)CN(C(=O)OC(C)(C)C)C1 ; CC(C)(C)OC(=O)N1CC(=O)CC2(CC2)C1]

Tert-butyl 7-methoxy-5-azaspiro[2. 5]oct-7-ene-5-carboxylate (8.8 g, 33.5 mmol) was dissolved in THF (50 mL), p-toluenesulfonic acid monohydrate (2 g, 10.5 mmol) was added thereto under nitrogen protection and stirred for 15 hours at room temperature. The mixture was washed with saturated $NaHCO_3$ aqueous solution, the organic phase was dried over anhydrous sodium sulfate, concentrated to obtain the crude product, and purified by column chromatography (EtOAc/Petro ether=10:1) to obtain the target product tert-butyl 7-carbonyl-5-azaspiro[2. 5]octane-5-carboxylate (4.5 g, yield: 60%).

Step 4: Preparation of tert-butyl (Z)-8-((dimethylamino)methylene)-7-carbonyl-5-azaspiro[2. 5]octane-5-carboxylate

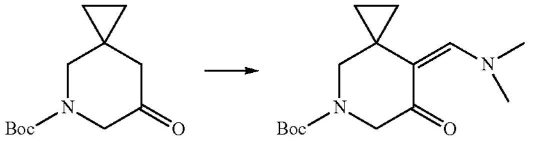 [SMILES: CC(C)(C)OC(=O)N1CC(=O)CC2(CC2)C1 ; CN(C)/C=C1\C(=O)CN(C(=O)OC(C)(C)C)CC12CC2]

Tert-butyl 7-carbonyl-5-azaspiro[2. 5]octane-5-carboxylate (4.3 g, 19.1 mmol) was dissolved in DMF-DMA (10 mL), and the mixture was stirred at 100° C. for 5 hours under nitrogen protection. The mixture was concentrated to obtain the crude target product tert-butyl (Z)-8-((dimethylamino)methylene)-7-carbonyl-5-azaspiro[2. 5]octane-5-carboxylate (4.5 g), directly used in the next step reaction.

MS m/z (ESI): 281.1 $[M+H]^+$.

Step 5: Preparation of tert-butyl 2'-hydroxy-6'H-spiro[cyclopropane-1, 5'-pyrido[3, 4-d]pyrimidine]-7'(8'H)-carboxylate

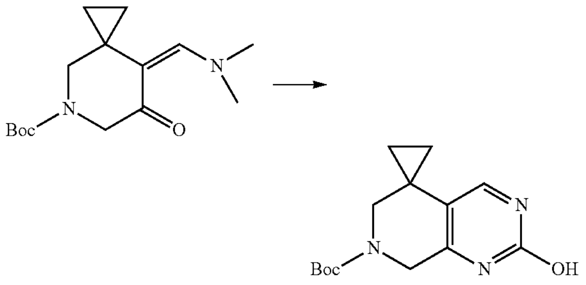

Tert-butyl (Z)-8-((dimethylamino)methylene)-7-carbonyl-5-azaspiro[2. 5]octane-5-carboxylate (4.5 g, 19.1 mmol) was dissolved in EtOH (20 mL), urea (1.7 g, 28.7 mmol) was added thereto and stirred at 100° C. for 15 hours. The mixture was cooled to room temperature, water was added thereto, and extracted three times with ethyl acetate (20 mL). The organic phases were combined, dried over anhydrous sodium sulfate, concentrated to obtain the crude product, and purified by column chromatography ($CH_2Cl_2$/MeOH=10:1) to obtain the target product tert-butyl 2'-hydroxy-6'H-spiro[cyclopropane-1, 5'-pyrido[3, 4-d]pyrimidine]-7'(8'H)-carboxylate (4.6 g, yield: 69%).

MS m/z (ESI): 278.1 $[M+H]^+$.

Step 6: Preparation of tert-butyl (S)-2'-((1-methylpyrrolidine-2-yl)methoxy)-6'H-spiro[cyclopropane-1, 5'-pyrido[3, 4-d]pyrimidine]-7'(8'H)-carboxylate

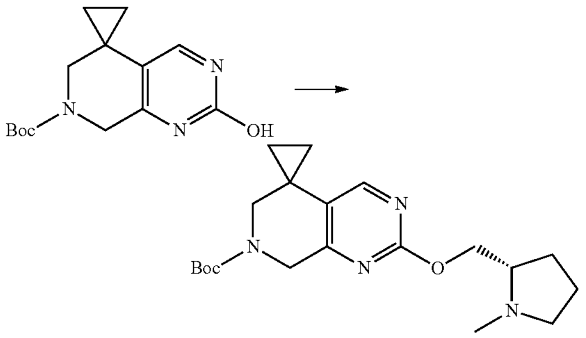

Tert-butyl 2'-hydroxy-6'H-spiro[cyclopropane-1, 5'-pyrido[3, 4-d]pyrimidine]-7'(8'H)-carboxylate (1 g, 3.6 mmol) was dissolved in DMF (100 mL), (S)-(1-methylpyrrolidin-2-yl)methyl-methanesulfonate (1 g, 5.2 mmol) and $K_2CO_3$ (1.5 g, 10.8 mmol) were added thereto, and stirred for 15 hours at room temperature. Water was added thereto and the mixture was extracted three times with ethyl acetate (30 mL). The organic phases were combined, dried over anhydrous sodium sulfate, concentrated to obtain the crude product, purified by column chromatography ($CH_2Cl_2$/MeOH=10:1) to obtain the target product tert-butyl (S)-2'-((1-methylpyrrolidin-2-yl)methoxy)-6'H-spiro[cyclopropane-1, 5'-pyrido[3, 4-d]pyrimidine]-7'(8'H)-carboxylate (1.1 g, yield: 82%).

MS m/z (ESI): 375.1 $[M+H]^+$.

Step 7: Preparation of (S)-7'-(8-methylnaphthalen-1-yl)-2'-((1-methylpyrrolidin-2-yl)methoxy)-7', 8'-dihydro-6'H-spiro[cyclopropane-1, 5'-pyrido[3, 4-d]pyrimidine]

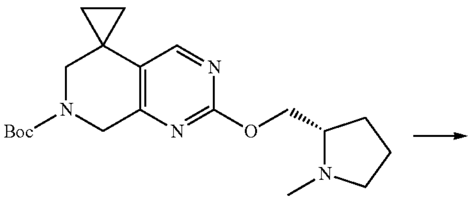

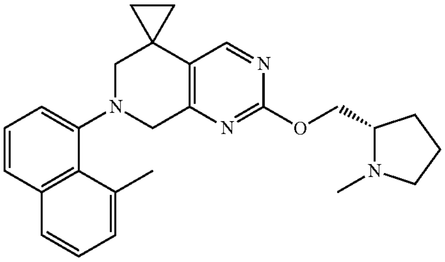

Tert-butyl (S)-2'-((1-methylpyrrolidin-2-yl)methoxy)-6'H-spiro[cyclopropane-1, 5'-pyrido[3, 4-d]pyrimidine]-7'(8'H)-carboxylate (1 g, 2.7 mmol) was dissolved in dichloromethane (20 mL), trifluoroacetic acid (2 mL) was added thereto, and the mixture was stirred at room temperature for 3 hours, then concentrated to obtain the crude product. The residue was dissolved in toluene (20 mL), 1-bromo-8-methylnaphthalen (1.2 g, 5.4 mmol), $Pd_2(dba)_3$ (275 mg, 0.3 mmol), RuPhos (280 mg, 0.6 mmol) and $Cs_2CO_3$ (326 mg, 1.0 mmol) were added thereto, and replaced with nitrogen for 3 times, the reaction mixture was stirred at 100° C. for 15 hours. The mixture was concentrated to remove toluene and extracted with water and ethyl acetate (3*30 mL). The organic phases were combined, dried over anhydrous sodium sulfate, concentrated to obtain the crude product, purified by column chromatography ($CH_2Cl_2$/MeOH=10:1) to obtain the target product (S)-2'-((1-methylpyrrolidin-2-yl)methoxy)-7', 8'-dihydro-6'H-spiro[cyclopropan-1, 5'-pyrido[3, 4-d]pyrimidine]///(S)-7'-(8-methylnaphthalen-1-yl)-2'-((1-methylpyrrolidin-2-yl)methoxy)-7', 8'-dihydro-6'H-spiro[cyclopropane-1, 5'-pyrido[3, 4-d]pyrimidine] (450 mg, yield: 41%).

MS m/z (ESI): 415.1 $[M+H]^+$.

Step 8: Preparation of (S)-4'-chloro-7'-(8-methylnaphthalen-1-yl)-2'-((1-methylpyrrolidin-2-yl)methoxy)-7', 8'-dihydro-6'H-spiro[cyclopropane-1, 5'-pyrido[3, 4-d]pyrimidine

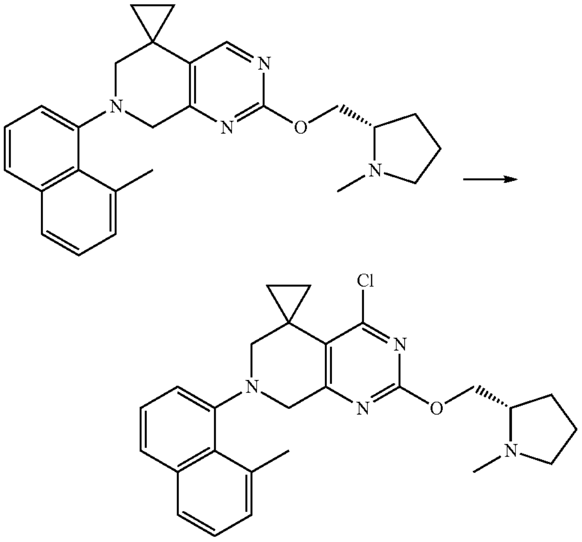

(S)-7'-(8-Methylnaphthalen-1-yl)-2'-((1-methylpyrrolidin-2-yl)methoxy)-7', 8'-dihydro-6'H-spiro[cyclopropane-1, 5'-pyrido[3, 4-d]pyrimidine] (400 mg, 0.97 mmol) was dissolved in DMF (10 mL), NCS (150 mg, 1.13 mmol) was added thereto under nitrogen protection, and the mixture was stirred at 80° C. for 15 hours. Water was added thereto and the mixture was extracted three times with ethyl acetate (20 mL). The organic phases were combined, dried over anhydrous sodium sulfate, concentrated to obtain the crude product, purified by column chromatography ($CH_2Cl_2$/MeOH=10:1) to obtain the target product (S)-4'-chloro-7'-(8-methylnaphthalen-1-yl)-2'-((1-methylpyrrolidin-2-yl)methoxy)-7', 8'-dihydro-6'H-spiro[cyclopropane-1, 5'-pyrido[3, 4-d]pyrimidine] (180 mg, yield: 41%).

MS m/z (ESI): 449.1 $[M+H]^+$.

Step 9: Preparation of tert-butyl (S)-4-(7'-(8-methylnaphthalen-1-yl)-2'-((1-methylpyrrolidin-2-yl)methoxy)-7', 8'-dihydro-6'H-spiro[cyclopropane-1, 5'-pyrido[3, 4-d]pyrimidin]-4'-yl)piperazine-1-carboxylate

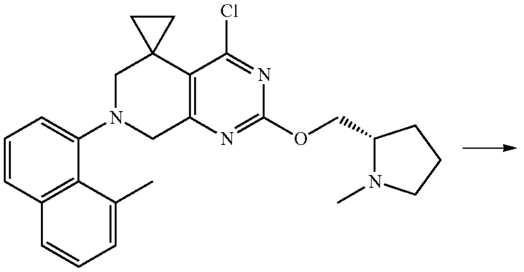

-continued

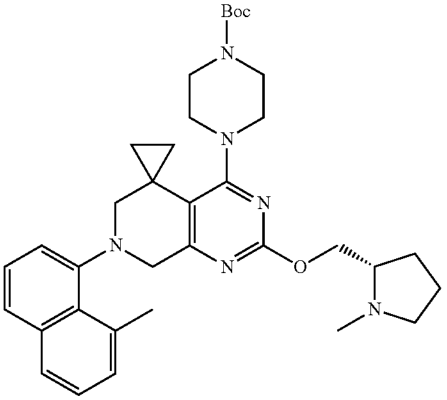

-continued

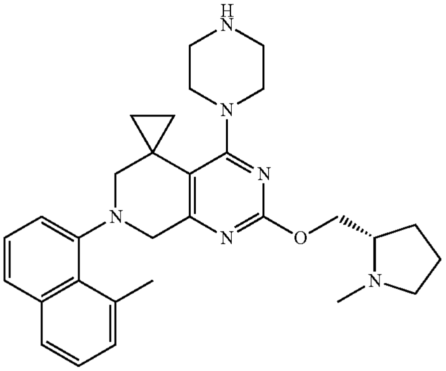

(S)-4'-chloro-7'-(8-methylnaphthalen-1-yl)-2'-((1-methylpyrrolidin-2-yl)methoxy)-7', 8'-dihydro-6'H-spiro[cyclopropane-1, 5'-pyrido [3, 4-d]pyrimidine] (180 mg, 0.40 mmol) was dissolved in DMF (10 mL); N-tert-butoxyacylpiperazine (224 mg, 1.20 mmol), DIPEA (155 mg, 1.20 mmol) were added thereto and the mixture was stirred at 80° C. for 3 hours under nitrogen protection. The mixture was cooled down, water was added thereto, and the mixture was extracted with ethyl acetate (3*20 mL). The organic phases were combined, dried over anhydrous sodium sulfate, concentrated to obtain the crude product, purified by column chromatography ($CH_2Cl_2$/MeOH=10:1) to obtain the target product tert-butyl (S)-4-(7'-(8-methylnaphthalen-1-yl)-2'-((1-methylpyrrolidin-2-yl)methoxy)-7', 8'-dihydro-6'H-spiro[cyclopropane-1, 5'-pyrido[3, 4-d]pyrimidin]-4'-yl)piperazine-1-carboxylate (120 mg, yield: 50%).

MS m/z (ESI): 599.1 $[M+H]^+$.

Step 10: Preparation of (S)-7'-(8-methylnaphthalen-1-yl)-2'-((1-methylpyrrolidin-2-yl)methoxy)-4'-(piperazin-1-yl)-7', 8'-dihydro-6'H-spiro[cyclopropane-1, 5'-pyrido[3, 4-d]pyrimidine]

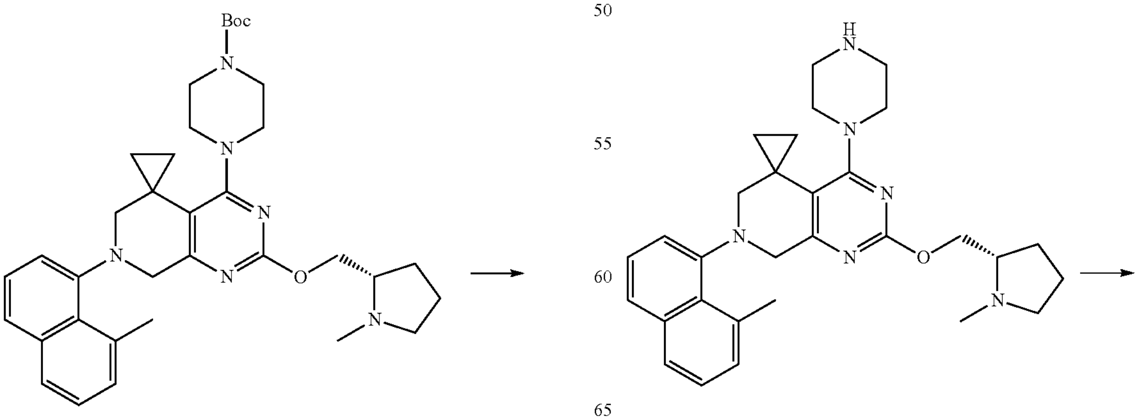

Tert-butyl (S)-4-(7'-(8-methylnaphthalen-1-yl)-2'-((1-methylpyrrolidin-2-yl)methoxy)-7', 8'-dihydro-6'H-spiro [cyclopropane-1, 5'-pyrido[3, 4-d]pyrimidin]-4'-yl)piperazine-1-carboxylate (110 mg, 0.18 mmol) was dissolved in dichloromethane (10 mL), TFA (0.5 mL) was added thereto and the mixture was stirred at room temperature for 2 hours. The mixture was adjusted to neutral with saturated $NaHCO_3$ aqueous solution and extracted three times with dichloromethane (3*20 mL). The organic phases were combined, dried over anhydrous sodium sulfate, and concentrated to obtain the target product (S)-7'-(8-methylnaphthalen-1-yl)-2'-((1-methylpyrrolidin-2-yl)methoxy)-4'-(piperazin-1-yl)-7', 8'-dihydro-6'H-spiro[cyclopropan-1, 5'-pyrido[3, 4-d]pyrimidine] (130 mg, crude product).

MS m/z (ESI): 499.1 $[M+H]^+$.

Step 11: Preparation of (S)-1-(4-(7'-(8-methylnaphthalen-1-yl)-2'-((1-methylpyrrolidin-2-yl)methoxy)-7', 8'-dihydro-6'H-spiro[cyclopropane-1, 5'-pyrido[3, 4-d]pyrimidin]-4'-yl)piperazin-1-yl)prop-2-en-1-one -continued

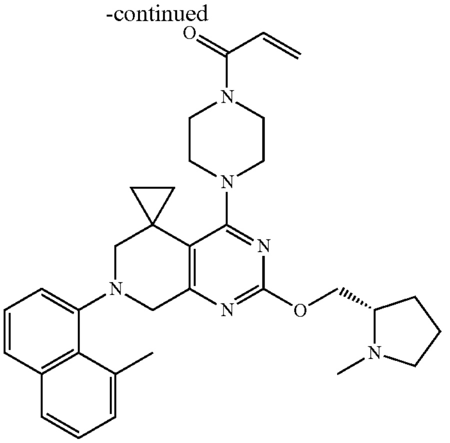

(S)-7'-(8-methylnaphthalen-1-yl)-2'-((1-methylpyrrolidin-2-yl)methoxy)-4'-(piperazin-1-yl)-7', 8'-dihydro-6'H-spiro[cyclopropane-1, 5'-pyrido[3, 4-d]pyrimidine] (130 mg, 0.18 mmol) was dissolved in dichloromethane (10 mL), DIPEA (71 mg, 0.55 mmol)) was added thereto, then acryloyl chloride (20 mg, 0.22 mmol) was added dropwise at room temperature, and the stirring was continued after the addition for 1 hour. The reaction mixture was quenched with water and extracted three times with dichloromethane (10 mL). The organic phases were combined, dried over anhydrous sodium sulfate, concentrated to obtain the crude product, and purified by preparative HPLC to obtain the target product (S)-1-(4-(7'-(8-methylnaphthalen-1-yl)-2'-((1-methylpyrrolidin-2-yl)methoxy)-7', 8'-dihydro-6'H-spiro[cyclopropane-1, 5'-pyrido[3, 4-d]pyrimidin]-4'-yl)piperazin-1-yl)prop-2-en-1-one (32 mg, yield: 32%).

MS m/z (ESI): 553.1 $[M+H]^+$.

The synthesis of embodiments 32-35 were carried out with reference to embodiment 31.

Embodiment 36

Preparation of 4-((2S, 5R)-4-acryloyl-2, 5-dimethylpiperazin-1-yl)-1-(4-fluoro-2-isopropylpyridin-3-yl)-7-(2-fluoro-6-hydroxyphenyl)-5, 6, 7, 8-tetrahydropyrido[3, 4-d]pyrimidin-2(1H)-one

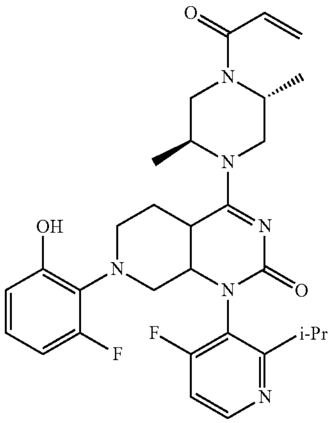 [SMILES: C=CC(=O)N1C[C@H](C)N(c2nc(=O)n(-c3c(F)ccnc3C(C)C)c3c2CCN(c2c(O)cccc2F)C3)C[C@H]1C]

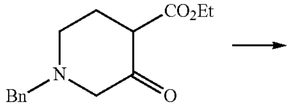

-continued

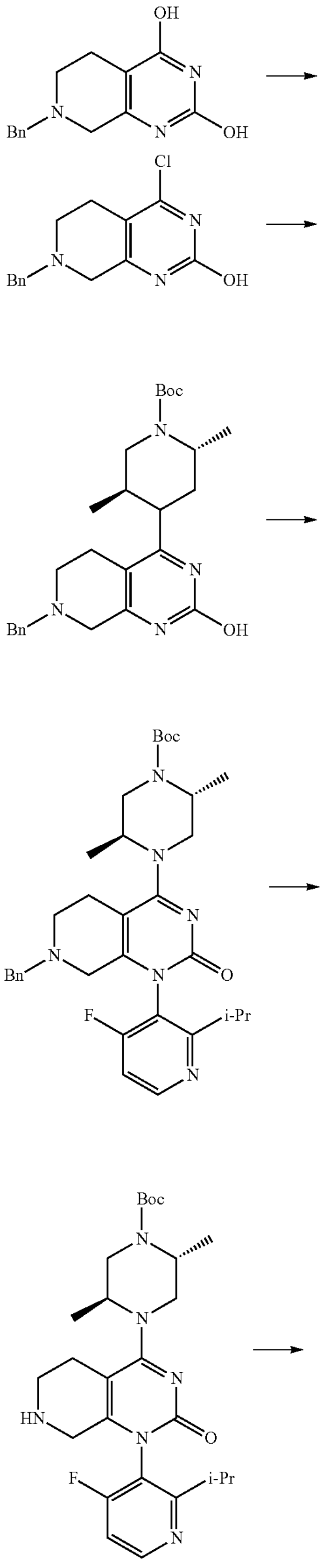

-continued

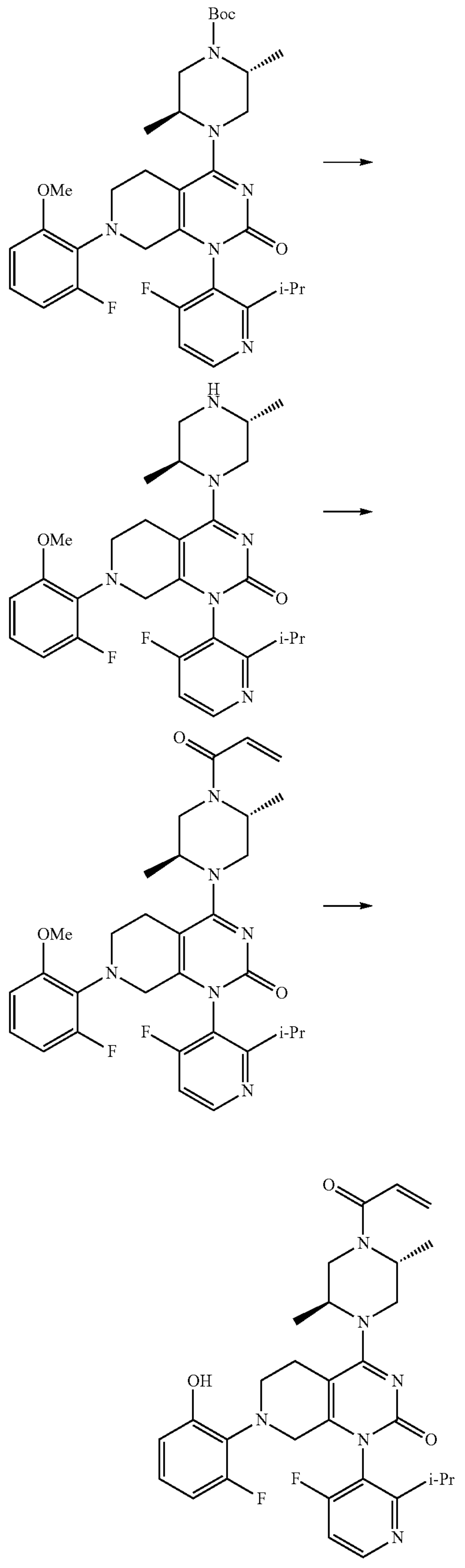

Step 1: Preparation of 7-benzyl-5, 6, 7, 8-tetrahydropyrido[3, 4-d]pyrimidin-2, 4-diol

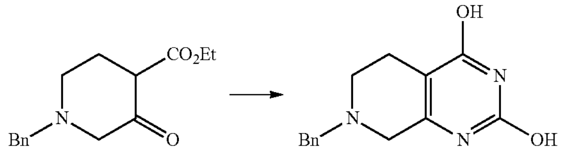 [SMILES: CCOC(=O)C1CCN(Cc2ccccc2)CC1=O ; Oc1nc(O)c2c(n1)CN(Cc1ccccc1)CC2]

Ethyl 1-benzyl-3-carbonylpiperidine-4-carboxylate (10 g, 38.3 mmol) was dissolved in EtOH (100 mL), urea (3.4 g, 57.5 mmol) was added thereto, and the mixture was stirred at 100° C. for 15 hours. The mixture was cooled to room temperature, water was added thereto, and extracted three times with ethyl acetate (20 mL). The organic phases were combined, dried over anhydrous sodium sulfate, concentrated to obtain the crude product, and purified by column chromatography ($CH_2Cl_2$/MeOH=10:1) to obtain the target product 7-benzyl-5, 6, 7, 8-tetrahydropyrido[3, 4-d]pyrimidin-2, 4-diol (8.7 g, yield: 89%).

MS m/z (ESI): 258.1 $[M+H]^+$.

Step 2: Preparation of 7-benzyl-4-chloro-5, 6, 7, 8-tetrahydropyrido[3, 4-d]pyrimidin-2-ol

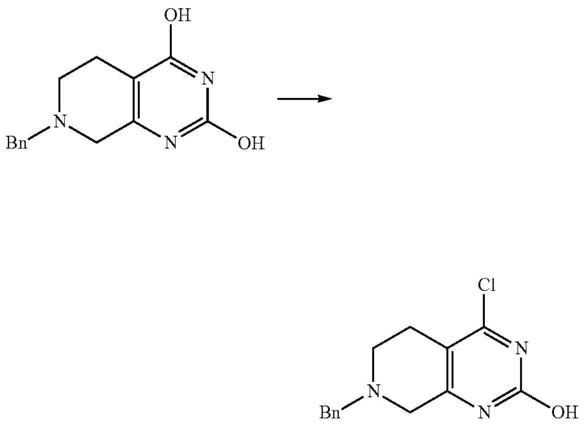

7-Benzyl-5, 6, 7, 8-tetrahydropyrido[3, 4-d]pyrimidin-2, 4-diol (8 g, 31.1 mmol) was dissolved in 100 mL of dioxane, the mixture was heat to 100° C., a dioxane solution (20 mL) of Lawson's reagent (6.3 g, 15.5 mmol) was added dropwise, and the reaction was carried out for 1 hour after the addition; then the temperature was cooled to room temperature, and the mixture was concentrated to remove the solvent, the solid was washed with a small amount of acetic acid, then washed with water and dried, $SOCl_2$ (50 mL) was added to the crude product in an ice-water bath, gradually warmed to room temperature, and stirred for 10 hours, then concentrated to remove excess $SOCl_2$ to obtain the crude target product 7-benzyl-4-chloro-5, 6, 7, 8-tetrahydropyrido[3, 4-d]pyrimidin-2-ol (7.5 g, crude product), which was directly used in the next reaction.

MS m/z (ESI): 276.1 $[M+H]^+$, 278.1$[M+2+H]^+$.

Step 3: Preparation of tert-butyl (2R, 5S)-4-(7-benzyl-2-hydroxy-5, 6, 7, 8-tetrahydropyrido[3, 4-d] pyrimidin-4-yl)-2, 5-dimethylpiperazine-1-carboxylate

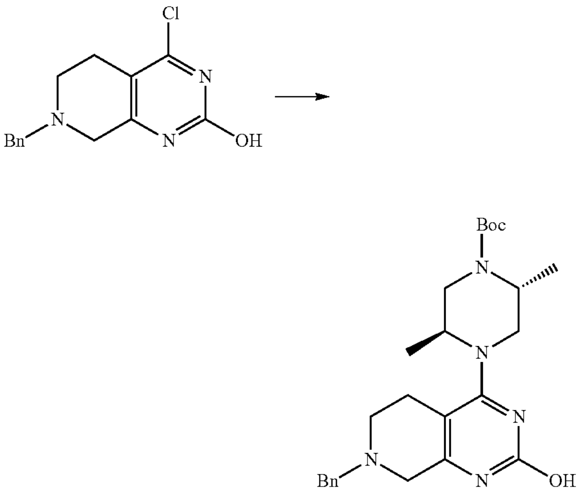

7-Benzyl-4-chloro-5, 6, 7, 8-tetrahydropyrido[3, 4-d]pyrimidin-2-ol (7.5 g, crude product) was dissolved in DMF (50 mL); tert-butyl (2R, 5S)-2, 5-dimethylpiperazine-1-carboxylate (8.7 g, 40.8 mmol) and DIPEA (10.5 g, 81.6 mmol) were added, then the mixture was stirred at 80° C. for 3 hours under nitrogen protection. The mixture was cooled down, water was added thereto, and the mixture was extracted with ethyl acetate (3*50 mL). The organic phases were combined, dried over anhydrous sodium sulfate, concentrated to obtain the crude product, and purified by column chromatography ($CH_2Cl_2$/MeOH=10:1) to obtain the target product tert-butyl (2R, 5S)-4-(7-benzyl-2-hydroxy-5, 6, 7, 8-tetrahydropyrido[3, 4-d]pyrimidin-4-yl)-2, 5-dimethylpiperazine-1-carboxylate (5.3 g, two-step yield: 38%).

MS m/z (ESI): 454.1 $[M+H]^+$.

Step 4: Preparation of tert-butyl (2R, 5S)-4-(7-benzyl-1-(4-fluoro-2-isopropylpyridin-3-yl)-2-carbonyl-1, 2, 5, 6, 7, 8-hexahydropyrido[3, 4-d]pyrimidin-4-yl)-2, 5-dimethylpiperazine-1-carboxylate

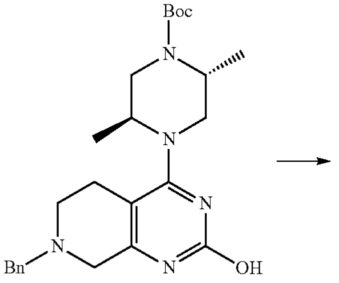

-continued

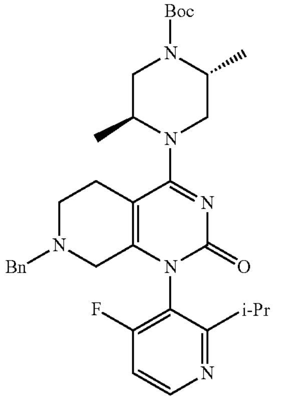

Tert-butyl (2R, 5S)-4-(7-benzyl-2-hydroxy-5, 6, 7, 8-tetrahydropyrido[3, 4-d]pyrimidin-4-yl)-2, 5-dimethylpiperazine-1-carboxylate (1 g, 2.2 mmol) was dissolved in dichloromethane (50 mL); (4-fluoro-2-isopropylpyridin-3-yl) boric acid (806 mg, 4.4 mmol), copper acetate (72 mg, 0.4 mmol), pyridine (348 mg, 4.4 mmol) and molecular sieve were added, the mixture was stirred overnight at room temperature under open conditions. The mixture was washed with saturated $Na_2CO_3$ aqueous solution and water, the organic phase was dried over anhydrous sodium sulfate, concentrated to obtain the crude product, and purified by column chromatography ($CH_2Cl_2$/MeOH=10:1) to obtain the target product tert-butyl (2R, 5S)-4-(7-benzyl-1-(4-fluoro-2-isopropylpyridin-3-yl)-2-carbonyl-1, 2, 5, 6, 7, 8-hexahydropyrido[3, 4-d]pyrimidin-4-yl)-2, 5-dimethylpiperazine-1-carboxylate (650 mg, yield: 50%).

MS m/z (ESI): 591.1 $[M+H]^+$.

Step 5: Preparation of tert-butyl (2R, 5S)-4-(1-(4-fluoro-2-isopropylpyridin-3-yl)-2-carbonyl-1, 2, 5, 6, 7, 8-hexahydropyrido[3, 4-d]pyrimidin-4-yl)-2, 5-dimethylpiperazine-1-carboxylate

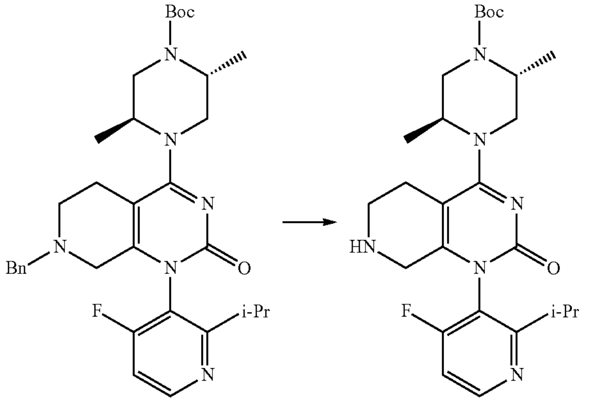 [SMILES: CC(C)c1nccc(F)c1-n1c2c(c(N3C[C@@H](C)N(C(=O)OC(C)(C)C)C[C@@H]3C)nc1=O)CCN(Cc1ccccc1)C2 ; CC(C)c1nccc(F)c1-n1c2c(c(N3C[C@@H](C)N(C(=O)OC(C)(C)C)C[C@@H]3C)nc1=O)CCNC2]

Tert-buty (2R, 5S)-4-(7-benzyl-1-(4-fluoro-2-isopropylpyridin-3-yl)-2-carbonyl-1, 2, 5, 6, 7, 8-hexahydropyrido[3, 4-d]pyrimidin-4-yl)-2, 5-dimethylpiperazine-1-carboxylate (600 mg, 1.0 mmol) was dissolved in EtOH (20 mL), $Pd(OH)_2/C$ (60 mg) was added, the mixture was replaced with hydrogen for 3 times and stirred for 15 hours at room temperature under hydrogen balloon. The mixture was filtered, washed with ethanol, and concentrated to obtain the target product tert-butyl (2R, 5S)-4-(1-(4-fluoro-2-isopropylpyridin-3-yl)-2-carbonyl-1, 2, 5, 6, 7, 8-hexahydropyrido[3, 4-d]pyrimidin-4-yl)-2, 5-dimethylpiperazine-1-carboxylate (420 mg, yield: 83%).

MS m/z (ESI): 501.1 $[M+H]^+$.

Step 6: Preparation of tert-butyl (2R, 5S)-4-(1-(4-fluoro-2-isopropylpyridin-3-yl)-7-(2-fluoro-6-methoxyphenyl)-2-carbonyl-1, 2, 5, 6, 7, 8-hexahydropyrido[3, 4-d]pyrimidin-4-yl)-2, 5-dimethylpiperazine-1-carboxylate

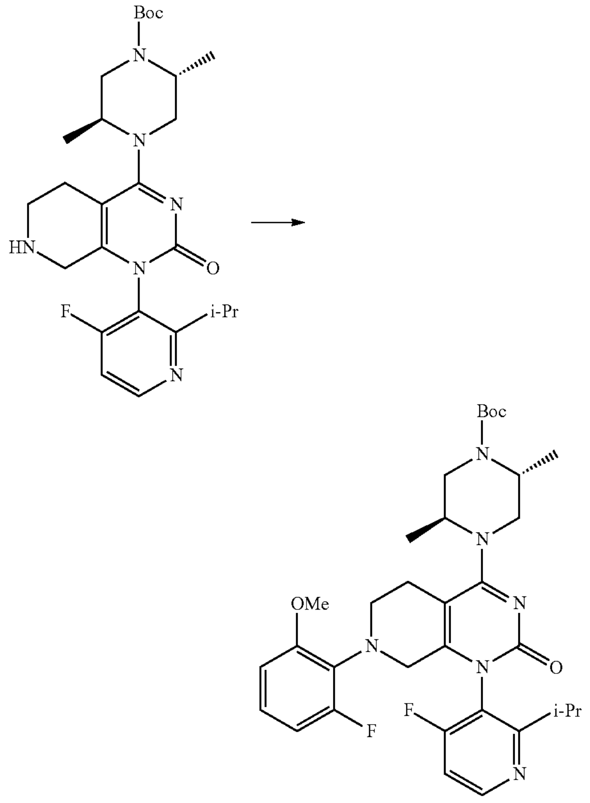

Tert-butyl (2R, 5S)-4-(1-(4-fluoro-2-isopropylpyridin-3-yl)-2-carbonyl-1, 2, 5, 6, 7, 8-hexahydropyrido[3, 4-d]pyrimidin-4-yl)-2, 5-dimethylpiperazine-1-carboxylate (400 mg, 0.8 mmol) was dissolved in toluene (20 mL); and 2-bromo-1-fluoro-3-methoxybenzene (326 mg, 1.6 mmol), $Pd_2(dba)_3$ (92 mg, 0.1 mmol), RuPhos (93 mg, 0.2 mmol) and $Cs_2CO_3$ (105 mg, 3.2 mmol) were added thereto, the mixture was replaced with nitrogen for 3 times, and the reaction mixture was stirred at 100° C. for 15 hours. The mixture was concentrated to remove toluene and extracted with water and ethyl acetate (3*30 mL). The organic phases were combined, dried over anhydrous sodium sulfate, concentrated to obtain the crude product, and purified by column chromatography ($CH_2Cl_2$/MeOH=10:1) to obtain the target product tert-butyl (2R, 5S)-4-(1-(4-fluoro-2-isopropylpyridin-3-yl)-7-(2-fluoro-6-methoxyphenyl)-2-carbonyl-1, 2, 5, 6, 7, 8-hexahydropyrido[3, 4-d]pyrimidin-4-yl)-2, 5-dimethylpiperazine-1-carboxylate (270 mg, yield: 54%).

MS m/z (ESI): 625.1 $[M+H]^+$.

Step 7: Preparation of 4-((2S, 5R)-2, 5-dimethylpiperazin-1-yl)-1-(4-fluoro-2-isopropylpyridin-3-yl)-7-(2-fluoro-6-methoxyphenyl)-5, 6, 7, 8-tetrahydropyrido[3, 4-d]pyrimidin-2(1H)-one

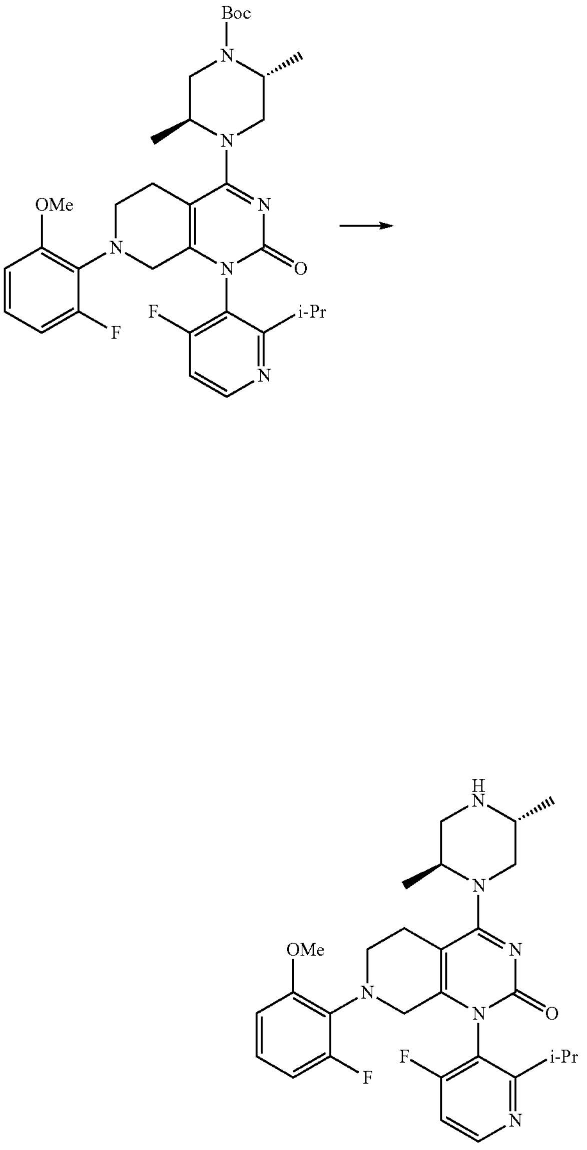

Tert-butyl (2R, 5S)-4-(1-(4-fluoro-2-isopropylpyridin-3-yl)-7-(2-fluoro-6-methoxyphenyl)-2-carbonyl-1, 2, 5, 6, 7, 8-hexahydropyrido[3, 4-d]pyrimidin-4-yl)-2, 5-dimethylpiperazine-1-carboxylate (250 mg, 0.4 mmol) was dissolved in dichloromethane (10 mL), trifluoroacetic acid (0.5 mL) was added thereto, and the mixture was stirred at room temperature for 3 hours, then concentrated to obtain the crude target product 4-((2S, 5R)-2, 5-dimethylpiperazin-1-yl)-1-(4-fluoro-2-isopropylpyridin-3-yl)-7-(2-fluoro-6-methoxyphenyl)-5, 6, 7, 8-tetrahydropyrido[3, 4-d]pyrimidin-2(1H)-one (320 mg, crude product).

MS m/z (ESI): 525.1 $[M+H]^+$.

Step 8: Preparation of 4-((2S, 5R)-4-acryloyl-2, 5-dimethylpiperazin-1-yl)-1-(4-fluoro-2-isopropylpyridin-3-yl)-7-(2-fluoro-6-methoxyphenyl)-5, 6, 7, 8-tetrahydropyrido[3, 4-d]pyrimidin-2(1H1)-one

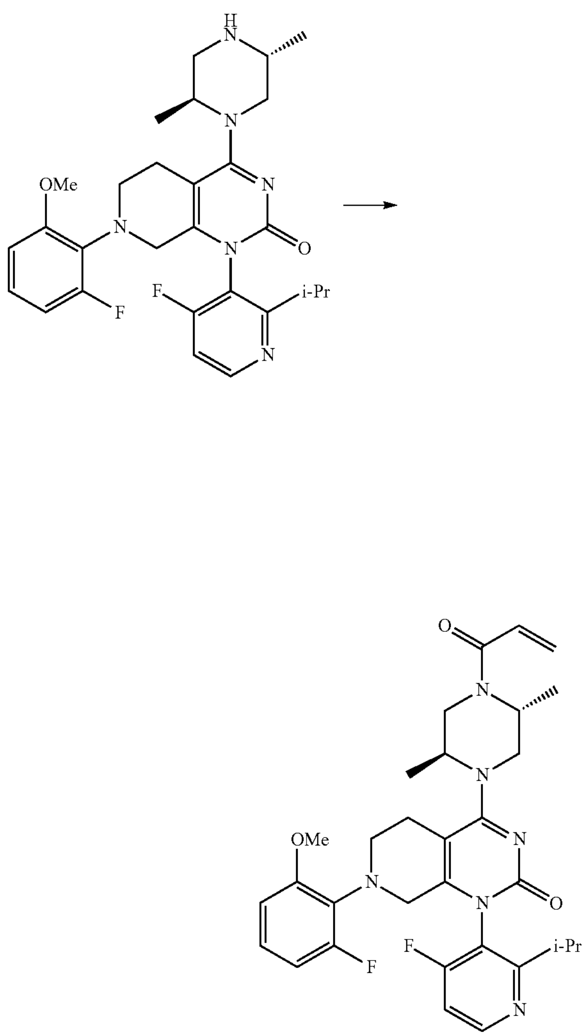

4-((2S, 5R)-2, 5-dimethylpiperazin-1-yl)-1-(4-fluoro-2-isopropylpyridin-3-yl)-7-(2-fluoro-6-methoxyphenyl)-5, 6, 7, 8-tetrahydropyrido[3, 4-d]pyrimidin-2(1H)-one (320 mg, 0.4 mmol) was dissolved in dichloromethane (10 mL), DIPEA (155 mg, 1.2 mmol) was added, acryloyl chloride (45 mg, 0.5 mmol) was added dropwise at room temperature, and the stirring was continued after the addition for 1 hour. The reaction mixture was quenched with water and extracted three times with dichloromethane (10 mL). The organic phases were combined, dried over anhydrous sodium sulfate, concentrated to obtain the crude product, and purified by column chromatography ($CH_2Cl_2$/MeOH=10:1) to obtain the target product 4-((2S, 5R)-4-acryloyl-2, 5-dimethylpiperazin-1-yl)-1-(4-fluoro-2-isopropylpyridin-3-yl)-7-(2-fluoro-6-methoxyphenyl)-5, 6, 7, 8-tetrahydropyrido[3, 4-d]pyrimidin-2(1H)-one (170 mg, yield: 74%).

MS m/z (ESI): 579.1 $[M+H]^+$.

Step 9: Preparation of 4-((2S, 5R)-4-acryloyl-2, 5-dimethylpiperazin-1-yl)-1-(4-fluoro-2-isopropylpyridin-3-yl)-7-(2-fluoro-6-hydroxyphenyl)-5, 6, 7, 8-tetrahydropyrido[3, 4-d]pyrimidin-2(1H)-one

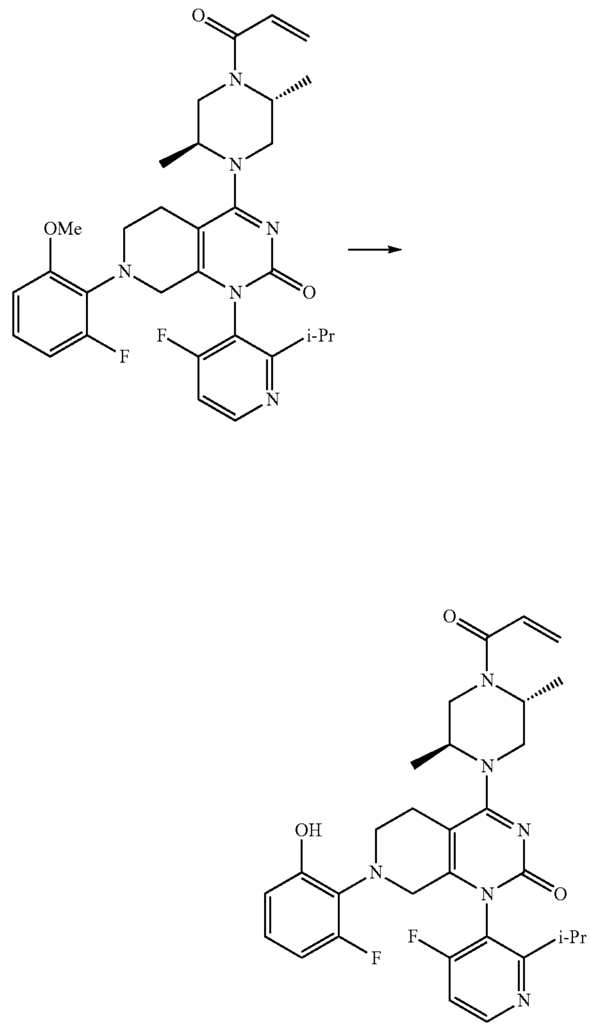

4-((2S, 5R)-4-acryloyl-2, 5-dimethylpiperazin-1-yl)-1-(4-fluoro-2-isopropylpyridin-3-yl)-7-(2-fluoro-6-methoxyphenyl)-5, 6, 7, 8-tetrahydropyrido[3, 4-d]pyrimidin-2(1H)-one (150 mg, 0.26 mmol) was dissolved in dichloromethane (10 mL) and the mixture was cooled to −40° C., $BBr_3$ (650 mg, 2.60 mmol) was added dropwise, then the mixture was brought to room temperature and stirred for 1 hour. The mixture was quenched with saturated $NaHCO_3$ aqueous solution and extracted with dichloromethane (3*20 mL). The organic phases were combined, dried over anhydrous sodium sulfate, concentrated to obtain the crude product, and purified by preparative HPLC to obtain the target product 4-((2S, 5R)-4-acryloyl-2, 5-dimethylpiperazin-1-yl)-1-(4-fluoro-2-isopropylpyridin-3-yl)-7-(2-fluoro-6-hydroxyphenyl)-5, 6, 7, 8-tetrahydropyrido[3, 4-d]pyrimidin-2(1H)-one (52 mg, yield: 36%).

MS m/z (ESI): 565.1 $[M+H]^+$.

The synthesis of embodiments 37-50 were carried out with reference to embodiment 36.

Embodiment 51

Preparation of 6-fluoro-7-(2-fluoro-6-hydroxyphenyl)-1-(2-isopropyl-4-methylpyridin-3-yl)-4-(4-(3-methyl-2-oxopyrrolindin-1-yl)piperidin-1-yl)pyrido [2, 3-d]pyrimidin-2(1H)-one

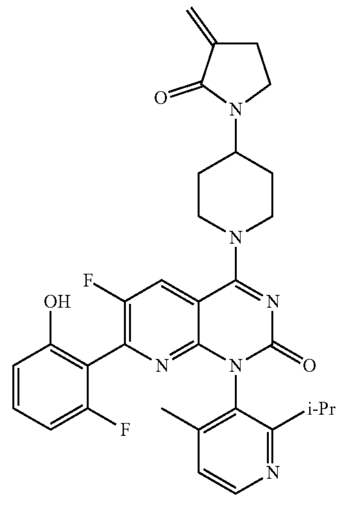 [SMILES: C=C1CCN(C2CCN(c3nc(=O)n(-c4c(C)ccnc4C(C)C)c4nc(-c5c(O)cccc5F)c(F)cc34)CC2)C1=O]

Step 1: Preparation of tert-butyl 4-(4-chlorobutanamido)piperidine-1-carboxylate

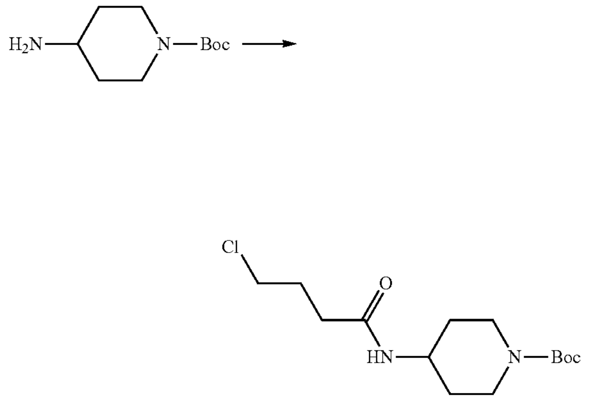

Tert-butyl 4-aminopiperidine-1-carboxylate (5 g, 24.9 mmol) and 4-chlorobutyryl chloride (4.2 g, 29.8 mmol) were dissolved in $CH_2Cl_2$ (50 mL), DIPEA (6.5 g, 49.8 mmol) was added thereto under ice bath conditions and the mixture was stirred for 4 hours at room temperature. Water was added thereto and the mixture was extracted three times with $CH_2Cl_2$ (50 mL). The organic phases were combined, dried over anhydrous sodium sulfate, filtered, concentrated to obtain the crude product, and purified by column chromatography (Petro ether/EtOAc=4:1) to obtain the target product tert-butyl 4-(4-chlorobutanamido)piperidine-1-carboxylate (7.2 g, yield: 94%).

MS m/z (ESI): 305.2 $[M+H]^+$.

Step 2: Preparation of tert-butyl 4-(2-oxopyrrolindin-1-yl)piperidine-1-carboxylate

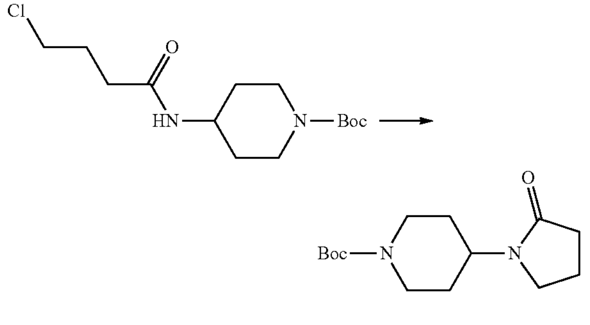

Tert-butyl 4-(4-chlorobutanamido)piperidine-1-carboxylate (1.0 g, 3.3 mmol) was dissolved in THF (10 mL), NaH (0.26 g, 6.6 mmol) was added under an ice bath, the temperature was raised to reflux and stirred for 16 hours, the mixture was extracted three times with water and ethyl acetate (50 mL). The organic phases were combined, dried over anhydrous sodium sulfate, filtered, concentrated to obtain the crude product, and purified by column chromatography (Petro ether/EtOAc=2:1) to obtain the target product tert-butyl 4-(2-oxopyrrolindin-1-yl)piperidine-1-carboxylate (0.85 g, yield: 94%).

MS m/z (ESI): 269.1 $[M+H]^+$.

Step 3: Preparation of tert-butyl 4-(3-(ethoxycarbonyl)-2-oxopyrrolindin-1-yl)piperidine-1-carboxylate

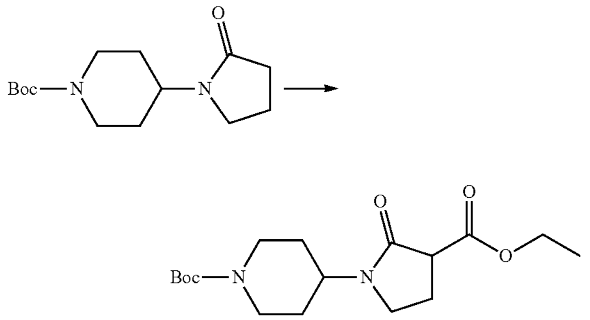

Tert-butyl 4-(2-oxopyrrolindin-1-yl)piperidin2-1-carboxylate (0.5 g, 1.86 mmol) was dissolved in anhydrous THF (10 mL), and the mixture was cooled to −78° C. under nitrogen protection, then LiHMDS (3.8 mL, 3.72 mmol) was added, and the mixture was stirred for 1 hour. Diethyl carbonate (0.44 g, 3.72 mmol) was added thereto and the mixture was stirred at −78° C. for 1 hour, then gradually brought to room temperature. The stirring was continued for 2 hours. The reaction mixture was then quenched with water, then extracted three times with ethyl acetate (3*10 mL) and water. The organic phases were combined, dried over anhydrous sodium sulfate, filtered, and concentrated to obtain the crude product tert-butyl 4-(3-(ethoxycarbonyl)-2-oxopyrrolindin-1-yl)piperidine-1-carboxylate (0.6 g, crude product).

Step 4: Preparation of 1-(1-(tert-butoxycarbonyl) piperidin-4-yl)-2-oxopyrrolindine-3-carboxylic acid

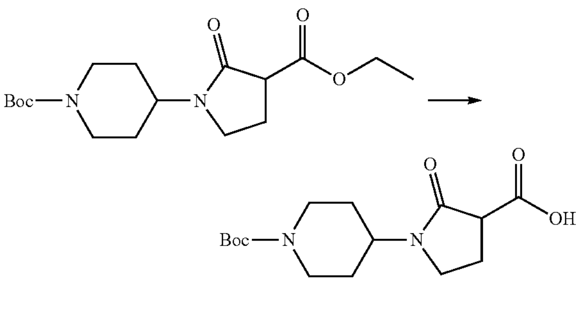

Tert-butyl 4-(3-(ethoxycarbonyl)-2-oxopyrrolindin-1-yl) piperidine-1-carboxylate (0.6 g, crude product) was dissolved in MeOH/$H_2O$ (1:1, 20 mL), and lithium hydroxide (89 mg, 2.1 mmol) was added and the mixture was stirred at room temperature overnight. The pH value of the mixture was adjusted to 5.0-6.0 by adding 20% acetic acid aqueous solution. The reaction mixture was extracted with dichloromethane (3*15 mL) and water. The organic phases were combined, dried over anhydrous sodium sulfate, filtered, and concentrated to obtain the crude target product 1-(1-(tert-butoxycarbonyl)piperidin-4-yl)-2-oxopyrrolindin-3-carboxylic acid (0.52 g, yield: 79%).

MS m/z (ESI): 311.1 $[M+H]^+$.

Step 5: Preparation of tert-butyl 4-(3-methylene-2-oxopyrrolindin-1-yl)piperidine-1-carboxylate

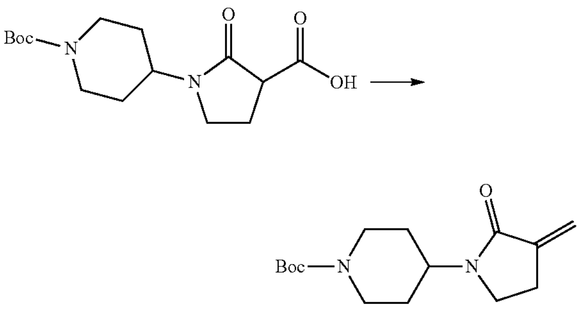

1-(1-(Tert-butoxycarbonyl)piperidin-4-yl)-2-oxopyrrolindin-3-carboxylic acid (0.5 g, crude product), paraformaldehyde (72 mg, 2.4 mmol) were dissolved in ethyl acetate (10 mL), diethylamine (0.14 g, 1.9 mmol) was added to the reaction mixture under ice bath condition, and then the reaction mixture was moved to reflux under heating and stirred for 3 hours. The mixture was cooled down, water was added thereto, and the mixture was extracted with ethyl acetate (3*10 mL). The organic phases were combined, dried over anhydrous sodium sulfate, filtered, concentrated, and purified by column chromatography (Petro ether/EtOAc=2:1) to obtain the target product tert-butyl 4-(3-methylene-2-oxopyrrolindin-1-yl)piperidine-1-carboxylate (0.36 g, yield: 80%).

MS m/z (ESI): 281.1 $[M+H]^+$.

Step 6: Preparation of 3-methylene-1-(piperidin-4-yl)pyrrolindin-2-one hydrochloride

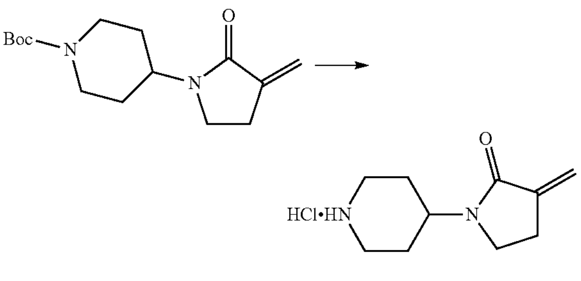

Tert-butyl 4-(3-methylene-2-oxopyrrolindin-1-yl)piperidine-1-carboxylic acid (100 mg, 0.35 mmol) was dissolved in 2M HCl/EtOH (5 mL), the mixture was stirred at room temperature for 2 hours, concentrated to remove solvent to obtain the crude product 3-methylene-1-(piperidin-4-yl) pyrrolindin-2-one hydrochloride (80 mg, crude product).

MS m/z (ESI): 181.1 $[M+H]^+$.

Step 7: Preparation of 7-chloro-6-fluoro-1-(2-isopropyl-4-methylpyridin-3-yl)-4-(4-(3-methyl-2-oxopyrrolindin-1-yl) piperidin-1-yl) pyrido[2, 3-d] pyrimidin-2 (1H)-one

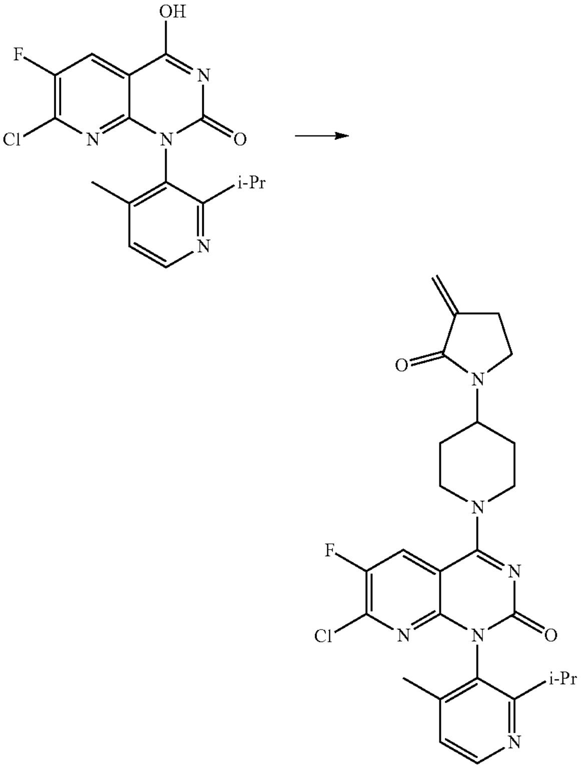

N, N-diisopropylethylamine (0.14 g, 1.11 mmol) was added to a solution of 7-chloro-6-fluoro-4-hydroxy-1-(2-isopropyl-4-methylpyridin-3-yl)pyrido[4, 3-d]pyrimidin-2 (1H)-one (130 mg, 0.37 mmol) in acetonitrile (10 mL), then phosphorus oxychloride (167 mg, 1.11 mmol) was added thereto and the mixture was stirred at 80° C. for 1 hour at room temperature. Then the mixture was cooled to room temperature. N, N-diisopropylethylamine (0.14 g, 1.11 mmol) was added to the reaction mixture and stirred for 5 minutes after the addition, 3-methylene-1-(piperidin 4-yl) pyrrolindin-2-one hydrochloride (80 mg, crude product) was added and stirred for 1 hour. The reaction mixture was quenched with ammonium chloride aqueous solution (10 mL), extracted with ethyl acetate (30 mL×3), the organic phase was washed with sodium chloride aqueous solution (10 mL) and evaporated to dryness, then purified by preparative chromatography [eluent: dichloromethane:methanol=20:1] to obtain a pale yellow solid product 7-chloro-6-fluoro-1-(2-isopropyl-4-methylpyridin-3-yl)-4-(4-(3-methyl-2-oxopyrrolindin-1-yl)piperidin-1-yl)pyrido[2, 3-d] pyrimidin-2 (1H)-one (52 mg, yield: 27%).

MS m/z (ESI): 511.2 [M+H]+.

Step 7: Preparation of 6-fluoro-7-(2-fluoro-6-hydroxyphenyl)-1-(2-isopropyl-4-methylpyridin-3-yl)-4-(4-(3-methyl-2-oxopyrrolindin-1-yl)piperidin-1-yl) pyrido[2, 3-d]pyrimidin-2(1H)-one

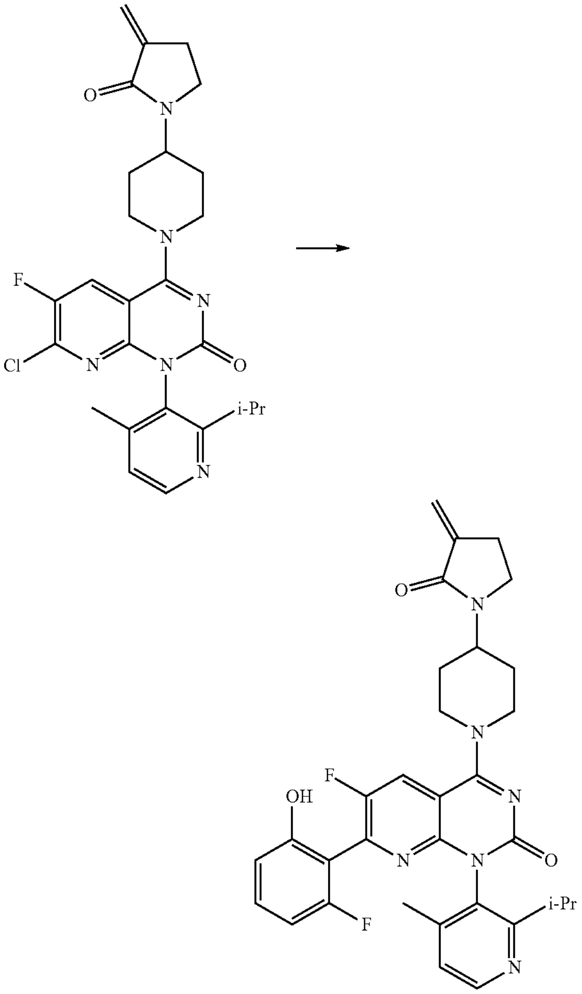

7-Chloro-6-fluoro-1-(2-isopropyl-4-methylpyridin-3-yl)-4-(4-(3-methyl-2-oxopyrrolindin-1-yl) piperidin-1-yl) pyrido[2, 3-d] pyrimidin-2 (1H)-one (52 mg, 0.10 mmol), (2-fluoro-6-hydroxyphenyl) boric acid (34 mg, 0.2 mmol), 1, 1'-bis(diphenylphphino) ferrocene-palladium (II) dichloride dichloromethane complex (9 mg, 0.01 mmol) and cesium carbonate (97 mg, 0.3 mmol) were dissolved in dioxane (4 mL) and water (1 mL), and the mixture was stirred at 100° C. under microwave for 1 hour. The reaction mixture was evaporated to dryness and purified by preparative HPLC to obtain the yellow solid product 6-fluoro-7-(2-fluoro-6-hydroxyphenyl)-1-(2-isopropyl-4-methylpyridin-3-yl)-4-(4-(3-methyl-2-oxopyrrolidin-1-yl)piperidin-1-yl)pyrido[2,3-d]pyrimidin-2(1H)-one (15 mg, yield: 25%).

MS m/z (ESI): 589.3 [M+H]+.

$^1$H NMR (400 MHz, $CDCl_3$) δ 9.39 (s, 1H), 8.65 (s, 1H), 7.96 (d, J=9.0 Hz, 1H), 7.30 (s, 2H), 6.82-6.57 (m, 2H), 6.04 (s, 1H), 5.39 (s, 1H), 4.75 (s, 2H), 4.50 (s, 1H), 3.45 (s, 4H), 2.83 (s, 2H), 2.06 (d, J=29.5 Hz, 7H), 1.29 (s, 3H), 1.12 (s, 3H).

The synthesis of embodiments 52 and 58-74 were carried out with reference to embodiment 51.

Embodiment 60

4-((S)-4-acryloyl-2-methylpiperazin-1-yl)-6-fluoro-7-(2-fluoro-6-hydroxyphenyl)-1-(2-isopropyl-4-(methylthio)pyridin-3-yl)pyrido[2, 3-d]pyrimidin-2 (1H)-one

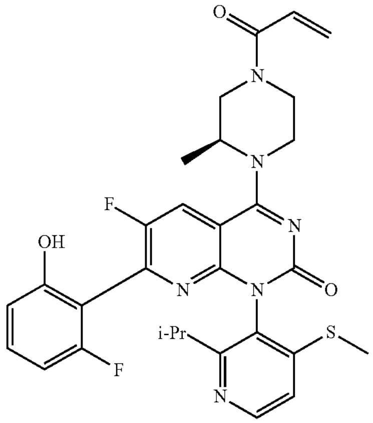

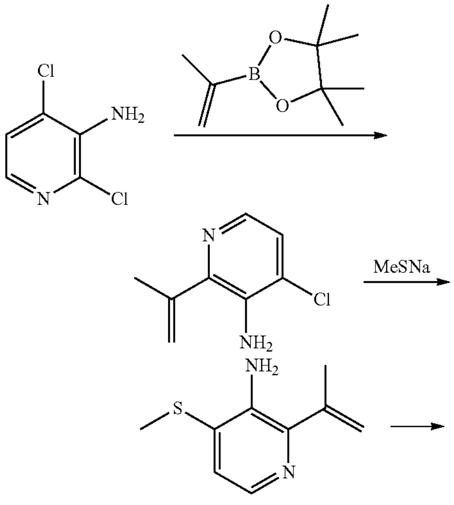

-continued
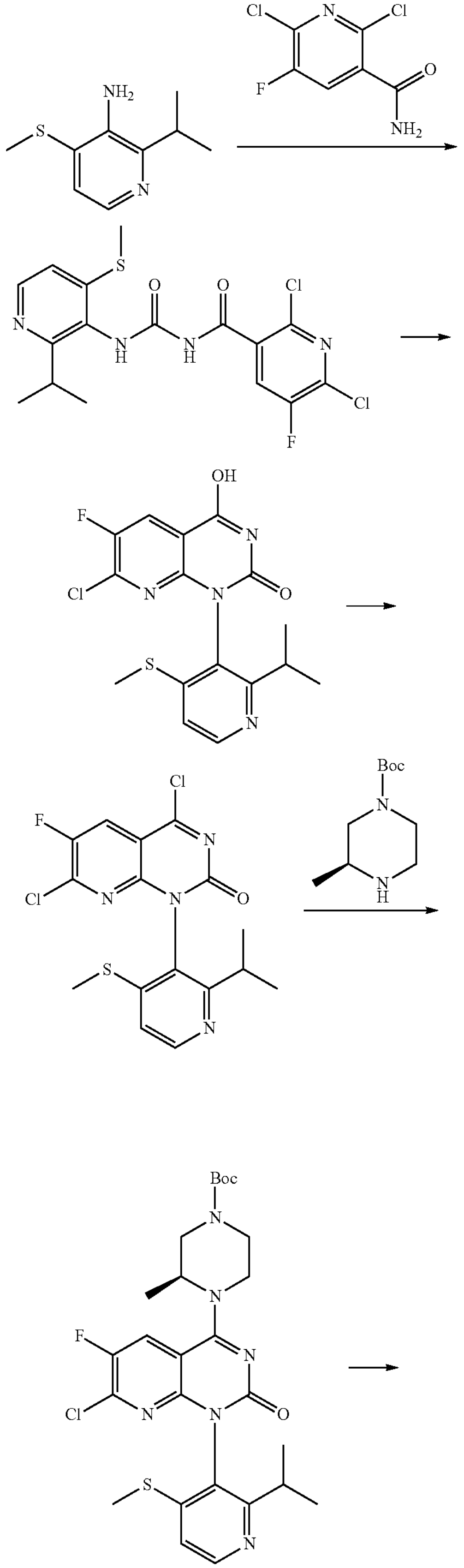
-continued
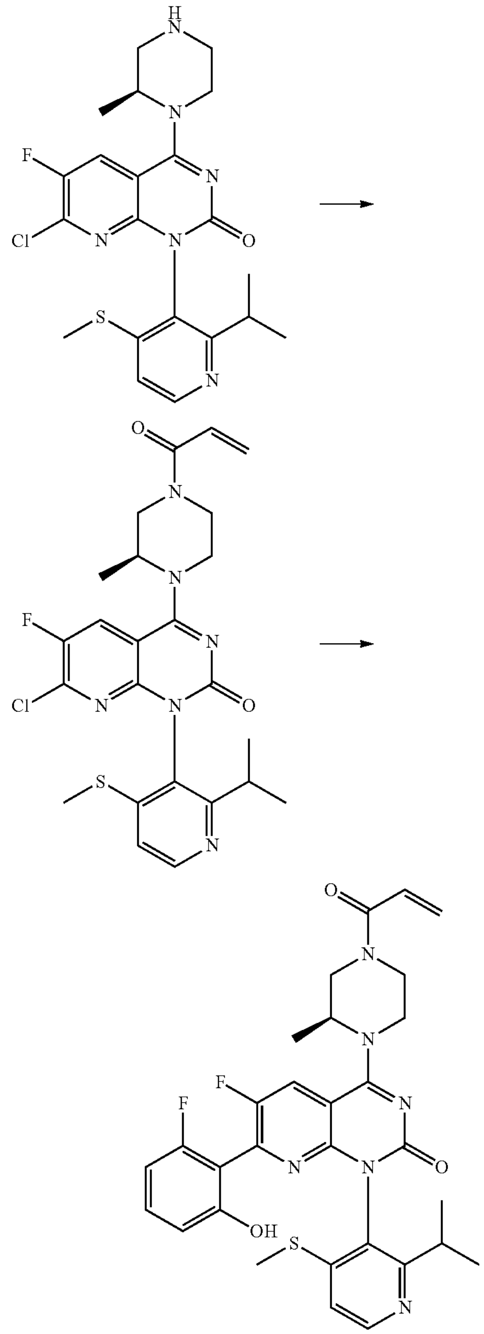
Step 1: Preparation of 4-chloro-2-(prop-1-en-2-yl) pyridin-3-amine
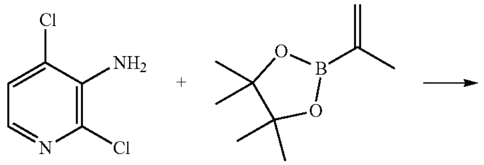

-continued

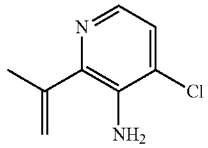

2, 4-Dichloropyridin-3-amine (4.5 g, 27.78 mmol), 4, 4, 5, 5-trimethyl-2-(prop-1-en-2-yl)-1, 3, 2-dioxaborolane (5.13 g, 30.56 mmol), potassium carbonate (11.5 g, 83.34 mmol), $Pd(PPh_3)_4$ were added to dioxane (120 mL), and the reaction mixture was uniformly mixed and stirred overnight under the condition of oil bath at 100° C. The mixture was concentrated under reduced pressure and purified by rapid silica gel column chromatography to obtain the target compound 4-chloro-2-(prop-1-en-2-yl) pyridin-3-amine as a colorless oily liquid (4.5 g, yield: 96%).

MS m/z (ESI): 169.1 $[M+H]^+$.

Step 2: Preparation of 4-(methylthio)-2-(prop-1-en-2-yl) pyridin-3-amine

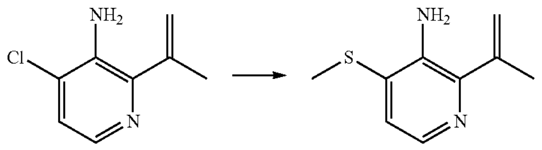

4-Chloro-2-(prop-1-en-2-yl)pyridin-3-amine (2 g, 11.9 mmol) and sodium thiomethoxide (10 mL, 20% aqueous solution) were added to dioxane (3 mL), the reaction mixture was uniformly mixed, the reaction mixture was reacted at 100° C. for 2 days, cooled to room temperature, and concentrated under reduced pressure, the crude product was separated and purified by rapid silica gel column chromatography to obtain the compound 4-(methylthio)-2-(prop-1-en-2-yl) pyridin-3-amine as a pale yellow liquid (1.7 g, yield: 79%).

MS m/z (ESI): 181.2 $[M+H]^+$.

Step 3: Preparation of 2-isopropyl-4-(methylthio) pyridin-3-amine

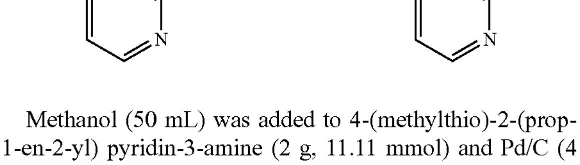

Methanol (50 mL) was added to 4-(methylthio)-2-(prop-1-en-2-yl) pyridin-3-amine (2 g, 11.11 mmol) and Pd/C (4 g), the reaction mixture was uniformly mixed, and then the reaction was carried out overnight at room temperature and the mixture was concentrated under reduced pressure. The resulting crude product was added to a mixed solution of methanol (5 mL), N, N-diisopropylethylamine (0.5 mL) and acrylonitrile (1 mL) and the reaction was carried out at room temperature for 2 hours. The mixture was concentrated under reduced pressure and purified by rapid silica gel column chromatography to obtain the compound 2-isopropyl-4-(methylthio)pyridin-3-amine as a colorless liquid (500 mg, yield: 25%).

MS m/z (ESI): 183.2 $[M+H]^+$.

Step 4: Preparation of 2, 6-dichloro-5-fluoro-N-(2-isopropyl-4-(methylthio) pyridin-3-yl) carbamoyl) nicotinamide

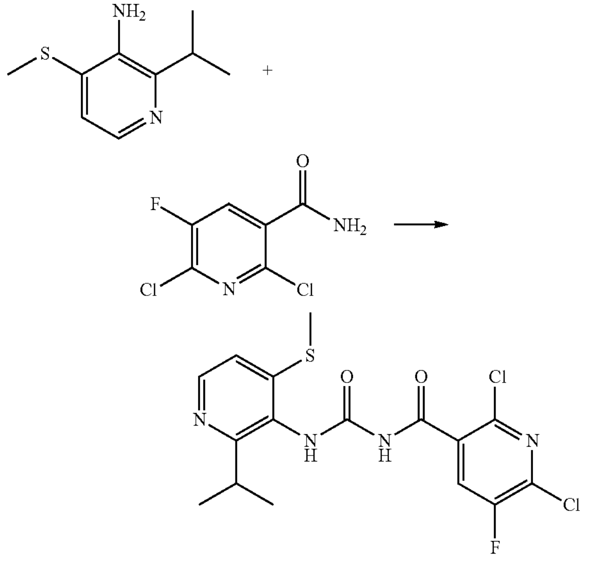

THF (10 mL) was added to 2, 6-dichloro-5-fluoronicotinamide (500 mg, 2.44 mmol) and oxalyl chloride (1.32 mL, 2.54 mmol), and the reaction mixture was uniformly mixed and the reaction was carried out at 60° C. for 3 hours, the reaction temperature was reduced to room temperature, and triethylamine (680 mg, 6.6 mmol) and 2-isopropyl-4-(methylthio)pyridin-3-amine (400 mg, 2.2 mmol) were added, and the reaction was carried out at room temperature for 1 hour, the crude product was purified by rapid silica gel column chromatography to obtain the compound 2, 6-dichloro-5-fluoro-N-((2-isopropyl-4-(methylthio)pyridin-3-yl)carbamoyl)nicotinamide as a white solid (800 mg, yield: 87%).

MS m/z (ESI): 417.1 $[M+H]^+$.

Step 5: Preparation of 7-chloro-6-fluoro-4-hydroxy-1-(2-isopropyl-4-(methylthio) pyridin-3-yl) pyrido [2, 3-d] pyrimidin-2 (1H)-one

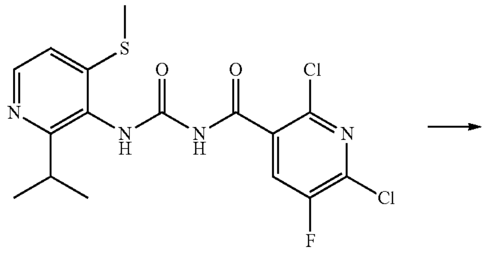

-continued

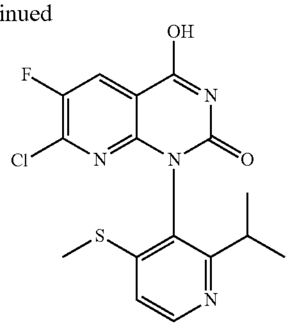

2, 6-Dichloro-5-fluoro-N-((2-isopropyl-4-(methylthio) pyridin-3-yl)carbamoyl)nicotinamide (800 mg, 1.92 mmol) was added to THF (20 mL), and the reaction mixture was uniformly mixed, KHMDS (4.8 mL, 4.8 mmol) was added slowly at 0° C., and the reaction was carried out at room temperature for 1 hour, the crude product was concentrated under reduced pressure and purified by rapid silica gel column chromatography to obtain the compound 7-chloro-6-fluoro-4-hydroxy-1-(2-isopropyl-4-(methylthio)pyridin-3-yl) pyrido[2, 3-d]pyrimidin-2(1H)-one as a white solid (600 mg, yield: 82%).

MS m/z (ESI): 381.1 [M+H]$^+$.

Step 6: Preparation of tert-butyl (S)-4-(7-chloro-6-fluoro-1-(2-isopropyl-4-(methylthio)pyridin-3-yl)-2-carbonyl-1, 2-dihydropyrido[2, 3-d]pyrimidin-4-yl)-3-methylpiperazine-1-carboxylate

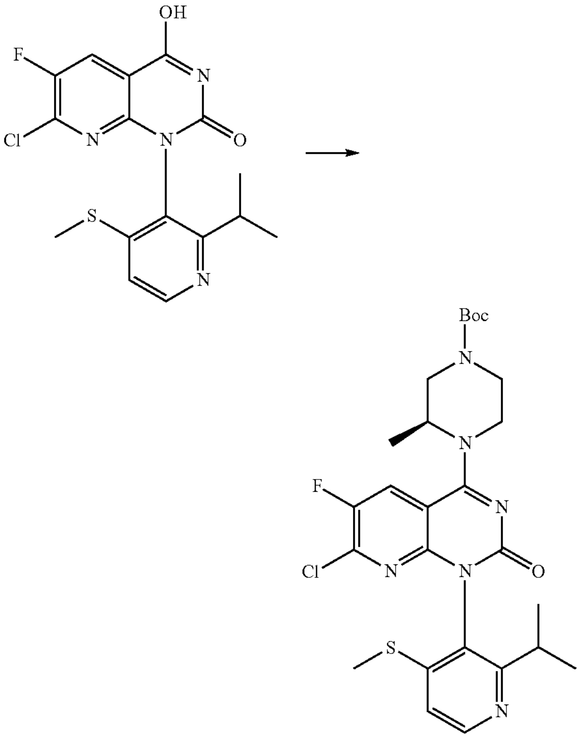

7-Chloro-6-fluoro-4-hydroxy-1-(2-isopropyl-4-(methylthio)pyridin-3-yl)pyrido[2, 3-d]pyrimidin-2 (1H)-one (300 mg, 0.79 mmol), phosphorus oxychloride (600 mg, 3.95 mmol), DIPEA (1 g, 7.9 mmol) were added to THF (40 mL), the reaction mixture was uniformly mixed, and the reaction was carried out at 80° C. for 1 hour, the reaction temperature was cooled to room temperature, and tert-butyl (S)-3-methylpiperazine-1-carboxylate (240 mg, 1.19 mmol) was slowly added to the reaction solution, then the reaction was carried out at room temperature for 1 hour, the mixture was concentrated under reduced pressure, and the crude product was separated and purified by rapid silica gel column chromatography to obtain tert-butyl (S)-4-(7-chloro-6-fluoro-1-(2-isopropyl-4-(methylthio)pyridin-3-yl)-2-carbonyl-1, 2-dihydropyrido [2, 3-d] pyrimidin-4-yl)-3-methylpiperazine-1-carboxylate as a white solid (400 mg, yield: 90%).

MS m/z (ESI): 563.1 [M+H]$^+$.

Step 7: Preparation of (S)-4-(4-acryloyl-2-methylpiperazin-1-yl)-7-chloro-6-fluoro-1-(2-isopropyl-4-(methylthio)pyridin-3-yl)pyrido[2, 3-d]pyrimidin-2(1H)-one

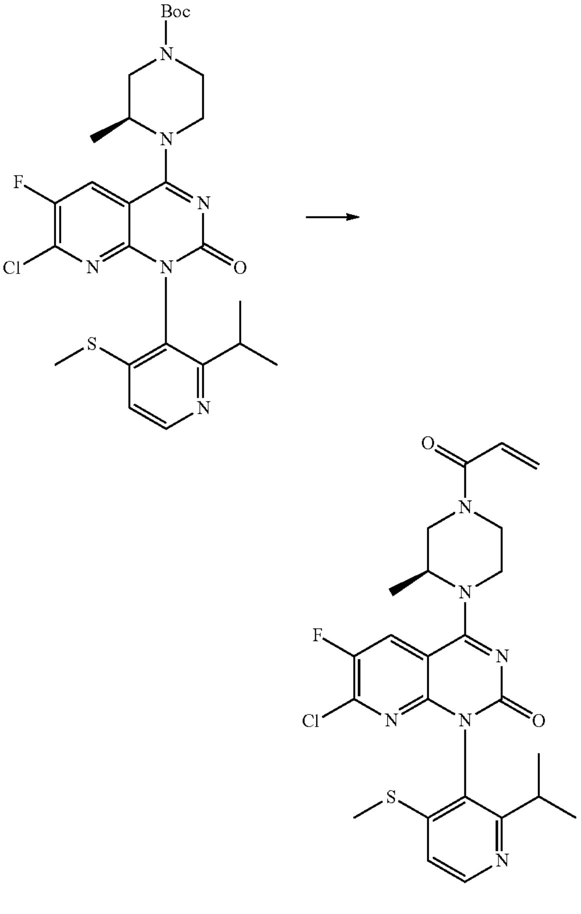

Tert-butyl (S)-4-(7-chloro-6-fluoro-1-(2-isopropyl-4-(methylthio) pyridin-3-yl)-2-carbonyl-1, 2-dihydropyrido [2, 3-d] pyrimidin-4-yl)-3-methylpiperazine-1-carboxylate (400 mg, 0.71 mmol), TFA (2 mL) were added to $CH_2Cl_2$ (30 mL), the reaction mixture was uniformly mixed, and the reaction was carried out at room temperature for 1 hour, then the mixture was concentrated under reduced pressure, $CH_2Cl_2$ (20 mL) and DIPEA (0.3 mL) were added to the crude product, the reaction temperature was reduced to 0° C., acryloyl chloride (0.1 mL) was slowly added thereto, and the reaction was carried out at room temperature for 1 hour, the mixture was then concentrated under reduced pressure. The resulting crude product was separated and purified by rapid silica gel column chromatography to obtain the compound (S)-4-(4-acryloyl-2-methylpiperazin-1-yl)-7-chloro-6-fluoro-1-(2-isopropyl-4-(methylthio) pyridin-3-yl) pyrido [2, 3-d]pyrimidin-2 (1H)-one as a yellow solid (200 mg, yield: 55%).

MS m/z (ESI): 517.1 [M+H]$^+$.

Step 8: Preparation of 4-((S)-4-acryloyl-2-methylpiperazin-1-yl)-6-fluoro-7-(2-fluoro-6-hydroxyphenyl)-1-(2-isopropyl-4-(methylthio) pyridin-3-yl) pyrido [2, 3-d] pyrimidin-2 (1H)-one

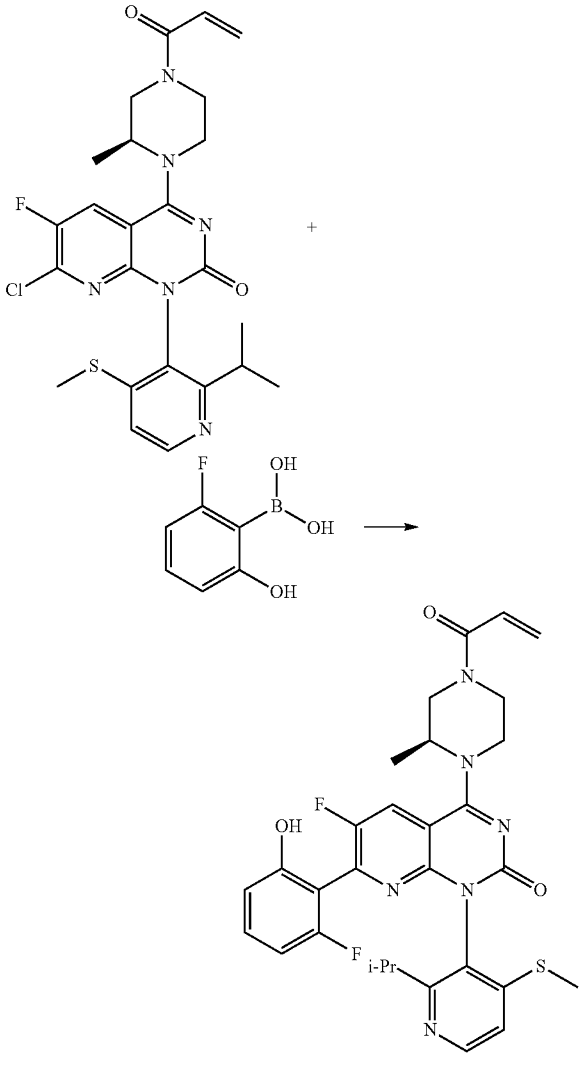

(S)-4-(4-acryloyl-2-methylpiperazin-1-yl)-7-chloro-6-fluoro-1-(2-isopropyl-4-(methylthio) pyridin-3-yl) pyrido [2, 3-d] pyrimidin-2 (1H)-one (50 mg, 0.1 mmol), (2-fluoro-6-hydroxyphenyl) boric acid (30 mg, 0.2 mmol), Pd(dppf) $Cl_2$ (16 mg, 0.02 mmol) and cesium carbonate (100 mg, 0.3 mmol) were added to dixoane (1.5 mL), the reaction mixture was uniformly mixed, and then the reaction was carried out at 100° C. under microwave for 1 hour, then the mixture was concentrated under reduced pressure, $CH_2Cl_2$ (20 mL) and DIPEA (0.3 mL) were added into the crude product, and the reaction temperature was reduced to 0° C., acryloyl chloride (0.1 mL) was slowly added thereto, and the reaction was carried out at room temperature for 1 hour, then the mixture was concentrated under reduced pressure. The resulting crude product was separated and purified by Pre-HPLC to obtain the compound 4-((S)-4-acryloyl-2-methylpiperazin-1-yl)-6-fluoro-7-(2-fluoro-6-hydroxyphenyl)-1-(2-isopropyl-4-(methylthio)pyridin-3-yl) pyrido [2, 3-d] pyrimidin-2 (1H)-one as a white solid (14 mg, yield: 24%).

MS m/z (ESI): 593.1 [M+H]$^+$.

$^1$H NMR (400 MHz, MeOD-$d_4$) δ 8.40 (d, J=5.6 Hz, 1H), 8.22-8.27 (m, 1H), 7.21-7.27 (m, 2H), 6.79-6.88 (m, 1H), 6.58-6.66 (m, 2H), 6.28-6.34 (m, 1H), 5.84 (d, J=12.0 Hz, 1H), 5.06 (s, 1H), 4.43-4.59 (m, 2H), 4.07-4.23 (s, 1H), 3.57-3.85 (m, 2H), 3.20-3.48 (m, 1H), 2.79-2.85 (m, 1H), 2.41 (s, 3H), 1.47 (d, J=4.8 Hz, 3H), 1.20 (d, J=6.4 Hz, 3H), 1.06 (d, J=6.8 Hz, 3H).

Embodiment 60-1 and Embodiment 60-2

(M/P-4-((S)-4-acryloyl-2-methylpiperazin-1-yl)-6-fluoro-7-(2-fluoro-6-hydroxyphenyl)-1-(2-isopropyl-4-(methylthio)pyridin-3-yl)pyrido[2, 3-d]pyrimidin-2(1H)-one)

60-1

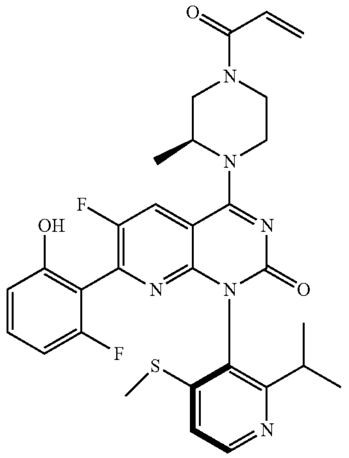

60-2

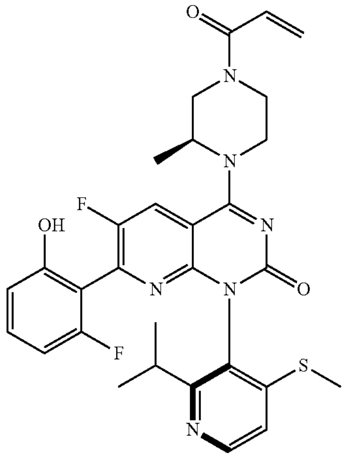

-continued

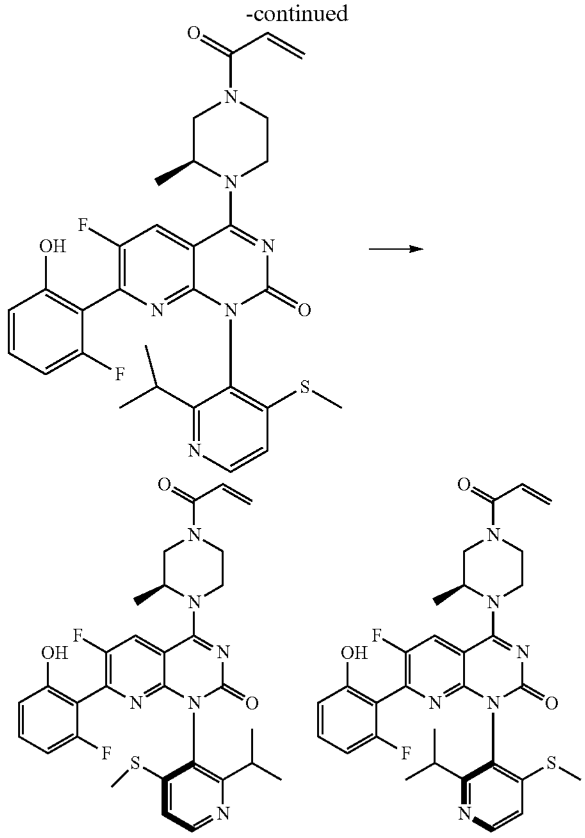

Embodiment 60 was resolved by SFC to obtain two axial chiral isomers, embodiment 60-1 and embodiment 60-2, SFC: chiral preparation conditions:

TABLE 13

| | |
|---|---|
| Instrument | SFC-150 (Thar, Waters) |
| Column type | IC 20*250 mm, 10 μm (Daicel) |
| Column pressure | 100 bar |
| Mobile phase | $CO_2$/Methanol (0.2% Methanol Ammonia) = 50/50 |
| Flow rate | 120 g/min |
| Detection wavelength | UV 214 nm |
| Column temperature | 35° C. |

Chiral Analysis Conditions:

TABLE 14

| | |
|---|---|
| Instrument | SFC Method Station (Thar, Waters) |
| Column type | Celluloe-SC 4.6 × 100 mm, 5 um (YMC) |
| Column pressure | 120 bar |
| Mobile phase | A: $CO_2$; B: Methanol [0.2% NH3(7M in methanol)]; A:B = 60:40 |
| Flow rate | 4 mL/min |
| Detection wavelength | UV 214 nm |
| Column temperature | 40° C. |

Embodiment 60-1

$t_R$=1.92 min

MS m/z (ESI): 593.1 $[M+H]^+$.

$^1$H NMR (400 MHz, MeOD-$d_4$) δ 8.40 (d, J=5.6 Hz, 1H), 8.22-8.27 (m, 1H), 7.21-7.27 (m, 2H), 6.79-6.88 (m, 1H), 6.58-6.66 (m, 2H), 6.28-6.34 (m, 1H), 5.84 (d, J=12.0 Hz, 1H), 5.06 (s, 1H), 4.43-4.59 (m, 2H), 4.07-4.23 (s, 1H), 3.57-3.85 (m, 2H), 3.20-3.48 (m, 1H), 2.79-2.85 (m, 1H), 2.41 (s, 3H), 1.47 (d, J=4.8 Hz, 3H), 1.20 (d, J=6.4 Hz, 3H), 1.06 (d, J=6.8 Hz, 3H).

Embodiment 60-2

$t_R$=2.43 min

MS m/z (ESI): 593.1 $[M+H]^+$.

$^1$HNMR (400 MHz, MeOD-$d_4$) δ 8.40 (d, J=5.6 Hz, 1H), 8.25 (t, J=10.8 Hz, 1H), 7.21-7.27 (m, 2H), 6.79-6.90 (m, 1H), 6.58-6.66 (m, 2H), 6.28-6.34 (m, 1H), 5.83 (dd, J=10.8 Hz, 2.0 Hz, 1H), 5.05-5.10 (m, 1H), 4.41-4.57 (m, 2H), 4.07-4.21 (m, 1H), 3.61-3.87 (m, 2H), 3.24-3.36 (m, 1H), 2.77-2.83 (m, 1H), 2.41 (s, 3H), 1.46-1.49 (m, 3H), 1.19 (d, J=6.8 Hz, 3H), 1.06 (d, J=6.8 Hz, 3H).

The synthesis of embodiments 70, 81-84, 114-117, 130-134 and 139-141 were carried out with reference to embodiment 60.

Embodiment 75

Preparation of (S)-4-(4-acryloyl-2-methylpiperazin-1-yl)-6-fluoro-7-(2-fluoro-6-(methylthio)phenyl)-1-(2-isopropyl-4-methylpyridin-3-yl) pyrido[2, 3-d] pyrimidin-2 (1H)-one

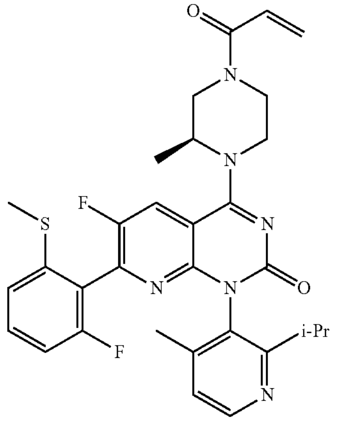 [SMILES: C=CC(=O)N1CCN(c2nc(=O)n(-c3c(C)ccnc3C(C)C)c3nc(-c4c(F)cccc4SC)c(F)cc23)[C@@H](C)C1]

Step 1: Preparation of (2-fluoro-6-(methylthio) phenyl) boric acid

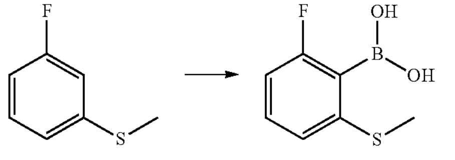

Lithium diisopropylamine (5.3 mL, 10.6 mmol) was added dropwise into a solution of (3-fluorophenyl)(methyl) sulfane (500 mg, 3.52 mmol) in tetrahydrofuran (15 mL) at −78° C., after addition, the dry ice bath was removed and the temperature was slowly raised to room temperature and stirred for 1 hour. The reaction mixture was quenched with hydrochloric acid (2N, 20 mmol) and stirred for another 30 minutes. The reaction mixture was extracted with ethyl acetate (40 mL×3), the organic phase was washed with saline (30 mL), concentrated and purified by column chromatography [eluent: petroleum ether-ethyl acetate/petroleum ether from 0% to 30%] to obtain (2-fluoro-6-(methylthio) phenyl) boric acid (73 mg, yield: 11%) as a white solid.

$^1$H NMR (400 MHz, $CDCl_3$) δ 7.43-7.33 (m, 1H), 7.24 (d, J=8 Hz, 1H), 7.01-6.93 (m, 1H), 6.08 (br, 2H), 2.51 (s, 3H).

Step 2: Preparation of (S)-4-(4-acryloyl-2-methylpiperazin-1-yl)-6-fluoro-7-(2-fluoro-6-(methylthio) phenyl)-1-(2-isopropyl-4-methylpyridin-3-yl) pyrido [2, 3-d] pyrimidin-2 (1H)-one

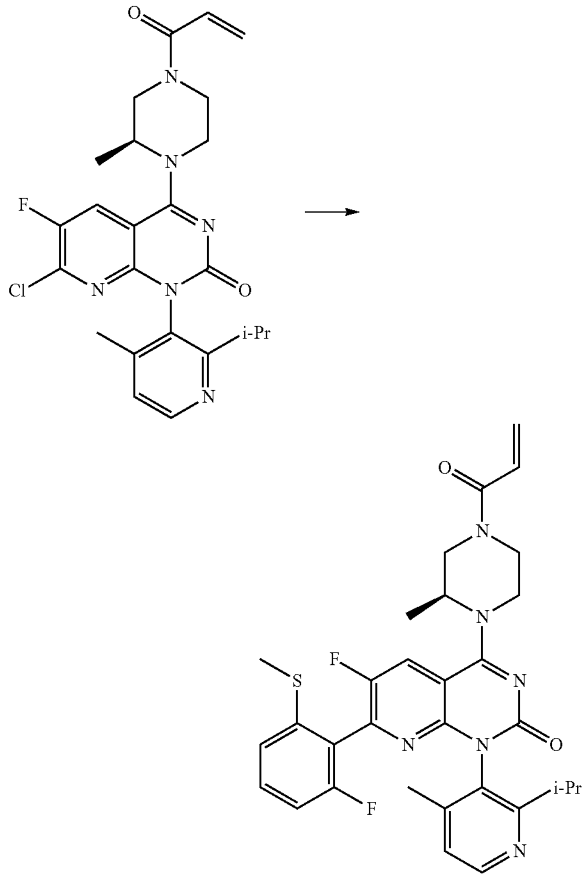

(S)-4-(4-acryloyl-2-methylpiperazin-1-yl)-7-chloro-6-fluoro-1-(2-isopropyl-4-methylpyridin-3-yl)pyrido[2, 3-d] pyrimidin-2(1H)-one (50 mg, 0.103 mmol), (2-fluoro-6-(methylthio)phenyl) boric acid (55 mg, 0.296 mmol), 1, 1'-bis(diphenylphosphino)ferrocene-palladium(II) dichloride dichloromethane complex (17 mg, 0.0206 mmol) and cesium carbonate (100 mg, 0.309 mmol) were dissolved in dioxane (2.5 mL) and water (3 drops), and the mixture was stirred at 100° C. for 1 hour under microwave. The reaction mixture was concentrated and purified by preparative chromatography [eluent: dichloromethane/methanol=12/1] to obtain 4-((S)-4-acryloyl-2-methylpiperazin-1-yl)-6-fluoro-7-(2-fluoro-6-(methylthio) phenyl)-1-(2-isopropyl-4-methylpyridin-3-yl) pyrido [2, 3-d] pyrimidin-2 (1H)-one (25 mg, yield: 41%) as a yellow solid.

MS m/z (ESI): 591.2 [M+H].

$^1$H NMR (400 MHz, MeOD-$d_4$) δ 8.42-8.24 (m, 2H), 7.49-7.39 (m, 1H), 7.27-7.16 (m, 2H), 6.97 (t, J=12 Hz, 1H), 6.85 (m, 1H), 6.31 (d, J=12 Hz, 1H), 5.83 (d, J=12 Hz, 1H), 5.22-5.00 (m, 1H), 4.65-4.37 (m, 2H), 4.28-4.02 (m, 1H), 3.99-3.54 (m, 2H), 3.49-3.35 (m, 1H), 2.94-2.70 (m, 1H), 2.33 (s, 3H), 2.04 (s, 3H), 1.60-1.41 (m, 3H), 1.18 (d, J=8 Hz, 3H), 1.00 (s, 3H).

Embodiment 75-1 and Embodiment 75-2

(M/P-4-((S)-4-acryloyl-2-methylpiperazin-1-yl)-6-fluoro-7-(2-fluoro-6-(methylthio)phenyl)-1-(2-isopropyl-4-methylpyridin-3-yl)pyrido[2, 3-d]pyrimidin-2(1H)-one)

75-1

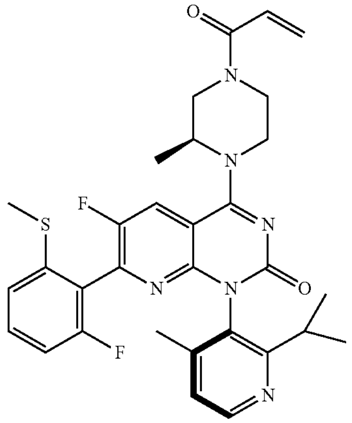

75-2

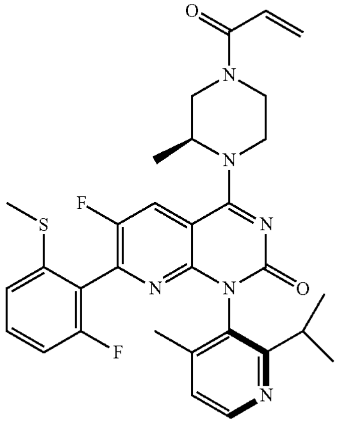

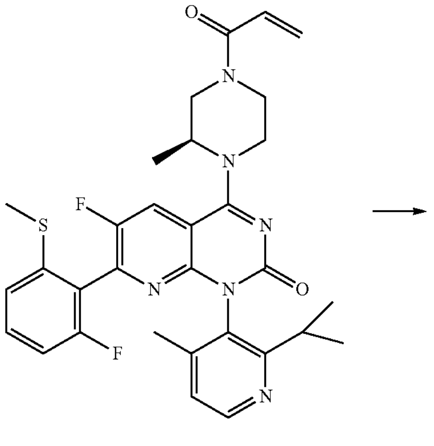

-continued

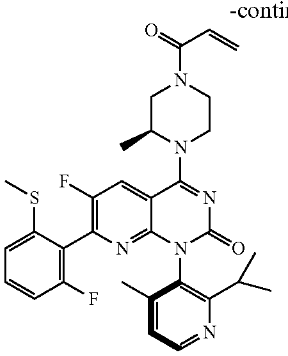

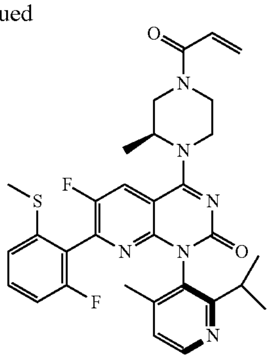

Embodiment 75 was resolved by SFC to obtain two axial chiral isomers, embodiment 75-1 and embodiment 75-2, SFC: chiral preparation conditions:

TABLE 15

| | |
|---|---|
| Instrument | SFC-150 (Thar, Waters) |
| Column type | IC 20 * 250 mm, 10 μm (Daicel) |
| Column pressure | 100 bar |
| Mobile phase | $CO_2$/Methanol (0.2% Methanol Ammonia) = 45/55 |
| Flow rate | 110 g/min |
| Detection wavelength | UV 214 nm |
| Column temperature | 35° C. |

Chiral Analysis Conditions:

TABLE 16

| | |
|---|---|
| Instrument | SFC Method Station (Thar, Waters) |
| Column type | Celluloe-SC 4.6% x 100 mm, 5 μm (YMC) |
| Column pressure | 120 bar |
| Mobile phase | A: $CO_2$; B: Methanol [0.2% NH3(7M in methanol)]; A:B = 60:40 |
| Flow rate | 4 mL/min |
| Detection wavelength | UV 214 nm |
| Column temperature | 40° C. |

Embodiment: 75-1

$t_R$=1.97 min

MS m/z (ESI): 591.2 $[M+H]^+$.

$^1$H NMR (400 MHz, MeOD-$d_4$) δ 8.42-8.24 (m, 2H), 7.49-7.39 (m, 1H), 7.27-7.16 (m, 2H), 6.97 (t, J=12 Hz, 1H), 6.85 (m, 1H), 6.31 (d, J=12 Hz, 1H), 5.83 (d, J=12 Hz, 1H), 5.22-5.00 (m, 1H), 4.65-4.37 (m, 2H), 4.28-4.02 (m, 1H), 3.99-3.54 (m, 2H), 3.49-3.35 (m, 1H), 2.94-2.70 (m, 1H), 2.33 (s, 3H), 2.04 (s, 3H), 1.60-1.41 (m, 3H), 1.18 (d, J=8 Hz, 3H), 1.00 (s, 3H).

Embodiment 75-2

$t_R$=3.75 min

MS m/z (ESI): 591.2 $[M+H]^+$.

$^1$H NMR (400 MHz, MeOD-$d_4$) δ 8.40-8.23 (m, 2H), 7.48-7.38 (m, 1H), 7.25-7.16 (m, 2H), 6.96 (t, J=12 Hz, 1H), 6.85 (m, 1H), 6.31 (d, J=12 Hz, 1H), 5.82 (d, J=12 Hz, 1H), 5.20-5.00 (m, 1H), 4.64-4.36 (m, 2H), 4.28-4.02 (m, 1H), 3.99-3.54 (m, 2H), 3.48-3.34 (m, 1H), 2.93-2.70 (m, 1H), 2.33 (s, 3H), 2.04 (s, 3H), 1.58-1.40 (m, 3H), 1.18 (d, J=8 Hz, 3H), 1.00 (s, 3H).

Embodiment 77

Preparation of (S)-4-(4-acryloyl-2-methylpiperazin-1-yl)-6-fluoro-1-(2-isopropyl-4-methylpyridin-3-yl)-7-(2-(methylsulfonyl-6-fluoro) phenyl) pyrido [2, 3-d] pyrimidin-2 (1H)-one

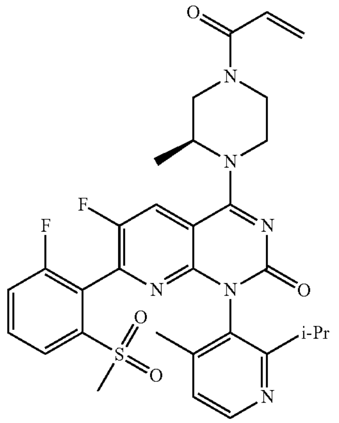 [SMILES: C=CC(=O)N1CCN(c2nc(=O)n(-c3c(C)ccnc3C(C)C)c3nc(-c4c(F)cccc4S(C)(=O)=O)c(F)cc23)[C@@H](C)C1]

MS m/z (ESI): 623.1 $[M+H]^+$.

$^1$H NMR (400 MHz, MeOD-$d_4$) δ 8.37 (d, J=4 Hz, 2H), 7.92 (d, J=4 Hz, 1H), 7.86-7.73 (m, 1H), 7.62 (t, J=8 Hz, 1H), 7.27-7.15 (m, 1H), 6.95-6.74 (m, 1H), 6.39-6.23 (m, 1H), 5.89-5.79 (m, 1H), 5.32-5.00 (m, 1H), 4.66-4.31 (m, 2H), 4.28-4.03 (m, 1H), 3.97-3.51 (m, 2H), 3.48-3.34 (m, 2H), 2.70 (s, 3H), 2.13 (s, 3H), 1.60-1.37 (m, 3H), 1.17-1.09 (m, 3H), 0.92 (d, J=8 Hz, 3H).

Embodiment 85

Preparation of 4-(4-acryloyl-2-vinylpiperazin-1-yl)-6-fluoro-7-(2-fluoro-6-hydroxyphenyl)-1-(2-isopropyl-4-methylpyridin-3-yl)pyrido[2, 3-d]pyrimidin-2 (1H)-one

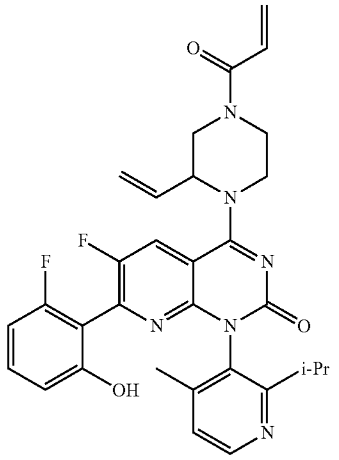

-continued
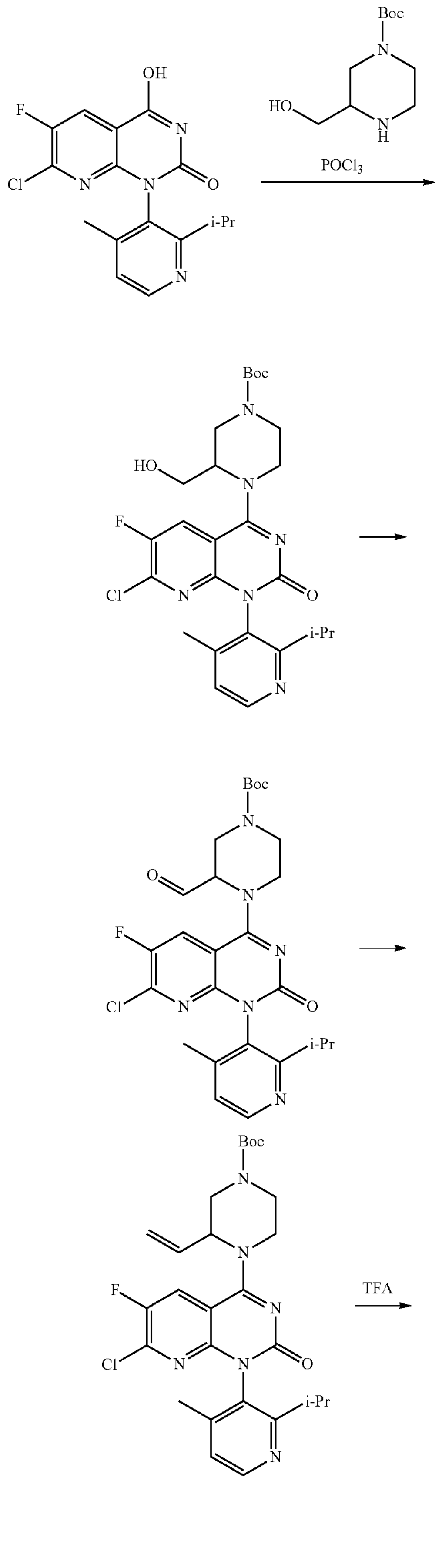
-continued
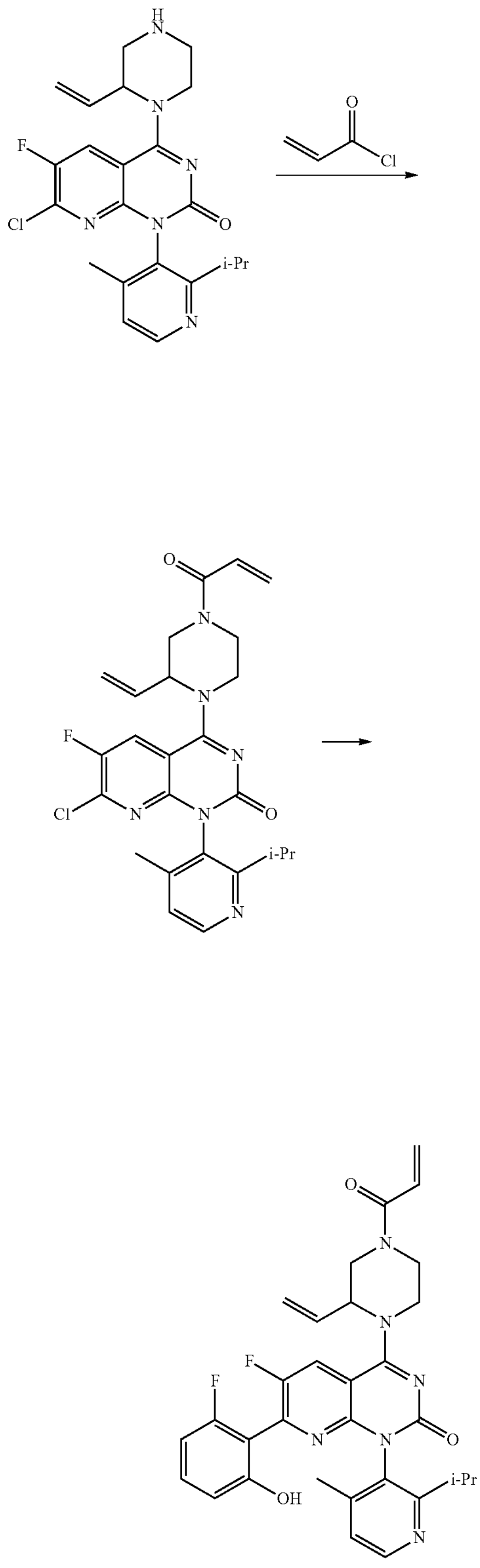

Step 1: Preparation of tert-butyl 4-(7-chloro-6-fluoro-1-(2-isopropyl-4-methylpyridin-3-yl)-2-carbonyl-1, 2-dihydropyrido[2, 3-d]pyrimidin-4-yl)-3-(hydroxymethyl)piperazine-1-carboxylate

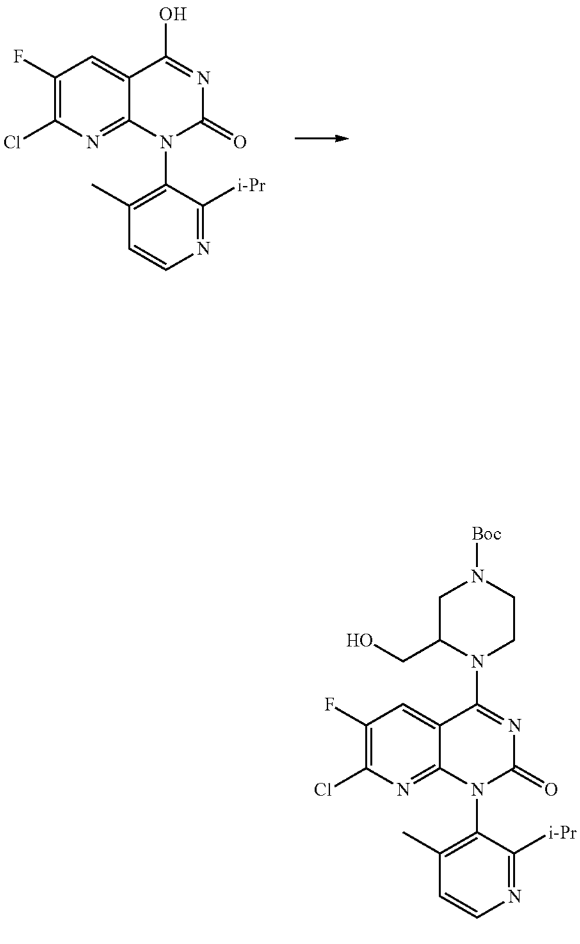

N, N-diisopropylethylamine (1.63 g, 12.9 mmol) was added to a solution of 7-chloro-6-fluoro-1-(2-isopropyl-4-methylpyridin-3-yl)pyrido[2, 3-d]pyrimidin-2, 4(1H, 3H)-dione (1.5 g, 4.3 mmol) in acetonitrile (50 mL) at room temperature, and then phosphorus oxychloride (1.94 g, 12.9 mmol) was added thereto, and the mixture was stirred at 80° C. for 1 hour. Then the mixture was cooled to room temperature. N, N-diisopropylethylamine (1.63 g, 12.9 mmol) was added to the reaction mixture and stirred for 5 minutes, then tert-butyl 3-(hydroxymethyl) piperazine-1-carboxylate (2.8 g, 12.9 mmol) was added thereto and stirred for 1 hour. The reaction mixture was quenched with ammonium chloride aqueous solution (10 mL), extracted with ethyl acetate (50 mL×3), washed with sodium chloride aqueous solution (30 mL), dried over anhydrous sodium sulfate, filtered, concentrated and purified by column chromatography ($CH_2Cl_2$:MeOH=10:1) to obtain tert-butyl 4-(7-chloro-6-fluoro-1-(2-isopropyl-4-methylpyridin-3-yl)-2-carbonyl-1, 2-dihydropyrido [2, 3-d] pyrimidin-4-yl)-3-(hydroxymethyl) piperazine-1-carboxylate (1.9 g, yield: 81%).

MS m/z (ESI): 547.1 $[M+H]^+$, 549.1 $[M+H+2]^+$.

Step 2: Preparation of tert-butyl 4-(7-chloro-6-fluoro-1-(2-isopropyl-4-methylpyridin-3-yl)-2-carbonyl-1, 2-dihydropyrido [2, 3-d] pyrimidin-4-yl)-3-formylpiperazine-1-carboxylate

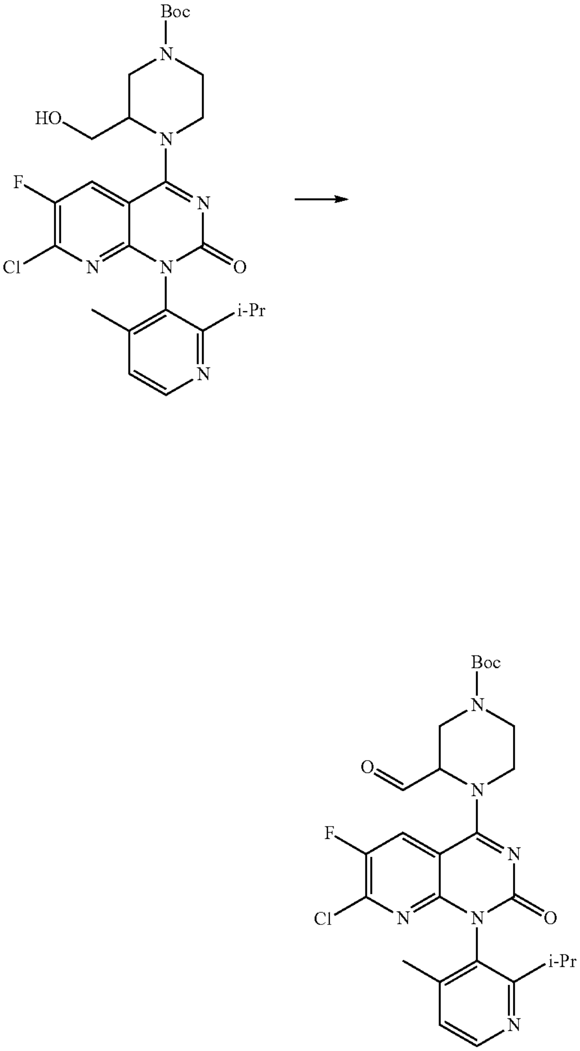

Tert-butyl 4-(7-chloro-6-fluoro-1-(2-isopropyl-4-methylpyridin-3-yl)-2-carbonyl-1, 2-dihydropyrido[2, 3-d]pyrimidin-4-yl)-3-(hydroxymethyl)piperazine-1-carboxylate (1.8 g, 3.3 mmol) was dissolved in dichloromethane (100 mL), Dess-Martin oxidant DMP (1.7 g, 4.0 mmol) was added thereto in batches at room temperature and stirred for 3 hours, the mixture was then filtered through celite, the filtrate was washed with saturated $NaHCO_3$ aqueous solution (30 mL) and then washed with saturated saline (30 mL), dried over anhydrous sodium sulfate, filtered, concentrated to obtain the crude product, and purified by column chromatography (Petro ether/EtOAc=5:1-1:1) to obtain the target product tert-butyl 4-(7-chloro-6-fluoro-1-(2-isopropyl-4-methylpyridin-3-yl)-2-carbonyl-1, 2-dihydropyrido[2, 3-d]pyrimidin-4-yl)-3-formylpiperazine-1-carboxylate (1.2 g, yield: 67%).

MS m/z (ESI): 545.1 $[M+H]^+$, 547.1 $[M+H+2]^+$.

Step 3: Preparation of tert-butyl 4-(7-chloro-6-fluoro-1-(2-isopropyl-4-methylpyridin-3-yl)-2-carbonyl-1, 2-dihydropyrido [2, 3-d] pyrimidin-4-yl)-3-vinylpiperazine-1-carboxylate

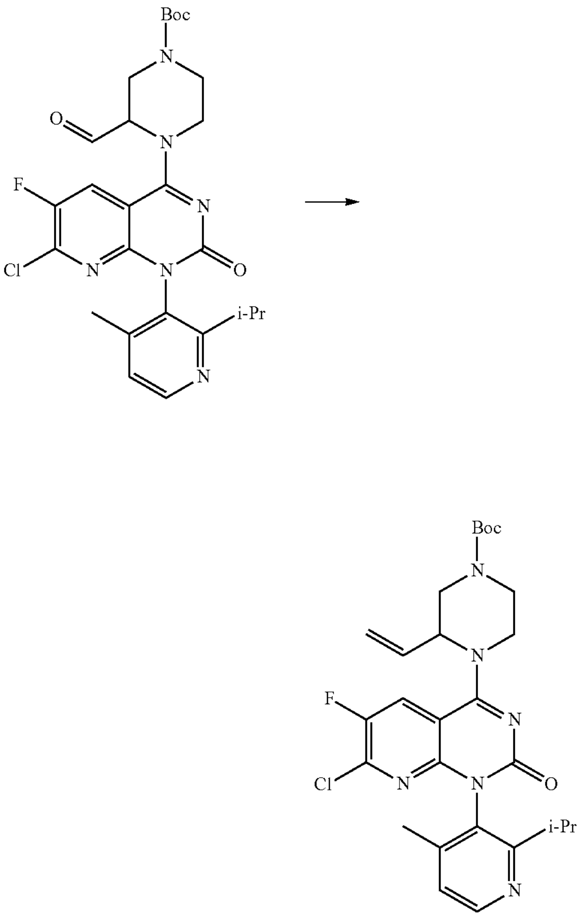 [SMILES: Cc1ccnc(C(C)C)c1-n1c(=O)nc(N2CCN(C(=O)OC(C)(C)C)CC2CO)c2cc(F)c(Cl)nc21 ; Cc1ccnc(C(C)C)c1-n1c(=O)nc(N2CCN(C(=O)OC(C)(C)C)CC2C=O)c2cc(F)c(Cl)nc21]

Methyltriphenylphosphonium bromide (295 mg, 0.83 mmol) was dissolved in anhydrous THF (20 mL), cooled to −78° C. under nitrogen protection, n-BuLi (3 mL, 0.75 mmol, 2.5 M in hexane) was added thereto and stirred for 10 minutes, then the temperature was raised to room temperature, and the mixture was stirred for 1 hour. Then the mixture was cooled to −78° C., tert-butyl 4-(7-chloro-6-fluoro-1-(2-isopropyl-4-methylpyridin-3-yl)-2-carbonyl-1, 2-dihydropyrido [2, 3-d] pyrimidin-4-yl)-3-formylpiperazine-1-carboxylate (300 mg, 0.55 mmol) was added thereto dropwise and stirred for 1 hour. The temperature was gradually raised to room temperature and the stirring was continued for 2 hours. The reaction mixture was then quenched with saturated ammonium chloride aqueous solution, then extracted three times with ethyl acetate (3*10 mL) and water. The organic phases were combined, dried over anhydrous sodium sulfate, filtered, concentrated to obtain the crude product, and purified by column chromatography (Petro ether/EtOAc=5:1-1:1) to obtain tert-butyl 4-(7-chloro-6-fluoro-1-(2-isopropyl-4-methylpyridin-3-yl)-2-carbonyl-1, 2-dihydropyrido [2, 3-d] pyrimidin-4-yl)-3-vinylpiperazine-1-carboxylate (160 mg, yield: 54%).

MS m/z (ESI): 543.1 $[M+H]^+$, 545.1 $[M+H+2]^+$.

Step 4: Preparation of 7-chloro-6-fluoro-1-(2-isopropyl-4-methylpyridin-3-yl)-4-(2-vinylpiperazin-1-yl) pyrido [2, 3-d] pyrimidin-2 (1H)-one

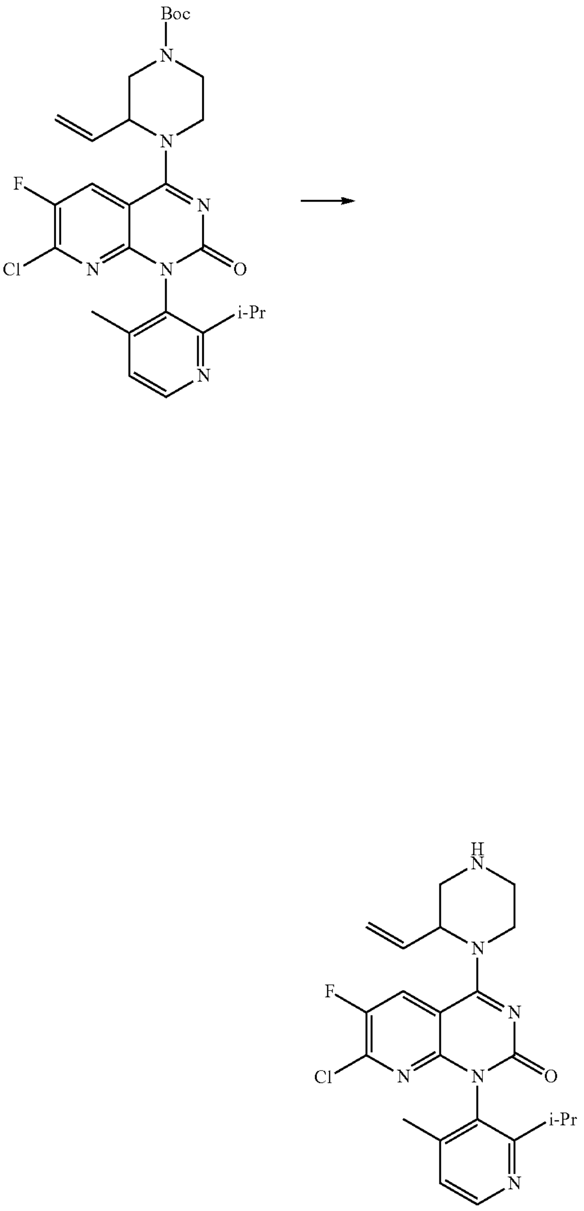

Tert-butyl 4-(7-chloro-6-fluoro-1-(2-isopropyl-4-methylpyridin-3-yl)-2-carbonyl-1, 2-dihydropyrido [2, 3-d] pyrimidin-4-yl)-3-vinylpiperazine-1-carboxylate (150 mg, 0.28 mmol) was dissolved in dichloromethane (10 mL), trifluoroacetic acid (1 mL) was added thereto, and stirred at room temperature for 1 hour, then the mixture was concentrated to obtain the crude target product 7-chloro-6-fluoro-1-(2-isopropyl-4-methylpyridin-3-yl)-4-(2-vinylpiperazine-1-yl) pyrido [2, 3-d] pyrimidin-2 (1H)-one (220 mg, crude).

MS m/z (ESI): 443.1 $[M+H]^+$, 445.1 $[M+H+2]^+$.

Step 5: Preparation of 4-(4-acryloyl-2-vinylpiperazine-1-yl)-7-chloro-6-fluoro-1-(2-isopropyl-4-methylpyridin-3-yl) pyrido [2, 3-d] pyrimidin-2 (1H)-one

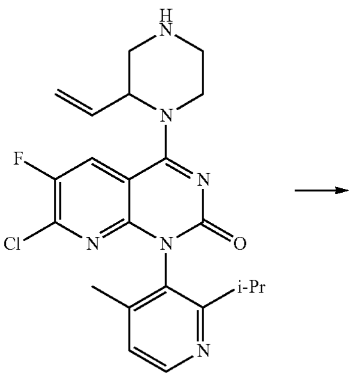

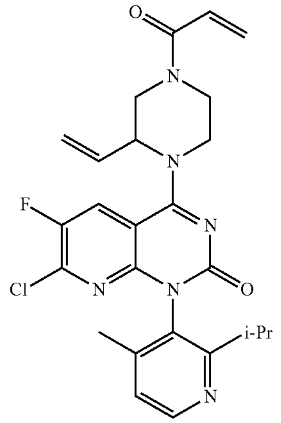

7-Chloro-6-fluoro-1-(2-isopropyl-4-methylpyridin-3-yl)-4-(2-vinylpiperazin-1-yl) pyrido [2, 3-d]pyrimidin-2(1H)-one (220 mg, 0.28 mmol) was dissolved in dichloromethane (10 mL), DIPEA (108 mg, 0.84 mmol) was added, then acryloyl chloride (30 mg, 0.34 mmol) was added thereto dropwise at room temperature, and the stirring was continued for 1 hour. The reaction mixture was quenched with water and extracted three times with dichloromethane (10 mL). The organic phases were combined, dried over anhydrous sodium sulfate, concentrated and purified by column chromatography ($CH_2Cl_2$/MeOH=10:1) to obtain the target product 4-(4-acryloyl-2-vinylpiperazin-1-yl)-7-chloro-6-fluoro-1-(2-isopropyl-4-methylpyridin-3-yl) pyrido [2, 3-d] pyrimidin-2 (1H)-one (75 mg, total yield of two steps: 54%).

MS m/z (ESI): 497.1 $[M+H]^+$, 499.1 $[M+H+2]^+$.

Step 6: Preparation of 4-(4-acryloyl-2-vinylpiperazin-1-yl)-6-fluoro-7-(2-fluoro-6-hydroxyphenyl)-1-(2-isopropyl-4-methylpyridin-3-yl)pyrido[2, 3-d] pyrimidin-2(1H)-one

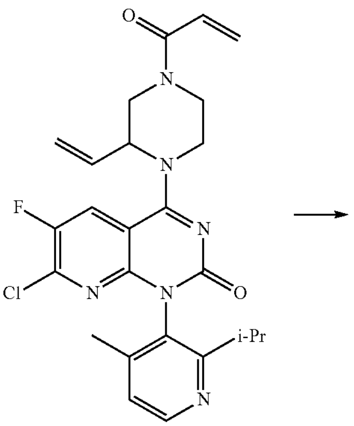

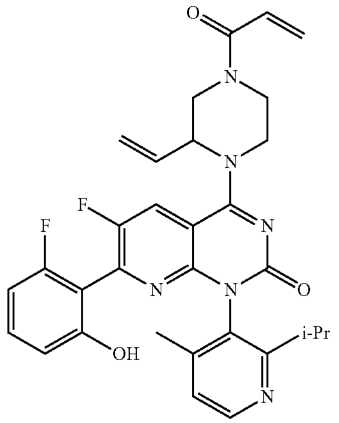

4-(4-Acryloyl-2-vinylpiperazin-1-yl)-7-chloro-6-fluoro-1-(2-isopropyl-4-methylpyridin-3-yl)pyrido[2, 3-d]pyrimidin-2(1H)-one (50 mg, 0.10 mmol), (2-fluoro-6-hydroxyphenyl) boric acid (34 mg, 0.2 mmol), 1, 1'-bis (diphenylphosphino)ferrocene-palladium(II)dichloride dichloromethane complex (9 mg, 0.01 mmol) and cesium carbonate (97 mg, 0.3 mmol) were dissolved in dioxane (4 mL) and water (1 mL), and the mixture was stirred at 100° C. for 1 hour under microwave. The reaction mixture was concentrated and purified by preparative HPLC to obtain the product 4-(4-acryloyl-2-vinylpiperazin-1-yl)-6-fluoro-7-(2-fluoro-6-hydroxyphenyl)-1-(2-isopropyl-4-methylpyridin-3-yl)pyrido[2, 3-d]pyrimidin-2(1H)-one (8 mg, yield: 14%).

MS m/z (ESI): 573.1 $[M+H]^+$.

The synthesis of embodiments 76-80, 85-113 and 118-129 were carried out with reference to embodiment 75.

Embodiment 114

Preparation of 4-((2S, 5R)-4-acryloyl-2, 5-dimethylpiperazin-1-yl)-6-fluoro-7-(2-fluoro-6-hydroxyphenyl)-1-(2-isopropyl-4-(methylthio) pyridin-3-yl) pyrido [2, 3-d] pyrimidin-2 (1H)-one

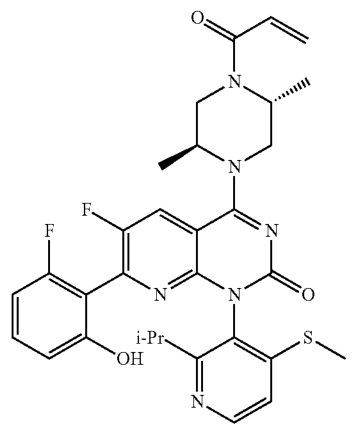 [SMILES: C=CC(=O)N1C[C@H](C)N(c2nc(=O)n(-c3c(SC)ccnc3C(C)C)c3nc(-c4c(O)cccc4F)c(F)cc23)C[C@H]1C]

Step 1: Preparation of 4, 7-dichloro-6-fluoro-1-(2-isopropyl-4-(methylthio)pyridin-3-yl) pyrido [2, 3-d] pyrimidin-2 (1H)-one

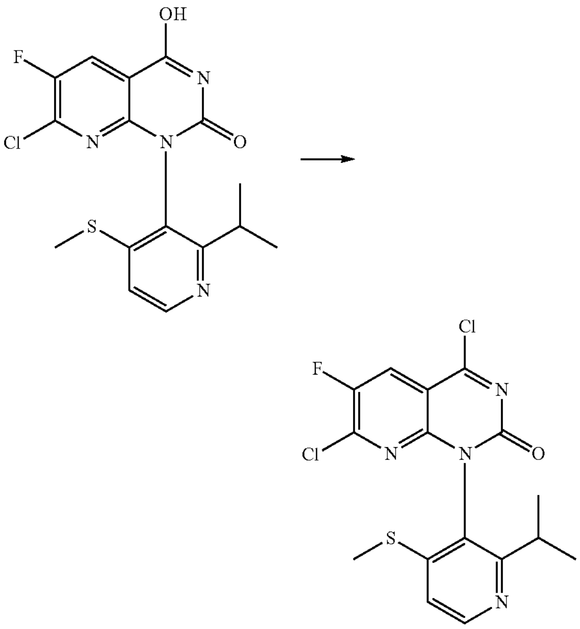

N, N-diisopropylethylamine (407 mg, 3.16 mmol) was added to a solution of 7-chloro-6-fluoro-4-hydroxy-1-(2-isopropyl-4-(methylthio) pyridin-3-yl) pyrido [2, 3-d] pyrimidin-2 (1H)-one (200 mg, 0.526 mmol) in acetonitrile (10 mL), phosphorus oxychloride (242 mg, 1.58 mmol) was added thereto and the mixture was stirred at 80° C. for 1 hour at room temperature. The mixture was cooled to room temperature and directly used for the next reaction.

Step 2: Preparation of tert-butyl (2R, 5S)-4-(7-chloro-6-fluoro-1-(2-isopropyl-4-(methylthio) pyridin-3-yl)-2-carbonyl-1, 2-dihydropyrido [2, 3-d] pyrimidin-4-yl)-2, 5-dimethylpiperazine-1-carboxylate

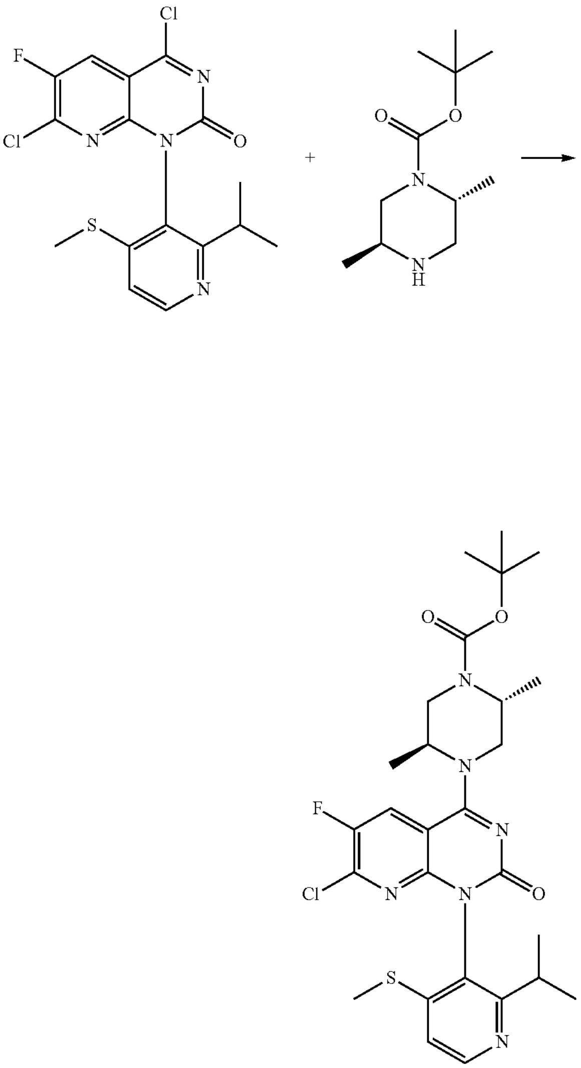

N, N-diisopropylethylamine (678 mg, 5.26 mmol) and tert-butyl (2R, 5S)-2, 5-dimethylpiperazine-1-carboxylate (224 mg, 1.005 mmol) were added to the reaction mixture of the previous step and stirred for 1 hour at room temperature after the addition. Water (60 mL) was added thereto and the mixture was extracted with ethyl acetate (40 mL×3), the organic phase was washed with ammonium chloride aqueous solution (40 mL) and then washed with sodium chloride aqueous solution (30 mL), concentrated and then purified by column chromatography [eluent: dichloromethane-methanol/dichloromethane from 0% to 2.2%] to obtain tert-butyl (2R, 5S)-4-(7-chloro-6-fluoro-1-(2-isopropyl-4-(methylthio) pyridin-3-yl)-2-carbonyl-1, 2-dihydropyrido [2, 3-d] pyrimidin-4-yl)-2, 5-dimethylpiperazine-1-carboxylate (200 mg, two-step yield: 66%) as a yellow solid.

MS m/z (ESI): 577.2 $[M+H]^+$, 579.2$[M+2+H]^+$.

Step 3: Preparation of 7-chloro-4-((2S, 5R)-2, 5-dimethylpiperazin-1-yl)-6-fluoro-1-(2-isopropyl-4-(methylthio) pyridin-3-yl) pyrido [2, 3-d] pyrimidin-2 (1H)-one trifluoroacetate

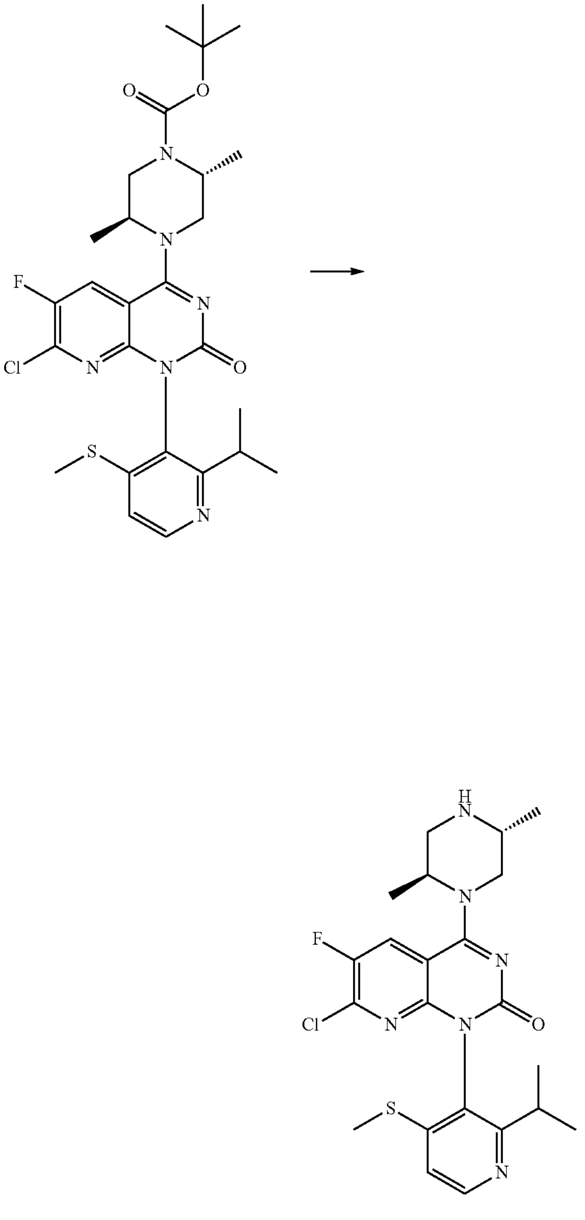

Trifluoroacetic acid (1.2 mL) was added to a solution of tert-butyl (2R, 5S)-4-(7-chloro-6-fluoro-1-(2-isopropyl-4-(methylthio)pyridin-3-yl)-2-carbonyl-1, 2-dihydropyrido [2, 3-d] pyrimidin-4-yl)-2, 5-dimethylpiperazine-1-carboxylate (200 mg, 0.347 mmol) in dichloromethane (6 mL), and the mixture was stirred at room temperature for 1.5 hours. Then the mixture was concentrated at low temperature to obtain 7-chloro-4-((2S, 5R)-2, 5-dimethylpiperazin-1-yl)-6-fluoro-1-(2-isopropyl-4-(methylthio) pyridin-3-yl) pyrido [2, 3-d] pyrimidin-2 (1H)-one trifluoroacetate (200 mg) as a red oil, which was used rapidly in the next reaction.

MS m/z (ESI): 477.2 $[M+H]^+$, 479.2 $[M+H+2]^+$.

Step 4: Preparation of 4-((2S, 5R)-4-acryloyl-2, 5-dimethylpiperazin-1-yl)-7-chloro-6-fluoro-1-(2-isopropyl-4-(methylthio) pyridin-3-yl) pyrido [2, 3-d] pyrimidin-2 (1H)-one

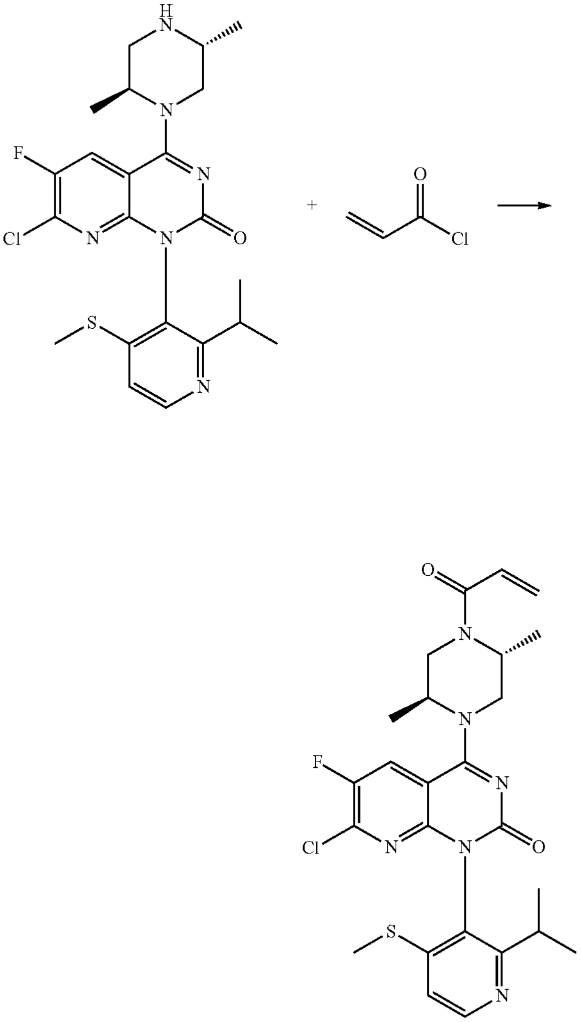

N, N-diisopropylethylamine (447 mg, 3.47 mmol) was added to a solution of 7-chloro-4-((2S, 5R)-2, 5-dimethylpiperazin-1-yl)-6-fluoro-1-(2-isopropyl-4-(methylthio) pyridin-3-yl)pyrido[2, 3-d]pyrimidin-2(1H)-one trifluoroacetate (200 mg, 0.347 mmol) in dichloromethane (15 mL), then acryloyl chloride (63 mg, 0.694 mmol) was added dropwise at 0° C., and the mixture was stirred for 1 hour after the addition. The reaction mixture was quenched with ammonium chloride aqueous solution (30 mL), extracted with dichloromethane (30 mL×3), the dichloromethane phase was washed with saturated NaCl aqueous solution (20 mL), dried over anhydrous sodium sulfate, concentrated and then purified by column chromatography [eluent: dichloromethane-methanol/dichloromethane from 0% to 2.5%] to obtain 4-((2S, 5R)-4-acryloyl-2, 5-dimethylpiperazin-1-yl)-7-chloro-6-fluoro-1-(2-isopropyl-4-(methylthio)pyridin-3-yl)pyrido[2, 3-d]pyrimidin-2(1H)-one (130 mg, two-step yield: 71%) as a yellow solid.

MS m/z (ESI): 530.2 $[M+H]^+$, 532.2 $[M+H+2]^+$.

Step 5: Preparation of 4-((2S, 5R)-4-acryloyl-2, 5-dimethylpiperazin-1-yl)-6-fluoro-7-(2-fluoro-6-hydroxyphenyl)-1-(2-isopropyl-4-(methylthio) pyridin-3-yl) pyrido [2, 3-d] pyrimidin-2 (1H)-one

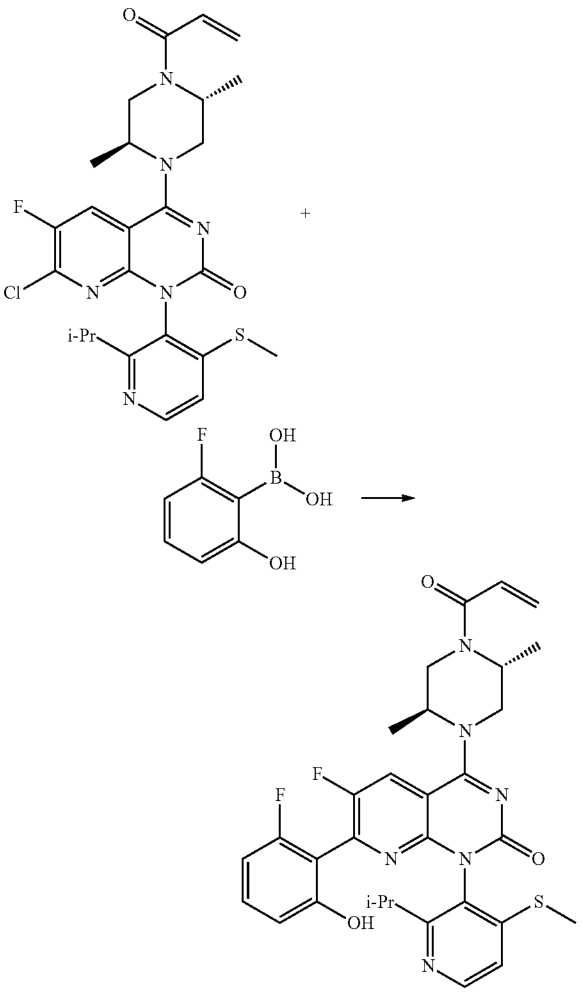

4-((2S, 5R)-4-acryloyl-2, 5-dimethylpiperazin-1-yl)-7-chloro-6-fluoro-1-(2-isopropyl-4-(methylthio)pyridin-3-yl) pyrido[2, 3-d]pyrimidin-2(1H)-one (130 mg, 0.246 mmol), (2-fluoro-6-hydroxyphenyl) boric acid (77 mg, 0.491 mmol), 1, 1'-bis(diphenylphosphino)ferrocene-palladium (II)dichloride dichloromethane complex (40 mg, 0.0491 mmol) and cesium carbonate (240 mg, 0.738 mmol) were added to dioxane (4 mL) and water (1 mL), the mixture was replaced with nitrogen, and stirred at 100° C. for 1 hour under microwave. The reaction mixture was concentrated, then purified by column chromatography [eluent: dichloromethane-methanol/dichloromethane from 0% to 2.5%] to obtain 4-((2S, 5R)-4-acryloyl-2, 5-dimethylpiperazin-1-yl)-6-fluoro-7-(2-fluoro-6-hydroxyphenyl)-1-(2-isopropyl-4-(methylthio)pyridin-3-yl)pyrido[2, 3-d]pyrimidin-2(1H)-one (90 mg, yield: 60%) as a yellow solid.

MS m/z (ESI): 606.2 $[M+H]^+$.

$^1H$ NMR (400 MHz, MeOD-$d_4$) δ 8.40 (d, J=8 Hz, 1H), 8.29-8.18 (m, 1H), 7.30-7.18 (m, 2H), 6.93-6.73 (m, 1H), 6.70-6.56 (m, 2H), 6.36-6.20 (m, 1H), 5.89-5.75 (m, 1H), 5.15-4.98 (m, 1H), 4.63-4.22 (m, 2H), 4.11-3.82 (m, 2H), 3.68-3.40 (m, 1H), 2.88-2.65 (m, 1H), 2.40 (d, J=4 Hz, 3H), 1.53-1.43 (m, 3H), 1.36 (t, J=8 Hz, 1H), 1.28 (t, J=8 Hz, 2H), 1.23-1.16 (m, 3H), 1.10-1.01 (m, 3H).

Embodiment 114-1 and Embodiment 114-2

(M/P-4-((2S, 5R)-4-acryloyl-2, 5-dimethylpiperazin-1-yl)-6-fluoro-7-(2-fluoro-6-hydroxyphenyl)-1-(2-isopropyl-4-(methylthio)pyridin-3-yl)pyrido[2, 3-d]pyrimidin-2(1H)-one)

114-1

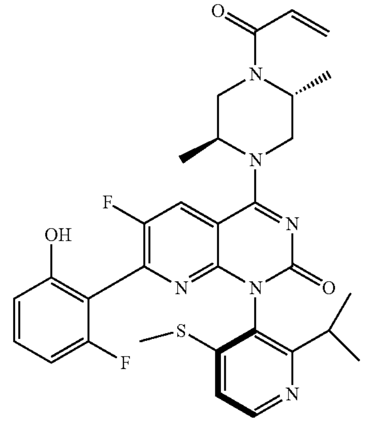

114-2

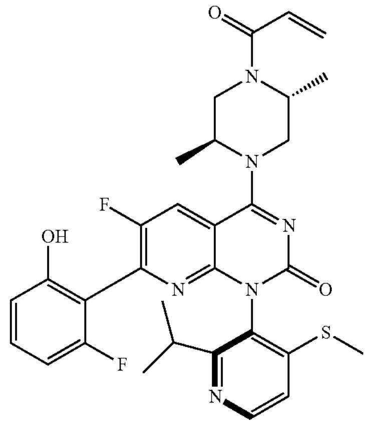

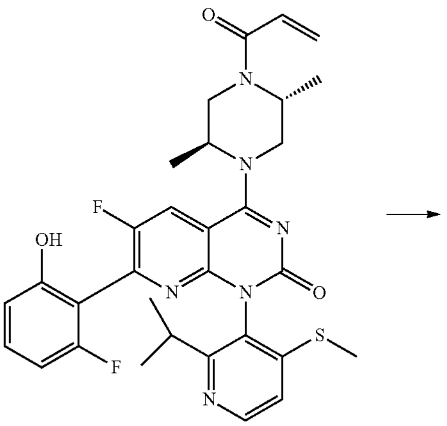

-continued

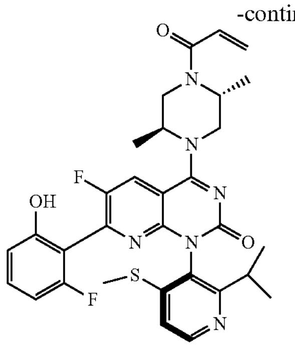

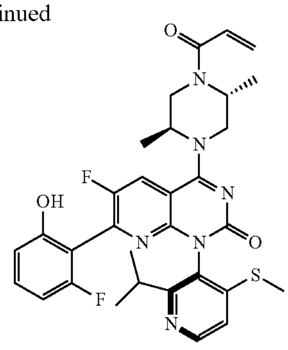

Embodiment 114 was resolved by SFC to obtain two axial chiral isomers, embodiment 114-1 and embodiment 114-2, SFC: chiral preparation conditions:

TABLE 17

| | |
|---|---|
| Instrument | SFC-150 (Thar, Waters) |
| Column type | IC 20 * 250 mm, 10 μm (Daicel) |
| Column pressure | 100 bar |
| Mobile phase | $CO_2$/Methanol (0.2% Methanol Ammonia) = 60/40 |
| Flow rate | 100 g/min |
| Detection wavelength | UV 214 nm |
| Column temperature | 35° C. |

Chiral Analysis Conditions:

TABLE 18

| | |
|---|---|
| Instrument | SFC Method Station (Thar, Waters) |
| Column type | Celluloe-SC 4.6% × 100 mm, 5 μm (YMC) |
| Column pressure | 120 bar |
| Mobile phase | A: $CO_2$; B: Ethanol [1.0% NH3(7M in methanol)]; A:B = 65:35 |
| Flow rate | 4 mL/min |
| Detection wavelength | UV 214 nm |
| Column temperature | 40° C. |

Embodiment 114-1

$t_R$=1.99 min

MS m/z (ESI): 606.2 $[M+H]^+$.

$^1$H NMR (400 MHz, MeOD-$d_4$) δ 8.40 (d, J=8 Hz, 1H), 8.29-8.18 (m, 1H), 7.30-7.18 (m, 2H), 6.93-6.73 (m, 1H), 6.70-6.56 (m, 2H), 6.36-6.20 (m, 1H), 5.89-5.75 (m, 1H), 5.15-4.98 (m, 1H), 4.63-4.22 (m, 2H), 4.11-3.82 (m, 2H), 3.68-3.40 (m, 1H), 2.88-2.65 (m, 1H), 2.40 (d, J=4 Hz, 3H), 1.53-1.43 (m, 3H), 1.36 (t, J=8 Hz, 1H), 1.28 (t, J=8 Hz, 2H), 1.23-1.16 (m, 3H), 1.10-1.01 (m, 3H).

Embodiment 114-2

$t_R$=2.87 min

MS m/z (ESI): 606.2 $[M+H]^+$.

$^1$H NMR (400 MHz, MeOD-$d_4$) δ 8.40 (d, J=8 Hz, 1H), 8.27-8.18 (m, 1H), 7.30-7.19 (m, 2H), 6.94-6.74 (m, 1H), 6.70-6.56 (m, 2H), 6.36-6.20 (d, J=16 Hz, 1H), 5.90-5.75 (m, 1H), 5.14-4.98 (m, 1H), 4.63-4.22 (m, 2H), 4.12-3.82 (m, 2H), 3.68-3.41 (m, 1H), 2.87-2.65 (m, 1H), 2.40 (d, J=4 Hz, 3H), 1.53-1.42 (m, 3H), 1.36 (t, J=8 Hz, 1H), 1.28 (t, J=8 Hz, 2H), 1.23-1.16 (d, J=4 Hz, 3H), 1.10-1.01 (d, J=4 Hz, 3H).

Embodiment 115

Preparation of 4-((3S, 5R)-4-acryloyl-3, 5-dimethylpiperazin-1-yl)-6-fluoro-7-(2-fluoro-6-hydroxyphenyl)-1-(2-isopropyl-4-(methylthio) pyridin-3-yl) pyrido [2, 3-d] pyrimidin-2 (1H)-one

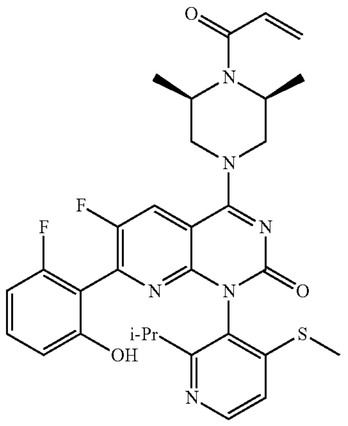 [SMILES: C=CC(=O)N1[C@H](C)CN(c2nc(=O)n(-c3c(SC)ccnc3C(C)C)c3nc(-c4c(O)cccc4F)c(F)cc23)C[C@@H]1C]

4-((3S, 5R)-4-acryloyl-3, 5-dimethylpiperazin-1-yl)-6-fluoro-7-(2-fluoro-6-hydroxyphenyl)-1-(2-isopropyl-4-(methylthio)pyridin-3-yl)pyrido[2, 3-d]pyrimidin-2(1H)-one was prepared with reference to embodiment 114.

MS m/z (ESI): 607.1 $[M+H]^+$.

$^1$H NMR (400 MHz, Methanol-$d_4$) δ 8.39-8.34 (m, 2H), 7.25-7.20 (m, 2H), 6.86-6.80 (m, 1H), 6.67-6.58 (m, 2H), 6.32-6.27 (dd, J=16.6, 4.0 Hz, 1H), 5.83-5.79 (dd, J=12.0, 4.0 Hz, 1H), 4.65-4.48 (m, 4H), 3.84-3.72 (m, 2H), 2.82-2.75 (m, 1H), 2.38 (s, 3H), 1.50-1.44 (dd, J=16.0, 8.0 Hz, 6H), 1.20-1.18 (d, J=8.0 Hz, 3H), 1.07-1.05 (d, J=8.0 Hz, 3H).

Embodiment 133

Preparation of 4-((S)-4-acryloyl-2-methylpiperazin-1-yl)-6-fluoro-7-(2-fluoro-6-hydroxyphenyl)-1-(2-isopropyl-4-(methylsulfonyl) pyridin-3-yl) pyrido [2, 3-d] pyrimidin-2 (1H)-one

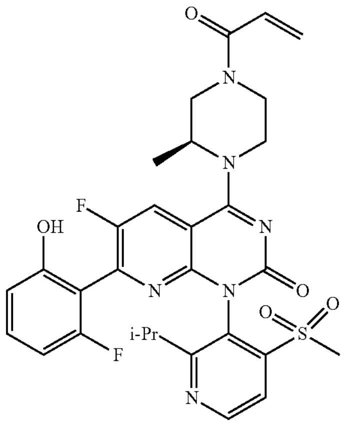 [SMILES: C=CC(=O)N1CCN(c2nc(=O)n(-c3c(S(C)(=O)=O)ccnc3C(C)C)c3nc(-c4c(O)cccc4F)c(F)cc23)[C@@H](C)C1]

Step 1: Preparation of 4-((S)-4-acryloyl-2-methylpiperazin-1-yl)-6-fluoro-7-(2-fluoro-6-hydroxyphenyl)-1-(2-isopropyl-4-(methylsulfonyl) pyridin-3-yl) pyrido [2, 3-d] pyrimidin-2 (1H)-one

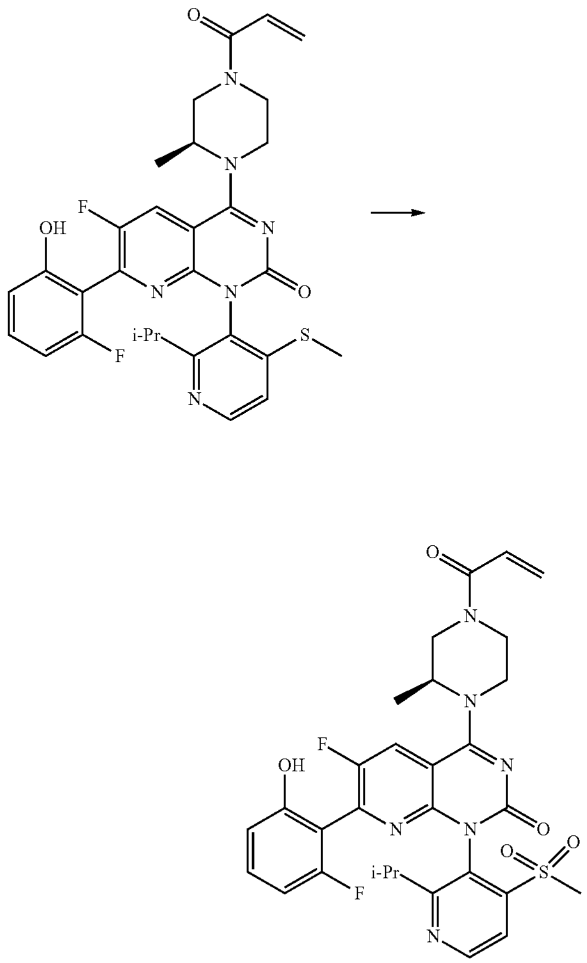 [SMILES: C=CC(=O)N1CCN(c2nc(=O)n(-c3c(SC)ccnc3C(C)C)c3nc(-c4c(O)cccc4F)c(F)cc23)[C@@H](C)C1 ; C=CC(=O)N1CCN(c2nc(=O)n(-c3c(S(C)(=O)=O)ccnc3C(C)C)c3nc(-c4c(O)cccc4F)c(F)cc23)[C@@H](C)C1]

4-((S)-4-acryloyl-2-methylpiperazin-1-yl)-6-fluoro-7-(2-fluoro-6-hydroxyphenyl)-1-(2-isopropyl-4-(methylthio) pyridin-3-yl) pyrido [2, 3-d] pyrimidin-2 (1H)-one (80 mg, 0.14 mmol) and potassium peroxymonosulfate complex salt (520 mg, 0.84 mmol) were added to solvent (acetonitrile: water=2:1) (9 mL) and the reaction was carried out overnight at room temperature, the crude product was separated and purified by preparative-HPLC to obtain the target compound 4-((S)-4-acryloyl-2-methylpiperazin-1-yl)-6-fluoro-7-(2-fluoro-6-hydroxyphenyl)-1-(2-isopropyl-4-(methylsulfonyl)pyridin-3-yl) pyrido [2, 3-d] pyrimidin-2 (1H)-one as a white solid (13 mg, yield: 15%).

MS m/z (ESI): 625.1 $[M+H]^+$.

$^1$H NMR (400 MHz, MeOD-$d_4$) δ 8.88 (d, J=4.8 Hz, 1H), 8.23-8.29 (m, 1H), 7.87 (d, J=5.2 Hz, 1H), 7.23 (dd, $J_1$=14.8 Hz, $J_2$=8.0 Hz, 1H), 6.78-6.85 (m, 1H), 6.57-6.65 (m, 2H), 6.31 (dd, $J_1$=16.4 Hz, $J_2$=3.2 Hz, 1H), 5.83 (dd, $J_1$=10.8 Hz, $J_2$=1.6 Hz, 1H), 5.08 (s, 1H), 4.43-4.55 (m, 2H), 4.06-4.23 (s, 1H), 3.61-3.86 (m, 2H), 3.11-3.40 (m, 1H), 2.94-2.99 (m, 4H), 1.46-1.50 (m, 3H), 1.20-1.22 (m, 3H), 1.07-1.09 (m, 3H).

Embodiment 134

Preparation of 4-((S)-4-acryloyl-2-methylpiperazin-1-yl)-7-(2-amino-6-fluorophenyl)-6-fluoro-1-(2-isopropyl-4-(methylthio) pyridin-3-yl) pyrido [2, 3-d] pyrimidin-2 (1H)-one

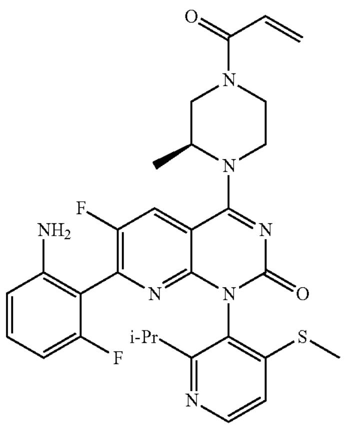

Step 1: Preparation of N-(4-chloro-3-fluorophenyl)-2, 2, 2-trifluoroacetamide

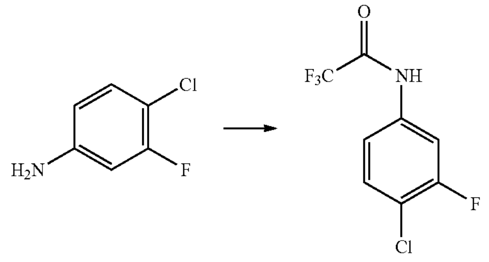 [SMILES: Nc1ccc(Cl)c(F)c1 ; O=C(Nc1ccc(Cl)c(F)c1)C(F)(F)F]

4-Chloro-3-fluoroaniline (1.45 g, 0.01 mol) was dissolved in THF (150 mL), $Na_2CO_3$ (3.18 g, 0.03 mol) was added thereto, the mixture was cooled to 0° C. under the protection of nitrogen, trifluoroacetic anhydride (4.2 mL, 0.03 mol) was added thereto dropwise, and the mixture was then stirred at room temperature for 10 hours. The reaction mixture was added to water (150 mL). The mixture was then extracted three times with ethyl acetate (100 mL). The organic phases were combined, dried over anhydrous sodium sulfate, concentrated to obtain the crude product, purified by column chromatography (PE/EA=5:1) to obtain a white solid target product N-(4-chloro-3-fluorophenyl)-2, 2, 2-trifluoroacetamide (2.3 g, yield: 95%).

$^1$H NMR (400 MHz, MeOD-$d_4$) δ 7.70 (dd, J=11.1, 2.0 Hz, 1H), 7.49-7.40 (m, 2H);

$^{19}$F NMR (376 MHz, MeOD-$d_4$) δ −77.17 (s);

MS m/z (ESI): 242.1 $[M+H]^+$.

Step 2: Preparation of (6-amino-3-chloro-2-fluorophenyl) boric acid

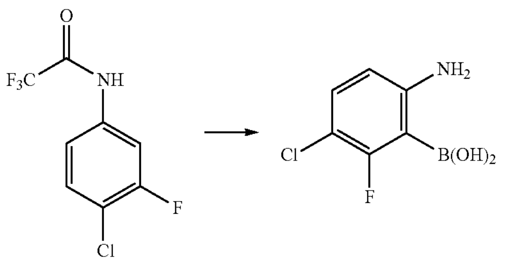 [SMILES: O=C(Nc1ccc(Cl)c(F)c1)C(F)(F)F ; Nc1ccc(Cl)c(F)c1B(O)O]

N-(4-chloro-3-fluorophenyl)-2, 2, 2-trifluoroacetamide (2.3 g, 9.5 mmol) was dissolved in THF (40 mL), the mixture was cooled to −78° C. under the protection of nitrogen, and n-BuLi (7.9 mL, 19.0 mmol, 2.4 m) was added dropwise, then the mixture was stirred at −50° C. for 50 minutes. The reaction mixture was cooled to −78° C., triisopropyl borate (2.3 g, 9.5 mmol) (4.8 mL, 20.9 mmol) was added dropwise, the mixture was stirred at the same temperature for 20 minutes, the dry ice bath was removed, and the mixture was stirred at room temperature for 2 hours. Then, the reaction mixture was cooled to 0° C., dilute hydrochloric acid (19 mL, 1M) was added dropwise, the temperature was raised to 40° C., and the mixture was stirred for 1 hour. The mixture was then extracted three times with ethyl acetate (100 mL). The organic phases were combined, dried over anhydrous sodium sulfate, concentrated to obtain the crude product, purified by column chromatography (PE/EA=4:1) to obtain a gray solid target product (6-amino-3-chloro-2-fluorophenyl) boric acid (1.1 g, yield: 56%).

MS m/z (ESI): 190.0 $[M+H]^+$.

Step 3: Preparation of (2-amino-6-fluorophenyl) boric acid

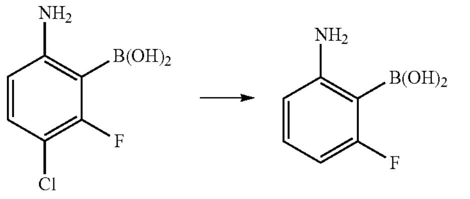 [SMILES: Nc1ccc(Cl)c(F)c1B(O)O ; Nc1cccc(F)c1B(O)O]

(6-Amino-3-chloro-2-fluorophenyl) boric acid (100 mg, 0.53 mmol) was dissolved in MeOH (20 mL), Pd/C (20 mg) was added, the mixture was replaced with hydrogen for three times, then stirred for 2 hours at 15 psi, and the reaction was detected by TLC (PE/EA 1:1) until the reaction was completed. The mixture was filtered, and the filtrate was concentrated to obtain a yellow solid target product (2-amino-6-fluorophenyl) boric acid (80 mg, yield: 97%), which was used directly in the next reaction without purification.

MS m/z (ESI): 156.0 $[M+H]^+$.

Step 4: Preparation of 4-((S)-4-acryloyl-2-methylpiperazin-1-yl)-7-(2-amino-6-fluorophenyl)-6-fluoro-1-(2-isopropyl-4-(methylthio) pyridin-3-yl) pyrido [2, 3-d] pyrimidin-2 (1H)-one

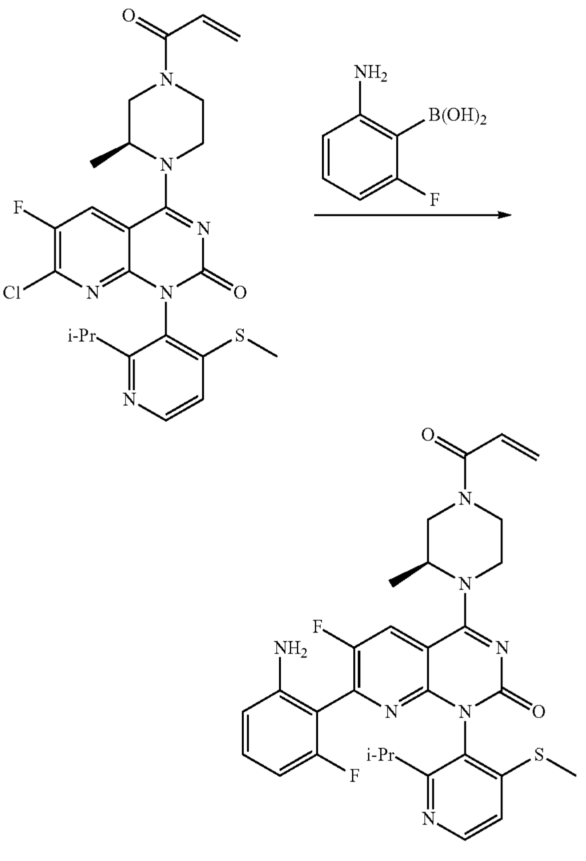

(S)-4-(4-acryloyl-2-methylpiperazin-1-yl)-7-chloro-6-fluoro-1-(2-isopropyl-4-(methylthio) pyridin-3-yl)pyrido [2, 3-d] pyrimidin-2 (1H)-one (26 mg, 0.05 mmol), (6-amino-3-chloro-2-fluorophenyl) boric acid (23.2 mg, 0.15 mmol) and cesium carbonate (48.87 mg, 0.15 mmol) were dissolved in dioxane/$H_2O$ (1.5 mL/0.3 m L). The mixture was replaced with nitrogen for 1 minute, and the reaction was carried out at 100° C. for 1 hour under microwave conditions. When the reaction was completed, the reaction mixture was concentrated, purified by column chromatography ($CH_2Cl_2$/MeOH=20:1) and then purified by preparation HPLC to obtain a yellow solid target product 4-((S)-4-acryloyl-2-methylpiperazin-1-yl)-7-(2-amino-6-fluorophenyl)-6-fluoro-1-(2-isopropyl-4-(methylthio) pyridin-3-yl) pyrido [2, 3-d]pyrimidin-2 (1H)-one (7.0 mg, yield: 24%).

$^1H$ NMR (400 MHz, MeOD-$d_4$) δ 8.46 (d, J=5.4 Hz, 1H), 8.25 (dd, J=21.2, 12.0 Hz, 1H), 7.27 (d, J=5.5 Hz, 1H), 7.11 (dd, J=14.7, 8.2 Hz, 1H), 6.84 (d, J=14.2 Hz, 1H), 6.49 (d, J=8.3 Hz, 1H), 6.41-6.27 (m, 2H), 5.83 (dd, J=10.6, 1.6 Hz, 1H), 4.48 (dd, J=52.4, 11.6 Hz, 2H), 4.30-3.83 (m, 2H), 3.74 (d, J=9.7 Hz, 2H), 3.22 (s, 1H), 2.98-2.80 (m, 1H), 2.43 (d, J=0.7 Hz, 3H), 1.56-1.40 (m, 3H), 1.22 (d, J=6.6 Hz, 3H), 1.01 (d, J=6.6 Hz, 3H).

$^{19}F$ NMR (376 MHz, MeOD-$d_4$) δ −114.58-−114.95 (m), −114.95-−115.34 (m), −125.12-−126.48 (m).

MS m/z (ESI): 592.2 $[M+H]^+$.

Embodiment 136

Preparation of (S)-4-(4-acryloyl-2-methylpiperazin-1-yl)-6-fluoro-1-(2-isopropyl-4-methylpyridin-3-yl)-7-(2-(methylthio) pyridin-3-yl) pyrido [2, 3-d] pyrimidin-2 (1H)-one

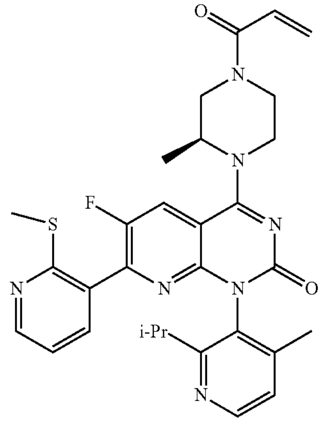 [SMILES: C=CC(=O)N1CCN(c2nc(=O)n(-c3c(C)ccnc3C(C)C)c3nc(-c4cccnc4SC)c(F)cc23)[C@@H](C)C1]

Step 1: Preparation of 6-fluoro-7-(2-fluoropyridin-3-yl)-1-(2-isopropyl-4-methylpyridin-3-yl) pyrido [2, 3-d] pyrimidin-2, 4 (1H, 31H)-dione

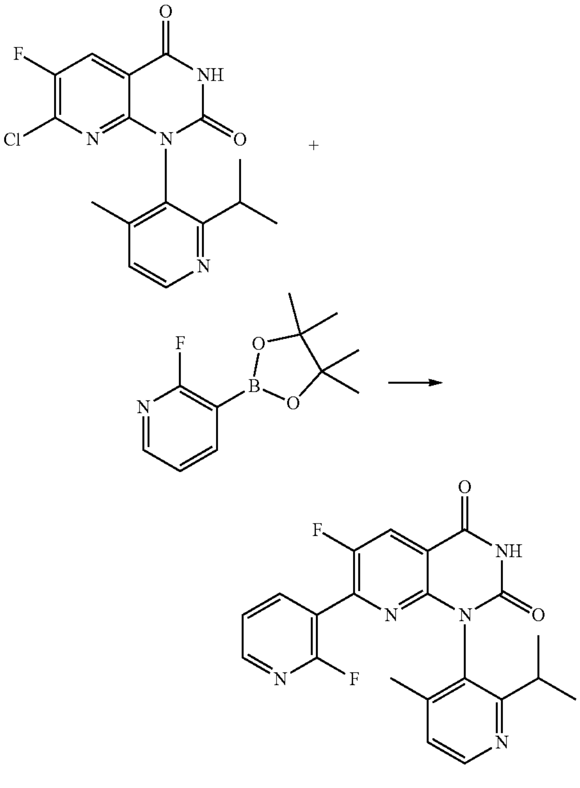

7-Chloro-6-fluoro-1-(2-isopropyl-4-methylpyridin-3-yl) pyrido[2, 3-d]pyrimidin-2, 4(1H, 3H)-dione (200 mg, 0.575 mmol), 2-fluoro-3-(4, 4, 5, 5-trimethyl-1, 3, 2-dioxaborolan- 2-yl)pyridine (192 mg, 0.862 mmol), 1, 1'-bis(diphenylphosphino)ferrocene-palladium(II)dichloride dichloromethane complex (47 mg, 0.0575 mmol) and cesium carbonate (561 mg, 1.725 mmol) were dissolved in dioxane (8 mL) and water (1 mL), and the mixture was stirred at 100° C. for 1 hour under microwave. The reaction mixture was concentrated, then purified by column chromatography [eluent: dichloromethane-methanol/dichloromethane from 0% to 3%] to obtain 6-fluoro-7-(2-fluoropyridin-3-yl)-1-(2-isopropyl-4-methylpyridin-3-yl) pyrido [2, 3-d] pyrimidin-2, 4 (1H, 3H)-dione (200 mg, yield: 85%) as a yellow solid.

MS m/z (ESI): 410.1 $[M+H]^+$.

Step 2: Preparation of 6-fluoro-7-(2-fluoropyridin-3-yl)-1-(2-isopropyl-4-methylpyridin-3-yl) pyrido [2, 3-d] pyrimidin-2, 4 (1H, 3H)-dione

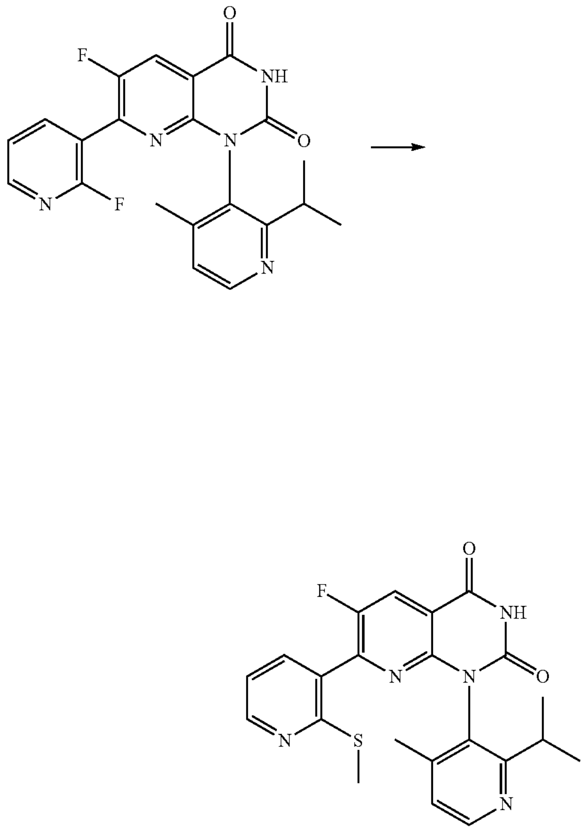

6-Fluoro-7-(2-fluoropyridin-3-yl)-1-(2-isopropyl-4-methylpyridin-3-yl) pyrido [2, 3-d]pyrimidin-2, 4 (1H, 3H)-dione (170 mg, 0.416 mmol) and 20% sodium methyl mercaptide aqueous solution (218 mg, 0.623 mmol) in dimethyl sulfoxide (5 mL) were stirred at 85° C. for 4 hours. Water (40 mL) was added thereto, and the mixture was extracted with ethyl acetate (30 mL×3), the organic phase was washed with sodium chloride aqueous solution (30 mL), concentrated and purified by column chromatography [eluent: dichloromethane-methanol/dichloromethane from 0% to 2.5%] to obtain 6-fluoro-7-(2-fluoropyridin-3-yl)-1-(2-isopropyl-4-methylpyridin-3-yl) pyrido [2, 3-d] pyrimidin-2, 4 (1H, 3H)-dione (128 mg, yield: 70%) as a yellow solid.

MS m/z (ESI): 438.1 $[M+H]^+$.

Step 3: Preparation of 4-chloro-6-fluoro-1-(2-isopropyl-4-methylpyridin-3-yl)-7-(2-(methylthio)pyridin-3-yl) pyrido [2, 3-d] pyrimidin-2 (1H)-one

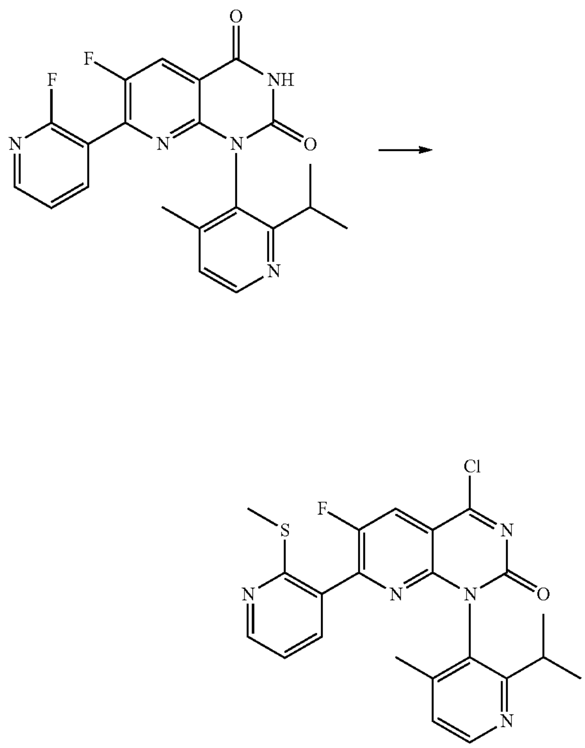

N, N-diisopropylethylamine (354 mg, 2.75 mmol) was added to a solution of 6-fluoro-7-(2-fluoropyridin-3-yl)-1-(2-isopropyl-4-methylpyridin-3-yl)pyrido[2, 3-d]pyrimidin-2, 4(1H, 3H)-dione (200 mg, 0.458 mmol) in acetonitrile (20 mL); phosphorus oxychloride (210 mg, 1.37 mmol) was added thereto and the mixture was stirred at 80° C. for 1 hour at room temperature. The mixture was cooled to room temperature and directly used for the next reaction.

Step 4: Preparation of tert-butyl (S)-4-(6-fluoro-1-(2-isopropyl-4-methylpyridin-3-yl)-7-(2-(methylthio) pyridin-3-yl)-2-carbonyl-1, 2-dihydropyrido [2, 3-d] pyrimidin-4-yl)-3-methylpiperazine-1-carboxylate

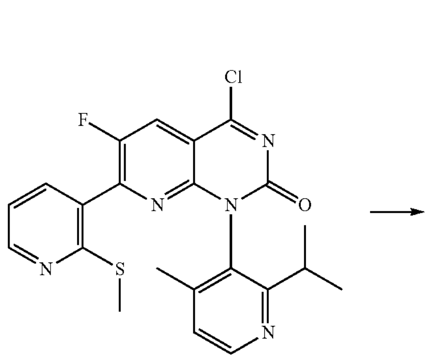

-continued

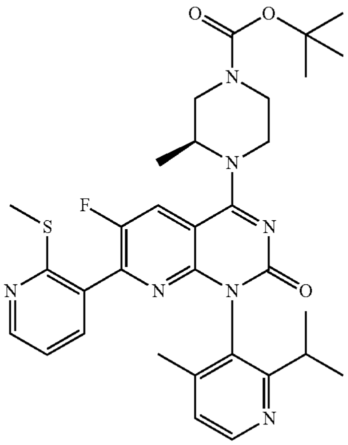

N, N-diisopropylethylamine (588 mg, 4.58 mmol) and tert-butyl (2R, 5S)-2, 5-dimethylpiperazine-1-carboxylate (183 mg, 4.5 mmol) were added to the reaction mixture of the previous step and stirred for 0.5 hours at room temperature after the addition. The reaction mixture was quenched with ammonium chloride aqueous solution (60 mL), extracted with ethyl acetate (40 mL×3), washed with sodium chloride aqueous solution (30 mL), concentrated and purified by column chromatography [eluent: dichloromethane-methanol/dichloromethane from 0% to 2.8%] to obtain tert-butyl (S)-4-(6-fluoro-1-(2-isopropyl-4-methylpyridin-3-yl)-7-(2-(methylthio)pyridin-3-yl)-2-carbonyl-1, 2-dihydropyrido[2, 3-d]pyrimidin-4-yl)-3-methylpiperazine-1-carboxylate (220 mg, two-step yield: 78%) as a yellow solid.

MS m/z (ESI): 620.3 $[M+H]^+$.

Step 5: Preparation of (S)-6-fluoro-1-(2-isopropyl-4-methylpyridin-3-yl)-4-(2-methylpiperazin-1-yl)-7-(2-(methylthio)pyridin-3-yl) pyrido [2, 3-d] pyrimidin-2 (1H)-one trifluoroacetate

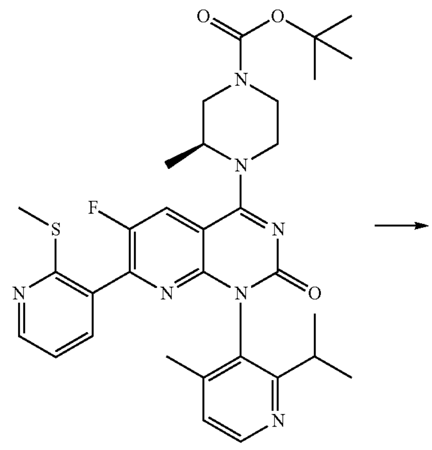

-continued

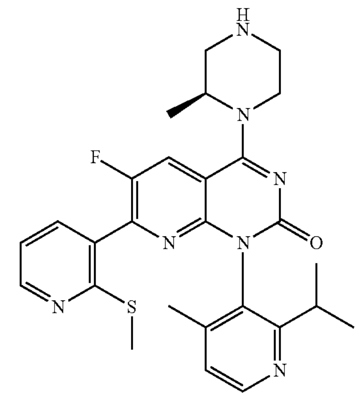

Trifluoroacetic acid (1 mL) was added to a solution of tert-butyl (S)-4-(6-fluoro-1-(2-isopropyl-4-methylpyridin-3-yl)-7-(2-(methylthio) pyridin-3-yl)-2-carbonyl-1, 2-dihydropyrido [2, 3-d] pyrimidin-4-yl)-3-methylpiperazine-1-carboxylate (75 mg, 0.121 mmol) in dichloromethane (5 mL), after the addition, the mixture was stirred at room temperature for 0.5 hours. The reaction mixture was concentrated at low temperature to obtain (S)-6-fluoro-1-(2-isopropyl-4-methylpyridin-3-yl)-4-(2-methylpiperazin-1-yl)-7-(2-(methylthio) pyridin-3-yl) pyrido [2, 3-d] pyrimidin-2 (1H)-one trifluoroacetate (80 mg) as a yellow oil, which was rapidly used in the next step.

MS m/z (ESI): 520.2 $[M+H]^+$.

Step 6: Preparation of (S)-4-(4-acryloyl-2-methylpiperazin-1-yl)-6-fluoro-1-(2-isopropyl-4-methylpyridin-3-yl)-7-(2-(methylthio) pyridin-3-yl) pyrido [2, 3-d] pyrimidin-2 (1H)-one

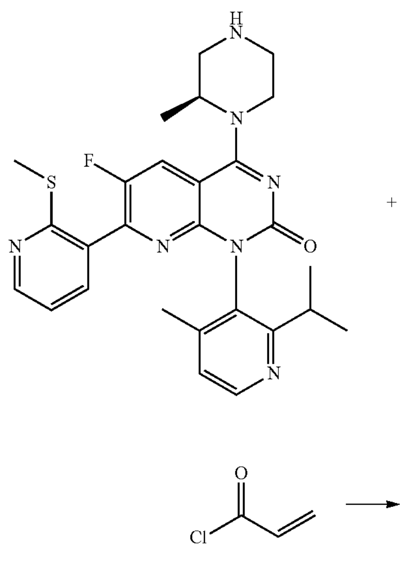

-continued

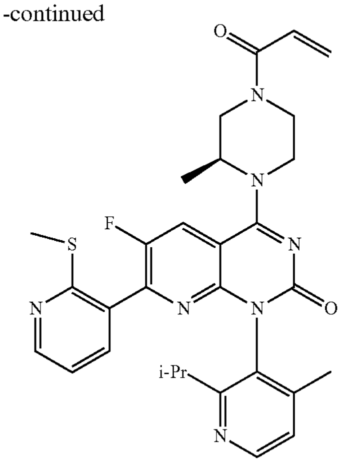

N, N-diisopropylethylamine (156 mg, 1.21 mmol) was added to a solution of (S)-6-fluoro-1-(2-isopropyl-4-methylpyridin-3-yl)-4-(2-methylpiperazin-1-yl)-7-(2-(methylthio)pyridin-3-yl)pyrido[2, 3-d]pyrimidin-2(1H)-one trifluoroacetate (80 mg, 0.121 mmol) in dichloromethane (10 mL), then acryloyl chloride (33 mg, 0.363 mmol) was added dropwise at 0° C. and stirred for 1 hour after the addition. The reaction mixture was quenched with ammonium chloride aqueous solution (30 mL), extracted with dichloromethane (30 mL×3), washed with saturated saline aqueous solution (20 mL), dried over anhydrous sodium sulfate, and purified by preparative chromatography [eluent: dichloromethane/methanol=12/1] to obtain (S)-4-(4-acryloyl-2-methylpiperazin-1-yl)-6-fluoro-1-(2-isopropyl-4-methylpyridin-3-yl)-7-(2-(methylthio)pyridin-3-yl) pyrido [2, 3-d] pyrimidin-2 (1H)-one (26 mg, two-step yield: 37%) as a yellow solid.

$^1H$ NMR (400 MHz, MeOD-$d_4$) δ 8.50-8.45 (m, 1H), 8.40 (d, J=4 Hz, 1H), 8.36-8.24 (m, 1H), 7.67 (d, J=8 Hz, 1H), 7.26 (d, J=8 Hz, 1H), 7.18-7.09 (m, 1H), 6.94-6.76 (m, 1H), 6.38-6.26 (m, 1H), 5.89-5.79 (m, 1H), 5.23-4.93 (m, 2H), 4.63-4.36 (m, 2H), 4.28-4.02 (m, 1H), 3.99-3.52 (m, 2H), 2.90-2.72 (m, 1H), 2.37 (s, 3H), 2.07 (s, 3H), 1.58-1.40 (m, 3H), 1.18 (d, J=8 Hz, 3H), 1.01 (d, J=8 Hz, 3H).

MS m/z (ESI): 574.2 [M+H].

Embodiment 143

Preparation of 6-fluoro-7-(2-fluoro-6-(methylthio) phenyl)-4-((S)-4-(2-fluoroacryloyl)-2-methylpiperazin-1-yl)-1-(2-isopropyl-4-methylpyridin-3-yl) pyrido [2, 3-d] pyrimidin-2 (1H)-one

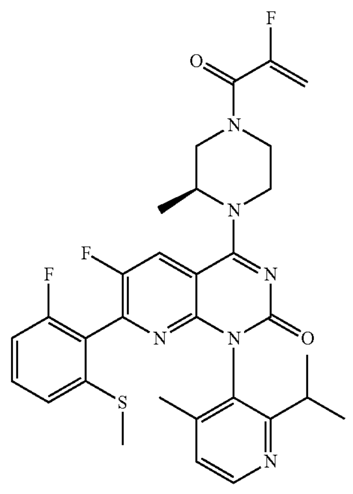 [SMILES: C=C(F)C(=O)N1CCN(c2nc(=O)n(-c3c(C)ccnc3C(C)C)c3nc(-c4c(F)cccc4SC)c(F)cc23)[C@@H](C)C1]

Step 1: Preparation of tert-butyl (3S)-4-(6-fluoro-7-(2-fluoro-6-(methylthio) phenyl)-1-(2-isopropyl-4-methylpyridin-3-yl)-2-carbonyl-1, 2-dihydropyrido [2, 3-d] pyrimidin-4-yl)-3-methylpiperazine-1-carboxylate

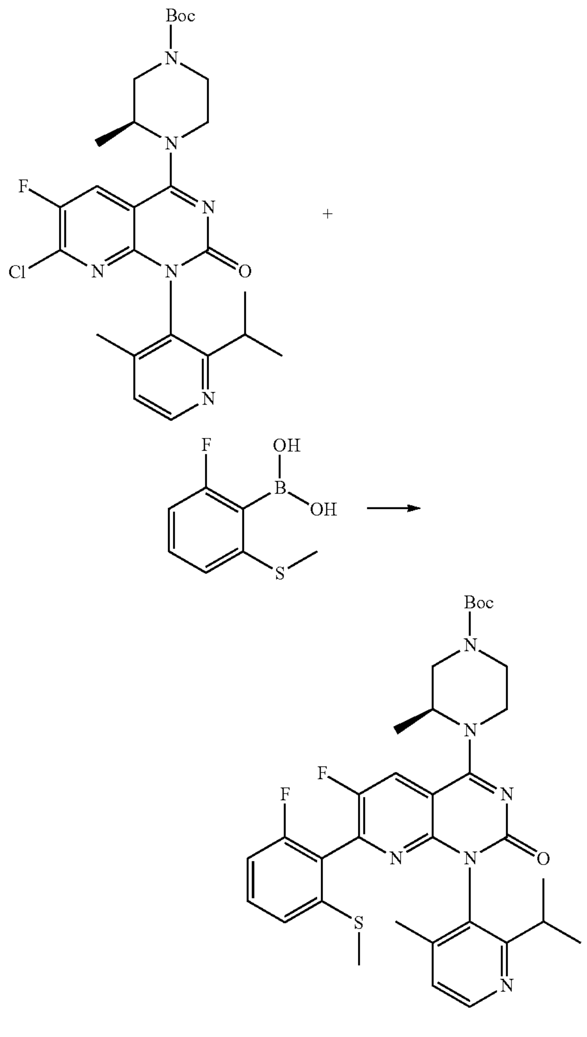

Tert-butyl (S)-4-(7-chloro-6-fluoro-1-(2-isopropyl-4-methylpyridin-3-yl)-2-carbonyl-1, 2-dihydropyrido [2, 3-d] pyrimidin-4-yl)-3-methylpiperazine-1-carboxylate (250 mg, 0.472 mmol), (2-fluoro-6-(methylthio) phenyl) boric acid (132 mg, 0.708 mmol), 1, 1'-bis (diphenylphosphino)) ferrocene-palladium (II) dichloride dichloromethane complex (96 mg, 0.118 mmol) and cesium carbonate (460 mg, 1.42 mmol) were dissolved in dioxane (8 mL) and water (1 mL), and the mixture was stirred at 100° C. for 1 hour under microwave. The reaction mixture was evaporated to dryness, then purified by column chromatography [eluent: dichloromethane/methanol from 0% to 3.5%] to obtain tert-butyl (3S)-4-(6-fluoro-7-(2-fluoro-6-(methylthio) phenyl)-1-(2-isopropyl-4-methylpyridin-3-yl)-2-carbonyl-1, 2-dihydropyrido [2, 3-d] pyrimidin-4-yl)-3-methylpiperazine-1-carboxylate (230 mg, yield: 77%) as a yellow solid.

MS m/z (ESI): 637.3 $[M+H]^+$.

Step 2: Preparation of 6-fluoro-7-(2-fluoro-6-(methylthio) phenyl)-1-(2-isopropyl-4-methylpyridin-3-yl)-4-((S)-2-methylpiperazin-1-yl) pyrido [2, 3-d] pyrimidin-2 (1H)-one trifluoroacetate

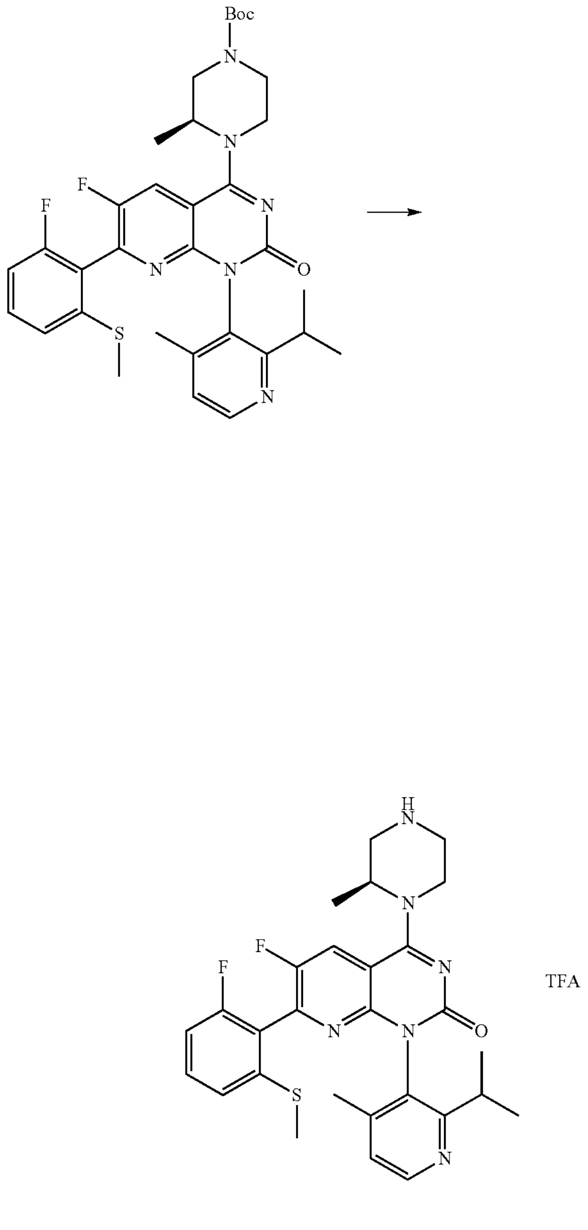

Trifluoroacetic acid (1.2 mL) was added to a solution of tert-butyl (3S)-4-(6-fluoro-7-(2-fluoro-6-(methylthio)phenyl)-1-(2-isopropyl-4-methylpyridin-3-yl)-2-carbonyl-1, 2-dihydropyrido[2, 3-d]pyrimidin-4-yl)-3-methylpiperazine-1-carboxylate (50 mg, 0.0786 mmol) in dichloromethane (6 mL), and the mixture was stirred at room temperature for 1 hour. The mixture was evaporated to dryness at low temperature to obtain 6-fluoro-7-(2-fluoro-6-(methylthio) phenyl)-1-(2-isopropyl-4-methylpyridin-3-yl)-4-((S)-2-methylpiperazin-1-yl) pyrido [2, 3-d] pyrimidin-2 (1H)-one trifluoroacetate (51 mg, yield: 100%) as a red oil, which was rapidly used in the next reaction.

Step 3: Preparation of 6-fluoro-7-(2-fluoro-6-(methylthio)phenyl)-4-((S)-4-(2-fluoroacryloyl)-2-methylpiperazin-1-yl)-1-(2-isopropyl-4-methylpyridin-3-yl) pyrido [2, 3-d]pyrimidin-2 (1H)-one

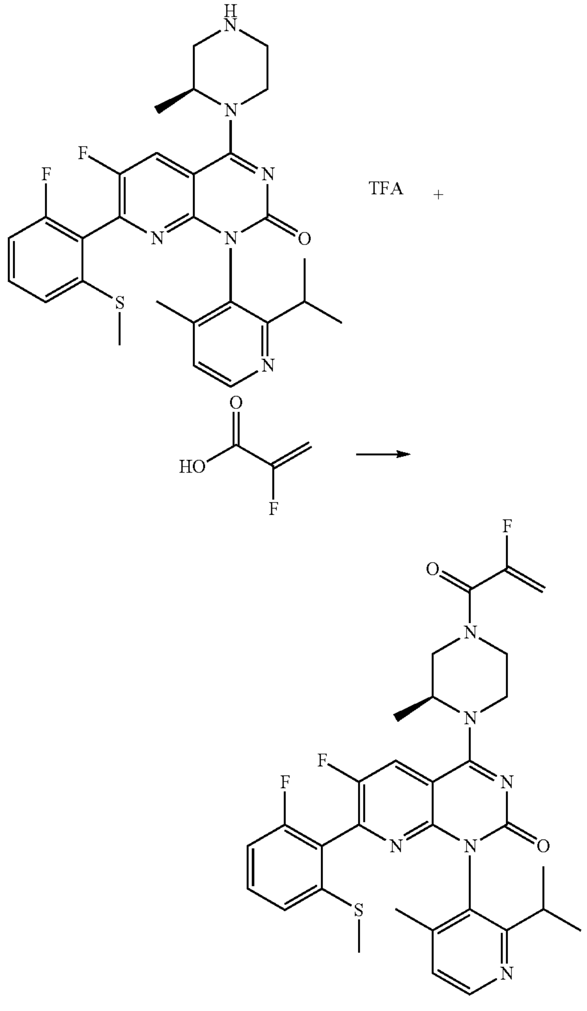

2-Fluoropropenoic acid (21 mg, 0.233 mmol) and 1-n-propyl phosphorous anhydride (100 mg, 0.314 mmol) were added to a solution of 6-fluoro-7-(2-fluoro-6-(methylthio) phenyl)-1-(2-isopropyl-4-methylpyridin-3-yl)-4-((S)-2-methylpiperazin-1-yl) pyrido [2, 3-d] pyrimidin-2 (1H)-one trifluoroacetate (51 mg, 0.0786 mmol) and N-methylmorpholine (55 mg, 0.55 mmol) in dichloromethane (10 mL) at 0° C., the mixture was stirred at 0° C. for 1 hour. Water (20 mL) was added thereto, and the mixture was extracted with dichloromethane (20 mL*2), the organic phase was concentrated and purified by preparative chromatography [eluent: dichloromethane/methanol=12/1] to obtain 6-fluoro-7-(2-fluoro-6-(methylthio) phenyl)-4-((S)-4-(2-fluoroacryloyl)-2-methylpiperazin-1-yl)-1-(2-isopropyl-4-methylpyridin-3-yl) pyrido [2, 3-d] pyrimidin-2 (1H)-one (35 mg, yield: 61%) as a yellow solid.

$^1$H NMR (400 MHz, MeOD-$d_4$) δ 8.38 (d, J=4 Hz, 1H), 8.35-8.25 (m, 1H), 7.49-7.39 (m, 1H), 7.26-7.17 (m, 2H), 6.98 (t, J=8 Hz, 1H), 5.41-5.31 (m, 1H), 5.31-5.24 (m, 1H), 5.21-4.94 (m, 2H), 4.59-3.68 (m, 4H), 3.54-3.38 (m, 1H), 2.81 (s, 1H), 2.33 (s, 3H), 2.05 (s, 3H), 1.59-1.42 (m, 3H), 1.18 (d, J=8 Hz, 3H), 0.99 (brd, 3H).

MS m/z (ESI): 609.2 [M+H]$^+$.

The synthesis of embodiments 144-149 were carried out with reference to embodiment 143.

Embodiment 150

Preparation of 4-((S)-4-acryloyl-2-methylpiperazin-1-yl)-7-(6-amino-3-chloro-2-fluorophenyl)-6-chloro-1-(2-isopropyl-4-(methylthio) pyridin-3-yl) pyrido [2, 3-d] pyrimidin-2 (1H)-one

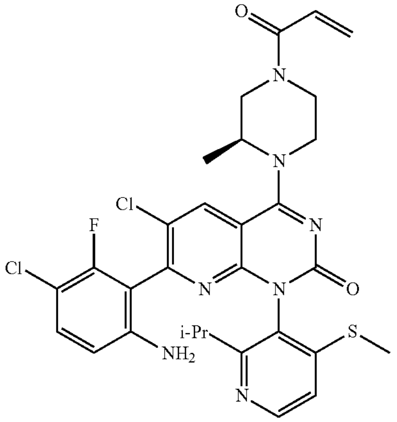 [SMILES: C=CC(=O)N1CCN(c2nc(=O)n(-c3c(SC)ccnc3C(C)C)c3nc(-c4c(N)ccc(Cl)c4F)c(Cl)cc23)[C@@H](C)C1]

(S)-4-(4-acryloyl-2-methylpiperazin-1-yl)-7-chloro-6-chloro-1-(2-isopropyl-4-(methylthio) pyridin-3-yl) pyrido [2, 3-d] pyrimidin-2 (1H)-one (26.7 mg, 0.05 mmol), (6-amino-3-chloro-2-fluorophenyl) boric acid (28.4 mg, 0.15 mmol) and potassium acetate (15.0 mg, 0.15 mmol) were dissolved in dioxane/$H_2O$ (1.5 mL/0.3 mL). The mixture was replaced with nitrogen for 1 minute, and the reaction was carried out at 100° C. for 1 hour under microwave conditions. When the reaction was completed, the reaction mixture was concentrated, purified by column chromatography ($CH_2Cl_2$/MeOH=20:1) to obtain the crude product, and then purified by preparative-HPLC to obtain the yellow solid target product 4-((S)-4-acryloyl-2-methylpiperazin-1-yl)-7-(2-amino-6-fluorophenyl)-6-fluoro-1-(2-isopropyl-4-(methylthio) pyridin-3-yl) pyrido [2, 3-d] pyrimidin-2 (1H)-one (3.7 mg, yield: 14%).

MS m/z (ESI): 642.1 [M+H]$^+$.

$^1$H NMR (400 MHz, MeOD-$d_4$) δ 8.56-8.39 (m, 2H), 7.24 (t, J=5.3 Hz, 1H), 7.15 (dd, J=15.4, 6.9 Hz, 1H), 6.84 (d, J=9.9 Hz, 1H), 6.53-6.46 (m, 1H), 6.32 (d, J=15.9 Hz, 1H), 5.84 (d, J=12.2 Hz, 1H), 4.68-4.36 (m, 3H), 4.10 (dd, J=45.7, 31.6 Hz, 2H), 3.76 (s, 1H), 2.94 (s, 2H), 2.42 (d, J=6.2 Hz, 3H), 1.57-1.43 (m, 3H), 1.22 (d, J=6.7 Hz, 3H), 1.06 (dd, J=42.4, 6.7 Hz, 3H). $^{19}$F NMR (376 MHz, MeOD) δ −117.04-−117.24 (m), −117.24-−117.51 (m).

Embodiment 150-1 and Embodiment 150-2

(M/P-4-((S)-4-acryloyl-2-methylpiperazin-1-yl)-7-(2-amino-6-fluorophenyl)-6-fluoro-1-(2-isopropyl-4-(methylthio)pyridin-3-yl)pyrido[2, 3-d]pyrimidin-2(1H)-one)

150-1

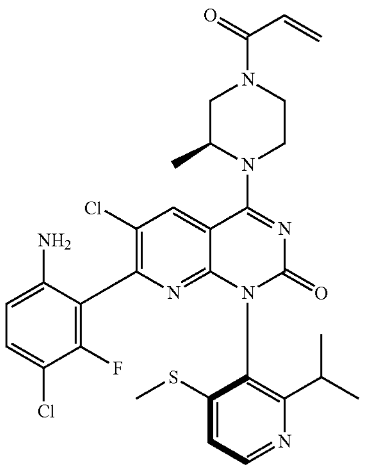

150-2

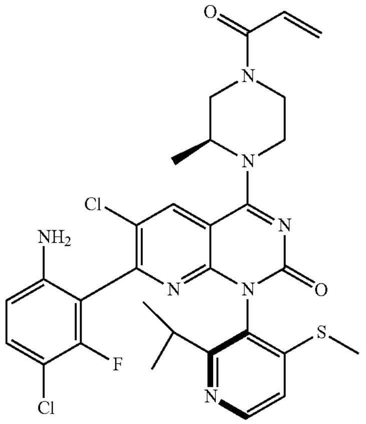

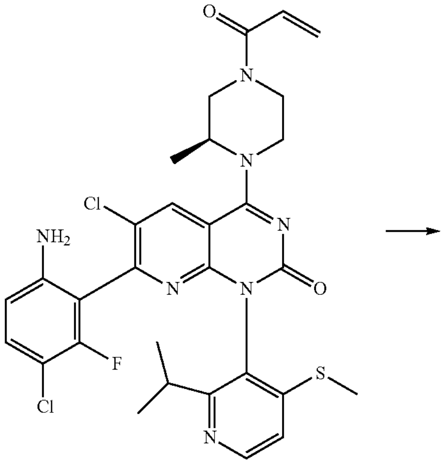

-continued

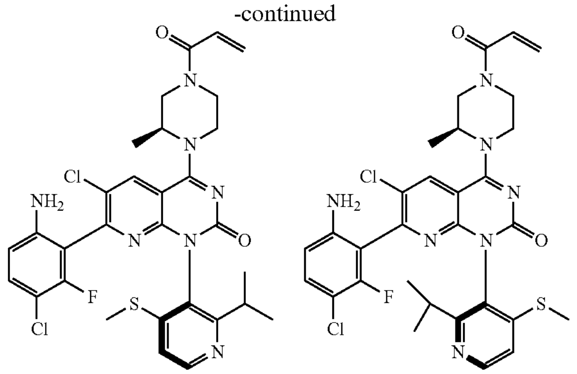

Embodiment 150 was resolved by SFC to obtain two axial chiral isomers, embodiment 150-1 and embodiment 150-2, SFC: chiral preparation conditions:

TABLE 19

| | |
|---|---|
| Instrument | SFC-80 (Thar, Waters) |
| Column type | IC 20 * 250 mm, 10 μm (Daicel) |
| Column pressure | 100 bar |
| Mobile phase | $CO_2$/Methanol (0.2% Methanol Ammonia) = 45/55 |
| Flow rate | 80 g/min |
| Detection wavelength | UV 214 nm |
| Column temperature | 35° C. |

Chiral Analysis Conditions:

TABLE 20

| | |
|---|---|
| Instrument | SFC Method Station (Thar, Waters) |
| Column type | OX-H 4.6 * 100 mm, 5 μm (Daicel) |
| Column pressure | 120 bar |
| Mobile phase | A: $CO_2$; B: Methanol [0.2% NH3(7M in methanol)]; A:B = 65:35 |
| Flow rate | 4 mL/min |
| Detection wavelength | UV 214 nm |
| Column temperature | 40° C. |

Embodiment 150-1

$t_R$=1.87 min

MS m/z (ESI): 642.1 $[M+H]^+$.

$^1$H NMR (400 MHz, MeOD-$d_4$) δ 8.56-8.39 (m, 2H), 7.24 (t, J=5.3 Hz, 1H), 7.15 (dd, J=15.4, 6.9 Hz, 1H), 6.84 (d, J=9.9 Hz, 1H), 6.53-6.46 (m, 1H), 6.32 (d, J=15.9 Hz, 1H), 5.84 (d, J=12.2 Hz, 1H), 4.68-4.36 (m, 3H), 4.10 (dd, J=45.7, 31.6 Hz, 2H), 3.76 (s, 1H), 2.94 (s, 2H), 2.42 (d, J=6.2 Hz, 3H), 1.57-1.43 (m, 3H), 1.22 (d, J=6.7 Hz, 3H), 1.06 (dd, J=42.4, 6.7 Hz, 3H).

$^{19}$F NMR (376 MHz, MeOD-$d_4$) δ −117.04-−117.24 (m), −117.24-−117.51 (m).

Embodiment 150-2

$t_R$=2.80 min

MS m/z (ESI): 642.1 $[M+H]^+$.

$^1$H NMR (400 MHz, MeOD-$d_4$) δ 8.56-8.39 (m, 2H), 7.27-7.10 (m, 2H), 6.84 (dd, J=28.3, 17.7 Hz, 1H), 6.50 (d, J=8.8 Hz, 1H), 6.32 (d, J=16.9 Hz, 1H), 5.83 (d, J=11.7 Hz, 1H), 4.63-4.41 (m, 2H), 4.23-4.02 (m, 1H), 3.79-3.57 (m, 2H), 3.36 (s, 2H), 2.99-2.86 (m, 1H), 2.41 (d, J=7.6 Hz, 3H), 1.51 (d, J=25.9 Hz, 3H), 1.21 (d, J=6.6 Hz, 3H), 1.05 (dd, J=44.8, 6.7 Hz, 3H).

Embodiment 151

Preparation of 4-((S)-4-acryloyl-2-methylpiperazin-1-yl)-7-(6-amino-3-chloro-2-fluorophenyl)-6-fluoro-1-(2-isopropyl-4-(methylthio)pyridin-3-yl)pyrido[2, 3-d]pyrimidin-2(1H)-one

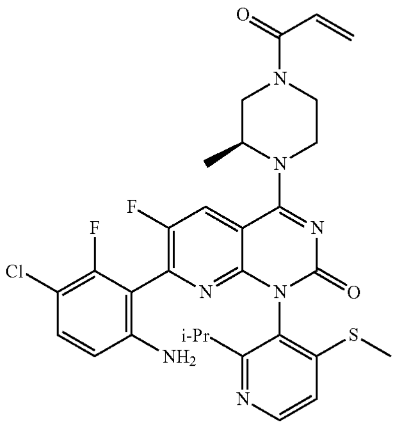 [SMILES: C=CC(=O)N1CCN(c2nc(=O)n(-c3c(SC)ccnc3C(C)C)c3nc(-c4c(N)ccc(Cl)c4F)c(F)cc23)[C@@H](C)C1]

(S)-4-(4-acryloyl-2-methylpiperazin-1-yl)-7-chloro-6-fluoro-1-(2-isopropyl-4-(methylthio) pyridin-3-yl) pyrido [2, 3-d] pyrimidin-2 (1H)-one (26 mg, 0.05 mmol), (6-amino-3-chloro-2-fluorophenyl) boric acid (28.4 mg, 0.15 mmol) and cesium carbonate (48.8 mg, 0.15 mmol) were dissolved in dioxane/$H_2O$ (1.5 mL/0.3 mL). The mixture was replaced with nitrogen for 1 minute, and the reaction was carried out at 100° C. for 1 hour under microwave conditions. When the reaction was completed, the reaction mixture was evaporated to dryness, purified by column chromatography ($CH_2Cl_2$/MeOH=20:1) to obtain the crude product, and then purified by preparative-HPLC to obtain the yellow solid target product 4-((S)-4-acryloyl-2-methylpiperazin-1-yl)-7-(2-amino-6-fluorophenyl)-6-fluoro-1-(2-isopropyl-4-(methylthio) pyridin-3-yl) pyrido [2, 3-d] pyrimidin-2 (1H)-one (4.4 mg, yield: 14%).

$^1$H NMR (400 MHz, MeOD-$d_4$) δ 8.47 (d, J=5.4 Hz, 1H), 8.38-8.24 (m, 1H), 7.27 (d, J=5.4 Hz, 1H), 7.17 (t, J=8.6 Hz, 1H), 6.85 (d, J=14.9 Hz, 1H), 6.49 (d, J=8.9 Hz, 1H), 6.32 (d, J=16.3 Hz, 1H), 5.84 (d, J=10.5 Hz, 1H), 4.57 (d, J=23.5 Hz, 2H), 4.42 (s, 1H), 4.24-3.89 (m, 2H), 3.73 (dd, J=14.4, 7.9 Hz, 1H), 2.92 (s, 1H), 2.43 (s, 3H), 1.54-1.40 (m, 3H), 1.22 (d, J=6.7 Hz, 3H), 1.01 (d, J=6.6 Hz, 3H).

$^{19}$F NMR (376 MHz, MeOD-$d_4$) δ −116.46-−116.73 (m), −116.87 (dd, J=39.0, 8.4 Hz), −126.18 (dd, J=24.9, 15.2 Hz).

MS m/z (ESI): 626.1 [M+H]$^+$.

Embodiment 152

Preparation of 4-((S)-4-acryloyl-2-methylpiperazin-1-yl)-6-fluoro-7-(2-fluoro-6-hydroxyphenyl)-1-(2-isopropyl-6-methyl-4-(methylthio) pyridin-3-yl) pyrido [2, 3-d] pyrimidin-2 (1H)-one

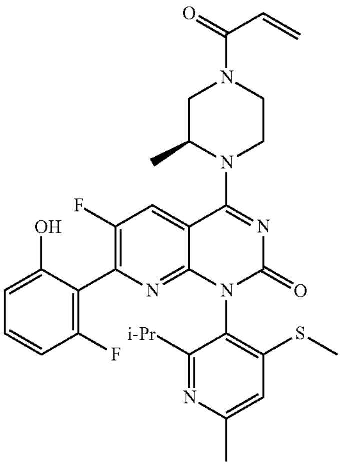 [SMILES: C=CC(=O)N1CCN(c2nc(=O)n(-c3c(SC)cc(C)nc3C(C)C)c3nc(-c4c(O)cccc4F)c(F)cc23)[C@@H](C)C1]

Step 1: Preparation of 6-bromo-2-isopropyl-4-(methylthio) pyridin-3-amine

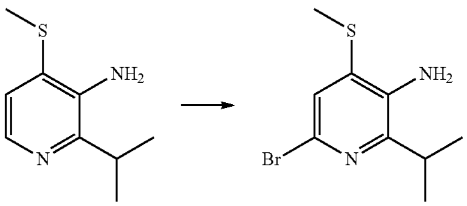

2-Isopropyl-4-(methylthio) pyridin-3-amine (1 g, 5.5 mmol) was dissolved in acetonitrile (15 mL), N-bromosuccinimide (970 mg, 5.5 mmol) was added thereto at 0° C., and the mixture was stirred at room temperature for 1 hour. The reaction mixture was cooled to 0° C., and quenched by adding saturated $Na_2SO_3$ dropwise, then extracted with water and dichloromethane (3*10 mL). The organic phases were combined, dried over anhydrous sodium sulfate, filtered, concentrated to obtain the crude product, and purified by column chromatography (Petro ether/EtOAc=10:1 to 3:1) to obtain the target product 6-bromo-2-isopropyl-4-(methylthio) pyridin-3-amine (480 mg, yield: 34%).

MS m/z (ESI): 261.1 [M+H]$^+$.

Step 2: Preparation of 2-isopropyl-6-methyl-4-(methylthio) pyridin-3-amine

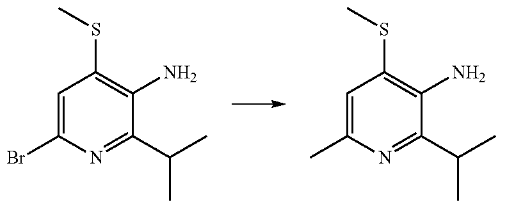

Under the protection of $N_2$, 6-bromo-2-isopropyl-4-(methylthio) pyridin-3-amine (480 mg, 1.85 mmol) was dissolved in a mixture of 1, 4-dioxane and water (3 mL: 0.1 mL), methyl boric acid (560 mg, 9.25 mmol), Pd(dppf) $Cl_2$·DCM (100 mg, 0.2 mmol) and $K_2CO_3$ (510 mg, 3.7 mmol) were added thereto and the reaction was carried out at 100° C. for 1 hour under microwave. The reaction mixture was extracted with dichloromethane (3*10 mL) and water. The organic phases were combined, dried over anhydrous sodium sulfate, filtered, concentrated to obtain the crude product, and purified by column chromatography (Petro ether/EtOAc=3:1 to 1:1) to obtain the target product 2-isopropyl-6-methyl-4-(methylthio)pyridin-3-amine (200 mg, yield: 55%).

MS m/z (ESI): 197.1 $[M+H]^+$.

Step 3: Preparation of 2, 6-dichloro-5-fluoro-N-(2-isopropyl-6-methyl-4-(methylthio) pyridin-3-yl) carbamoyl) nicotinamide

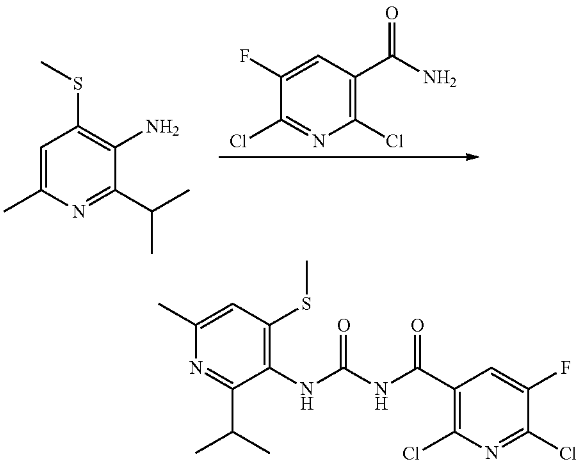

Under the protection of $N_2$, 2, 6-dichloro-5-fluoronicotinamide (220 mg, 1.05 mmol) was dissolved in THF (20 mL), oxalyl chloride (0.6 mL, 1.2 mmol) (2 m/L dichloromethane solution) was added dropwise at −78° C., and the mixture was stirred at −78° C. for 10 minutes, then stirred at 60° C. for 3 hours, then cooled to 0° C., triethylamine (1 mL, 3.2 mmol) was added dropwise, a solution of 2-isopropyl-6-methyl-4-(methylthio) pyridin-3-amine (200 mg, 1.05 mmol) in THF was added dropwise, and the mixture was stirred at room temperature for 2 hours. The reaction mixture was quenched with saline, extracted with water and ethyl acetate (3*50 mL), the organic phases were combined, dried over anhydrous sodium sulfate, filtered and concentrated to obtain the crude product, then purified by column chromatography (DCM/MeOH=100:1 to 70:1) to obtain the target product 2, 6-dichloro-5-fluoro-N-((2-isopropyl-6-methyl-4-(methylthio)pyridin-3-yl)carbamoyl)nicotinamide (320 mg, yield: 67%).

MS m/z (ESI): 457.1 $[M+H]^+$.

Step 4: Preparation of 7-chloro-6-fluoro-1-(2-isopropyl-6-methyl-4-(methylthio) pyridin-3-yl) pyrido [2, 3-d] pyrimidin-2, 4 (1H, 3H)-dione

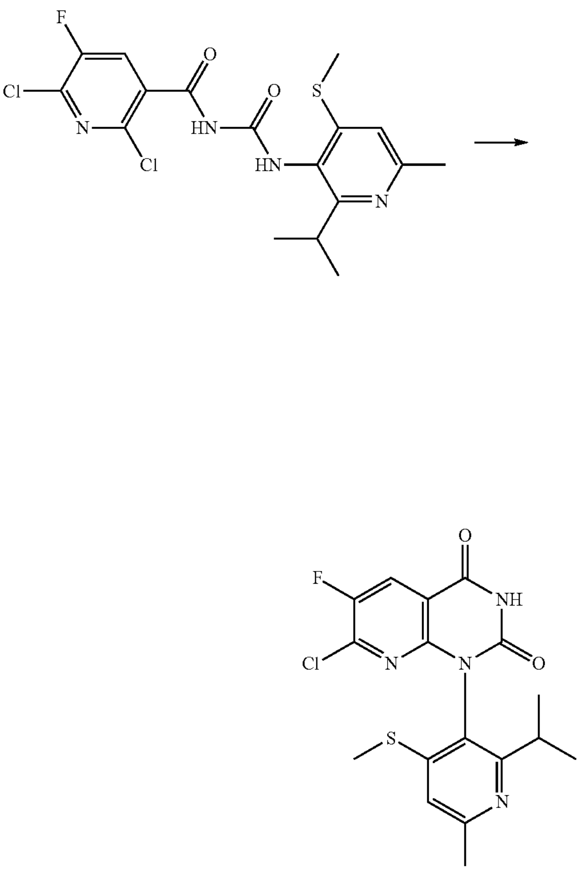

2, 6-Dichloro-5-fluoro-N-((2-isopropyl-6-methyl-4-(methylthio) pyridin-3-yl) carbamoyl) nicotinamide (320 mg, 0.75 mmol) was dissolved in anhydrous THF (20 mL), cooled to 0° C. under nitrogen protection, KHMDS (1.5 mL, 1.5 mmol) was added thereto dropwise, and the mixture was stirred for 0.5 hours. The reaction mixture was then quenched with saturated ammonium chloride aqueous solution, then extracted three times with water and ethyl acetate (3*50 mL). The organic phases were combined, dried over anhydrous sodium sulfate, filtered, concentrated to obtain the crude product, and purified by column chromatography (DCM/MeOH=200:1 to 80:1) to obtain the target product 7-chloro-6-fluoro-1-(2-isopropyl-6-methyl-4-(methylthio) pyridin-3-yl) pyrido [2, 3-d] pyrimidin-2, 4 (1H, 3H)-dione (270 mg, yield: 91%).

MS m/z (ESI): 395.1 $[M+H]^+$.

Step 5: Preparation of 4, 7-dichloro-6-fluoro-1-(2-isopropyl-6-methyl-4-(methylthio) pyridin-3-yl) pyrido [2, 3-d] pyrimidin-2 (1H)-one

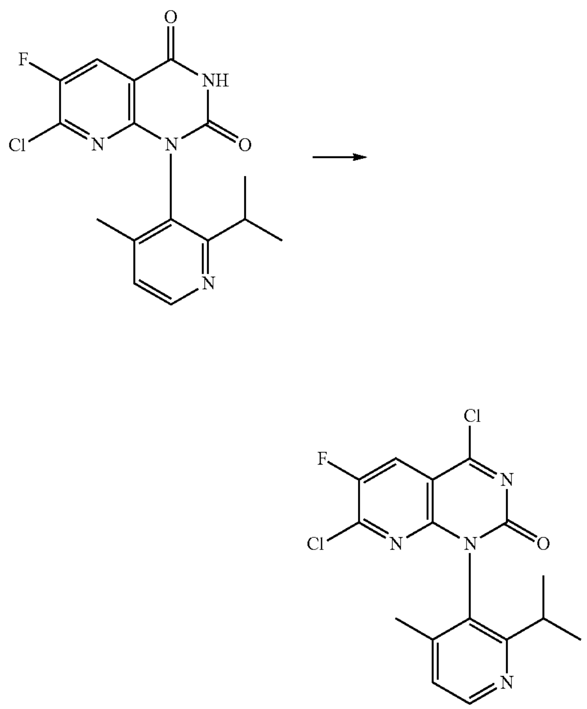 [SMILES: Cc1ccnc(C(C)C)c1-n1c(=O)[nH]c(=O)c2cc(F)c(Cl)nc21 ; Cc1ccnc(C(C)C)c1-n1c(=O)nc(Cl)c2cc(F)c(Cl)nc21]

7-Chloro-6-fluoro-1-(2-isopropyl-6-methyl-4-(methylthio) pyridin-3-yl) pyrido [2, 3-d]pyrimidin-2, 4 (1H, 3H)-dione (270 mg, 0.57 mmol) was dissolved in acetonitrile (10 mL); DIEA (1.2 mL, 2.3 mmol) and $POCl_3$ (0.12 mL, 1.1 mmol) were added thereto, and the mixture was stirred at 80° C. for 0.5 hours. The residue was used in the next reaction.

MS m/z (ESI): 413.1 $[M+H]^+$.

Step 6: Preparation of tert-butyl (S)-4-(7-chloro-6-fluoro-1-(2-isopropyl-6-methyl-4-(methylthio) pyridin-3-yl)-2-carbonyl-1, 2-dihydropyrido [2, 3-d] pyrimidin-4-yl)-3-methylpiperazine-1-carboxylate

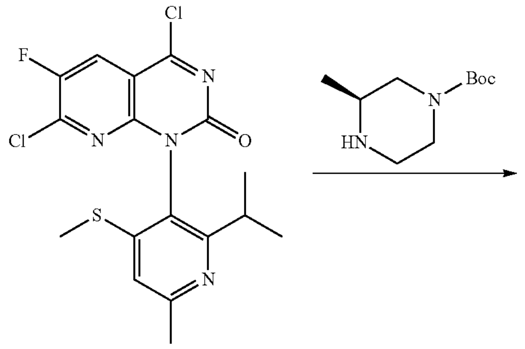

-continued

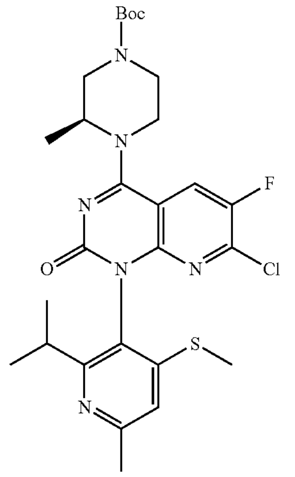

DIEA (1.2 mL, 2.3 mmol) was added to a solution of 4, 7-dichloro-6-fluoro-1-(2-isopropyl-6-methyl-4-(methylthio) pyridin-3-yl)pyrido[2, 3-d]pyrimidin-2(1H)-one (230 mg, 0.57 mmol) in acetonitrile (10 mL), tert-butyl (S)-3-methylpiperazine-1-carboxylate (230 mg, 1.1 mmol) was added thereto, and the mixture was stirred for 1 hour at room temperature. The reaction mixture was then quenched with water, then extracted three times with ethyl acetate (3*50 mL) and water. The organic phases were combined, dried over anhydrous sodium sulfate, filtered, concentrated to obtain the crude product, and purified by column chromatography ($CH_2Cl_2$/MeOH=30:1) to obtain the target product tert-butyl (S)-4-(7-chloro-6-fluoro-1-(2-isopropyl-6-methyl-4-(methylthio)pyridin-3-yl)-2-carbonyl-1, 2-dihydropyrido [2, 3-d]pyrimidin-4-yl)-3-methylpiperazine-1-carboxylate (290 mg, yield: 88%).

MS m/z (ESI): 577.1 $[M+H]^+$.

Step 7: Preparation of (S)-7-chloro-6-fluoro-1-(2-isopropyl-6-methyl-4-(methylthio) pyridin-3-yl)-4-(2-methylpiperazin-1-yl) pyrido [2, 3-d] pyrimidin-2 (1H)-one

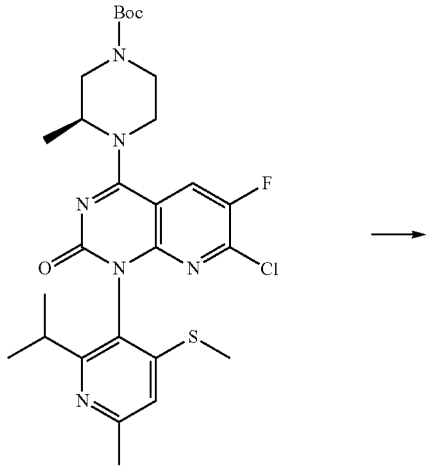

-continued

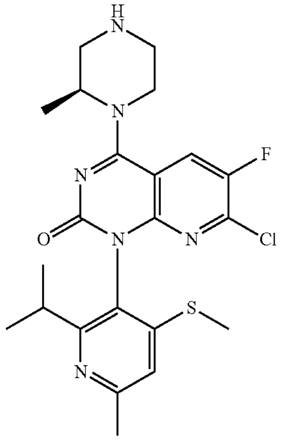

-continued

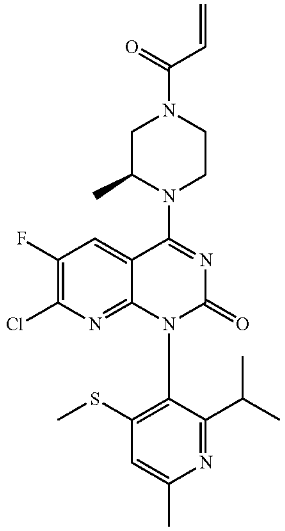

Tert-butyl (S)-4-(7-chloro-6-fluoro-1-(2-isopropyl-6-methyl-4-(methylthio) pyridin-3-yl)-2-carbonyl-1, 2-dihydropyrido [2,3-d] pyrimidin-4-yl)-3-methylpiperazine-1-carboxylate (290 mg, 0.5 mmol) was dissolved in dichloromethane (6 mL), TFA (1 mL) was added thereto, and the mixture was stirred at room temperature for 1 hour. The mixture was concentrated to obtain the crude target product (S)-7-chloro-6-fluoro-1-(2-isopropyl-6-methyl-4-(methylthio)pyridin-3-yl)-4-(2-methylpiperazin-1-yl)pyrido [2, 3-d]pyrimidin-2(1H)-one (240 mg, yield: 100%).

MS m/z (ESI): 477.1 $[M+H]^+$.

Step 8: Preparation of 4-((S)-4-acryloyl-2-methylpiperazin-1-yl)-7-chloro-6-fluoro-1-(2-isopropyl-6-methyl-4-(methylthio) pyridin-3-yl) pyrido [2, 3-d] pyrimidin-2 (1H)-one

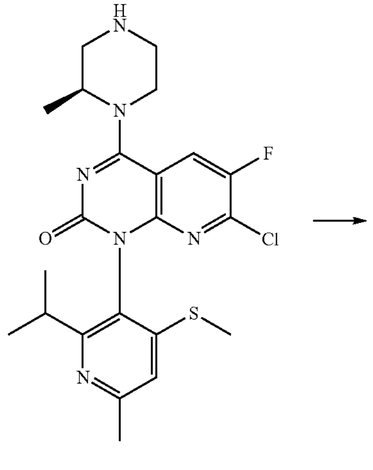

(S)-7-chloro-6-fluoro-1-(2-isopropyl-6-methyl-4-(methylthio) pyridin-3-yl)-4-(2-methylpiperazin-1-yl) pyrido [2, 3-d] pyrimidin-2 (1H)-one (240 mg, 0.5 mmol) was dissolved in dichloromethane (10 mL), DIEA (3 mL, 5 mmol) was added thereto, then acryloyl chloride (45 mg, 0.5 mmol) was added and the mixture was stirred at room temperature for 1 hour. The reaction mixture was then quenched with water, then extracted three times with water and ethyl acetate (3*50 mL). The organic phases were combined, dried over anhydrous sodium sulfate, filtered, concentrated, and purified by column chromatography ($CH_2Cl_2$/MeOH=20:1) to obtain the target product 4-((S)-4-acryloyl-2-methylpiperazin-1-yl)-7-chloro-6-fluoro-1-(2-isopropyl-6-methyl-4-(methylthio) pyridin-3-yl) pyrido [2, 3-d] pyrimidin-2 (1H)-one (300 mg, yield: 100%).

MS m/z (ESI): 531.1 $[M+H]^+$.

Step 9: Preparation of 4-((S)-4-acryloyl-2-methylpiperazin-1-yl)-6-fluoro-7-(2-fluoro-6-hydroxyphenyl)-1-(2-isopropyl-6-methyl-4-(methylthio) pyridin-3-yl) pyrido [2, 3-d] pyrimidin-2 (1H)-one

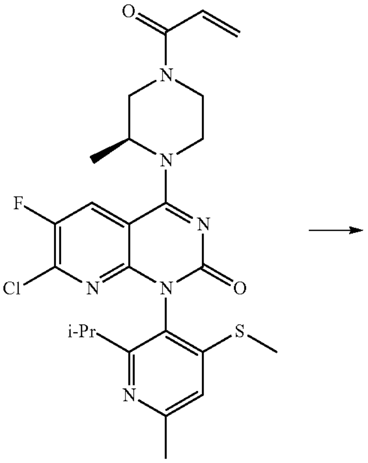

-continued

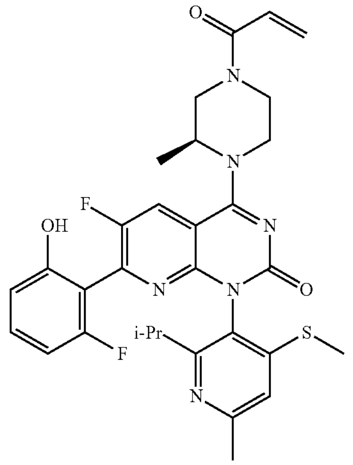

Under the protection of $N_2$, 4-((S)-4-acryloyl-2-methylpiperazin-1-yl)-7-chloro-6-fluoro-1-(2-isopropyl-6-methyl-4-(methylthio)pyridin-3-yl)pyrido[2, 3-d]pyrimidin-2(1H)-one (300 mg, 0.57 mmol) and (2-fluoro-6-hydroxyphenyl) boric acid (177 mg, 1.1 mmol) were dissolved in a mixture of 1, 4-dioxane and water (6 mL: 0.3 mL); $Pd(dppf)Cl_2{\cdot}DCM$ (50 mg, 0.06 mmol) and $Cs_2CO_3$ (280 mg, 0.86 mmol) were added thereto and the reaction was carried out at 100° C. for 1 hour under microwave. The reaction mixture was then quenched with water, then extracted three times with water and ethyl acetate (3*50 mL). The organic phases were combined, dried over anhydrous sodium sulfate, filtered, concentrated, and purified by column chromatography ($CH_2Cl_2$/MeOH=200:1 to 80:1) to obtain the target product 4-((S)-4-acryloyl-2-methylpiperazin-1-yl)-6-fluoro-7-(2-fluoro-6-hydroxyphenyl)-1-(2-isopropyl-6-methyl-4-(methylthio)pyridin-3-yl)pyrido[2, 3-d]pyrimidin-2(1H)-one (90 mg, yield: 26%).

$^1$H NMR (400 MHz, Methanol-$d_4$) δ 8.38 (d, J=5.0 Hz, 1H), 8.30-8.22 (m, 1H), 7.56-7.41 (m, 3H), 7.25-7.19 (m, 2H), 6.91-6.80 (m, 1H), 6.34-6.29 (dd, J=17.0, 5.6 Hz, 1H), 5.84-5.82 (dd, J=10.6, 1.8 Hz, 1H), 5.11-5.04 (m, 2H), 4.53-4.46 (m, 2H), 4.23-4.07 (m, 1H), 3.90-3.73 (m, 2H), 2.81-2.79 (m, 1H), 2.28 (s, 3H), 2.05 (s, 3H), 1.50-1.46 (m, 3H), 1.19-1.17 (d, J=6.8 Hz, 3H), 1.01-0.99 (d, J=6.8 Hz, 3H).

MS m/z (ESI): 573.1 $[M+H]^+$.

Embodiment 143

Preparation of 6-fluoro-7-(2-fluoro-6-(methylthio)phenyl)-4-((S)-4-(2-fluoroacryloyl)-2-methylpiperazin-1-yl)-1-(2-isopropyl-4-methylpyridin-3-yl) pyrido [2, 3-d] pyrimidin-2 (1H)-one

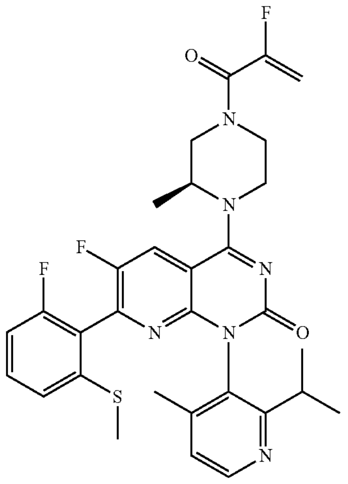

Embodiment 153

Preparation of 4-((S)-4-acryloyl-2-methylpiperazin-1-yl)-7-(2, 3-difluoro-6-hydroxyphenyl)-6-fluoro-1-(2-isopropyl-4-(methylthio) pyridin-3-yl) pyrido [2, 3-d] pyrimidin-2 (1H)-one

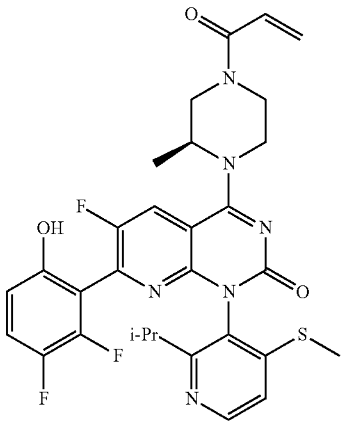 [SMILES: C=CC(=O)N1CCN(c2nc(=O)n(-c3c(SC)ccnc3C(C)C)c3nc(-c4c(O)ccc(F)c4F)c(F)cc23)[C@@H](C)C1]

Embodiment 143

Preparation of 6-fluoro-7-(2-fluoro-6-(methylthio) phenyl)-4-((S)-4-(2-fluoroacryloyl)-2-methylpiperazin-1-yl)-1-(2-isopropyl-4-methylpyridin-3-yl) pyrido [2, 3-d] pyrimidin-2 (1H)-one

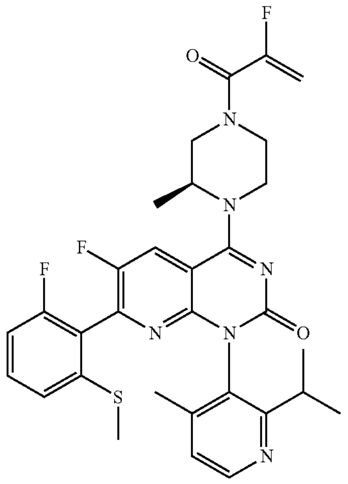

4-((S)-4-acryloyl-2-methylpiperazin-1-yl)-7-(2, 3-difluoro-6-hydroxyphenyl)-6-fluoro-1-(2-isopropyl-4-(methylthio)pyridin-3-yl)pyrido[2, 3-d]pyrimidin-2(1H)-one was prepared with reference to embodiment 114.

MS m/z (ESI): 611.1 $[M+H]^+$.

$^1$H NMR (400 MHz, MeOD-$d_4$) δ 8.41 (d, J=5.6 Hz, 1H), 8.32-8.25 (m, 1H), 7.25 (d, J=5.6 Hz, 1H), 7.20-7.13 (m, 1H), 6.92-6.82 (m, 1H), 6.62-6.58 (m, 1H), 6.34-6.28 (m, 1H), 5.83 (d, J=10.4 Hz, 1H), 5.14-5.04 (m, 1H), 4.64-4.42 (m, 2H), 4.25-4.07 (m, 1H), 3.89-3.61 (m, 3H), 2.88-2.77 (m, 1H), 2.42 (s, 3H), 1.52-1.46 (m, 3H), 1.20 (d, J=6.4 Hz, 3H), 1.05 (d, J=6.4 Hz, 3H).

Embodiment 154

Preparation of (S)-4-(4-acryloyl-2-methylpiperazin-1-yl)-7-(2, 6-difluorophenyl)-6-fluoro-1-(2-isopropyl-4-(methylthio)pyridin-3-yl)pyrido[2, 3-d]pyrimidin-2(1H)-one

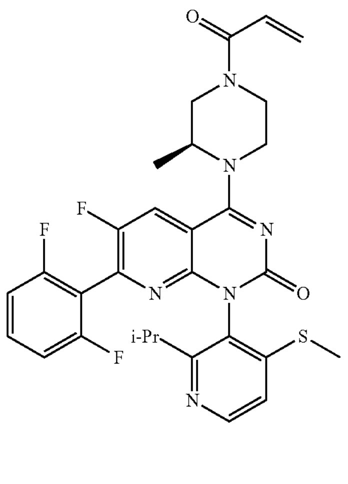 [SMILES: C=CC(=O)N1CCN(c2nc(=O)n(-c3c(SC)ccnc3C(C)C)c3nc(-c4c(F)cccc4F)c(F)cc23)[C@@H](C)C1]

(S)-4-(4-acryloyl-2-methylpiperazin-1-yl)-7-(2, 6-difluorophenyl)-6-fluoro-1-(2-isopropyl-4-(methylthio)pyridin-3-yl)pyrido[2, 3-d]pyrimidin-2(1H)-one was prepared with reference to embodiment 114.

MS m/z (ESI): 595.1 $[M+H]^+$.

$^1$H NMR (400 MHz, Methanol-$d_4$) δ 8.40-8.32 (m, 2H), 7.51 (t, J=7.6 Hz, 1H), 7.22 (d, J=5.4 Hz, 1H), 7.05 (t, J=8.4 Hz, 2H), 6.86-6.79 (m, 1H), 6.37-6.26 (m, 1H), 5.84 (d, J=10.6 Hz, 1H), 5.08 (m, 2H), 4.56-4.46 (m, 2H), 4.21-4.08 (m, 1H), 3.85-3.62 (m, 2H), 2.86-2.82 (m, 1H), 2.40 (s, 3H), 1.47 (d, J=6.6 Hz, 3H), 1.21-1.19 (d, J=6.8 Hz, 3H), 1.04 (d, J=6.8 Hz, 3H).

Embodiment 155

Preparation of 4-((S)-4-acryloyl-2-methylpiperazin-1-yl)-6-chloro-7-(2-fluoro-6-hydroxyphenyl)-1-(2-isopropyl-4-(methylsulfonyl) pyridin-3-yl) pyrido [2, 3-d] pyrimidin-2 (1H)-one

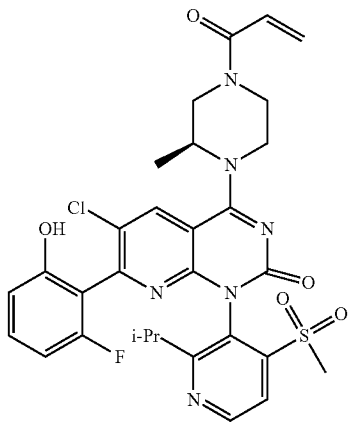 [SMILES: C=CC(=O)N1CCN(c2nc(=O)n(-c3c(S(C)(=O)=O)ccnc3C(C)C)c3nc(-c4c(O)cccc4F)c(Cl)cc23)[C@@H](C)C1]

4-((S)-4-acryloyl-2-methylpiperazin-1-yl)-6-chloro-7-(2-fluoro-6-hydroxyphenyl)-1-(2-isopropyl-4-(methylsulfonyl) pyridin-3-yl)pyrido[2, 3-d]pyrimidin-2(1H)-one was prepared with reference to embodiment 133.

MS m/z (ESI): 641.1 $[M+H]^+$.

$^1$H NMR (400 MHz, MeOD-$d_4$) δ 8.86 (d, J=5.2 Hz, 1H), 8.44-8.46 (m, 1H), 7.85 (d, J=4.8 Hz, 1H), 7.20 (dd, $J_1$=15.2 Hz, $J_2$=8.4 Hz, 1H), 6.82-6.85 (m, 1H), 6.55-6.64 (m, 2H), 6.31 (d, J=17.2 Hz, 1H), 5.82 (d, J=12.0 Hz, 1H), 5.07 (s, 1H), 4.43-4.58 (m, 2H), 4.06-4.23 (s, 1H), 3.38-3.86 (m, 3H), 2.94-2.98 (m, 4H), 1.46-1.51 (m, 3H), 1.18-1.22 (m, 3H), 1.07-1.09 (m, 3H).

Embodiment 165

Preparation of 4-((2S, 5R)-4-acryloyl-2, 5-dimethylpiperazin-1-yl)-7-(6-amino-3-chloro-2-fluorophenyl)-6-chloro-1-(2-isopropyl-4-(methylthio) pyridin-3-yl) pyrido [2, 3-d] pyrimidin-2 (1H)-one

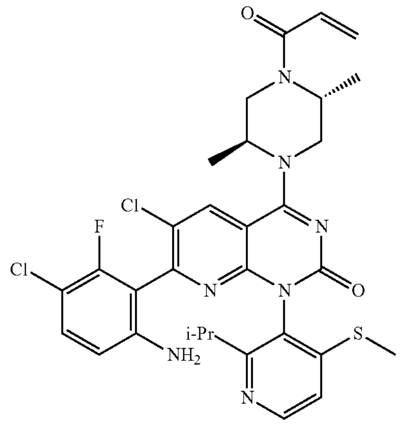 [SMILES: C=CC(=O)N1C[C@H](C)N(c2nc(=O)n(-c3c(SC)ccnc3C(C)C)c3nc(-c4c(N)ccc(Cl)c4F)c(Cl)cc23)C[C@H]1C]

Step 1: Preparation of 2, 5, 6-trichloro-N-(2-isopropyl-4-(methylthio) pyridin-3-yl) carbamoyl) nicotinamide

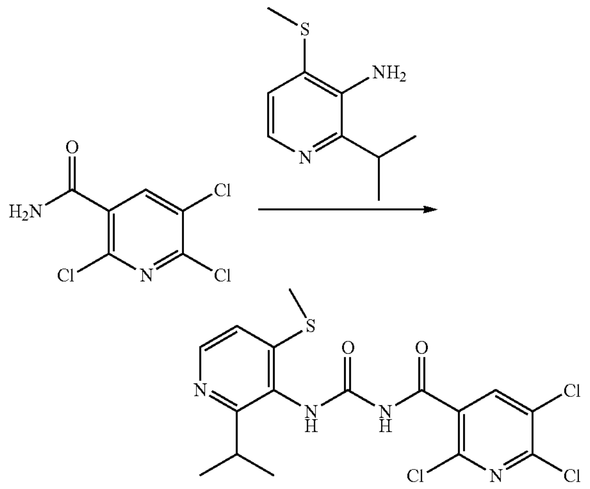

Under the protection of $N_2$, 2, 5, 6-trichloronicotinamide (6.2 g, 27.7 mmol) was dissolved in THF (60 mL), oxalyl chloride (15.2 mL, 31.5 mmol) (2 m/L dichloromethane solution) was added dropwise at −78° C., and the mixture was stirred at −78° C. for 10 minutes, then the mixture was stirred at 60° C. for 3 hours, then cooled to 0° C., triethylamine (18 mL, 111 mmol) was added dropwise, a solution of 2-isopropyl-6-methyl-4-(methylthio) pyridin-3-amine (5 g, 27.7 mmol) in THF was added dropwise, and the mixture was stirred at room temperature for 2 hours. The reaction mixture was quenched with saline, extracted with water and ethyl acetate (3*100 mL), the organic phases were combined, dried over anhydrous sodium sulfate, filtered and concentrated to obtain the crude product, then purified by column chromatography (DCM/MeOH=100:1 to 70:1) to obtain the target product 2, 5, 6-trichloro-N-((2-isopropyl-4-(methylthio)pyridin-3-yl)carbamoyl)nicotinamide (8.6 g, yield: 72%).

MS m/z (ESI): 433.1 $[M+H]^+$, 435.1 $[M+H+2]^+$.

Step 2: Preparation of 6, 7-dichloro-1-(2-isopropyl-4-(methylthio) pyridin-3-yl) pyrido [2, 3-d]pyrimidin-2, 4 (1H, 3H)-dione

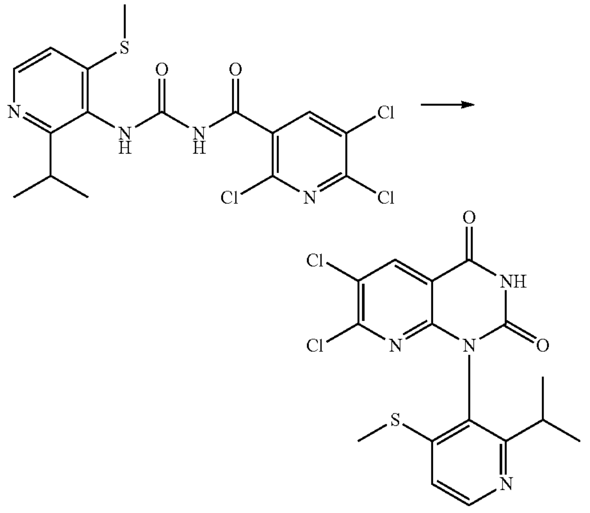

2, 5, 6-Trichloro-N-((2-isopropyl-4-(methylthio)pyridin-3-yl)carbamoyl)nicotinamide (10.4 g, 24.1 mmol) was dissolved in anhydrous THF (80 mL), cooled to 0° C. under nitrogen protection, KHMDS (48 mL, 48.2 mmol) was added thereto dropwise, and the mixture was stirred for 0.5 hours. The reaction mixture was then quenched with saturated ammonium chloride aqueous solution, then extracted three times with water and ethyl acetate (3*100 mL). The organic phases were combined, dried over anhydrous sodium sulfate, filtered, concentrated to obtain the crude product, and slurried with ethyl acetate to obtain the target product 6, 7-dichloro-1-(2-isopropyl-4-(methylthio) pyridin-3-yl) pyrido [2, 3-d] pyrimidin-2, 4 (1H, 3H)-dione (8 g, yield: 84%).

MS m/z (ESI): 397.1 $[M+H]^+$, 399.1 $[M+H+2]^+$.

Step 3: Preparation of 4, 6, 7-trichloro-1-(2-isopropyl-4-(methylthio) pyridin-3-yl) pyrido [2, 3-d]pyrimidin-2 (1H)-one

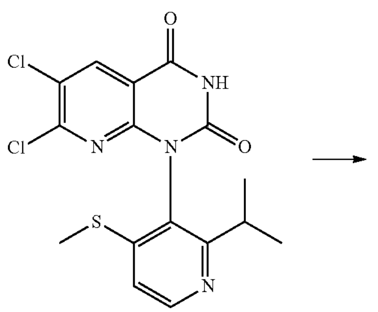

-continued

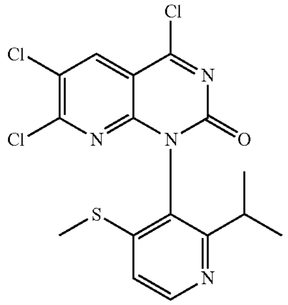

6, 7-Dichloro-1-(2-isopropyl-4-(methylthio) pyridin-3-yl) pyrido [2, 3-d] pyrimidin-2, 4 (1H, 3H)-dione (5.2 g, 13.1 mmol) was dissolved in ACN (50 mL); DIEA (23 mL, 66 mmol) and $POCl_3$ (3 mL, 19.7 mmol) were added thereto, and the mixture was stirred at 80° C. for 0.5 hours. The product was directly used in the next reaction.

MS m/z (ESI): 415.1 $[M+H]^+$, 417.1 $[M+H+2]^+$.

Step 4: Preparation of tert-butyl (2R, 5S)-4-(6, 7-dichloro-1-(2-isopropyl-4-(methylthio) pyridin-3-yl)-2-carbonyl-1, 2-dihydropyrido [2, 3-d] pyrimidin-4-yl)-2, 5-dimethylpiperazine-1-carboxylate

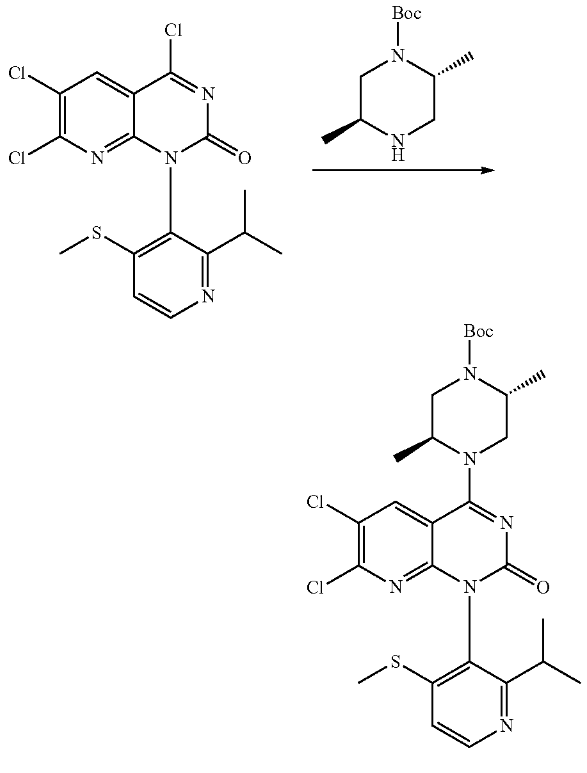

Tert-butyl (2R, 5S)-2, 5-dimethylpiperazine-1-carboxylate (6.2 g, 26.2 mmol) was added to a solution of 4, 6, 7-trichloro-1-(2-isopropyl-4-(methylthio) pyridin-3-yl) pyrido [2, 3-d] pyrimidin-2 (1H)-one in acetonitrile (50 mL); DIEA (23 mL, 66 mmol) was added thereto, and the mixture was stirred at room temperature for 1 hour. The reaction mixture was then quenched with water, then extracted three times with water and ethyl acetate (3*100 mL). The organic phases were combined, dried over anhydrous sodium sulfate, filtered, concentrated to obtain the crude product, and purified by column chromatography ($CH_2Cl_2$/MeOH=30:1) to obtain the target product tert-butyl (2R, 5S)-4-(6, 7-dichloro-1-(2-isopropyl-4-(methylthio) pyridin-3-yl)-2-carbonyl-1, 2-dihydropyrido[2, 3-d]pyrimidin-4-yl)-2, 5-dimethylpiperazine-1-carboxylate (6.1 g, yield: 77%).

MS m/z (ESI): 593.1 $[M+H]^+$, 595.1 $[M+H+2]^+$.

Step 5: Preparation of 6, 7-dichloro-4-((2S, 5R)-2, 5-dimethylpiperazin-1-yl)-1-(2-isopropyl-4-(methylthio) pyridin-3-yl) pyrido [2, 3-d] pyrimidin-2 (1H)-one

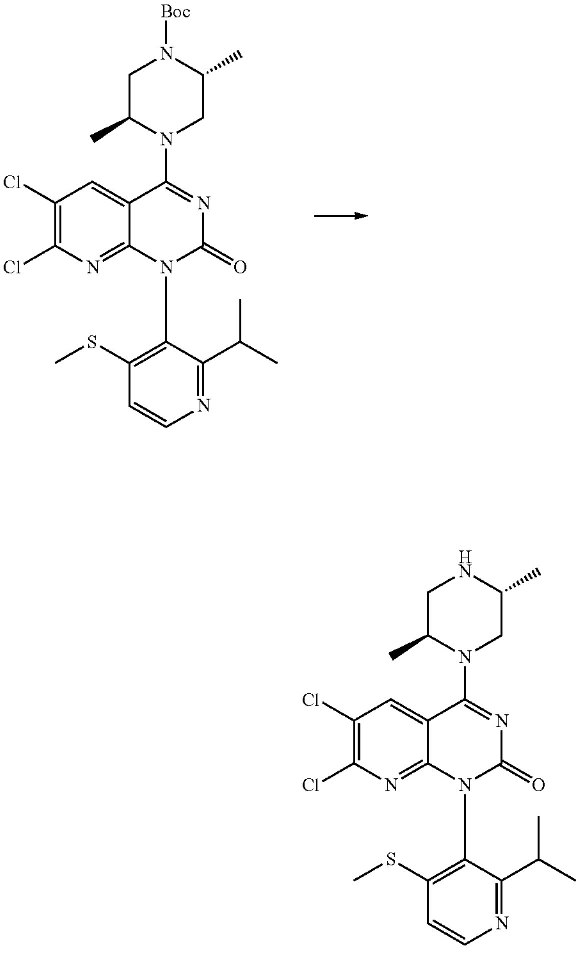 [SMILES: CSc1ccnc(C(C)C)c1-n1c(=O)nc(N2C[C@@H](C)N(C(=O)OC(C)(C)C)C[C@@H]2C)c2cc(Cl)c(Cl)nc21 ; CSc1ccnc(C(C)C)c1-n1c(=O)nc(N2C[C@@H](C)NC[C@@H]2C)c2cc(Cl)c(Cl)nc21]

Tert-butyl (2R, 5S)-4-(6, 7-dichloro-1-(2-isopropyl-4-(methylthio)pyridin-3-yl)-2-carbonyl-1, 2-dihydropyrido[2, 3-d]pyrimidin-4-yl)-2, 5-dimethylpiperazine-1-carboxylate (6.1 g, 10.3 mmol) was dissolved in dichloromethane (20 mL), TFA (20 mL) was added thereto, and the mixture was stirred at room temperature for 1 hour. The mixture was concentrated to obtain the crude target product 6, 7-dichloro-4-((2S, 5R)-2, 5-dimethylpiperazin-1-yl)-1-(2-isopropyl-4-(methylthio) pyridin-3-yl) pyrido [2, 3-d]pyrimidin-2 (1H)-one (6.1 g, yield: 100%).

MS m/z (ESI): 493.1 $[M+H]^+$, 495.1 $[M+H+2]^+$.

Step 6: Preparation of 4-((2S, 5R)-4-acryloyl-2, 5-dimethylpiperazin-1-yl)-6, 7-dichloro-1-(2-isopropyl-4-(methylthio) pyridin-3-yl) pyrido [2, 3-d] pyrimidin-2 (1H)-one

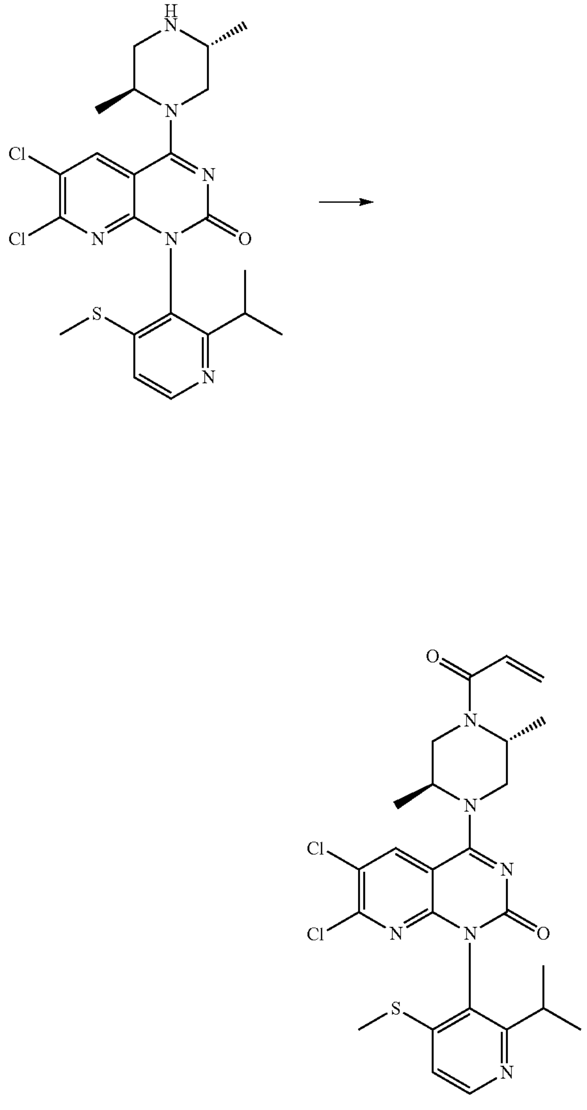

6, 7-Dichloro-4-((2S, 5R)-2, 5-dimethylpiperazin-1-yl)-1-(2-isopropyl-4-(methylthio) pyridin-3-yl) pyrido [2, 3-d] pyrimidin-2 (1H)-one (6 g, 12.2 mmol) was dissolved in dichloromethane (30 mL); DIEA (30 mL, 131 mmol), acryloyl chloride (1.08 mL, 13.13 mmol) were added thereto, and the mixture was stirred at room temperature for 1 hour. The reaction mixture was then quenched with water, then extracted three times with water and ethyl acetate (3*100 mL). The organic phases were combined, dried over anhydrous sodium sulfate, filtered, concentrated, and purified by column chromatography ($CH_2Cl_2$/MeOH=20:1) to obtain the target product 4-((2S, 5R)-4-acryloyl-2, 5-dimethylpiperazin-1-yl)-6, 7-dichloro-1-(2-isopropyl-4-(methylthio) pyridin-3-yl)pyrido[2, 3-d]pyrimidin-2(1H)-one (1.6 g, yield: 22%).

MS m/z (ESI): 547.1 $[M+H]^+$, 549.1 $[M+H+2]^+$.

Step 7: Preparation of 4-((2S, 5R)-4-acryloyl-2, 5-dimethylpiperazin-1-yl)-7-(6-amino-3-chloro-2-fluorophenyl)-6-chloro-1-(2-isopropyl-4-(methylthio) pyridin-3-yl) pyrido [2,3-d] pyrimidin-2 (1H)-one

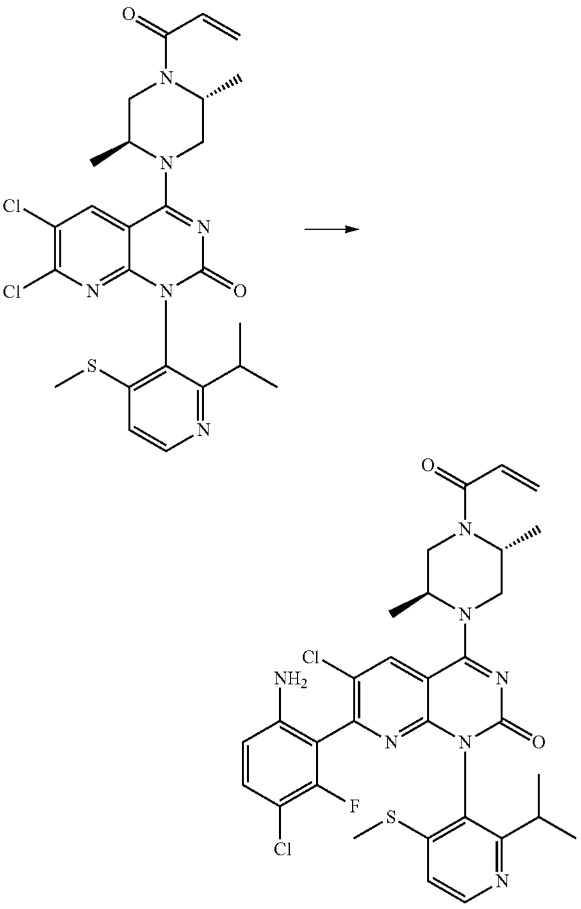

Under the protection of $N_2$, 4-((2S, 5R)-4-acryloyl-2, 5-dimethylpiperazin-1-yl)-6, 7-dichloro-1-(2-isopropyl-4-(methylthio)pyridin-3-yl)pyrido[2, 3-d] pyrimidin-2(1H)-one (700 mg, 1.3 mmol), (6-amino-3-chloro-2-fluorophenyl) boric acid (380 mg, 2.6 mmol) was dissolved in a mixture of 1, 4-dioxane and water (6 mL: 0.3 mL); and Pd(dppf) $Cl_2$·DCM (100 mg, 0.1 mmol) and KOAc (400 mg, 4 mmol) were added thereto, and the reaction was carried out at 100° C. for 1 hour under microwave. The reaction mixture was then quenched with water, then extracted three times with ethyl acetate (3*50 mL) and water. The organic phases were combined, dried over anhydrous sodium sulfate, filtered, concentrated to obtain the crude product, and purified by column chromatography ($CH_2Cl_2$/MeOH=200:1 to 80:1) to obtain the target product 4-((2S, 5R)-4-acryloyl-2, 5-dimethylpiperazin-1-yl)-7-(6-amino-3-chloro-2-fluorophenyl)-6-chloro-1-(2-isopropyl-4-(methylthio)pyridin-3-yl)pyrido [2, 3-d]pyrimidin-2(1H)-one (400 mg, yield: 48%).

MS m/z (ESI): 656.1 $[M+H]^+$, 658.1 $[M+H+2]^+$.

$^1H$ NMR (400 MHz, Methanol-$d_4$) δ 8.47-8.34 (m, 2H), 7.24-7.20 (m, 1H), 7.10-7.14 (m, 1H), 6.79-6.68 (m, 1H), 6.42-6.40 (d, J=8.0 Hz, 1H), 6.24-6.17 (m, 1H), 5.75-5.71 (m, 1H), 5.01-4.94 (m, 2H), 4.46-4.40 (m, 1H), 4.26-4.17

(m, 1H), 4.03-3.99 (m, 1H), 3.84-3.79 (m, 1H), 2.86-2.77 (m, 1H), 2.36 (s, 3H), 1.26-1.19 (m, 9H), 1.14-1.11 (m, 3H).

Embodiment 165-1 and Embodiment 165-2

(M/P-4-((2S, 5R)-4-acryloyl-2, 5-dimethylpiperazin-1-yl)-7-(6-amino-3-chloro-2-fluorophenyl)-6-chloro-1-(2-isopropyl-4-(methylthio)pyridin-3-yl)pyrido[2, 3-d]pyrimidin-2(1H)-one)

165-1

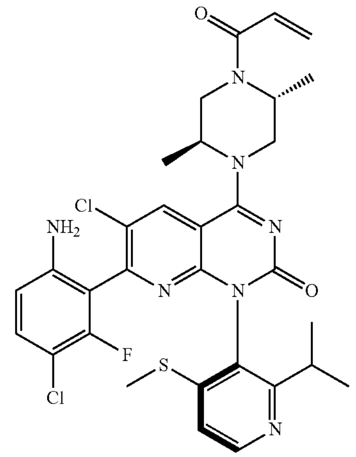

165-2

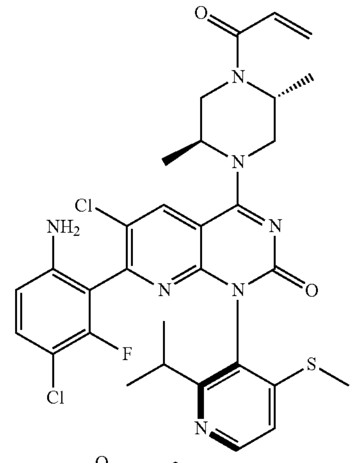

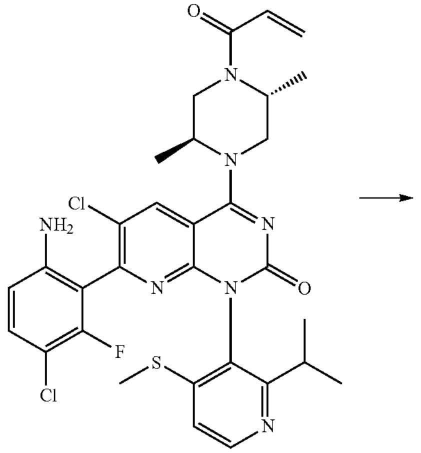

-continued

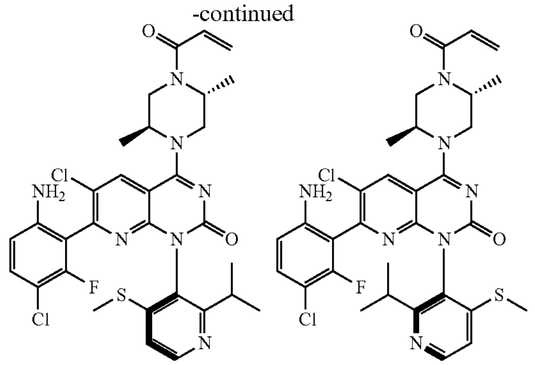

Embodiment 165 was resolved by SFC to obtain two axial chiral isomers, embodiment 165-1 and embodiment 165-2, SFC: chiral preparation conditions:

TABLE 21

| | |
|---|---|
| Instrument | SFC-150 (Thar, Waters) |
| Column type | IC 20 * 250 mm, 10 μm (Daicel) |
| Column pressure | 100 bar |
| Mobile phase | $CO_2$/Methanol (0.2% Methanol Ammonia) = 40/60 |
| Flow rate | 120 g/min |
| Detection wavelength | UV 214 nm |
| Column temperature | 35° C. |

Chiral Analysis Conditions:

TABLE 22

| | |
|---|---|
| Instrument | SFC Method Station (Thar, Waters) |
| Column type | OX-H 4.6 * 100 mm, 5 μm (Daicel) |
| Column pressure | 120 bar |
| Mobile phase | A: $CO_2$; B: Methanol [0.2% NH3(7M in methanol)];<br>A:B = 65:35 |
| Flow rate | 4 mL/min |
| Detection wavelength | UV 214 nm |
| Column temperature | 40° C. |

Embodiment 165-1

$t_R$=1.74 min

MS m/z (ESI): 656.1 $[M+H]^+$, 658.1 $[M+H+2]^+$.

$^1$H NMR (400 MHz, MeOD-$d_4$) δ 8.47-8.34 (m, 2H), 7.24-7.20 (m, 1H), 7.10-7.14 (m, 1H), 6.79-6.68 (m, 1H), 6.42-6.40 (d, J=8.0 Hz, 1H), 6.24-6.17 (m, 1H), 5.75-5.71 (m, 1H), 5.01-4.94 (m, 2H), 4.46-4.40 (m, 1H), 4.26-4.17 (m, 1H), 4.03-3.99 (m, 1H), 3.84-3.79 (m, 1H), 2.86-2.77 (m, 1H), 2.36 (s, 3H), 1.26-1.19 (m, 9H), 1.14-1.11 (m, 3H).

Embodiment 165-2

$t_R$=2.49 min

MS m/z (ESI): 656.1 $[M+H]^+$, 658.1 $[M+H+2]^+$.

$^1$H NMR (400 MHz, DMSO-$d_6$) δ 8.55-8.38 (m, 2H), 7.25-7.20 (m, 1H), 7.18-7.11 (m, 1H), 6.88-6.76 (m, 1H), 6.51-6.47 (d, J=8.0 Hz, 1H), 6.33-6.27 (m, 1H), 5.84-5.80 (m, 1H), 5.12-5.10 (m, 2H), 4.46-4.23 (m, 2H), 4.15-3.89 (m, 2H), 3.64-3.50 (m, 1H), 2.89-2.82 (m, 1H), 2.43 (s, 3H), 1.51-0.99 (m, 12H).

Embodiment 166

Preparation of 4-((2S, 5R)-4-acryloyl-2, 5-dimethylpiperazin-1-yl)-6-chloro-7-(2-fluoro-6-hydroxyphenyl)-1-(2-isopropyl-4-(methylthio) pyridin-3-yl) pyrido [2, 3-d] pyrimidin-2 (1H)-one

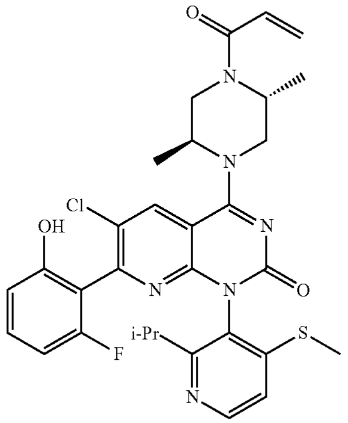 [SMILES: C=CC(=O)N1C[C@H](C)N(c2nc(=O)n(-c3c(SC)ccnc3C(C)C)c3nc(-c4c(O)cccc4F)c(Cl)cc23)C[C@H]1C]

4-((2S, 5R)-4-acryloyl-2, 5-dimethylpiperazin-1-yl)-6-chloro-7-(2-fluoro-6-hydroxyphenyl)-1-(2-isopropyl-4-(methylthio)pyridin-3-yl)pyrido[2, 3-d]pyrimidin-2(1H)-one was prepared with reference to embodiment 165.

MS m/z (ESI): 623.1 $[M+H]^+$, 625.1 $[M+H+2]^+$.

$^1$H NMR (400 MHz, Methanol-$d_4$) δ 8.47-8.34 (m, 2H), 7.21-7.20 (m, 2H), 6.89-6.77 (m, 1H), 6.64-6.55 (m, 2H), 6.32-6.26 (m, 1H), 5.84-5.80 (m, 1H), 5.08-5.03 (m, 2H), 4.56-4.49 (m, 1H), 4.34-4.26 (m, 1H), 4.13-4.04 (m, 1H), 3.92-3.88 (m, 1H), 2.79-2.72 (m, 1H), 2.40 (s, 3H), 1.55-1.43 (m, 3H), 1.35-1.27 (m, 3H), 1.20-1.17 (m, 3H), 1.08-1.05 (t, J=8.0 Hz, 3H).

Embodiment 166-1 and Embodiment 166-2

(M/P-4-((2S, 5R)-4-acryloyl-2, 5-dimethylpiperazin-1-yl)-6-chloro-7-(2-fluoro-6-hydroxyphenyl)-1-(2-isopropyl-4-(methylthio)pyridin-3-yl)pyrido[2, 3-d] pyrimidin-2(1H)-one)

166-1

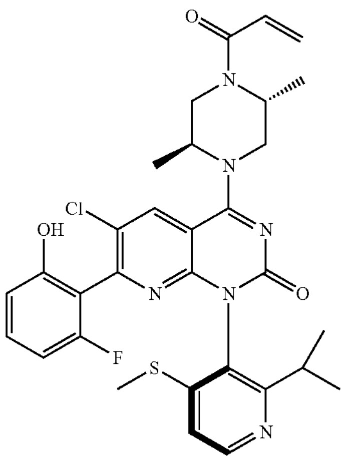

-continued 166-2

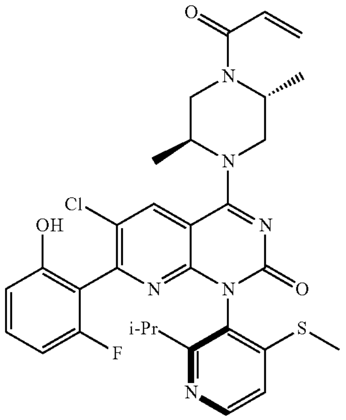

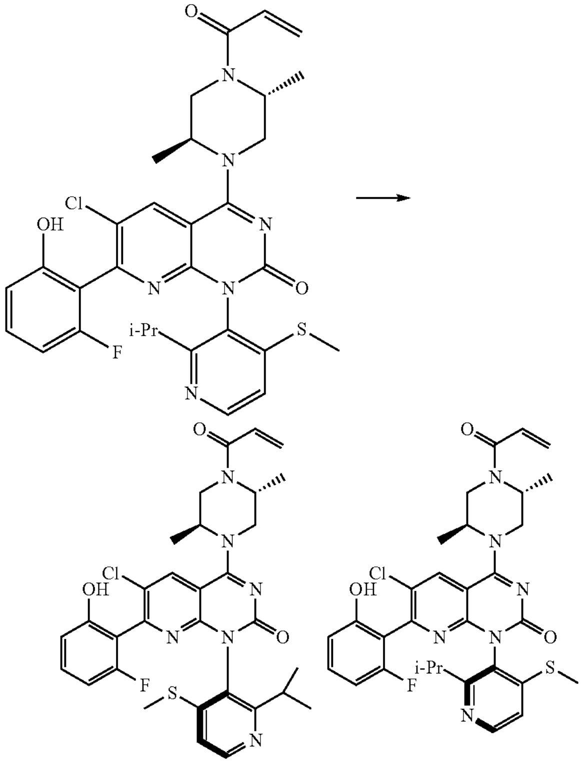

Embodiment 166 was resolved by SFC to obtain two axial chiral isomers, embodiment 166-1 and embodiment 166-2, SFC: chiral preparation conditions:

TABLE 23

| | |
|---|---|
| Instrument | SFC-150 (Thar, Waters) |
| Column type | IC 20 * 250 mm, 10 μm (Daicel) |
| Column pressure | 100 bar |
| Mobile phase | $CO_2$/Methanol (0.2% Methanol Ammonia) = 50/50 |
| Flow rate | 120 g/min |
| Detection wavelength | UV 214 nm |
| Column temperature | 35° C. |

Chiral Analysis Conditions:

TABLE 24

| | |
|---|---|
| Instrument | SFC Method Station (Thar, Waters) |
| Column type | IC 4.6*100 mm, 5 μm (Daicel) |

TABLE 24-continued

| | |
|---|---|
| Column pressure | 120 bar |
| Mobile phase | A: $CO_2$; B: Ethanol [1.0% $NH_3$(7M in methanol)]; A:B = 55:45 |
| Flow rate | 4 mL/min |
| Detection wavelength | UV 214 nm |
| Column temperature | 40° C. |

Embodiment 166-1

$t_R$=2.46 min

MS m/z (ESI): 623.1 $[M+H]^+$, 625.1 $[M+H+2]^+$.

$^1$H NMR (400 MHz, Methanol-$d_4$) δ 8.47-8.34 (m, 2H), 7.21-7.20 (m, 2H), 6.89-6.77 (m, 1H), 6.64-6.55 (m, 2H), 6.32-6.26 (m, 1H), 5.84-5.80 (m, 1H), 5.08-5.03 (m, 2H), 4.56-4.49 (m, 1H), 4.34-4.26 (m, 1H), 4.13-4.04 (m, 1H), 3.92-3.88 (m, 1H), 2.79-2.72 (m, 1H), 2.40 (s, 3H), 1.55-1.43 (m, 3H), 1.35-1.27 (m, 3H), 1.20-1.17 (m, 3H), 1.08-1.05 (t, J=8.0 Hz, 3H).

Embodiment 166-2

$t_R$=3.08 min

MS m/z (ESI): 623.1 $[M+H]^+$, 625.1 $[M+H+2]^+$.

$^1$H NMR (400 MHz, Methanol-$d_4$) δ 8.48-8.34 (m, 2H), 7.23-7.21 (m, 2H), 6.90-6.78 (m, 1H), 6.66-6.58 (m, 2H), 6.33-6.28 (m, 1H), 5.85-5.82 (m, 1H), 5.10-5.06 (m, 2H), 4.58-4.50 (m, 1H), 4.34-4.27 (m, 1H), 4.13-4.06 (m, 1H), 3.93-3.88 (m, 1H), 2.79-2.71 (m, 1H), 2.41 (s, 3H), 1.56-1.46 (m, 3H), 1.37-1.29 (m, 3H), 1.21-1.18 (m, 3H), 1.07-1.05 (t, J=8.0 Hz, 3H).

Embodiment 169

Preparation of (S)-4-(4-acryloyl-2-methylpiperazin-1-yl)-7-(2, 6-difluorophenyl)-6-fluoro-1-(2-isopropyl-4-(methylthio) pyridin-3-yl) pyrido [2, 3-d] pyrimidin-2 (1H)-one

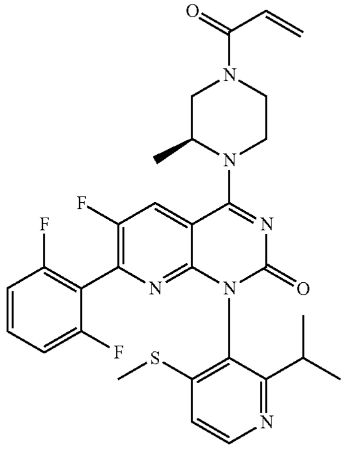 [SMILES: C=CC(=O)N1CCN(c2nc(=O)n(-c3c(SC)ccnc3C(C)C)c3nc(-c4c(F)cccc4F)c(F)cc23)[C@@H](C)C1]

(S)-4-(4-acryloyl-2-methylpiperazin-1-yl)-7-(2, 6-difluorophenyl)-6-fluoro-1-(2-isopropyl-4-(methylthio)pyridin-3-yl)pyrido[2, 3-d]pyrimidin-2(1H)-one was prepared with reference to embodiment 114.

MS m/z (ESI): 595.1 $[M+H]^+$.

$^1$H NMR (400 MHz, Methanol-$d_4$) δ 8.40-8.32 (m, 2H), 7.51 (t, J=7.6 Hz, 1H), 7.22 (d, J=5.4 Hz, 1H), 7.05 (t, J=8.4 Hz, 2H), 6.86-6.79 (m, 1H), 6.37-6.26 (m, 1H), 5.84 (d, J=10.6 Hz, 1H), 5.08 (m, 2H), 4.56-4.46 (m, 2H), 4.21-4.08 (m, 1H), 3.85-3.62 (m, 2H), 2.86-2.82 (m, 1H), 2.40 (s, 3H), 1.47 (d, J=6.6 Hz, 3H), 1.21-1.19 (d, J=6.8 Hz, 3H), 1.04 (d, J=6.8 Hz, 3H).

Embodiment 191

Preparation of 4-((s)-4-acryloyl-2-methylpiperazine-1-yl)-7-(2-amino-3, 5-dichloro-6-fluorophenyl)-6-chloro-1-(2-isopropyl-4-(methylthio) pyridin-3-yl) pyrido [2, 3-d] pyrimidin-2 (1H)-one

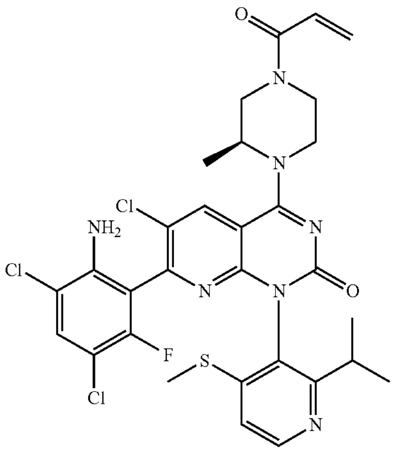 [SMILES: C=CC(=O)N1CCN(c2nc(=O)n(-c3c(SC)ccnc3C(C)C)c3nc(-c4c(N)c(Cl)cc(Cl)c4F)c(Cl)cc23)[C@@H](C)C1]

4-((S)-4-acryloyl-2-methylpiperazin-1-yl)-7-(2-amino-3, 5-dichloro-6-fluorophenyl)-6-chloro-1-(2-isopropyl-4-(methylthio)pyridin-3-yl)pyrido[2, 3-d]pyrimidin-2(1H)-one was prepared with reference to embodiment 165.

MS m/z (ESI): 676.1 $[M+H]^+$, 678.1 $[M+H+2]^+$.

$^1$H NMR (400 MHz, Methanol-$d_4$) δ 8.40-8.32 (m, 2H), 7.51 (t, J=7.6 Hz, 1H), 7.22 (d, J=5.4 Hz, 1H), 7.05 (t, J=8.4 Hz, 2H), 6.86-6.79 (m, 1H), 6.37-6.26 (m, 1H), 5.84 (d, J=10.6 Hz, 1H), 5.08 (m, 2H), 4.56-4.46 (m, 2H), 4.21-4.08 (m, 1H), 3.85-3.62 (m, 2H), 2.86-2.82 (m, 1H), 2.40 (s, 3H), 1.47 (d, J=6.6 Hz, 3H), 1.21-1.19 (d, J=6.8 Hz, 3H), 1.04 (d, J=6.8 Hz, 3H).

Embodiment 192

Preparation of 4-((S)-4-acryloyl-2-methylpiperazin-1-yl)-7-(2-amino-3, 5-dichloro-6-fluorophenyl)-6-chloro-1-(2-isopropyl-4-(methylsulfinyl)pyridin-3-yl) pyrido [2, 3-d] pyrimidin-2 (1H)-one

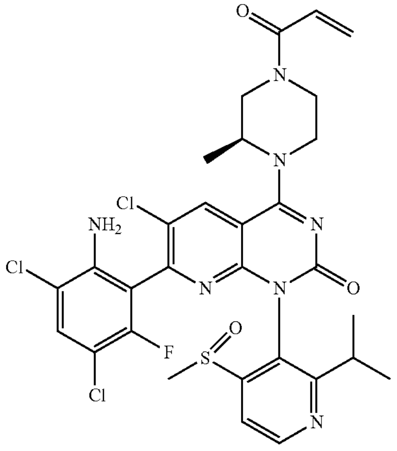 [SMILES: C=CC(=O)N1CCN(c2nc(=O)n(-c3c(S(C)=O)ccnc3C(C)C)c3nc(-c4c(N)c(Cl)cc(Cl)c4F)c(Cl)cc23)[C@@H](C)C1]

4-((S)-4-acryloyl-2-methylpiperazin-1-yl)-7-(2-amino-3, 5-dichloro-6-fluorophenyl)-6-chloro-1-(2-isopropyl-4-(methylsulfinyl) pyridin-3-yl) pyrido [2, 3-d] pyrimidin-2 (1H)-one was prepared with reference to embodiment 165.

MS m/z (ESI): 692.1 $[M+H]^+$, 694.1 $[M+H]^+$.

Embodiment 193

Preparation of 4-((2S, 5R)-4-acryloyl-2, 5-dimethylpiperazin-1-yl)-7-(2-amino-3, 5-dichloro-6-fluorophenyl)-6-chloro-1-(2-isopropyl-4-(methylthio) pyridin-3-yl) pyrido [2, 3-d] pyrimidin-2 (1H)-one

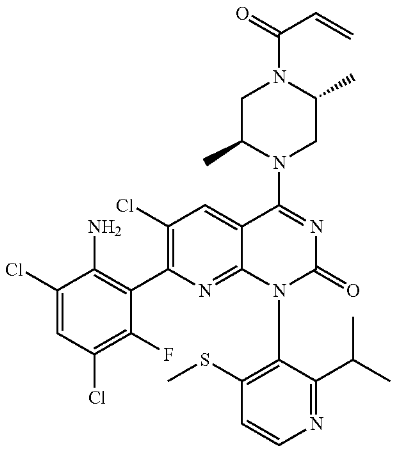 [SMILES: C=CC(=O)N1C[C@H](C)N(c2nc(=O)n(-c3c(SC)ccnc3C(C)C)c3nc(-c4c(N)c(Cl)cc(Cl)c4F)c(Cl)cc23)C[C@H]1C]

4-((2S, 5R)-4-acryloyl-2, 5-dimethylpiperazin-1-yl)-7-(2-amino-3, 5-dichloro-6-fluorophenyl)-6-chloro-1-(2-isopropyl-4-(methylthio)pyridin-3-yl)pyrido[2, 3-d]pyrimidin-2 (1H)-one was prepared with reference to embodiment 165.

MS m/z (ESI): 690.1 $[M+H]^+$, 692.1 $[M+H+2]^+$.

$^1H$ NMR (400 MHz, Methanol-$d_4$) δ 8.46-8.34 (m, 2H), 7.25-7.21 (m, 1H), 7.11-7.14 (m, 1H), 6.44-6.42 (d, J=8.0 Hz, 1H), 6.23-6.16 (m, 1H), 5.73-5.70 (m, 1H), 5.03-4.97 (m, 2H), 4.47-4.42 (m, 1H), 4.25-4.16 (m, 1H), 4.06-4.02 (m, 1H), 3.86-3.83 (m, 1H), 2.84-2.79 (m, 1H), 2.34 (s, 3H), 1.27-1.19 (m, 9H), 1.16-1.14 (m, 3H).

Embodiment 194

Preparation of 4-((S)-4-acryloyl-2-methylpiperazin-1-yl)-7-(2-amino-5-chloro-3, 6-difluorophenyl)-6-chloro-1-(2-isopropyl-4-(methylthio) pyridin-3-yl) pyrido [2, 3-d] pyrimidin-2 (1H)-one

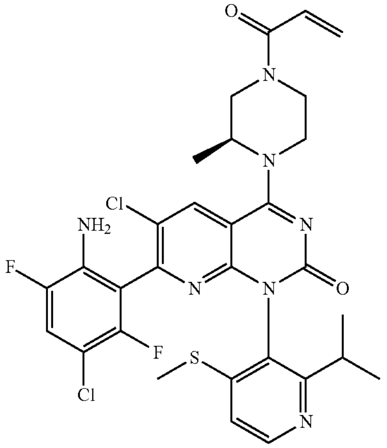 [SMILES: C=CC(=O)N1CCN(c2nc(=O)n(-c3c(SC)ccnc3C(C)C)c3nc(-c4c(N)c(F)cc(Cl)c4F)c(Cl)cc23)[C@@H](C)C1]

4-((S)-4-acryloyl-2-methylpiperazin-1-yl)-7-(2-amino-5-chloro-3, 6-difluorophenyl)-6-chloro-1-(2-isopropyl-4-(methylthio)pyridin-3-yl)pyrido[2, 3-d]pyrimidin-2(1H)-one was prepared with reference to embodiment 165.

MS m/z (ESI): 660.1 $[M+H]^+$, 662.1 $[M+H+2]^+$.

$^1H$ NMR (400 MHz, Methanol-$d_4$) δ 8.58-8.38 (m, 2H), 7.53-7.36 (m, 1H), 7.23-7.15 (m, 1H), 6.97-6.79 (m, 1H), 6.22 (d, J=16 Hz, 1H), 5.77 (d, J=8 Hz, 1H), 5.45-5.40 (m, 2H), 5.07-4.82 (m, 1H), 4.50-3.98 (m, 3H), 3.92-3.49 (m, 2H), 3.17-3.02 (m, 1H), 2.93-2.63 (m, 1H), 2.44-2.26 (m, 3H), 1.43-1.27 (m, 3H), 1.08 (d, J=4 Hz, 3H), 1.04-0.86 (m, 3H).

Embodiment 195

Preparation of 4-((S)-4-acryloyl-2-methylpiperazin-1-yl)-7-(2-amino-5, 6-difluoro-3-methylphenyl)-6-chloro-1-(2-isopropyl-4-(methylthio) pyridin-3-yl) pyrido [2, 3-d] pyrimidin-2 (1H)-one

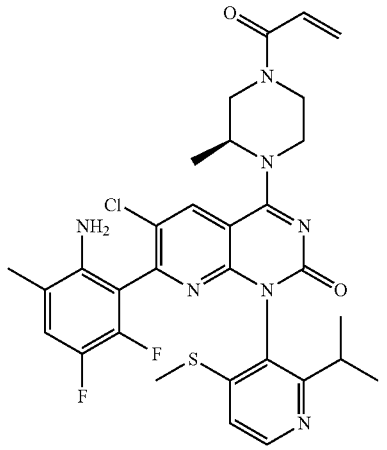 [SMILES: C=CC(=O)N1CCN(c2nc(=O)n(-c3c(SC)ccnc3C(C)C)c3nc(-c4c(N)c(C)cc(F)c4F)c(Cl)cc23)[C@@H](C)C1]

4-((S)-4-acryloyl-2-methylpiperazin-1-yl)-7-(2-amino-5, 6-difluoro-3-methylphenyl)-6-chloro-1-(2-isopropyl-4-(methylthio)pyridin-3-yl)pyrido[2, 3-d]pyrimidin-2(1H)-one was prepared with reference to embodiment 165.

MS m/z (ESI): 640.1 $[M+H]^+$, 642.1 $[M+H+2]^+$.

$^1$H NMR (400 MHz, Methanol-$d_4$) δ 8.57-8.35 (m, 3H), 7.25-7.04 (m, 2H), 6.96-6.79 (m, 1H), 6.29-6.14 (m, 1H), 5.77 (d, J=12 Hz, 1H), 5.09-4.82 (m, 1H), 4.76-4.58 (m, 2H), 4.48-3.98 (m, 3H), 3.94-3.59 (m, 2H), 2.93-2.69 (m, 1H), 2.44-2.29 (m, 3H), 2.10-1.95 (m, 3H), 1.42-1.26 (m, 3H), 1.08 (d, J=4 Hz, 3H), 1.05-0.87 (m, 3H).

Embodiment 196

Preparation of 4-((2S, 5R)-4-acryloyl-2, 5-dimethylpiperazin-1-yl)-7-(2-amino-5-chloro-3, 6-difluorophenyl)-6-chloro-1-(2-isopropyl-4-(methylthio) pyridin-3-yl) pyrido [2, 3-d] pyrimidin-2 (1H)-one

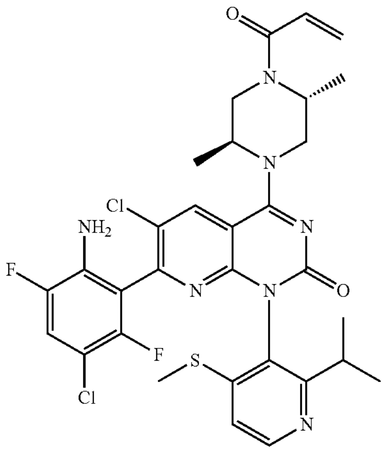 [SMILES: C=CC(=O)N1C[C@H](C)N(c2nc(=O)n(-c3c(SC)ccnc3C(C)C)c3nc(-c4c(N)c(F)cc(Cl)c4F)c(Cl)cc23)C[C@H]1C]

4-((2S, 5R)-4-acryloyl-2, 5-dimethylpiperazin-1-yl)-7-(2-amino-5-chloro-3, 6-difluorophenyl)-6-chloro-1-(2-isopropyl-4-(methylthio)pyridin-3-yl)pyrido[2, 3-d]pyrimidin-2 (1H)-one was prepared with reference to embodiment 165.

MS m/z (ESI): 674.1 $[M+H]^+$, 676.1 $[M+H+2]^+$.

$^1$H NMR (400 MHz, Methanol-$d_4$) δ 8.61-8.39 (m, 2H), 7.56-7.35 (m, 1H), 7.27-7.14 (m, 1H), 6.96-6.75 (m, 1H), 6.20 (d, J=16 Hz, 1H), 5.82-5.71 (m, 1H), 5.53-5.38 (m, 2H), 4.95-4.69 (m, 1H), 4.57-4.30 (m, 1H), 4.24-4.00 (m, 2H), 3.98-3.79 (m, 2H), 2.95-2.60 (m, 1H), 2.44-2.25 (m, 3H), 1.40-1.13 (m, 6H), 1.10-0.87 (m, 6H).

Embodiment 198

Preparation of 4-((S)-4-acryloyl-2-methylpiperazin-1-yl)-7-(2-amino-3, 6-difluorophenyl)-6-chloro-1-(2-isopropyl-4-(methylthio)pyridin-3-yl)pyrido[2, 3-d]pyrimidin-2(1H)-one

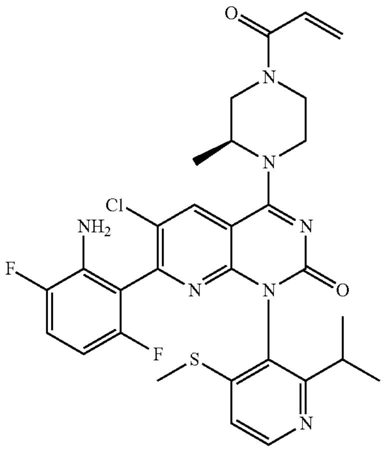 [SMILES: C=CC(=O)N1CCN(c2nc(=O)n(-c3c(SC)ccnc3C(C)C)c3nc(-c4c(F)ccc(F)c4N)c(Cl)cc23)[C@@H](C)C1]

4-((S)-4-acryloyl-2-methylpiperazin-1-yl)-7-(2-amino-3, 6-difluorophenyl)-6-chloro-1-(2-isopropyl-4-(methylthio) pyridin-3-yl)pyrido[2, 3-d]pyrimidin-2(1H)-one was prepared with reference to embodiment 165.

MS m/z (ESI): 626.1 $[M+H]^+$, 628.1 $[M+H+2]^+$.

$^1$H NMR (400 MHz, Methanol-$d_4$) δ 8.58-8.34 (m, 2H), 7.26-6.99 (m, 2H), 6.95-6.77 (m, 1H), 6.47-6.27 (m, 1H), 6.26-6.13 (m, 1H), 5.77 (d, J=16 Hz, 1H), 5.22 (s, 2H), 5.09-4.80 (m, 1H), 4.50-3.99 (m, 3H), 3.95-3.53 (m, 2H), 3.20-2.98 (m, 1H), 2.94-2.65 (m, 1H), 2.42-2.24 (m, 3H), 1.43-1.25 (m, 3H), 1.09 (d, J=4 Hz, 3H), 1.04-0.82 (m, 3H).

Embodiment 201

Preparation of 4-((2S, 5R)-4-acryloyl-2, 5-dimethylpiperazin-1-yl)-7-(2-amino-5, 6-difluoro-3-methylphenyl)-6-chloro-1-(2-isopropyl-4-(methylthio) pyridin-3-yl) pyrido [2, 3-d] pyrimidin-2 (1H)-one

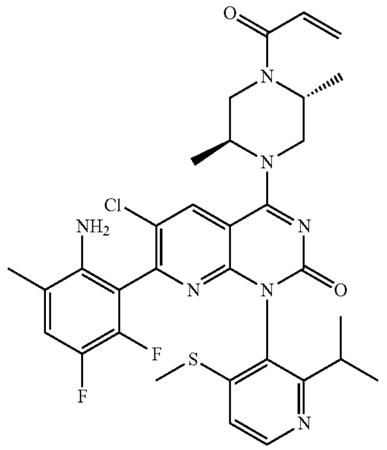 [SMILES: C=CC(=O)N1C[C@H](C)N(c2nc(=O)n(-c3c(SC)ccnc3C(C)C)c3nc(-c4c(N)c(C)cc(F)c4F)c(Cl)cc23)C[C@H]1C]

4-((2S, 5R)-4-acryloyl-2, 5-dimethylpiperazin-1-yl)-7-(2-amino-5, 6-difluoro-3-methylphenyl)-6-chloro-1-(2-isopropyl-4-(methylthio)pyridin-3-yl)pyrido[2, 3-d]pyrimidin-2 (1H)-one was prepared with reference to embodiment 165.

MS m/z (ESI): 654.1 [M+H]$^+$, 656.1 [M+H+2]$^+$.

$^1$H NMR (400 MHz, Methanol-$d_4$) δ 8.58-8.31 (m, 2H), 7.25-7.03 (m, 2H), 6.94-6.73 (m, 1H), 6.19 (d, J=16 Hz, 1H), 5.81-5.69 (m, 1H), 4.96-4.59 (m, 3H), 4.55-4.38 (m, 1H), 4.29-3.96 (m, 2H), 3.93-3.72 (m, 2H), 3.00-2.60 (m, 1H), 2.45-2.25 (m, 3H), 2.07-1.94 (m, 3H), 1.43-1.13 (m, 6H), 1.12-0.82 (m, 6H).

Embodiment 206

Preparation of 4-((S)-4-acryloyl-2-methylpiperazin-1-yl)-6-chloro-7-(2-fluoro-6-methylphenyl)-1-(2-isopropyl-4-(methylthio) pyridin-3-yl) pyrido [2, 3-d] pyrimidin-2 (1H)-one

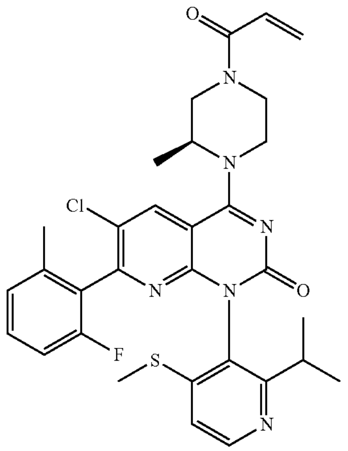 [SMILES: C=CC(=O)N1CCN(c2nc(=O)n(-c3c(SC)ccnc3C(C)C)c3nc(-c4c(C)cccc4F)c(Cl)cc23)[C@@H](C)C1]

4-((S)-4-acryloyl-2-methylpiperazin-1-yl)-6-chloro-7-(2-fluoro-6-methylphenyl)-1-(2-isopropyl-4-(methylthio)pyridin-3-yl)pyrido[2, 3-d]pyrimidin-2(1H)-one was prepared with reference to embodiment 165.

MS m/z (ESI): 607.1 [M+H]$^+$, 609.1 [M+H+2]$^+$.

$^1$H NMR (400 MHz, Methanol-$d_4$) δ 8.57-8.34 (m, 2H), 7.43-7.31 (m, 1H), 7.18 (d, J=4 Hz, 1H), 7.15-7.01 (m, 2H), 6.95-6.78 (m, 1H), 6.28-6.14 (m, 1H), 5.77 (d, J=12 Hz, 1H), 5.07-4.86 (m, 1H), 4.45-4.25 (m, 2H), 4.22-3.98 (m, 1H), 3.93-3.58 (m, 2H), 3.21-3.02 (m, 1H), 2.87-2.69 (m, 1H), 2.40-2.27 (m, 3H), 1.98-1.85 (m, 3H), 1.41-1.28 (m, 3H), 1.08 (d, J=8 Hz, 3H), 1.02-0.79 (m, 3H).

Embodiment 208

Preparation of 4-((S)-4-acryloyl-2-methylpiperazin-1-yl)-6-chloro-7-(2-chloro-6-fluorophenyl)-1-(2-isopropyl-4-(methylthio) pyridin-3-yl) pyrido [2, 3-d] pyrimidin-2 (1H)-one

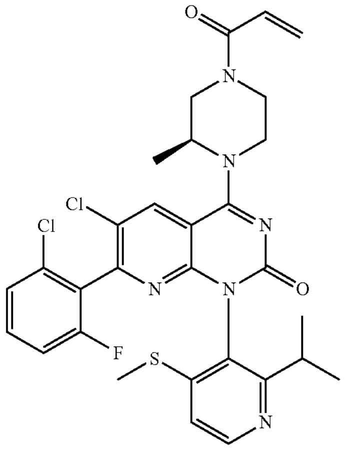 [SMILES: C=CC(=O)N1CCN(c2nc(=O)n(-c3c(SC)ccnc3C(C)C)c3nc(-c4c(F)cccc4Cl)c(Cl)cc23)[C@@H](C)C1]

4-((S)-4-acryloyl-2-methylpiperazin-1-yl)-6-chloro-7-(2-chloro-6-fluorophenyl)-1-(2-isopropyl-4-(methylthio)pyridin-3-yl)pyrido[2, 3-d]pyrimidin-2(1H)-one was prepared with reference to embodiment 165.

MS m/z (ESI): 627.1 [M+H]$^+$, 629.1 [M+H+2]$^+$.

$^1$H NMR (400 MHz, Methanol-$d_4$) δ 8.56-8.30 (m, 2H), 7.58-7.36 (m, 3H), 7.19 (s, 1H), 6.87 (s, 1H), 6.24-6.19 (d, J=20.0 Hz, 1H), 5.79-5.76 (d, J=12.0 Hz, 1H), 4.97 (s, 1H), 4.32-4.04 (m, 3H), 3.80-3.49 (m, 3H), 2.72 (s, 1H), 2.35 (s, 3H), 1.34-0.91 (m, 9H).

Embodiment 210

Preparation of (S)-4-(4-acryloyl-2-methylpiperazin-1-yl)-6-chloro-1-(2-isopropyl-4-(methylthio)pyridin-3-yl)-7-(o-phenylmethyl)pyrido[2, 3-d]pyrimidin-2(1H)-one

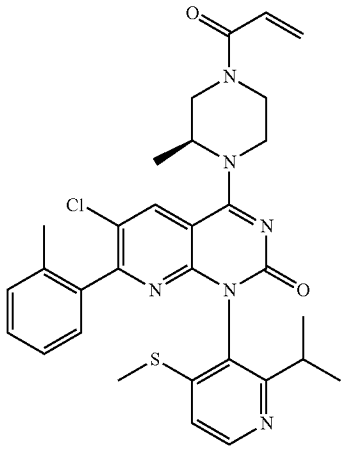 [SMILES: C=CC(=O)N1CCN(c2nc(=O)n(-c3c(SC)ccnc3C(C)C)c3nc(-c4ccccc4C)c(Cl)cc23)[C@@H](C)C1]

(S)-4-(4-acryloyl-2-methylpiperazin-1-yl)-6-chloro-1-(2-isopropyl-4-(methylthio)pyridin-3-yl)-7-(o-phenylmethyl)pyrido[2, 3-d]pyrimidin-2(1H)-one was prepared with reference to embodiment 165.

MS m/z (ESI): 589.1 $[M+H]^+$, 591.1 $[M+H+2]^+$.

Embodiment 213

Preparation of 4-((2S, 5R)-4-acryloyl-2, 5-dimethylpiperazin-1-yl)-6-chloro-1-(2-isopropyl-4-(methylthio) pyridin-3-yl)-7-(o-phenylmethyl) pyrido [2, 3-d] pyrimidin-2 (1H)-one

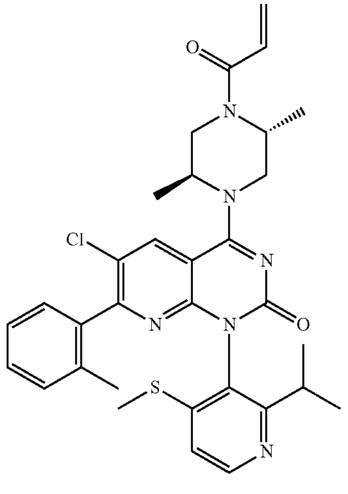 [SMILES: C=CC(=O)N1C[C@H](C)N(c2nc(=O)n(-c3c(SC)ccnc3C(C)C)c3nc(-c4ccccc4C)c(Cl)cc23)C[C@H]1C]

4-((2S, 5R)-4-acryloyl-2, 5-dimethylpiperazin-1-yl)-6-chloro-1-(2-isopropyl-4-(methylthio) pyridin-3-yl)-7-(o-phenylmethyl) pyrido [2, 3-d] pyrimidin-2 (1H)-one was prepared with reference to embodiment 165.

MS m/z (ESI): 603.1 $[M+H]^+$, 605.1 $[M+H+2]^+$.

Biological Test Evaluation

The present disclosure is further described below in conjunction with test embodiments to explain the disclosure, but these embodiments are not meant to limit the scope of the disclosure.

Test Embodiment 1: Determination of the Inhibitory Effect on NCI-H358/Mia PaCa-2 Cell Proliferation Activity 1.1 Experimental Purpose To determine the inhibitory effect of the compounds of the embodiment on the proliferation activity of KRAS G12C mutant cell lines NCI-H358 and Mia PaCa-2 cells.

1.2. Experimental Instruments and Reagents 1.2.1 Instrument:

Microplate reader (BioTek Synergy H1)

Pipette (Eppendorf & Rainin)

1.2.2 Reagents:

NCI-H358 was purchased from Nanjing Cobioer Biotechnology Co., Ltd.;

Mia PaCa-2 was purchased from ATCC;

Cell Titer-Glo cells were purchased from Promega Company, and the article number was G7573;

RPMI 1640 was purchased from Gibco, the article number was 22400089;

DMEM was purchased from Gibco, the article number is 11995065;

FBS was purchased from Gibco, the article number was 10091148;

PBS was purchased from Gibco, the article number was 10010023;

Trypsin was purchased from GIBCO, the article was 25200056;

The cell culture plate was purchased from Corning Company, the article number was 3610.

1.3. Experimental Methods

When NCI-H358 or Mia PaCa-2 cells were cultured to the appropriate fusion level, the NCI-H358 or Mia PaCa-2 cells were collected, and the cells were adjusted to the appropriate cell concentration using a complete medium, and the cell suspension was spread in a 96-well plate, 90 μL per well, and placed in a 37° C., 5% $CO_2$ incubator overnight; and compound solutions of different concentrations were prepared using DMSO and culture medium; and a solvent control was set, the compound solution was added to a 96-well plate, 10 μL per well, at 37° C. in a 5% $CO_2$ incubator for 72 hours; CellTiter-Glo solution was added thereto and the mixture was mixed well by shaking, incubated for 10 min in the dark, and read by BioTek Synergy H1 microplate reader.

1.4. Experimental Data Processing Methods

The luminescence signal values were used to calculate the inhibition rate, the concentration and the inhibition rate were fitted to a nonlinear regression curve using Graphpad Prism software, then the $IC_{50}$ value was obtained.

1.5. Experimental Results

The experimental results are shown in Table 25, $IC_{50}$ values of the inhibitory activity of the embodiment compound on the proliferation of NCI-H358 and Mia PaCa-2 cells.

TABLE 25

| Embodiment number | NCI-H358 $IC_{50}$ (nM) | Mia PaCa-2 $IC_{50}$ (nM) |
|---|---|---|
| Embodiment 60 | 40 | 60 |
| Embodiment 60-1 | 28 | 55 |
| Embodiment 75 | 24 | 34 |
| Embodiment 75-1 | 25 | 36 |
| Embodiment 77 | 117 | 120 |
| Embodiment 114 | 50 | 43 |
| Embodiment 114-1 | 35 | 29 |
| Embodiment 118 | 89 | 82 |
| Embodiment 130 | 14 | 41 |
| Embodiment 131 | 48 | 47 |
| Embodiment 133 | 25 | 46 |
| Embodiment 134 | 23 | 30 |
| Embodiment 138 | 67 | 104 |
| Embodiment 150 | 5.4 | 8.6 |
| Embodiment 150-1 | 6.6 | 3.5 |
| Embodiment 151 | 39 | 59 |
| Embodiment 152 | 45 | 91 |
| Embodiment 153 | 68 | 76 |
| Embodiment 154 | 79 | 68 |
| Embodiment 155 | 24 | 26 |
| Embodiment 156 | 95 | 86 |
| Embodiment 165 | 5.9 | 7.6 |
| Embodiment 165-1 | 6.6 | 3.3 |
| Embodiment 166 | 16 | 23 |
| Embodiment 166-1 | 17 | 11 |
| Embodiment 169 | 79 | 68 |
| Embodiment 191 | 32 | 16 |
| Embodiment 192 | 29 | 13 |
| Embodiment 193 | NT | 18 |
| Embodiment 194 | NT | 7 |
| Embodiment 195 | NT | 5.2 |
| Embodiment 196 | NT | 5.3 |
| Embodiment 198 | NT | 6.0 |
| Embodiment 201 | NT | 4.9 |
| Embodiment 206 | NT | 14 |
| Embodiment 208 | NT | 59 |

Note:
"NT" means not tested.

1.6. Experimental Conclusion

According to the data, the embodiment compounds of the present disclosure have a good inhibitory effect on the proliferation of NCI-H358 and Mia PaCa-2 cells.

Test Embodiment 2. Determination of the Ability of the Compound of the Present Disclosure to Improve the Binding Stability (Melting Temperature) of KRAS G12C Protein 2.1. Experimental Purpose To determine the ability of the compound to improve the stability of KRAS G12C protein (the degree of increase in protein melting temperature can be used to characterize the compound's ability to bind to KRAS G12C protein).

2.2. Experimental Reagents and Instruments 2.2.1 Experimental Instruments:

Quantitative PCR instrument (Quantstudio6 Flex) was purchased from Life Company;

Pipettes were purchased from Eppendorf or Rainin Company.

2.2.2 Experimental Reagents:

Protein Thermal Shift™ Dye Kit was purchased from Thermofisher Company, the article number was 4461146;

KRAS G12C protein was purchased from Beijing Sino-Biological Co., Ltd., the article number was 12259-H07E2;

HEPES, 1M Buffer Solution was purchased from Thermofisher Company, the article number was 15630080;

DTT was purchased from Sigma Company, the article number was 43816-50 mL;

NaCl was purchased from Sinopharm Chemical Reagent Co., Ltd., the article number was 10019318.

2.3 Experimental Methods

In this experiment, the thermal shift method was used to test the degree of change in the melting temperature (Tm) of the KRAS G12C protein before and after the binding of the compound, in order to characterize the ability of the compound to improve the stability of the KRAS G12C protein.

The specific experiment operation was as follows:

A solution containing 20 μM HEPES (pH 7.5), 1 mM DTT, 5×SYPRO Orange and 150 mM NaCl was prepared as the experimental buffer, and a final concentration of 5.37 μM human KRAS G12C protein was added thereto. The reaction mixture was divided into 8 rows of PCR tubes, each 19.5 μL, and 0.5 μL of the test compound or DMSO were added respectively, so that the total reaction system was 20 μL, the final concentration of the compound was 10 μM, and 2.5% DMSO was set as the solvent control. After incubating at room temperature in the dark for 1 hour, the PCR tube was put into the PCR instrument, QuantStudio Software v1.3 was opened, and the melting temperature of KRAS G12C protein in different treatment groups was detected by melt curve function (heating from 25° C. to 95° C., 0.03° C./s).

2.4. Experimental Data Processing Methods

The experimental data file of PCR instrument was imported into thermal shift software, and the melting temperature (Tm) of each treatment group was obtained, and the change value of melting temperature (Δ Tm) was obtained by subtracting the Tm of DMSO solvent control group.

2.5. Experimental Results

According to the above scheme, the compound of the present disclosure shows the ability to increase the melting temperature of the protein as shown in Table 26 in the experiment of improving the binding stability of KRAS G12C protein.

TABLE 26

| Embodiment number | Tm (° C.) DMSO | Tm (° C.) | ΔTm (° C.) |
|---|---|---|---|
| Embodiment 60 | 48.6 | 60.2 | 11.6 |
| Embodiment 73 | 48.6 | 55.5 | 6.9 |
| Embodiment 75 | 50.6 | 61.2 | 10.6 |

TABLE 26-continued

| Embodiment number | Tm (° C.) DMSO | Tm (° C.) | ΔTm (° C.) |
|---|---|---|---|
| Embodiment 77 | 50.6 | 60.4 | 9.8 |
| Embodiment 114 | 48.7 | 57.2 | 8.5 |
| Embodiment 115 | 48.6 | 55.2 | 6.6 |
| Embodiment 118 | 50.6 | 59.0 | 8.4 |
| Embodiment 130 | 50.6 | 61.5 | 10.9 |
| Embodiment 131 | 49.5 | 61.2 | 11.7 |
| Embodiment 134 | 48.6 | 64.4 | 15.8 |
| Embodiment 136 | 48.6 | 57.3 | 8.7 |
| Embodiment 138 | 50.6 | 59.4 | 8.8 |
| Embodiment 150 | 46.8 | 60.2 | 13.4 |
| Embodiment 152 | 48.6 | 60.0 | 11.4 |
| Embodiment 155 | 49.8 | 60.9 | 11.1 |
| Embodiment 156 | 49.8 | 61.4 | 11.6 |
| Embodiment 165 | 47.0 | 58.0 | 11.0 |

2.6 Experimental Conclusion

The above data show that the compound of the embodiment of the present disclosure has good binding ability to KRAS G12C protein.

Test Embodiment 3. The Inhibitory Activity of the Compound of the Present Disclosure on Miapaca-2 Cell P-ERK

3.1. Experimental Purpose

To determine the inhibitory activity of the embodiment compounds on the level of phosphorylated ERK in KRAS G12C mutant cells Mia PaCa-2.

3.2. Experimental Instruments 3.2.1 Instrument:
- Microplate reader (BioTek Synergy H1);
- Pipette (Eppendorf & Rainin).

3.2.2 Reagents:
- Phosphorylated ERK1/2 (T202-Y204) LANCE Ultra Cellular Detection Kit was purchased from PerkinElmer Company, the article number was TRF4000M;
- The cell culture plate was purchased from Corning, the article number was 3610;
- White opaque OptiPlate™-384 plate was purchased from PerkinElmer, the article number was 6007290.

3.3. Experimental Methods

When Mia PaCa-2 cells were cultured to the appropriate fusion level, Mia PaCa-2 cells were collected, and the cell density was adjusted to $1\times10^6$/mL using complete culture medium, the cell suspension was spread on a 96-well plate, 50 μL per well, and placed adherent to the wall in a 37° C., 5% $CO_2$ incubator overnight, compound solutions with different concentrations were prepared using DMSO and complete culture medium, a solvent control was set, the compound solution was added to a 96-well plate, 25 μL per well, and placed in a 37° C., 5% $CO_2$ incubator for 2 hours of continuous culture, the supernatant was discarded from the cell culture plate, 50 μL of lysis solution was added to each well, and lysing was performed for 30 minutes by shaking at room temperature, then the mixture was centrifuged at 1000 rpm for 1 minute, 15 μL of supernatant was transferred to 384 well plate, 5 μL of detection mixture (Eu-labeled anti-ERK1/2 (T202-Y204) antibody with final concentration of 0.5 nM and ULight labeled anti-ERK1/2 antibody with final concentration of 5 nM) was added to each well, centrifuged at 1000 rpm for 1 minute and mixed uniformly, the reaction was carried out overnight at room temperature, the plate was read with BioTek Synergy H1, and the signal values was detected at 620 nm and 665 nm emission wavelengths by time-resolved fluorescence program.

3.4. Experimental Data Processing Methods

The ratio of the signal values at 665 nm and 620 nm emission wavelength were calculated, and the ratio was used to calculate the inhibition rate, the concentration and the inhibition rate were fitted to a nonlinear regression curve using Graphpad Prism software, then the $IC_{50}$ value was obtained.

3.5. Experimental Results

TABLE 27

$IC_{50}$ values of pERK inhibition on Mia PaCa-2 cells

| Embodiment number | Mia PaCa-2 pERK $IC_{50}$ (nM) |
|---|---|
| Embodiment 114-1 | 38 |
| Embodiment 134 | 30 |
| Embodiment 150-1 | 5.0 |
| Embodiment 165-1 | 4.2 |
| Embodiment 166-1 | 20 |

3.6. Experimental Conclusion

The above data show that the embodiment compound of the present disclosure has a good inhibitory effect on pERK in Mia PaCa-2 cells.

Test Embodiment 4. Determination of Pharmacokinetics in Mice

4.1. Research Purpose

To study the pharmacokinetic behavior of the compound in mice (plasma) after oral administration using Balb/c mice as test animals.

4.2. Test Scheme 4.2.1 Test Drugs:

The compound of the embodiment of the present disclosure was self-made;

4.2.2 Test Animals:

Balb/c Mice, male, purchased from Shanghai Jiesijie Laboratory Animal Co., Ltd, Animal Production License No. (SCXK (Shanghai) 2013-0006 NO. 311620400001794).

4.2.3 Drug Preparation:

5 g of Hydroxyethyl cellulose (HEC, CMC-Na, viscosity: 800-1200 Cps) was weighed, dissolved in 1000 mL of purified water, and 10 g of Tween 80 was added. The mixture was mixed well to form a clear solution.

The embodiment compounds were weighed and added into 4-mL glass bottles, respectively, 2.4 mL of the solution was added, and ultrasound was performed for 10 minutes to obtain a colorless clear solution with a concentration of 1 mg/mL.

4.2.4 Administration:

Balb/C mice, males; PO, after overnight fasting, respectively, at a dose of 10 mg/kg, administered in a volume of 10 mL/kg.

4.2.5 Sample Collection:

Blood samples were collected before administration and 0.083 h, 0.25 h, 0.5 h, 1 h, 2 h, 4 h, 6 h and 8 h after administration, the blood was placed in EDTA-2K tube, centrifuged at 4° C. 6000 rpm for 6 min to separate plasma, and stored at −80° C.; food was consumed 4 hours after drug administration.

4.3 Experimental Results

The final determination results obtained by applying LCMS/MS method are shown in Table 28

TABLE 28

Pharmacokinetic parameters of the compounds in mice

| Embodiment number | Tmax (hr) | Cmax (ng/mL) | $AUC_{0-\infty}$ (ng/mL * hr) | $T_{1/2}$ (hr) | MRT (hr) |
|---|---|---|---|---|---|
| Embodiment 114 | 0.25 | 1529 | 1287 | 0.6 | 0.7 |
| Embodiment 114-1 | 0.25 | 1823 | 1373 | 0.6 | 0.7 |
| Embodiment 165-1 | 0.25 | 264 | 347 | 1.0 | 1.5 |
| Embodiment 165-FA | 0.25 | 1064 | 1018 | 0.5 | 0.8 |
| Embodiment 165-1-FA | 0.25 | 641 | 900 | 0.8 | 1.2 |

4.4 Experimental Conclusion

The above data show that the embodiment compounds of the present disclosure have good pharmacokinetic parameters in mice.

Test Embodiment 5. Tumor Inhibition Experiment on MiaPaca 2 Transplanted Tumor Model

5.1 Experimental Purpose

BALB/c nude mice were used as the test animals, and the human pancreatic cancer cell MiaPaca 2 xenograft (CDX) model was used for in vivo pharmacodynamic experiments to evaluate the antitumor effects of the test compounds.

5.2 Experimental Instruments and Reagents 5.2.1 Instrument:

Ultra Clean Bench (BSC-1300II A2, Shanghai Boxun Industrial Co., Ltd. Medical Equipment Factory);

$CO_2$ incubator (Thermo-311, Thermo);

Centrifuge (Centrifuge 5720R, Eppendorf);

Fully automatic cell counter (Countess II, Life Technologies);

Pipette (10-20 μL, Eppendorf);

Microscope (Ts 2, Nikon);

Vernier caliper (CD-6" AX, Mitutoyo Japan);

Cell culture flask (T25/T75/T225, Corning);

Constant temperature water tank (HWS12, Shanghai Yiheng Science).

5.2.2 Reagents:

DMEM (11995-065, Gibco);

Fetal bovine serum (FBS) (10091-148, Gibco);

0.25% trypsin (25200-056, GIBCO);

Penicillin double antibody (P/S) (SV30010, GE);

Phosphate buffer (PBS) (10010-023, Gibco);

Matrigel (356234, Corning);

Gln (25030-081, Gibco).

5.3 Experimental Operation

MiaPaca 2 cells were removed from the cell bank, revived and added to DMEM medium (containing 10% FBS, 1% Glu, 1% P/S) and incubated in a $CO_2$ incubator (incubator temperature was 37° C., $CO_2$ concentration was 5%). After the cells were spread to 80-90% of the bottom of the culture flask, the cells were continued to be cultured in the $CO_2$ incubator. The process was repeated until the number of cells met the in vivo pharmacological inoculation requirement, and the cells in logarithmic growth period were collected and counted with an automatic cell counter, resuspended with PBS and Matrigel (volume ratio 1:1) according to the count results, made into a cell suspension (the density was $8\times10^7$/mL), and placed in an ice box for use.

BALB/c nude mice, female, 6-8 weeks old, weighing about 18-22 g. The mice were kept in an environment free of special pathogens and in a single ventilated cage with 5 mice in each cage. All cages, bedding and water were sterilized before use, and all animals had free access to standard certified commercial laboratory diets. Nude mice were labeled with disposable universal ear tags for mice and rats before the start of the experiment, and the skin of the inoculation site was disinfected with 75% medical alcohol before inoculation, 0.1 mL (containing $8*10^6$ cells) of MiaPaca 2 tumor cells were inoculated subcutaneously on the right back of each mouse. When the tumor volume reached 100-200 $mm^3$, the group administration was started. The tested compounds were administered daily by oral intragastric administration, dosage/frequency (6 mg/kg QD×3 w), and the efficacy of each group at the end of the experiment was shown in Table 29.

5.4 Data Processing

The tumor volume ($mm^3$) was measured with vernier caliper twice a week, the calculation formula was V=0.5*D*D*D, wherein D and d were the long and short diameter of the tumor, respectively. The anti-tumor efficacy was determined by dividing the average tumor increased volume of the compound-treated animals by the average tumor increased volume of the untreated animals. The formula of tumor inhibition rate is: TGI (%)=1−[(Vt−V0) administration group/(Vt−V0) solvent control group] *100%. After the experiment, all animals were euthanized.

5.5 Experimental Results

TABLE 29

Pharmacodynamic parameters of the compounds in transplanted tumor mice

| Grouping | 100.80 ± 31.28 ($mm^3$, Mean ± SD) Day 0 | Day 21 | ΔT/ΔC(%) Day 21 | TGI (%) Day 21 |
|---|---|---|---|---|
| Vehicle QD × 3w | 178 ± 30 | 868 ± 234 | — | — |
| Embodiment 114-1 | 177 ± 38 | 67 ± 34 | −62.36 | 162.36 |
| Embodiment 150-1 | 178 ± 40 | 72 ± 18 | −59.56 | 159.56 |
| Embodiment 165-1 | 178 ± 34 | 41 ± 19 | −76.76 | 176.76 |

5.6 Experimental Conclusion

The above data show that after oral administration for 21 days, the embodiment compound of the present disclosure can significantly inhibit the growth of transplanted tumor in MiaPaca 2 nude mice under the condition of oral administration of 6 mg/kg every day.

Test Embodiment 6. In Vivo Pharmacodynamic Study on Human Lung Cancer NCI-H358 Cell Xenograft Tumor Model

6.1 Experimental Purpose

To evaluate the efficacy of the compound in vivo on xenograft tumor model of human lung cancer NCI-H358 cells.

6.2 Experimental Instruments and Reagents 6.2.1 Instrument:

- Biological safety cabinet (BSC-1300II A2, Shanghai Boxun Industrial Co., Ltd., Medical Equipment Factory);
- Ultra-clean bench (CJ-2F, Suzhou Fengshi Laboratory Animal Equipment Co.)
- $CO_2$ incubator (Thermo-311, Thermo);
- Centrifuge (Centrifuge 5720R, Eppendorf);
- Fully automatic cell counter (Countess II, Life Technologies);
- Vernier caliper (CD-6" AX, Mitutoyo Japan);
- Cell culture flask (T75/T225, Corning);
- Electronic balance (CPA2202S, Sartorius);
- Electronic balance (BSA2202S-CW, Sartorius);
- Electronic balance (BS124S, Sartorius).

6.2.2 Reagents:

- RPMI-1640 medium (22400-089, Gibco);
- DMEM medium (11995-065, Gibco);
- Fetal bovine serum (FBS) (10099-141C, Gibco);
- Phosphate buffer (PBS) (10010-023, Gibco);
- Tween 80 (30189828, Sinopharm reagent);
- Sodium carboxymethyl cellulose (30036365, Sinopharm reagent.)

6.3 Experimental Operation and Data Processing 6.3.1 Test Animals:

BALB/c nude mice, 6-8 weeks old, female, purchased from Shanghai Xipuer-Bikai Experimental Animal Co., Ltd.

6.3.2 Cell Culture and Cell Suspension Preparation

1) MiaPaca-2 cells were taken out from the cell bank and resuscitated with DMEM medium (DMEM+10% FBS), the resuscitated cells were placed in a cell culture flask (labeled with cell type, date, name of cultured person, etc.) and cultured in a $CO_2$ incubator (incubator temperature was 37° C., $CO_2$ concentration was 5%) (the method of resuscitating NCI-H358 cells was the same as MiaPaca-2 cells in test embodiment 5, and the culture medium was changed to RPMI-1640 medium).
2) Passage was conducted every three to five days, and the cells was continued to be cultured in $CO_2$ incubator after passage. The process was repeated until the cell count meets the in vivo pharmacodynamic requirements.
3) MiaPaca-2 cells were collected and counted by automatic cell counter, according to the counting results, the cells were re-suspended with PBS and Matrigel (ratio was 1:1) to make cell suspension (cell density was $5\times10^7$/mL), then placed in a ice box for use (NCI-H358 cells were re-suspended with PBS without adding Matrigel, cell density was $1\times10^8$/mL).

6.3.3 Sample Preparation:

1) Solvent: solvent (0.5% CMC-Na+1% Tween 80), storage condition: 4° C.

0.5 g of CMC-Na was weighted, dissolved in $ddH_2O$, then 1.0 mL of Tween 80 was added and the mixture was stirred to mix well, and the volume was finally set to 100 mL.

2) Compound to be tested (10 mg/kg) was prepared:

8.42 mg of AMG510 compound was weighted, 8.260 mL of solvent was added, a uniform solution was obtained by ultrasound, vortexing and stirring.

7.81 mg of embodiment compound 165-1 was weighted, 7.654 mL of solvent was added, a uniform solution was obtained by ultrasound, vortexing and stirring.

6.3.3 Cell Inoculation

1) Before inoculation, nude mice were labeled with disposable universal ear tags of rats and mice;
2) when inoculating, the cell suspension was mixed well, 0.1-1 mL cell suspension was extracted with a 1 mL syringe, bubbles were removed, and then the syringe was put on an ice bag for later use;
3) the nude mice was held with left hand, the right back of nude mice near the right shoulder (inoculation site) was disinfected with 75% alcohol, and inoculation was started after 30 seconds;
4) the experimental nude mice were inoculated in turn (each mouse was inoculated with 0.1 mL of cell suspension);

6.3.4 Tumor-Bearing Mouse were Measured, Grouped, and Administered:

1) According to the tumor growth, the tumor was measured on the 18th day after inoculation, and the tumor size was calculated.

tumor volume ($mm^3$)=length (mm)×width (mm)×width (mm)/2 Tumor volume calculation:

2) The tumor-bearing mice were grouped according to their body weight and tumor size using a randomized grouping method.
3) According to the grouping results, the administration of the test drug was started (administration method: oral administration; administration dose: 10 mg/kg; administration volume: 10 mL/kg; administration frequency: once a day; administration period: 21 days; solvents: 0.5% CMC/1% Tween 80).
4) The tumor was measured and weighed twice a week after the test drug was started to be given.
5) After the experiment, all animals were euthanized.
6) Data was processed with software such as Excel.

6.4 Data Processing

Calculation of TGI (%) of compound tumor inhibition rate: when there was no tumor regression, TGI (%)=[(1−(mean tumor volume at the end of the administration in a treatment group −mean tumor volume at the start of administration in the treatment group))/(mean tumor volume at the end of treatment in the solvent control group −mean tumor volume at the start of treatment in the solvent control group)]×100%.When there was tumor regression, TGI (%)=[1−(mean tumor volume at the end of dosing in a treatment group −mean tumor volume at the beginning of dosing in the treatment group)/mean tumor volume at the beginning of dosing in the treatment group]×100%.

6.5 Experimental Result

TABLE 30

Pharmacodynamic parameters of the compounds in transplanted tumor mice

| | 100.80 ± 31.28 ($mm^3$, Mean ± SD) | | ΔT/ΔC(%) | TGI (%) |
|---|---|---|---|---|
| Grouping | Day 0 | Day 15 | Day 15 | Day 15 |
| Vehicle QD × 3w | 202 ± 58 | 400 ± 111 | — | — |
| Embodiment 165-1 10 mpk | 203 ± 74 | 267 ± 155 | 32.59 | 67.41 |
| AMG-510 10 mpk | 202 ± 72 | 324 ± 204 | 61.98 | 38.02 |

6.6 Experimental Conclusion

The above data showed that after 15 days of continuous oral administration, the embodiment compounds of the disclosure significantly inhibited the growth of the tumors of nude mouse transplanted with human lung cancer NCI-H358 cells under the condition of 10 mg/kg oral daily administration, which was significantly better than the reference data.

Test Embodiment 7. hERG Potassium Channel Inhibitory Activity Test 7.1 Cell Preparation 7.1.1 CHO-hERG cells were cultured in a 175 $cm^2$ flask, when the cell density reached 60-80%, the culture medium was removed, the cells were washed with 7 mL PBS, and then digested with 3 mL Detachin.

7.1.2 After complete digestion, 7 mL culture medium was added to neutralize, then the mixture was centrifuged, the supernatant was aspirated, and then 5 mL culture medium was added to re-suspend, ensuring 2-5×$10^6$/mL of cell density.

7.2 Solution Preparation

TABLE 31

Composition of intracellular fluid and extracellular fluid

| Reagent | Extracelluar fluid (mM) | Intracellular fluid (mM) |
|---|---|---|
| $CaCl_2$ | 2 | 5.374 |
| $MgCl_2$ | 1 | 1.75 |
| KCl | 4 | 120 |
| NaCl | 145 | — |
| Glucose | 10 | — |
| HEPES | 10 | 10 |
| EGTA | — | 5 |
| Na-ATP | — | 4 |
| pH | 7.40 (adjusted with NaOH), Osmolarity~305 mOsm | 7.25 (adjusted with KOH), Osmolarity~290 mOsm |

7.3 Electrophysiological Recording Process

The process of single cell high impedance sealing and whole cell mode formation were all automatically completed by Qpatch instrument, after obtaining the whole cell recording mode, the cells were clamped at −80 mV, before giving a 5-second +40 mV depolarization stimulus, a 50 millisecond −50 mV prevoltage was given first, and then repolarized to −50 mV for 5 seconds, then returned to −80 mV. This voltage stimulation was applied every 15 seconds and recorded for 2 minutes before giving extracellular fluid recordings for 5 minutes, and then the administration process was started, the compound concentration was given from the lowest test concentration, each test concentration was given for 2.5 minutes, and the positive control compound 0.1 μM of Cisapride was given after all concentrations were continuously given. At least 3 cells (n≥3) were tested at each concentration.

7.4 Test Compound 7.4.1 20 mM of compound mother liquor was diluted with extracellular fluid, 5 μL of 20 mM compound mother liquor was added into 2495 μL of extracellular fluid and diluted 500-fold to 40 μM, and then the final concentration to be tested was obtained by sequential 3-fold serial dilutions in extracellular solution containing 0.2% DMSO.

7.4.2 The highest test concentration was 40 μM, in a total of 6 concentrations of 40, 13.33, 4.44, 1.48, 0.49 and 0.16 μM respectively.

7.4.3 The content of DMSO in the final test concentration was not more than 0.2%, and this concentration of DMSO had no effect on hERG potassium channel.

7.5 Data Analysis

The experimental data were analyzed by XLFit software.

7.6 Quality Control

Environment: humidity 20-50%, temperature 22~25° C.

Reagent: The experimental reagent used was purchased from Sigma Company, and the purity was >98%

The experimental data in the report must meet the following criteria:

Whole cell sealing impedance>100 MΩ

Tail current amplitude>400 pA

Pharmacological Parameters

The inhibitory effect of multiple concentrations of Cisapride on hERG channel was set as positive control.

7.7 Experimental Results

TABLE 32

Inhibition results of the embodiments of the present disclosure at multiple concentrations on hERG current

| Embodiment number | hERG (μM) |
|---|---|
| Embodiment 114-1 | >30 |
| Embodiment 150-1 | >30 |
| Embodiment 165-1 | >30 |
| Embodiment 166-1 | >30 |

7.8 Experimental Conclusion

The inhibition of drugs on the cardiac hERG potassium channel was the main cause of QT prolonged syndrome caused by drugs. It can be seen from the experimental results that the embodiment compound of the disclosure had no obvious inhibitory effect on the cardiac hERG potassium ion channel, and can avoid the toxic and side effects to the heart at a high dose.

Test Embodiment 8, Plasma Stability Test Scheme 8.1 Experimental Purpose

The purpose of this experiment was to examine the stability of the embodiment compounds in mouse, rat, dog and human plasma.

8.2 Experimental Purpose 8.2.1 Solution Preparation

1), Plasma preparation

Animal or human whole blood was collected, then the blood was put into a test tube containing anticoagulant, centrifuged at 3500 rpm for 10 min, and the upper layer of pale yellow plasma was collected.

2), 10 μM of tested compound (m/M/V=C)

The compound was weighed, the stock solution was prepared with DMSO and the working solution was prepared with 100 mM phosphate buffer.

3), 10 μM of positive control (1) Propantheline (Propantheline Mr=449.4 Da)

2.36 mg of Propantheline was weighed and diluted to 10 mM stock solution with 1 mL of DMSO; L of 10 mM stock solution was pipetted into 1 mL of 100 mM phosphate buffer to a final concentration of 100 μM.

(2) Mevinolin (Lovastatin Mr=404.5 Da)

4.05 mg of lovastatin was weighed and diluted to 10 mM stock solution with 1 mL of DMSO; 10 L of 10 mM stock solution was pipetted into 1 mL of 100 mM phosphate buffer to a final concentration of 100 μM.

8.2.2 Experimental Process 1) 285 μL of plasma and 15 μL of 10 μM compound (tested compound) were added in turn in a 96-well plate, and incubated at 37° C.
2) 40 μL was taken out at 0, 15, 30, 60, 90, 120 min, respectively, and 160 μL of acetonitrile termination solution containing internal standard was added.
3) After centrifugation (3500 rpm, 10 min), 50 μL of supernatant was taken out, and then diluted with 50 μL DDH2O and injected to LC-MS/MS.

8.3 Chromatographic Conditions

Instrument: Shimadzu LC-20 AD

Chromatographic column: phenomenex Gemiu® C18 (50*4.6 mm, 5 μM particle size);

mobile phase: A: acetonitrile, B: 0.1% formic acid solution 0-8 min: 5% A→95% A, 2.0-2.1 min: 90% A→5% A; flow rate: 0.8 mL/min; running time: 5.0 min; injection volume: 5 μL.

8.4 Mass Spectrum Condition

Instrument: API4000 Liquid Chromatography-Mass Spectrometry, AB, USA;

the ion source was electrospray ionization source (ESI);

the temperature of dry gas ($N_2$) was 500° C.;

electrospray voltage was 5500V;

the detection method was positive ion detection;

the scanning mode was selective response monitoring (MRM).

the scanning time was 0.1 s.

8.4 Experimental Results

TABLE 33

Plasma stability results of embodiment compounds

| Species and genus | Number | Residual rate (%) 0 min | 15 min | 30 min | 60 min | 120 min | $t_{1/2}$ (min) |
|---|---|---|---|---|---|---|---|
| human | Propantheline | 100.00 | 79.98 | 50.52 | 14.65 | 0.72 | 21.03 |
| | Embodiment 114-1 | 100.00 | 97.39 | 98.79 | 94.50 | 87.91 | 660.77 |
| | Embodiment 150-1 | 100.00 | 97.95 | 100.46 | 97.37 | 93.81 | 1383.71 |
| | Embodiment 166-1 | 100.00 | 99.15 | 94.74 | 89.14 | 78.85 | 338.58 |
| | Embodiment 165-1 | 100.00 | 102.34 | 100.28 | 90.27 | 87.22 | 500.87 |
| | AMG 510 | 100.00 | 93.77 | 85.72 | 82.51 | 64.44 | 198.80 |
| Rat | Lovastatin | 100.00 | 21.15 | 1.77 | 0.36 | 0.30 | 6.69 |
| | Embodiment 114-1 | 100.00 | 99.04 | 101.03 | 97.16 | 84.63 | 489.40 |
| | Embodiment 150-1 | 100.00 | 97.08 | 94.54 | 90.84 | 82.91 | 453.73 |
| | Embodiment 166-1 | 100.00 | 93.20 | 98.32 | 99.08 | 96.46 | 6505.51 |
| | Embodiment 165-1 | 100.00 | 95.57 | 96.73 | 93.97 | 91.93 | 1159.17 |
| | AMG 510 | 100.00 | 100.85 | 93.03 | 77.54 | 56.77 | 137.24 |
| mouse | Propantheline | 100.00 | 79.79 | 48.66 | 23.39 | 6.66 | 27.74 |
| | Embodiment 114-1 | 100.00 | 102.67 | 98.51 | 95.49 | 84.58 | 453.87 |
| | Embodiment 150-1 | 100.00 | 103.68 | 104.44 | 97.95 | 88.36 | 551.41 |
| | Embodiment 166-1 | 100.00 | 105.42 | 100.02 | 99.12 | 85.55 | 465.04 |
| | Embodiment 165-1 | 100.00 | 100.58 | 99.52 | 99.64 | 92.32 | 1015.92 |
| | AMG 510 | 100.00 | 97.50 | 82.58 | 81.82 | 63.23 | 184.89 |

TABLE 33-continued

Plasma stability results of embodiment compounds

| Species and genus | Number | Residual rate (%) 0 min | 15 min | 30 min | 60 min | 120 min | $t_{1/2}$ (min) |
|---|---|---|---|---|---|---|---|
| dog | Lovastatin | 100.00 | 95.25 | 95.45 | 75.66 | 36.25 | 80.22 |
| | Embodiment 114-1 | 100.00 | 97.87 | 96.23 | 92.42 | 85.48 | 534.11 |
| | Embodiment 150-1 | 100.00 | 96.78 | 94.25 | 92.45 | 89.54 | 830.19 |
| | Embodiment 166-1 | 100.00 | 99.98 | 98.79 | 93.69 | 86.16 | 532.60 |
| | Embodiment 165-1 | 100.00 | 97.71 | 96.32 | 94.86 | 92.49 | 1173.33 |
| | AMG 510 | 100.00 | 98.88 | 101.14 | 93.43 | 91.92 | 884.42 |

8.6 Experimental Conclusions

The above data show that the plasma stability of the embodiment compounds in the disclosure is high with little species difference.

Test Embodiment 9, CYP Enzyme Single Point Inhibition Test

9.1 Experimental Purpose

Using human liver microsomal incubation system, the inhibition of CYP450 enzyme subtypes by compounds was rapidly predicted by single point method.

9.2 Experimental Purpose 9.2.1 Solution Preparation 2.5 mM NADPH: 100 mM phosphate buffer was added to 4.165 mg of NADPH (reduced nicotinamide adenine dinucleotide phosphate) to 2 mL. 0.25 mg/mL microsome: 4 mL of 100 mM phosphate buffer was added to 50 μL of 20 mg/mL microsome and mixed well.

Preparation of Reaction Mixture for Compounds to be Tested

The embodiment compound to be tested was weighed and diluted to 10 mM with DMSO and then diluted to 100 μM with 100 mM phosphate buffer.

9.2.2 Experimental Process:

1. In a 96-well plate, 40 μL of liver microsomes, 10 μL of substrate, 10 μL of compound to be tested were pre-incubated for 3 min.
2. 40 μL of NADPH was added.
3. 300 μL of acetonitrile termination solution containing internal standard was added at 20 min.
4. Centrifugal injection.

9.3 Experimental Results

TABLE 34

Single point inhibition results of CYP enzyme of embodiment compounds

| Number | $IC_{50}$ (nM) 1A2 | 2C9 | 2C19 | 2D6 | 3A4-M | 3A4-T |
|---|---|---|---|---|---|---|
| Control | 0.064 | 0.459 | 0.293 | 0.099 | 0.089 | 0.117 |
| Embodiment 114-1 | >100 | 84.6 | >100 | >100 | 19.0 | >100 |

TABLE 34-continued

Single point inhibition results of CYP enzyme of embodiment compounds

| Number | $IC_{50}$ (nM) 1A2 | 2C9 | 2C19 | 2D6 | 3A4-M | 3A4-T |
|---|---|---|---|---|---|---|
| Embodiment 150-1 | 48.9 | 59.3 | 43.2 | 44.5 | 4.6 | 18.0 |
| Embodiment 165-1 | 66.7 | 58.8 | 28.8 | 21.2 | 4.7 | 9.1 |

Note:
Strong inhibition: $IC_{50} < 1$ μM;
moderate inhibition: 1 μM < $IC_{50}$ < 10 μM;
weak inhibition: $IC_{50} > 10$ μM

9.4 Experimental Conclusions

The above data show that the embodiment compound of the disclosure has no strong inhibition on each CYP enzyme subtype, and the risk of DDI is small.

Test Embodiment 10, Plasma Protein Binding Rate Test

10.1 Experimental Purpose

The purpose of this experimental method was to detect the plasma protein binding of the embodiment compounds in plasma.

10.2 Experimental Instruments and Material

Liquid-phase mass spectrometer, centrifuge, vortexer, pipette, continuous liquid dispenser, 96-well plate, tissue homogenizer (for tissue sample analysis), 50% methanol aqueous solution, acetonitrile solution with internal standard, blank matrix (plasma, urine or tissue homogenate, etc.)

10.3 Experimental Step 10.3.1 Preparation of the Stock Solution a for the Test Substance The embodiment compound was prepared into a 1 mM solution A with DMSO.

10.3.2 Preparation of Plasma Solution B

Solution A was added to the plasma solution and prepared into a 5 μM solution B.

10.3.3 Treatment Process 1) 200 μL of solution B was added into the membrane.

2) 350 μL of PBS was added to the outside of the membrane.
3) Incubating in a 37° C. water bath for 6 hours.
4) The samples were processed for dilution and detected by mass spectrometry.

10.4 Chromatographic Condition

Instrument: Shimadzu LC-20 AD;
Chromatographic column: phenomenex Gemiu® C18 (50*4.6 mm, 5 μM particle size);
Mobile phase: A: Acetonitrile, B: 0.1% formic acid solution 0-0.5 min: 5% A→90% A, 2.0-2.1 min: 90% A→5% A; flow rate: 0.8 mL/min; running time: 5.0 min; injection volume: 5 μL.

10.5 Mass Spectrum Condition

Instrument: API4000 Liquid Chromatography-Mass Spectrometry, AB, USA;
the ion source was electrospray ionization source (ESI);
the temperature of dry gas ($N_2$) was 500° C.;
electrospray voltage was 5500V;
the detection method was positive ion detection;
the scanning mode was selective response monitoring (MRM); the scanning time was 0.1 s.

10.6 Experimental Results

TABLE 35

Plasma protein binding rate of the embodiment compound

| Number | Human | Rat | Mouse | Dog |
|---|---|---|---|---|
| Embodiment 114-1 | 98.0 | 90.5 | 88.4 | 82.6 |
| Embodiment 150-1 | 99.8 | 94.9 | 90.1 | 98.7 |
| Embodiment 165-1 | 99.7 | 97.9 | 93.9 | 98.7 |
| Embodiment 166-1 | 96.8 | 95.4 | 96.3 | 92.5 |

10.7 Experimental Conclusions

The above data show that the embodiment compounds of the present disclosure exhibit high plasma protein binding rate with little species difference.

Test Embodiment 11. Determination of Pharmacokinetics in Tumor-Bearing Mice

11.1. Research Purpose

The pharmacokinetic behavior of embodiment compound 165 and AMG-510 compound, administered orally at a dose of 6 mg/kg, in mice (plasma, tumor tissue and intestine) was studied using MiaPaca 2 tumor-bearing mice as test animals.

11.2. Test Scheme 11.2.1 Test Drugs

Embodiment 165-1 of the present disclosure, AMG-510 compound, homemade.

11.2.2 Test Animals

24 MiaPaca 2 tumor-bearing mice, females. 3 for each time point (0 h, 1 h, 2 h, 4 h, 6 h, 8 h, 16 h, 24 h). Shanghai xipuer-bikai Laboratory Animal Co., Ltd, Animal Production License No. (SCXK (Shanghai) 2018-0006.

11.2.3 Drug Formulation 5 g of Hydroxymethyl cellulose was weighed, dissolved in 1000 mL of purified water, and 10 g of Tween 80 was added. The mixture was mixed well to form a clear solution.

Embodiment compound 165-1 and compound AMG-510 were weighed and dissolved in the solution, the mixture was shaken well, and ultrasound was performed for 15 minutes to obtain a uniform suspension with a concentration of 0.6 mg/mL.

11.2.4 Administration

MiaPaca 2 tumor-bearing mice were administered at a dose of 6 mg/kg in a volume of 10 mL/kg, respectively, based on body weight p.o. after fasting (animals were not administered at point 0 h).

11.2.5 Sample Collection

Before and after administration, mice were sacrificed with $CO_2$, 0.5 mL blood was collected from the heart and placed in EDTA-2K tube, centrifuged at 4° C. 6000 rpm for 6 min to separate plasma, and stored at −80° C.; after the tumor tissues were weighing, placed in a 2 mL centrifuge tube and stored at −80° C. The duodenum, ileum and colon tissues were cut with scissors, the contents were removed and cleaned twice with PBS, after absorbing water with absorbent paper, they were weighed, placed in a 2 mL centrifuge tube and stored at −80° C.

11.3 Experimental Results: The Final Determination Results Obtained by Applying LCMS/MS Method are Shown in Table 36

TABLE 36

Pharmacokinetic parameters of the compounds of the disclosure in mice

| Number of the compound | | Ratio (T/P) | $T_{1/2}$ (hr) | MRT (hr) |
|---|---|---|---|---|
| AMG-510 | Plasma | 0.42 | 0.3 | 0.8 |
| | Tumor | | 0.3 | 0.7 |
| Embodiment 165-1 | Plasma | 0.57 | 0.5 | 0.9 |
| | Tumor | | 0.9 | 1.5 |

11.4 Experimental Conclusions

At a dose of 6 mg/kg, the ratio of exposure of the embodiment compounds of the present disclosure in the tumor of the mouse to the exposure in the blood was higher than that of AMG-510, with longer $T_{1/2}$ and MRT.

Although the above describes specific embodiments of the present disclosure, it should be understood by those skilled in the art that these are merely illustrative embodiments and that a variety of changes or modifications can be made to these embodiments without departing from the principles and substance of the present disclosure. Therefore, the scope of protection of the present disclosure is defined by the appended claims.

The invention claimed is:

1. A compound represented by general formula (XI), a stereoisomer thereof or a pharmaceutically acceptable salt thereof:

(XI)

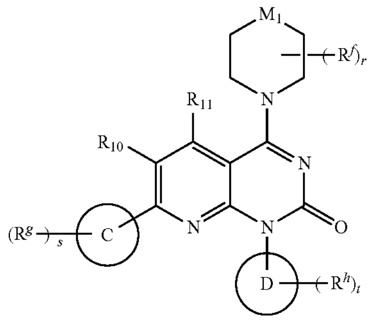

wherein:

$M_1$ is selected from $CR_{12}R_{13}$ or $NR_{12}$;

ring C is selected from $C_{6-14}$ aryl or 5-14 membered heteroaryl;

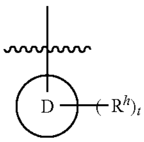

is selected from

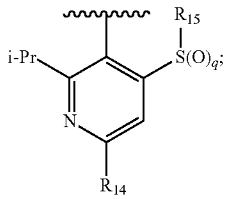

$R_{10}$ and $R_{11}$ are each independently selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl;

$R_{12}$ is selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, $C_{3-12}$ cycloalkyl, 3-12 membered heterocyclyl, $C_{6-12}$ aryl or 5-12 membered heteroaryl or $—(CH2)_{n2}C(O)CR_{ee}{=}CR_{ff}R_{gg}$;

$R_{13}$ is selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl;

$R_{14}$ is selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$alkyl, $C_{3-12}$ cycloalkyl, 3-12 membered heterocyclyl, $C_{6-12}$ aryl or 5-12 membered heteroaryl, the amino, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$aryl or 5-12 membered heteroaryl are optionally substituted by one or more substituents selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl and 5-12 membered heteroaryl;

$R_{15}$ is selected from $C_{1-6}$ alkyl;

$R^f$ is selected from hydrogen, deuterium, halogen, amino, hydroxyl, sulfhydryl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ alkylthio, $C_{1-6}$ alkylsulfinyl, $C_{1-6}$ alkylsulfonyl, $C_{1-6}$ haloalkoxy, $C_{1-6}$ hydroxyalkyl, $C_{3-12}$ cycloalkyl, 3-12 membered heterocyclyl, $C_{6-12}$ aryl, 5-12 membered heteroaryl or $—(CH_2)_nC(O)CH{=}CHR_{aa}$;

$R^g$ is selected from hydrogen, deuterium, halogen, amino, hydroxyl, cyano, nitro, $C_{1-6}$ alkyl, $C_{2-6}$ alkenyl, $C_{2-6}$ alkynyl, oxo, thio, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl, 5-12 membered heteroaryl, $—O(CH_2)_{n2}Ree$, $—OC(R_{ee}R_{ff})_{n2}(CH_2)_{m1}R_{gg}$, $—NR_{ee}(CH_2)_{n2}R_{ff}$, $—(CH_2)_{n2}SR_{ee}$, $—(CH_2)_{n2}R_{ee}$, $—(CH_2)_{n2}OR_{ee}$, $—(CH_2)_{n2}SR_{ee}$, $—(CH_2)_{n2}C(O)R_{ee}$, $—(CH_2)_{n2}C(O)OR_{ee}$, $—(CH_2)_{n2}S(O)_{m1}R_{ee}$, $—(CH_2)_{n2}C(O)NR_{ee}R_{ff}$, $—(CH_2)_{n2}NR_{ee}C(O)R_{ff}$ or $—(CH_2)_{n2}NR_{ee}S(O)_{m1}R_{ff}$;

$R_{aa}$ is selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl;

$R_{ee}$, $R_{ff}$ and $R_{gg}$ are each independently selected from hydrogen, deuterium, halogen, amino, hydroxyl, cyano, nitro, $C_{1-6}$ alkyl, $C_{2-6}$ alkenyl, $C_{2-6}$ alkynyl, $C_{1-6}$ deuterated alkyl, $C_{1-6}$ haloalkyl, $C_{1-6}$ alkoxy, $C_{1-6}$ haloalkoxy, $C_{1-6}$ hydroxyalkyl, cyano-substituted $C_{1-6}$ alkyl, $C_{3-12}$ cycloalkyl, 3-12 membered heterocyclyl, $C_{6-12}$ aryl or 5-12 membered heteroaryl;

r is an integer from 0 to 5;

s is an integer from 0 to 5;

t is an integer from 0 to 5;

n is an integer from 0, 1, 2, or 3;

n2 is an integer from 0 to 5; and m1 is 0, 1 or 2; and q is 0, 1 or 2.

2. The compound as defined in claim 1, the stereoisomer thereof or the pharmaceutically acceptable salt thereof, wherein, the compound is further represented by general formula (XI-B):

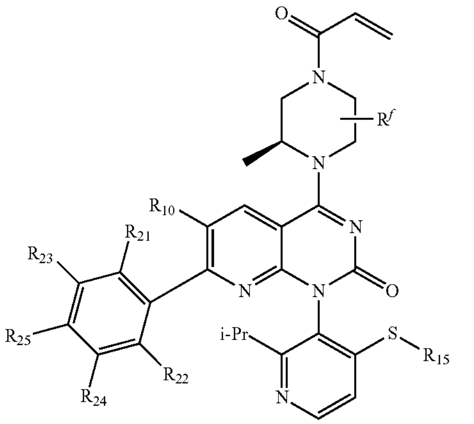

(XI-B)

wherein:

$R^f$ is selected from hydrogen, deuterium, halogen, amino, hydroxyl, sulfhydryl, cyano, nitro, methyl, ethyl, propyl, isopropyl, deuterated methyl, deuterated ethyl, deuterated propyl, deuterium isopropyl, halomethyl, haloethyl, halopropyl, haloisopropyl, methoxy, ethoxy, propoxy, isopropoxy, methylthio, ethylthio, propylthio, isopropylthio, halomethoxy, haloethoxy, halopropoxy, hydroxymethyl, hydroxyethyl, hydroxypropyl or hydroxyisopropyl;

$R_{10}$ is selected from hydrogen, deuterium, fluorine, chlorine, bromine, iodine, amino, hydroxyl, cyano, nitro, methyl, ethyl, propyl, isopropyl, deuterated methyl, deuterated ethyl, deuterated propyl, deuterium isopropyl, halomethyl, haloethyl, halopropyl, haloisopropyl, methoxy, ethoxy, propoxy, isopropoxy, halomethoxy, haloethoxy, halopropoxy, haloisopropoxy, hydroxymethyl, hydroxyethyl, hydroxypropyl or hydroxyisopropyl;

$R_{15}$ is selected from methyl, ethyl, propyl or isopropyl;

$R_{21}$ and $R_{22}$ are each independently selected from hydrogen, deuterium, fluorine, chlorine, bromine, iodine, amino, hydroxyl, cyano, nitro, methyl, ethyl, propyl, isopropyl, deuterated methyl, deuterated ethyl, deuterated propyl, deuterium isopropyl, halomethyl, haloethyl, halopropyl, haloisopropyl, methoxy, ethoxy, propoxy, isopropoxy, hydroxymethyl, hydroxyethyl, hydroxypropyl or hydroxyisopropyl;

$R_{23}$ and $R_{24}$ are each independently selected from hydrogen, deuterium, fluorine, chlorine, bromine, iodine, amino, hydroxyl, sulfhydryl, cyano, nitro, methyl, ethyl, propyl, isopropyl, deuterated methyl, deuterated ethyl, deuterated propyl, deuterium isopropyl, halomethyl, haloethyl, halopropyl, haloisopropyl, methoxy, ethoxy, propoxy, isopropoxy, hydroxymethyl, hydroxyethyl, hydroxypropyl or hydroxyisopropy;

$R_{25}$ is selected from hydrogen, deuterium, fluorine, chlorine, bromine, iodine, amino, hydroxyl, sulfhydryl, cyano, nitro, methyl, ethyl, propyl, isopropyl, deuterated methyl, deuterated ethyl, deuterated propyl, deuterium isopropyl, halomethyl, haloethyl, halopropyl, haloisopropyl, methoxy, ethoxy, propoxy, isopropoxy, hydroxymethyl, hydroxyethyl, hydroxypropyl or hydroxyisopropyl.

3. The compound as defined in claim 2, the stereoisomer thereof or the pharmaceutically acceptable salt thereof, wherein, the compound is further represented by general formula (XI-C) or (XI-D):

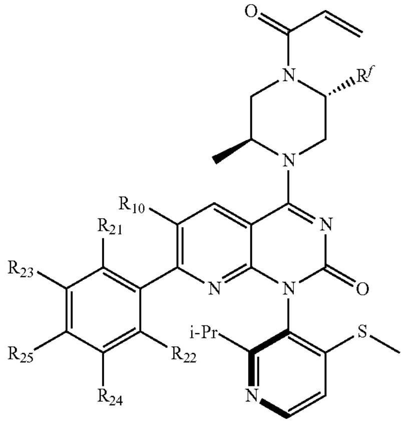

(XI-C)

or

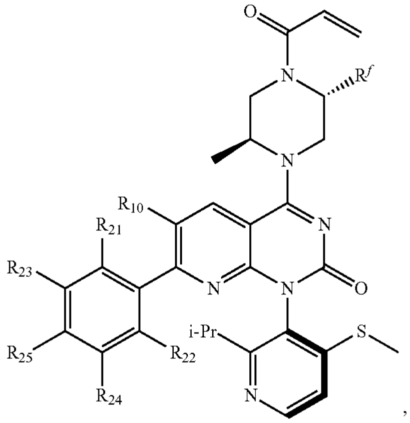

(XI-D)

, $R^f$ is selected from hydrogen or methyl;

$R_{10}$ is selected from hydrogen, fluorine, chlorine, bromine or methyl;

$R_{21}$ and $R_{22}$ are each independently selected from amino or fluorine, and $R_{23}$ and $R_{24}$ are each independently selected from hydrogen, fluorine, chlorine, bromine, methyl, ethyl, propyl or isopropyl;

or, $R_{21}$ and $R_{22}$ are each independently selected from hydroxyl or fluorine, and $R_{23}$ and $R_{24}$ are each independently selected from hydrogen, fluorine, chlorine, bromine, methyl, ethyl, propyl or isopropyl;

$R_{25}$ is selected from hydrogen, fluorine, chlorine, bromine or methyl.

4. A compound a stereoisomer thereof or a pharmaceutically acceptable salt thereof, wherein, the structure of the compound is as follows:

-continued
83
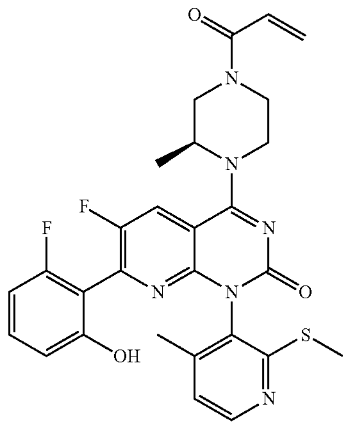
114
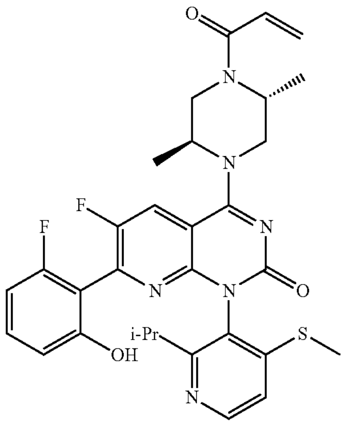
115
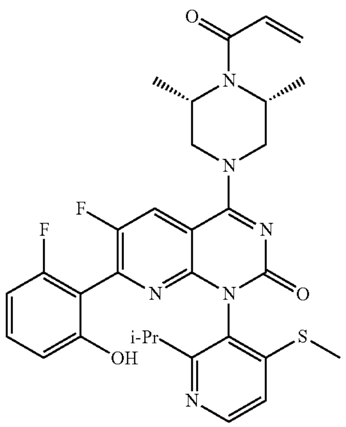
116
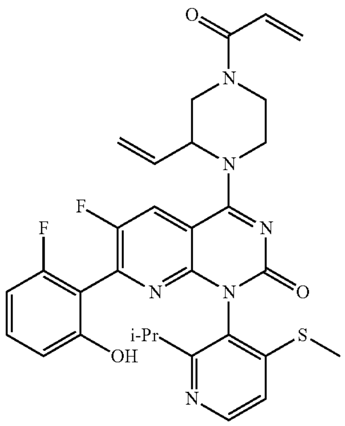
117
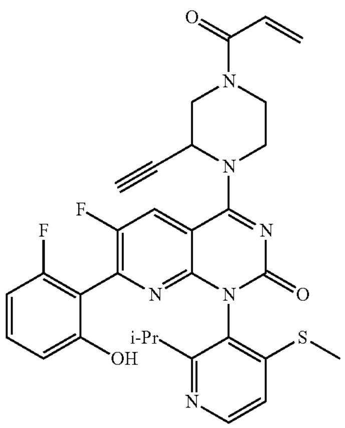
130
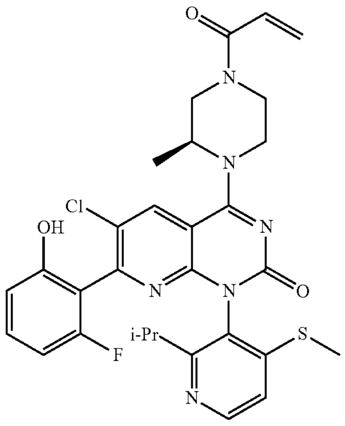

-continued
131
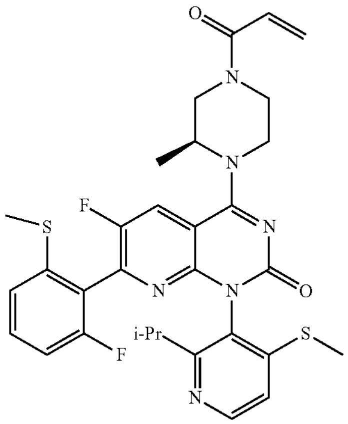
132
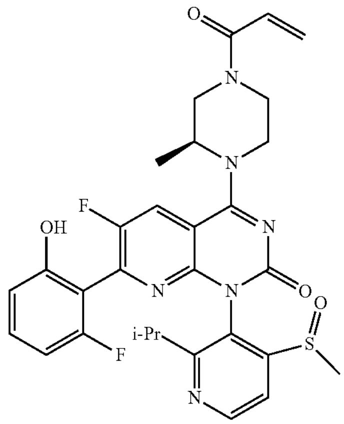
133
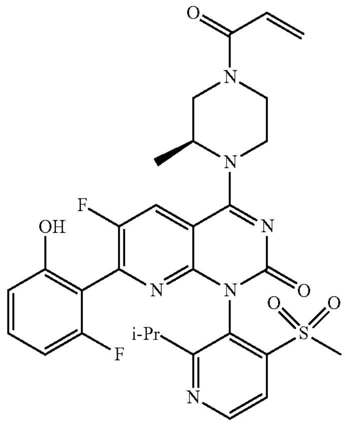
-continued
134
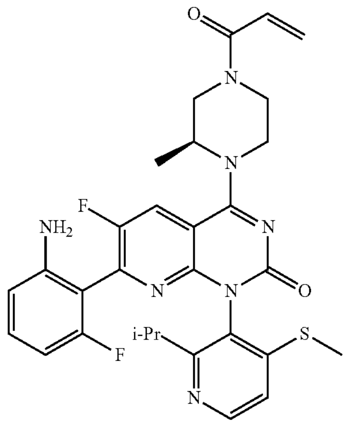
139
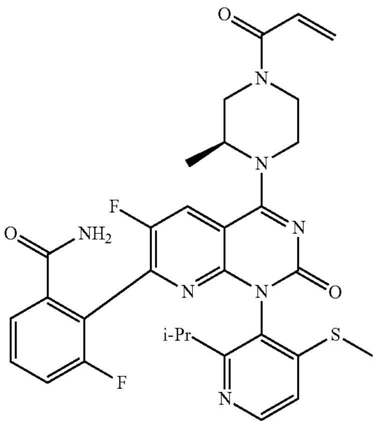
140
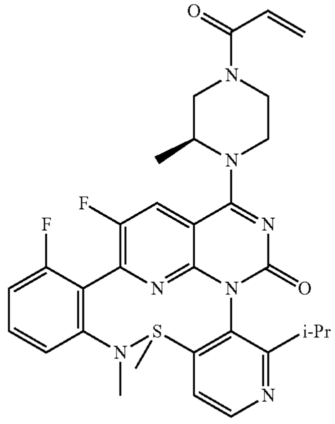

-continued
141
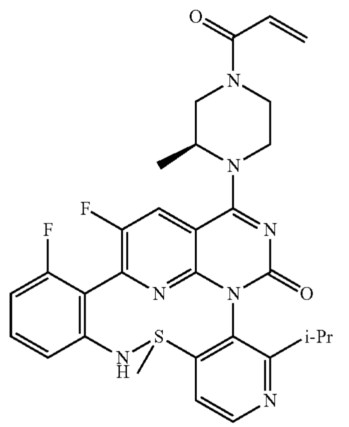
144
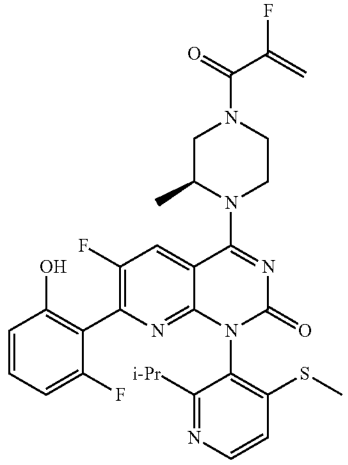
145
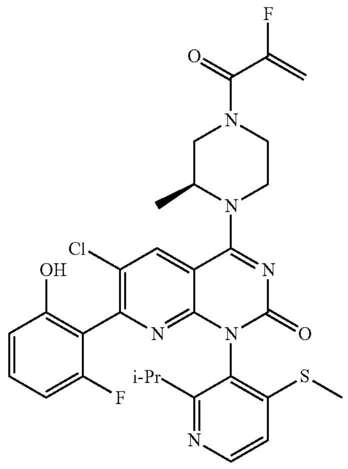
-continued
147
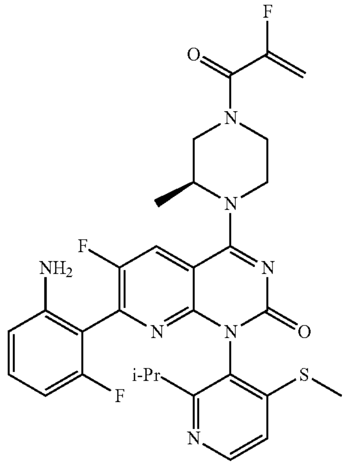
148
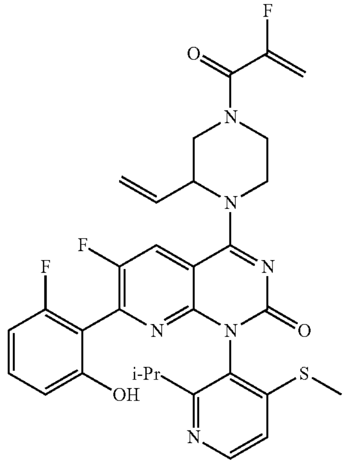
149
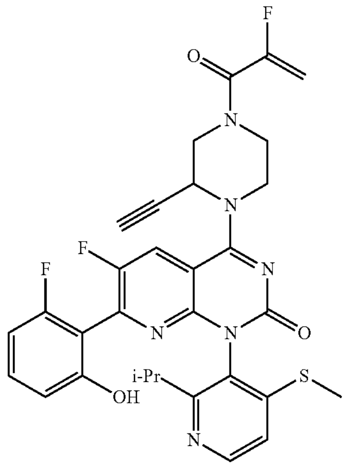

-continued
150
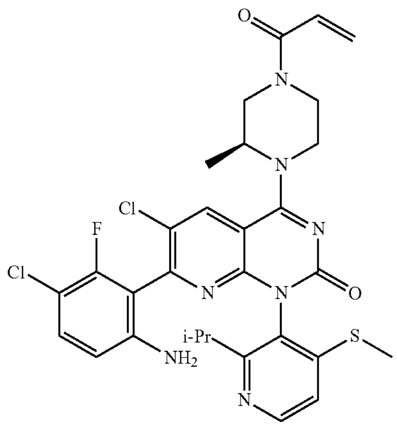
151
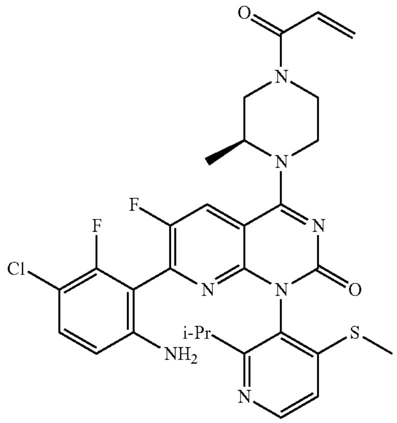
152
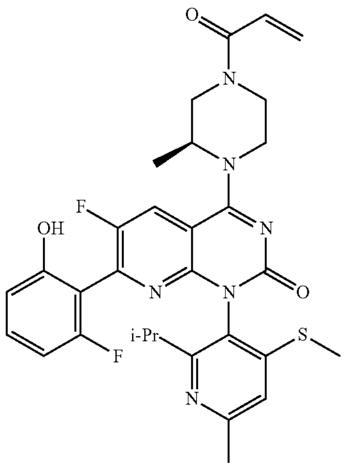
-continued
153
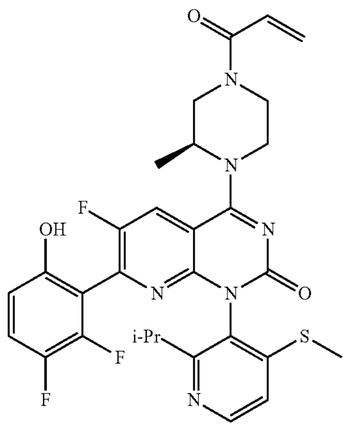
154
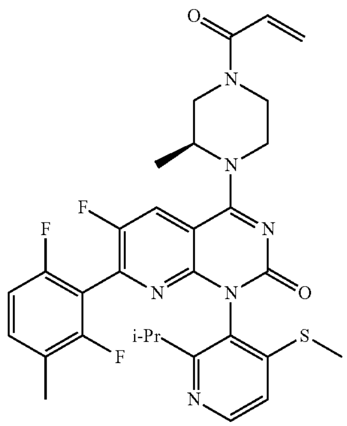
155
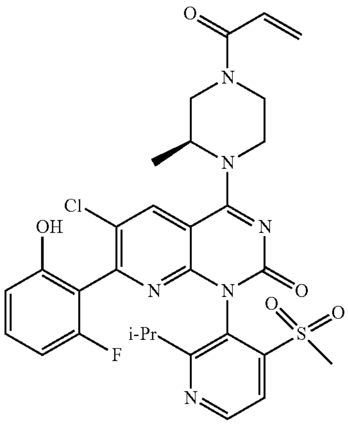

-continued
156
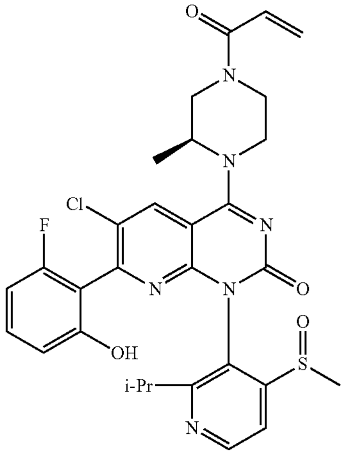
157
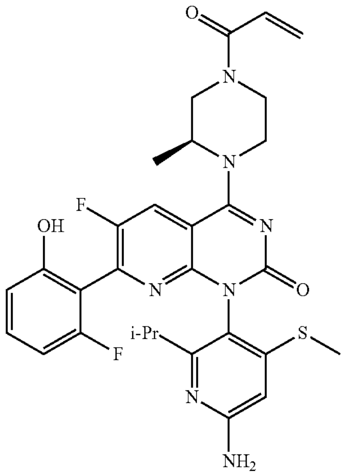
158
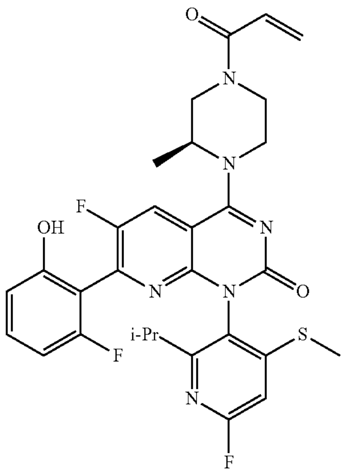
-continued
159
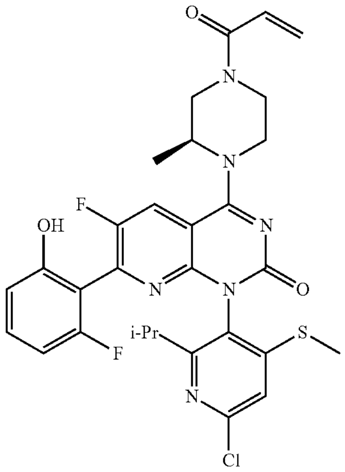
160
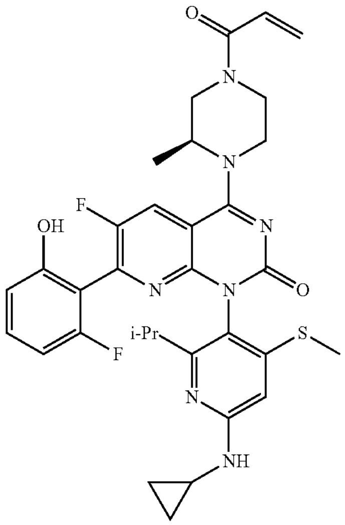
161
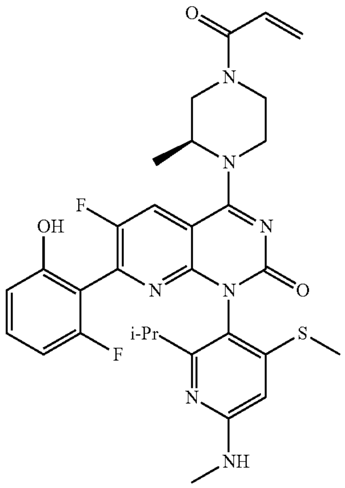

-continued
162
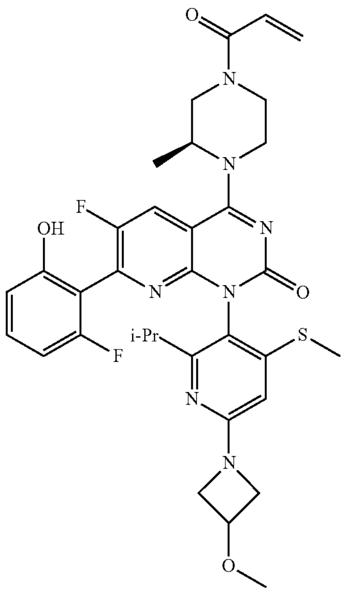
163
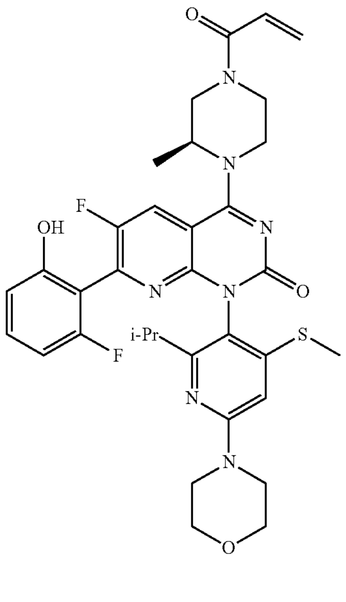
-continued
164
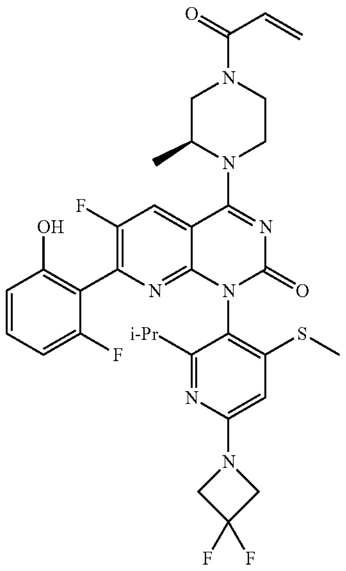
165
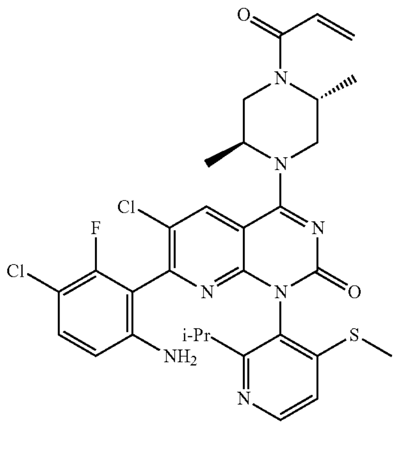
166
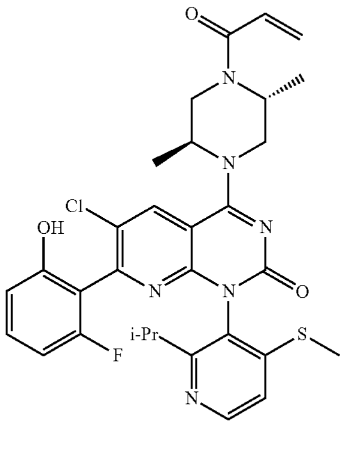

167
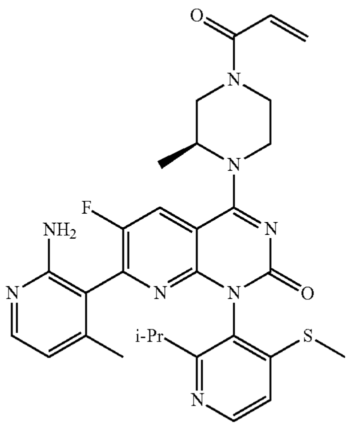
168
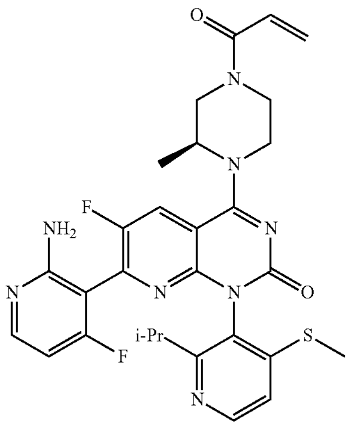
169
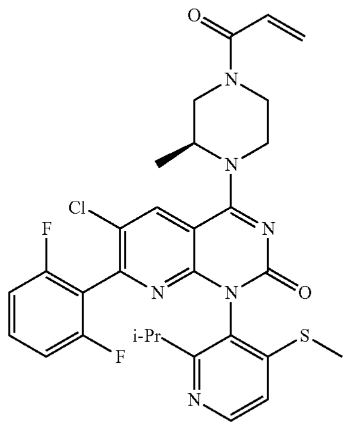
170
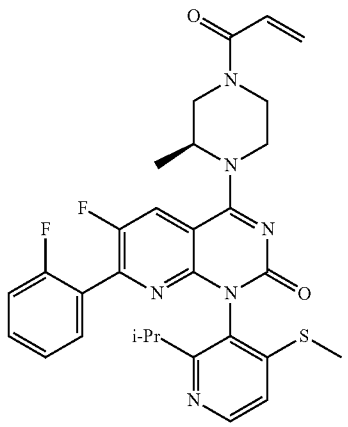
191
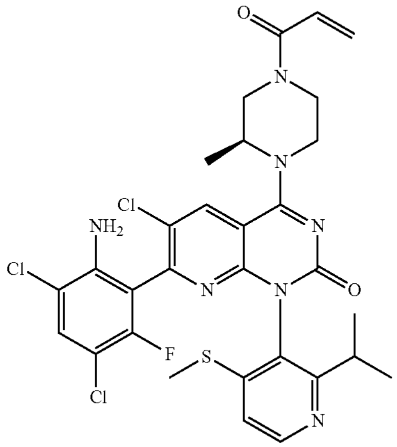
192
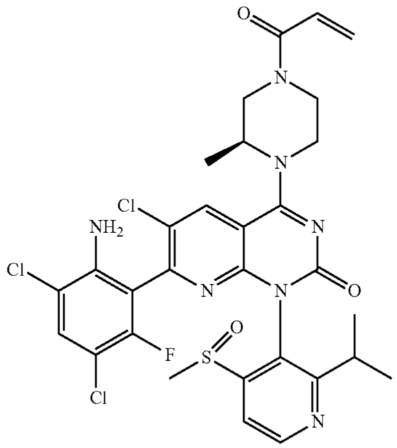

-continued
193
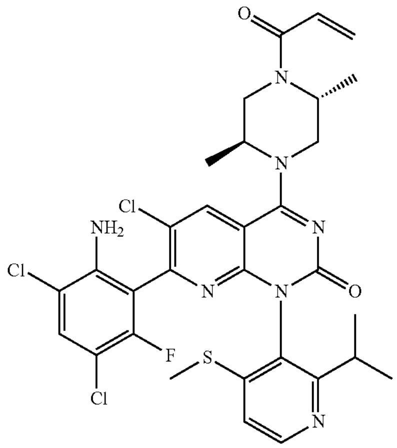
194
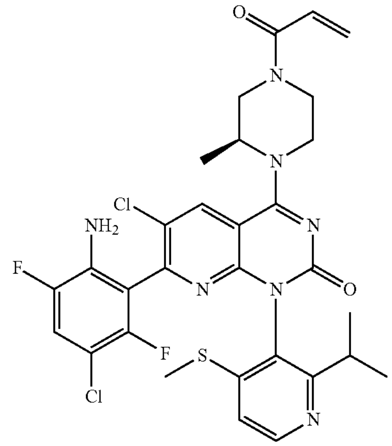
195
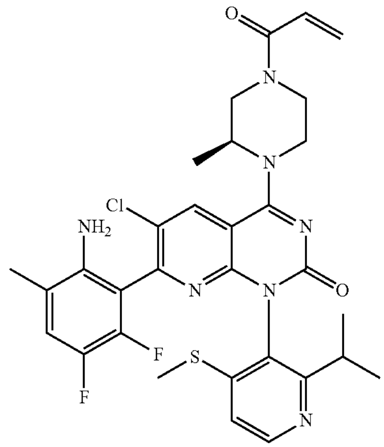
-continued
196
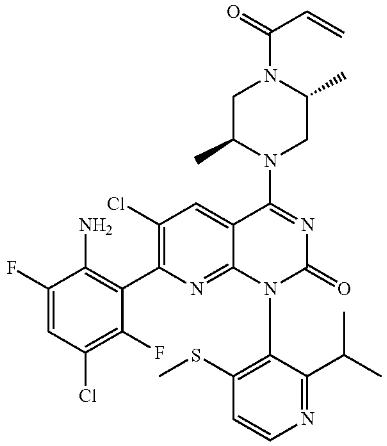
197
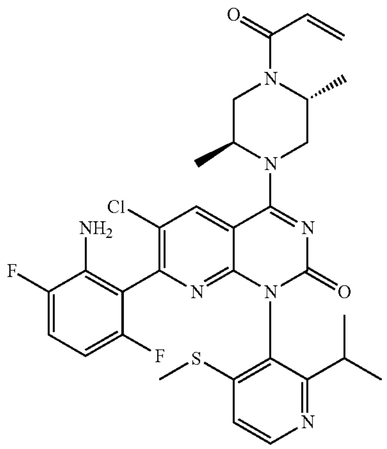
198
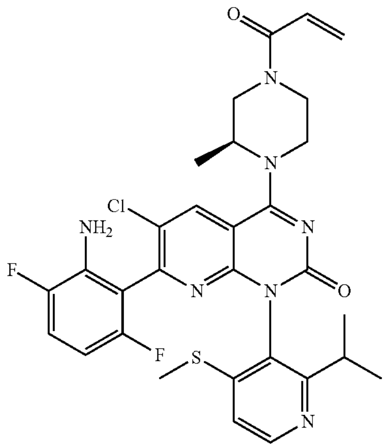

-continued
199
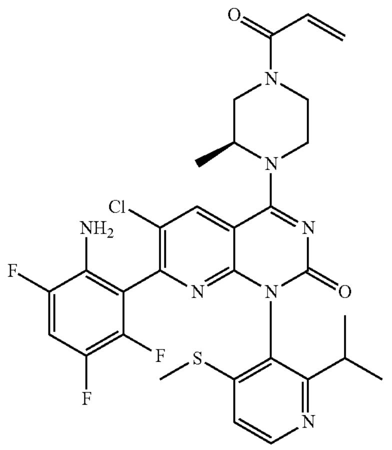
200
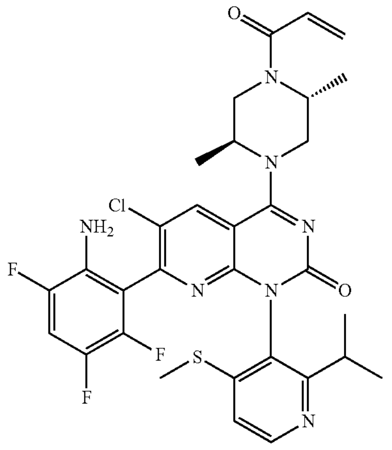
201
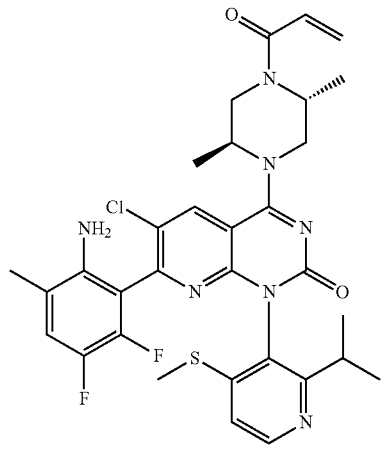
-continued
202
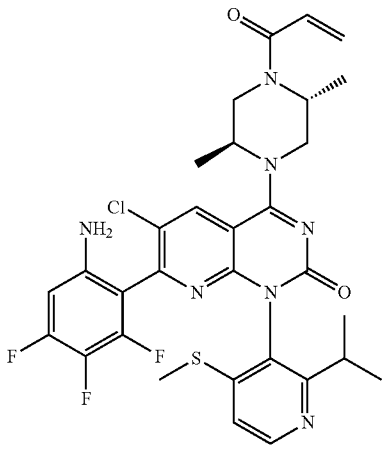
203
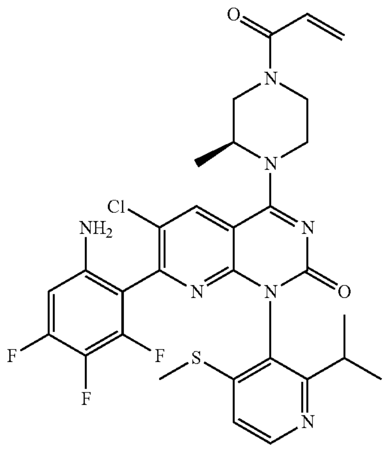
204
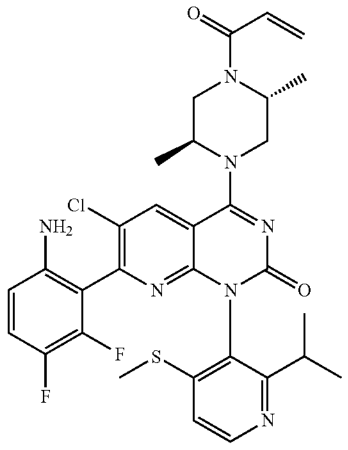

-continued
205
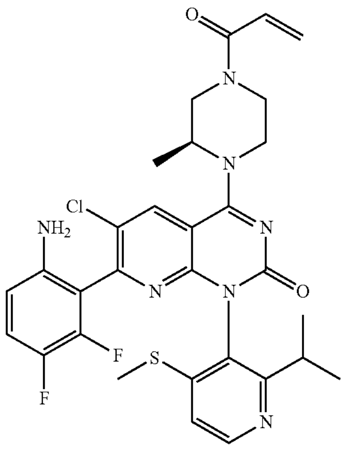
206
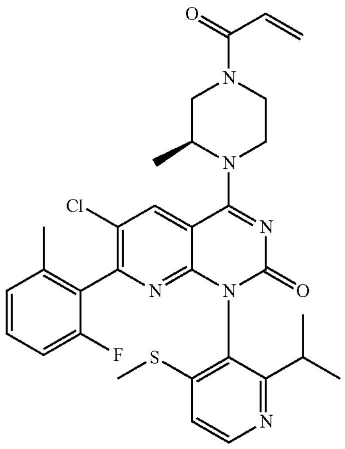
207
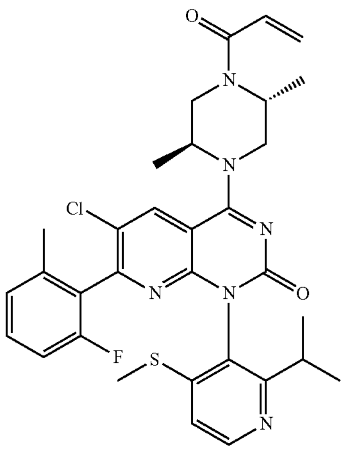
-continued
208
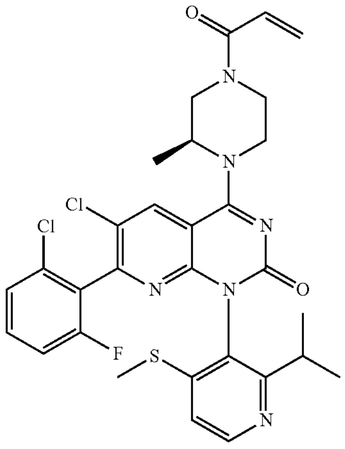
209
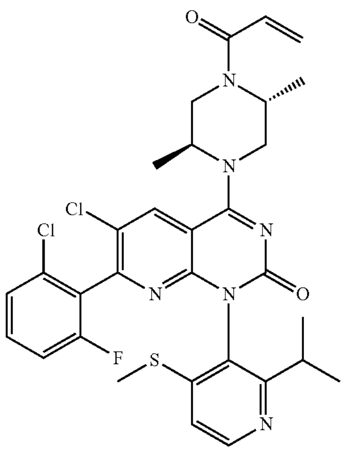
210
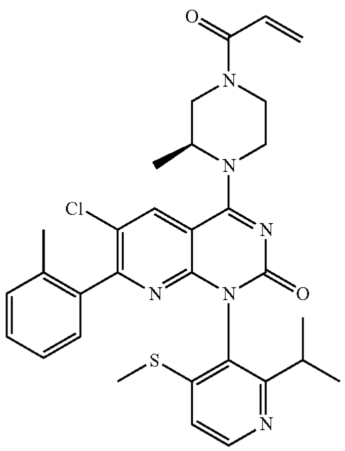

211
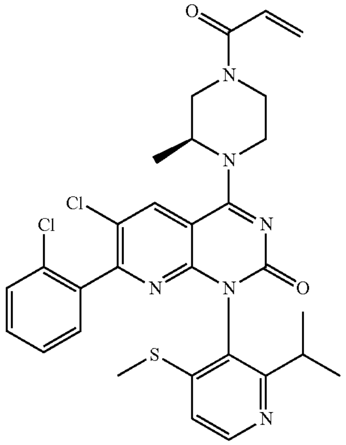
212
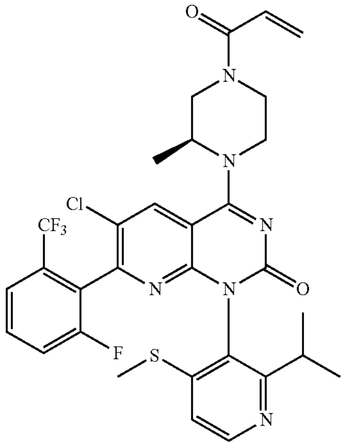
213
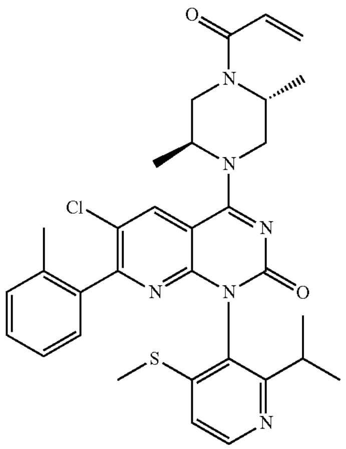
214
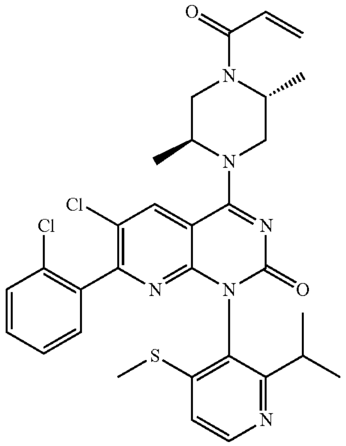
or
215
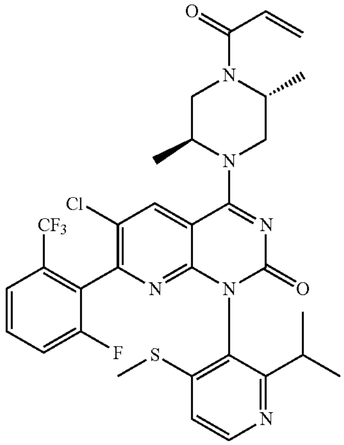
.
5. The compound as defined in claim 4, the stereoisomer thereof or the pharmaceutically acceptable salt thereof, wherein, when the compound is selected from the following compound structures, the compound is further separable into enantiomeric axially chiral isomers:
60
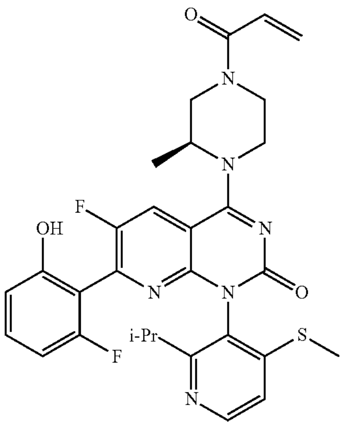

-continued
114
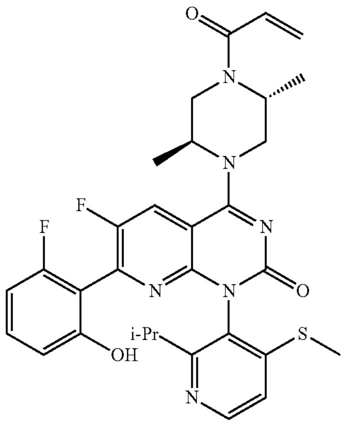
150
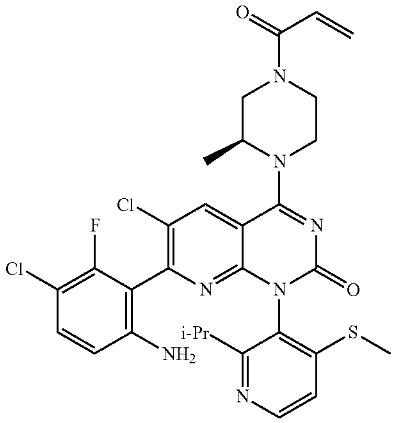
165
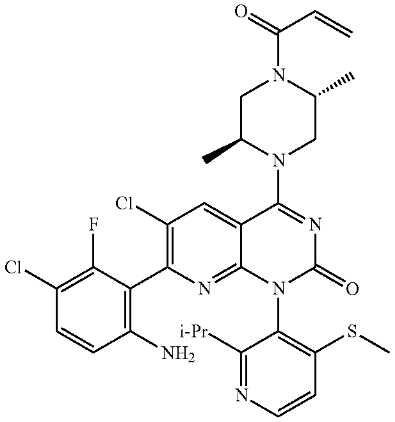
or
-continued
166
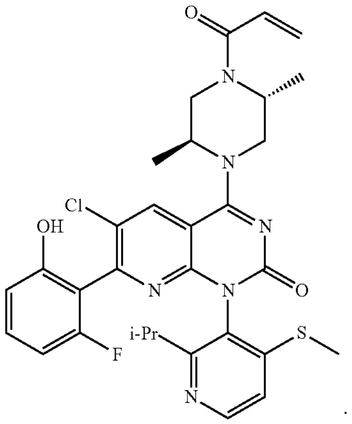
6. The compound as defined in claim 5, the stereoisomer thereof or the pharmaceutically acceptable salt thereof, wherein, the axially chiral isomer structure of the compound is as follows:
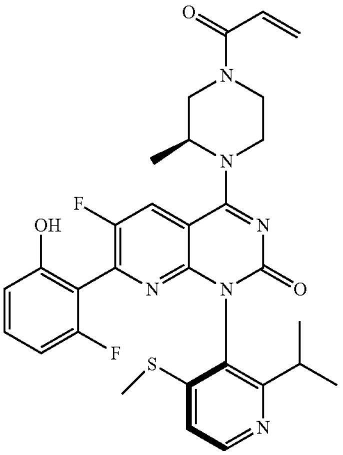
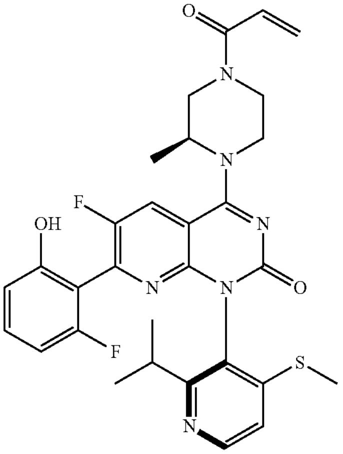

-continued
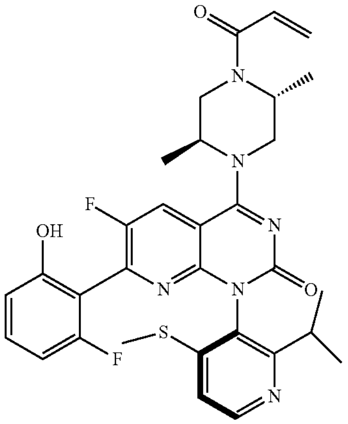
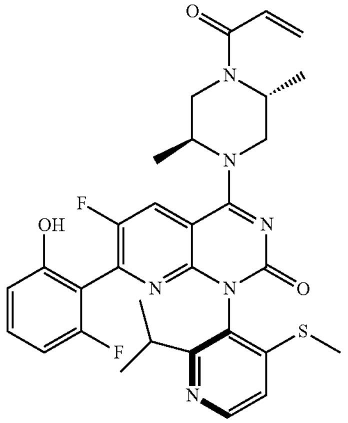
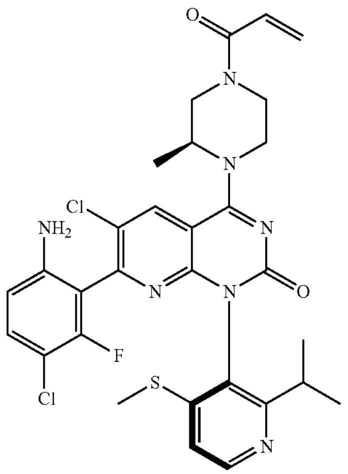
-continued
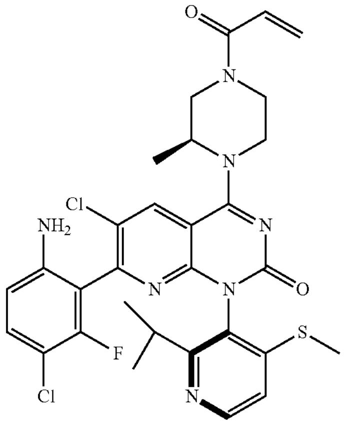
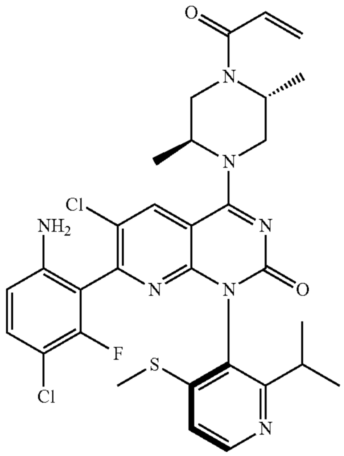
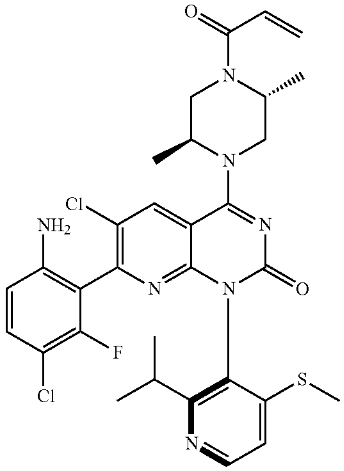

-continued

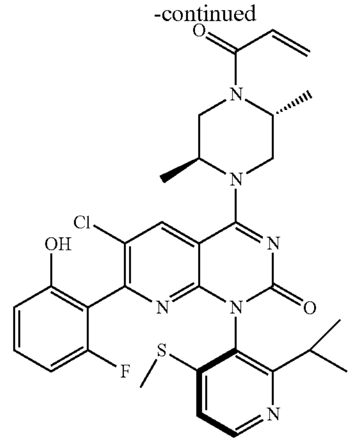

or

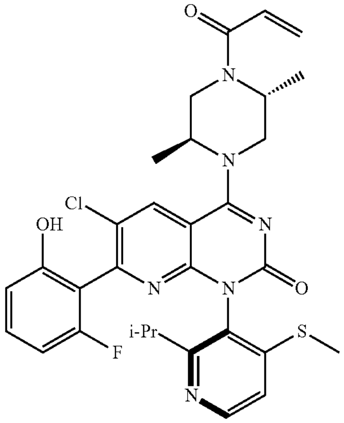

.

7. The compound as defined in claim 1, the stereoisomer thereof or the pharmaceutically acceptable salt thereof, wherein, M1 is selected from the following groups:

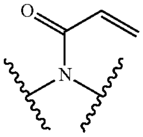

,

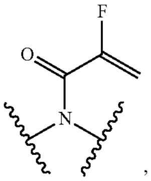

,

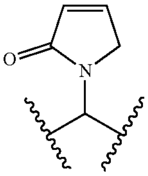

or

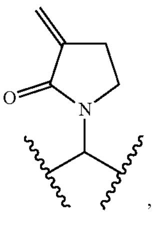

, ring C is selected from phenyl or pyridyl;

R12 is selected from 3-12 membered heterocyclyl or —(CH2)n2C(O)CRee=CRffRgg, and the 3-12 membered heterocyclyl is optionally substituted by one or more substituents selected from hydrogen, deuterium, halogen, amino, hydroxyl, cyano, nitro, oxo and methylene.

8. The compound as defined in claim 1, the stereoisomer thereof or the pharmaceutically acceptable salt thereof, wherein, ring C is selected from the following groups:

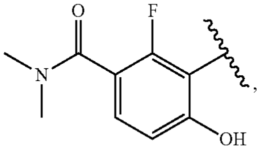
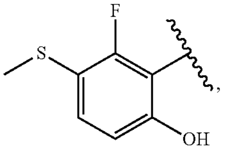
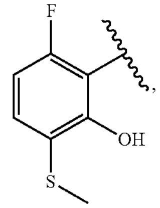
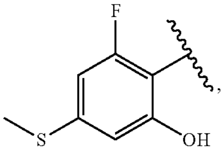
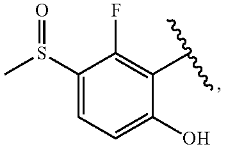
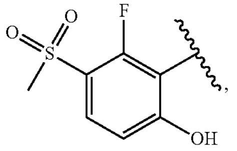
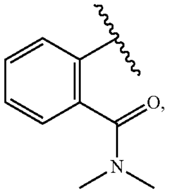
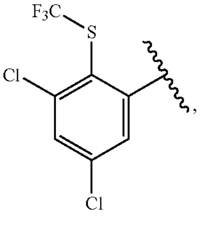
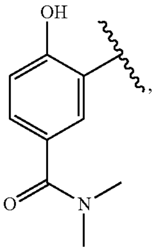
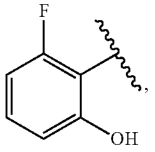
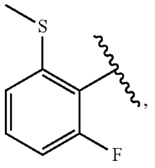
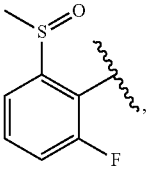
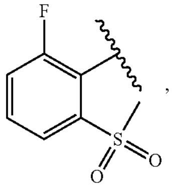

,

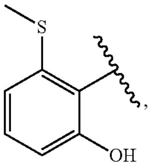
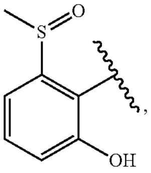
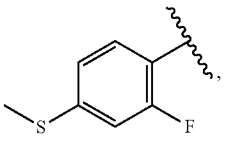
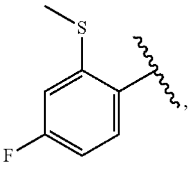
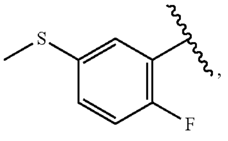
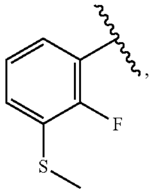
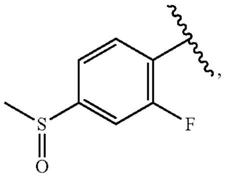
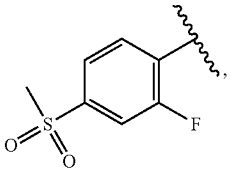

-continued

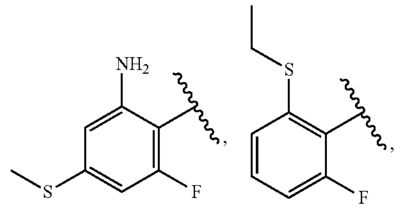

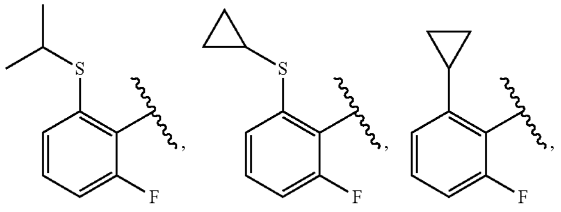

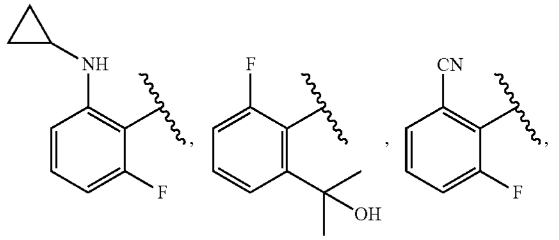

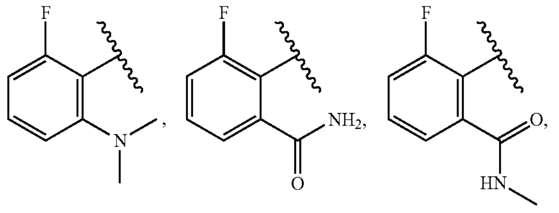

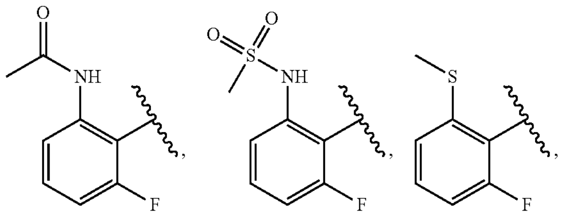

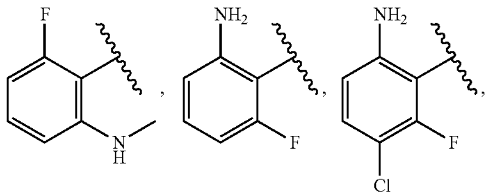

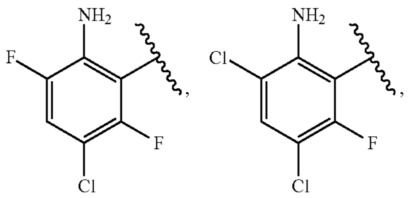

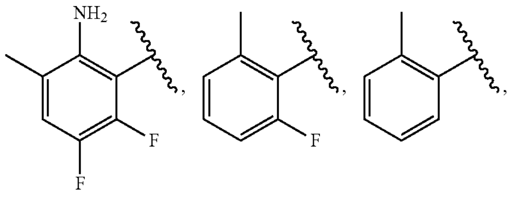

-continued

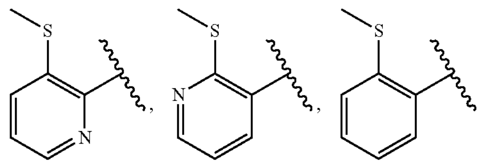

or

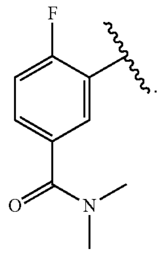

9. The compound as defined in claim 1, the stereoisomer thereof or the pharmaceutically acceptable salt thereof, wherein, $R_{14}$ is selected from hydrogen, halogen, amino, $C_{1-3}$ alkyl or 3-8 membered heterocyclyl, the amino, $C_{1-3}$ alkyl and 3-8 membered heterocyclyl are optionally substituted by one or more substituents selected from hydrogen, halogen, $C_{1-3}$ alkoxy and $C_{3-8}$ cycloalkyl;

$R_{15}$ is selected from $C_{1-3}$ alkyl.

10. The compound as defined in claim 1, the stereoisomer thereof or the pharmaceutically acceptable salt thereof, wherein, $R_{14}$ is selected from hydrogen, chlorine, fluorine, bromine, amino, methyl, methoxy, cyclopropyl, azetidinyl, morpholinyl, the amino, methyl, methoxy, cyclopropyl, azetidinyl and morpholinyl are optionally substituted by one or more substituents selected from hydrogen, fluorine, chlorine, bromine and cyclopropyl; and $R_{15}$ is selected from methyl.

11. The compound as defined in claim 1, the stereoisomer thereof or the pharmaceutically acceptable salt thereof, wherein, ring D is selected from the following groups:

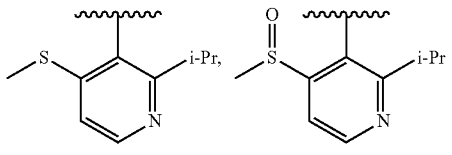

or

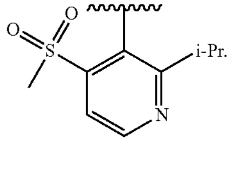

12. A pharmaceutical composition comprising a therapeutically effective amount of the compound of claim 1, the stereoisomer thereof or the pharmaceutically acceptable salt thereof, and one or more pharmaceutically acceptable carriers, diluents or excipients.

13. A method for preparing the compound represented by general formula (XI-B) as defined in claim 2, the stereoisomer thereof or the pharmaceutically acceptable salt thereof, wherein, comprising the following steps,

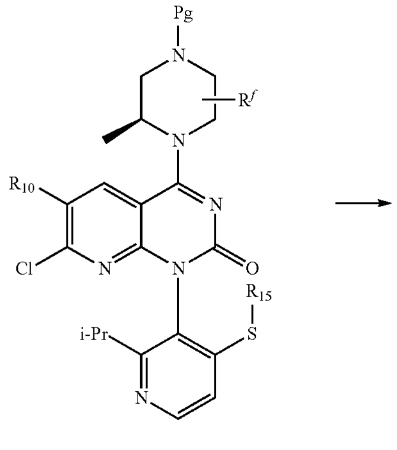

(XI-B4)

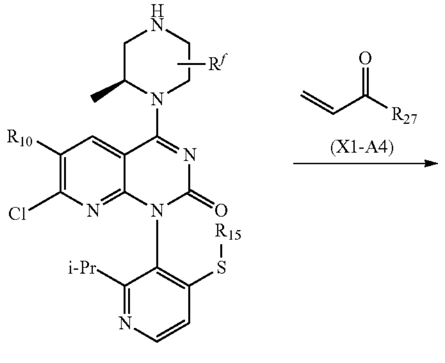

(X1-A4)

(XI-B3)

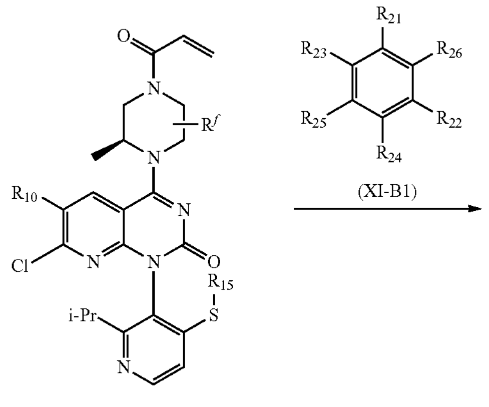

(XI-B1)

(XI-B2)

-continued

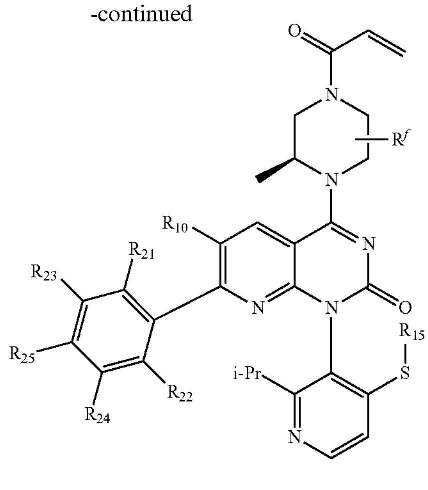

(XI-B)

a compound represented by general formula (XI-B4) is deprotected to obtain a compound represented by general formula (XI-B3) or a stereoisomer thereof and a pharmaceutically acceptable salt thereof;

a condensation reaction is carried out between the compound represented by general formula (XI-B3) and the compound represented by general formula (XI-A4) to obtain a compound represented by general formula (XI-B2) or a stereoisomer thereof and a pharmaceutically acceptable salt thereof;

a coupling reaction is carried out between the compound represented by general formula (XI-B2) and a compound represented by general formula (XI-B1) to obtain the compound represented by general formula (XI-B) or the stereoisomer thereof and the pharmaceutically acceptable salt thereof;

Pg is tert-butoxycarbonyl;

$R_{26}$ is —B(OH)$_2$;

$R_{27}$ is halogen.

14. A method for preparing the compound represented by general formula (XI-B) as defined in claim 2, the stereoisomer thereof or the pharmaceutically acceptable salt thereof, wherein, comprising the following steps,

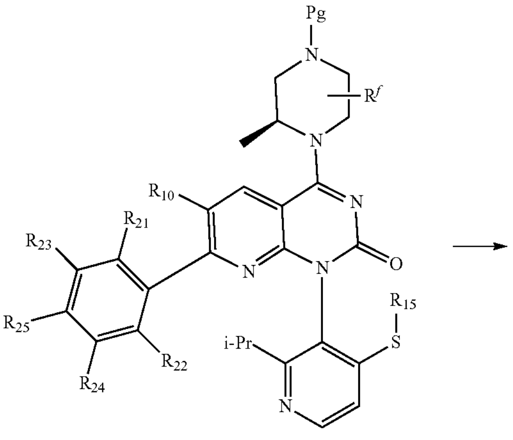

(XI-B6)

-continued

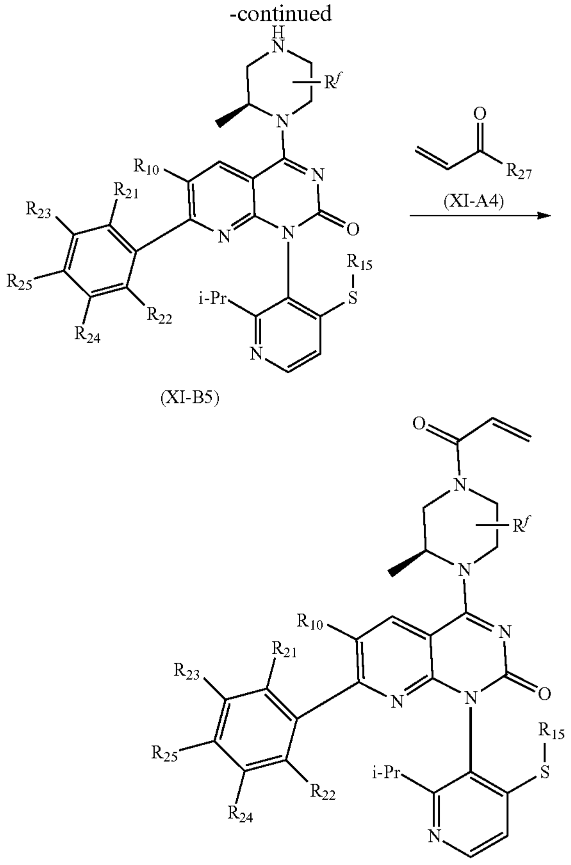

(XI-B5)

(XI-A4)

(XI-B)

a compound represented by general formula (XI-B6) is deprotected to obtain a compound represented by general formula (XI-B5) or a stereoisomer thereof and a pharmaceutically acceptable salt thereof;

a condensation reaction is carried out between the compound represented by general formula (XI-B5) and the compound represented by general formula (XI-A4) to obtain the compound represented by general formula (XI-B) or the stereoisomer thereof and the pharmaceutically acceptable salt thereof;

Pg is tert-butoxycarbonyl;

$R_{27}$ is halogen.

15. A method of treating a patient in need of KRAS inhibition, comprising administering a compound as defined in claim 1.

16. A method of treating Noonan syndrome, leopard syndrome, leukemia, neuroblastoma, melanoma, esophagus cancer, head and neck tumor, breast cancer, lung cancer, pancreatic cancer and colon cancer in a mammal in need thereof, the method comprising administering to the mammal a therapeutically effective amount of the compound as defined in claim 1, the stereoisomer thereof or the pharmaceutically acceptable salt thereof.

* * * * *